US008697708B2

(12) United States Patent
Blench et al.

(10) Patent No.: US 8,697,708 B2
(45) Date of Patent: Apr. 15, 2014

(54) AZABENZOTHIAZOLE COMPOUNDS, COMPOSITIONS AND METHODS OF USE

(75) Inventors: Toby Jonathan Blench, London (GB); Charles Ellwood, Chelmsford (GB); Simon Charles Goodacre, Sawbridgeworth (GB); Yingjie Lai, Cupertino, CA (US); Jun Liang, Palo Alto, CA (US); Calum Macleod, Bishops Stortford (GB); Steven R. Magnuson, Dublin, CA (US); Vickie H. Tsui, Burlingame, CA (US); Karen Williams, Bourne (GB); Birong Zhang, Union City, CA (US)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/232,778

(22) Filed: Sep. 14, 2011

(65) Prior Publication Data

US 2012/0202788 A1 Aug. 9, 2012

Related U.S. Application Data

(60) Provisional application No. 61/383,273, filed on Sep. 15, 2010.

(51) Int. Cl.
*A01N 43/90* (2006.01)
*A61K 31/519* (2006.01)
*C07D 471/00* (2006.01)
*C07D 487/00* (2006.01)
*C07D 491/00* (2006.01)
*C07D 495/00* (2006.01)

(52) U.S. Cl.
USPC .................. 514/260.1; 544/255; 544/278

(58) Field of Classification Search
None
See application file for complete search history.

(56) References Cited

U.S. PATENT DOCUMENTS

| 4,603,139 | A  | 7/1986  | King |
| 5,659,039 | A  | 8/1997  | Ogiso et al. |
| 7,132,439 | B2 | 11/2006 | Wang et al. |
| 7,199,119 | B2 | 4/2007  | Burkitt et al. |
| 7,335,652 | B2 | 2/2008  | Wischik et al. |
| 7,642,358 | B2 | 1/2010  | Zhao et al. |
| 7,714,009 | B2 | 5/2010  | Gyorkos et al. |
| 7,772,247 | B2 | 8/2010  | Vaisburg et al. |
| 2004/0092520 | A1 | 5/2004 | Griffith |
| 2004/0097485 | A1 | 5/2004 | Burkitt et al. |
| 2005/0153989 | A1 | 7/2005 | Grotzfeld et al. |
| 2005/0165029 | A1 | 7/2005 | Patel et al. |
| 2005/0245546 | A1 | 11/2005 | Cristalli |
| 2007/0032493 | A1 | 2/2007 | Foley et al. |
| 2008/0004309 | A1 | 1/2008 | Deng et al. |
| 2008/0085898 | A1 | 4/2008 | Lu et al. |
| 2008/0125417 | A1 | 5/2008 | Currie et al. |
| 2009/0099170 | A1 | 4/2009 | Nunes et al. |
| 2009/0163476 | A1 | 6/2009 | Milburn et al. |
| 2009/0170842 | A1 | 7/2009 | Jensen et al. |
| 2009/0197860 | A1 | 8/2009 | Ji et al. |
| 2009/0264405 | A1 | 10/2009 | Ali et al. |
| 2009/0281138 | A1 | 11/2009 | Bylund et al. |
| 2009/0306071 | A1 | 12/2009 | Young et al. |
| 2010/0029611 | A1 | 2/2010 | Cee et al. |
| 2010/0120805 | A1 | 5/2010 | Hsieh et al. |
| 2010/0160288 | A1 | 6/2010 | Astles et al. |

FOREIGN PATENT DOCUMENTS

| EP | 1 221 444 A1 | 7/2002 | |
| GB | 1421619 | 1/1976 | |
| WO | 94/14777 | 7/1994 | |
| WO | 98/14451 A1 | 4/1998 | |
| WO | 01/74786 A1 | 10/2001 | |
| WO | 02/075318 A2 | 9/2002 | |
| WO | 02/075318 A3 | 9/2002 | |
| WO | 2004/037823 A1 | 5/2004 | |
| WO | 2005/044793 A2 | 5/2005 | |
| WO | 2005/044793 A3 | 5/2005 | |
| WO | 2007/019346 A1 | 2/2007 | |
| WO | WO2007019344 | * 2/2007 | ........... C07D 513/04 |
| WO | 2007/039797 A1 | 4/2007 | |

(Continued)

OTHER PUBLICATIONS (Unverified translation for WO 2010/062038 A2—Database Thomson Innovation (Apr. 12, 2012)), pp. 23.

(Continued)

*Primary Examiner* — Jeffrey H Murray
(74) *Attorney, Agent, or Firm* — Tamara Kale; Genentech, Inc.

(57) ABSTRACT

Provided are compounds of Formula I, stereoisomers, tautomers, solvates, prodrugs and pharmaceutically acceptable salts thereof, wherein A, X, $R^1$, $R^2$, $R^4$ and $R^5$ are defined herein, a pharmaceutical composition that includes a compound of Formula I and a pharmaceutically acceptable carrier, adjuvant or vehicle, methods of using the compound or composition in therapy, and methods of manufacturing a compound of Formula I.

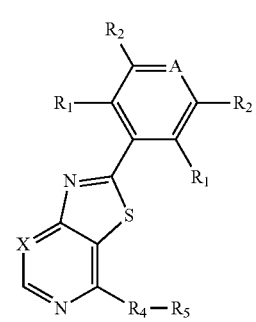

1 Claim, No Drawings

(56) References Cited

FOREIGN PATENT DOCUMENTS

| WO | 2007/054831 | A2 | 5/2007 |
|---|---|---|---|
| WO | 2007/054831 | A3 | 5/2007 |
| WO | 2007/070173 | A2 | 6/2007 |
| WO | 2007/070173 | A3 | 6/2007 |
| WO | 2007/115315 | A2 | 10/2007 |
| WO | 2007/115315 | A3 | 10/2007 |
| WO | 2008/051826 | | 5/2008 |
| WO | 2009/027732 | A1 | 3/2009 |
| WO | 2009/042607 | | 4/2009 |
| WO | 2009/061453 | A1 | 5/2009 |
| WO | 2009/061453 | A8 | 5/2009 |
| WO | 2009/065028 | A2 | 5/2009 |
| WO | 2009/065028 | A3 | 5/2009 |
| WO | 2009/073153 | A2 | 6/2009 |
| WO | 2009/073153 | A3 | 6/2009 |
| WO | 2010/010288 | A2 | 1/2010 |
| WO | 2010/010288 | A3 | 1/2010 |
| WO | 2010/019606 | A1 | 2/2010 |
| WO | 2010/019762 | A1 | 2/2010 |
| WO | 2010/062038 | A2 | 3/2010 |
| WO | 2010/062038 | A3 | 3/2010 |
| WO | 2010/045190 | A1 | 4/2010 |
| WO | 2010/089292 | A1 | 8/2010 |
| WO | 2010/094647 | A1 | 8/2010 |
| WO | 2011/002635 | A1 | 1/2011 |
| WO | 2011/048082 | A1 | 4/2011 |
| WO | 2011/113802 | A2 | 9/2011 |
| WO | 2011/134831 | A1 | 11/2011 |
| WO | 2013/041539 | A1 | 3/2013 |

OTHER PUBLICATIONS

Anderson et al., "Chemistry of the adenosine monophosphate site of rabbit muscle glycogen phosphorylase. I. Hydrophobic nature and affinity labeling of the allosteric site" Biochemistry 12(10):1895-900 (1973).
Barraclough et al., "Inotropic 'A' ring substituted sulmazole and isomazole analogues" J Med Chem. 33(8):2231-9 (1990).
Baslund et al., "Targeting interleukin-15 in patients with rheumatoid arthritis: a proof-of-concept study" Arthritis Rheum 52(9):2686-92 (Sep. 2005).
Borrmann et al., "Structure-activity relationships of adenine and deazaadenine derivatives as ligands for adenine receptors, a new purinergic receptor family" J Med Chem. 52:5974-89 (2009).
Cartwright et al., "Imidazopyridine and pyrimidinopyridine systems from perfluorinated pyridine derivatives" Tetrahedron 63(30) (Jun. 13, 2007).
CAS Registry Database, 1026421-43-1, (Database Registry), pp. 1 Jun. 8, 2008.
CAS Registry Database, 1026925-65-4, (Database Registry), pp. 1 Jun. 10, 2008.
CAS Registry Database, 1027012-36-7, (Database Registry), pp. 1, Jun. 8, 2008.
CAS Registry Database, 1027914-11-9, (Database Registry), pp. 1 Jun. 13, 2008.
CAS Registry Database, 1231299-64-1, (Database Registry), pp. 1 Jul. 12, 2010.
CAS Registry Database, 1240783-28-1,, pp. 1 Sep. 14, 2010.
CAS Registry Database, 501657-71-2, (Database Registry), pp. 1 Apr. 4, 2003.
CAS Registry Database, 734532-63-9, (Database Registry), pp. 1 Aug. 29, 2004.
CAS Registry Database, 741249-27-4, (Database Registry), pp. 1, Sep. 8, 2008.
CAS Registry Database, 777853-55-1, (Database Registry), pp. 1, Nov. 10, 2004.
Changelian et al., "Prevention of organ allograft rejection by a specific Janus kinase 3 inhibitor" Science 302:875-8 (Oct. 2003).
Couture et al., "2-Aryl-oxazolo- and thiazolopyridines. Synthesis via cyclization of N-(2-chloro-3-pyridinyl)arylamides and thioamides" Heterocycles 22(6):1383-1385 (1984).

Couture et al., "A Facile, One-Pot Synthesis of 2-Arylthiazolo[5,4-b]pyridines" Synthesis (Communications) 5:533-535 (1985).
Geldenhuys et al., "Virtual screening to identify novel antagonists for the G protein-coupled NK3 receptor" J Med Chem. 53:8080-8 (Nov. 2010).
Griffith et al., "Discovery of 1-[9-(4-chlorophenyl)-8-(2-chlorophenyl)-9H-purin-6-yl]-4-ethylaminopiperidine-4-carboxylic acid amide hydrochloride (CP-945,598), a novel, potent, and selective cannabinoid type 1 receptor antagonist" J Med Chem. 52(2):234-7 (Jan. 22, 2009).
Hasnik et al., "Cross-Coupling reactions of Halopurines with Aryl- and alkyltrifluoroborates; The Scope and Limitations in the Synthesis of Modified Purines" Synthesis 9:1309-17 (Mar. 25, 2009).
International Preliminary Report and Written Opinion for PCT/EP2011/065892, 2011.
International Preliminary Report on Patentability and Written Opinion for International Patent Application No. PCT/EP2011/053826, 2011.
International Preliminary Report on Patentability for International Patent Application No. PCT/EP2011/070313, 2011.
International Search Report on Patentability for International Patent Application No. PCT/EP2012/068380, 2012.
Kisseleva et al., "Signaling through the JAK/STAT pathway, recent advances and future challenges" Gene 285:1-24 (Feb. 2002).
Krueger et al., "A human interleukin-12/23 monoclonal antibody for the treatment of psoriasis" New Engl J Med 356(6):580-92 (Feb. 2007).
Levy et al., "Stats: transcriptional control and biological impact" Nat Rev Mol Cell Biol. 3(9):651-62 (2002).
MacNaught et al., Other Database, (IUPAC ED—Compendium of Chemical Terminolog, Blackwell Science, Oxford [U.A.], XP002585005, ISBN: 978-0-86542-684-9), pp. 1 Jan. 1, 1997.
MacNaught et al., Other Database, (IUPAC ED—Compendium of Chemical Terminology, Blackwell Science, Oxford [U.A.], XP002585006, ISBN: 978-0-86542-684-9), pp. 1 Jan. 1, 1997.
Mannon et al., "Anti-interleukin-12 antibody for active Crohn's disease" New Engl J Med 351(20):2069-79 (Nov. 2004).
McCloskey et al., "New insights into the design of inhibitors of human S-adenosylmethionine decarboxylase: studies of adenine C8 substitution in structural analogues S-adenosylmethionine" J Med Chem. 52(5):1388-407 (2009).
Medebielle et al., "Electrochemically induced SRNI substitution of fluorinated aryl halides. Application to the synthesis of fluorinated-aryl heterocycles" Electrochimica Acta 42(13):2049-55 (1997).
Millen et al., "Computational and experimental evidence for the structural preference of phenolic C-8 purine adducts" J Phys Chem A 112:3742-3753 (2008).
O'Shea et al., "Cytokine Signaling in 2002: New Surprises in the Jak/Stat Pathway" Cell 109:S121-S131 (Apr. 2002).
Ragan et al., "Development of a practical and Efficient Synthesis of CP-945,598-02,a CBI Antagonist for the Treatment of Obesity" Organic Process Research and Development 13(2):192 (Dec. 22, 2008).
Reich et al., "Ustekinumab" Nat Rev Drug Discov 8(5):355-6 (May 2009).
Sahnoun et al., "A site selective C—H arylation of free-(NH2) adenines with aryl chlorides: application to the synthesis of 6,8-disubstituted adenines" Org Biomol Chem. 7(20):4271-8 (Aug. 14, 2009).
Sahnoun et al., "Microwave-assisted Pd(OH)2-catalyzed direct C—H arylation of free-(NH2) adenines with aryl halides" Tetrahedron Letters 49(51):7279-83 (Dec. 15, 2008).
Sasaki et al., "Synthesis of Fused Heterocycles via cycloaddition of Hetaryne Studies on Heteroaromaticity, Part XLVII" Bulletin of the Chemical Sociey of Japen 44(3) (Jan. 1, 1971).
Scheinechker et al., "Tocilizumab" Nat Rev Drug Discov 8(4):273-4 (Apr. 2009).
Schindler, "JAK-STAT signaling: from interferons to cytokines" J Biol Chem 282(28):20059-63 (Jul. 2007).
Storr et al., "Pd(0)/Cu(I)—Mediated direct arylation of 2'-deoxyadenosines: mechanistic role of Cu(I) and reactivity comparisons with related purine nucleosides" J Org Chem 74(16):5810-21 (2009).
Watford et al., "Human tyk2 kinase deficiency: another primary imunodeficiency syndrome" Immunity 25:695-7 (Nov. 2006).

(56) References Cited

OTHER PUBLICATIONS

Wilks, "Two putative protein-tyrosine kinases identified by application of the polymerase chain reaction" P Natl Acad Sci USA 86:1603-1607 (1989).

Young et al., "Purine derivatives as competitive inhibitors of human erythrocyte membrane phosphatidylinositol 4-kinase" J Med Chem. 33(8):2073-80 (Aug. 1990).

* cited by examiner

AZABENZOTHIAZOLE COMPOUNDS, COMPOSITIONS AND METHODS OF USE

CROSS REFERENCE TO RELATED APPLICATIONS

This application, filed under 35 U.S.C. §111(a), claims the benefit under 35 U.S.C. §119(e) of U.S. Provisional Application Ser. No. 61/383,273 filed Sep. 15, 2010, which is incorporated by reference herein in its entirety for all purposes.

FIELD OF THE INVENTION

The present invention relates to organic compounds useful for therapy and/or prophylaxis in a patient, and in particular to inhibitors of TYK2 kinase useful for treating diseases mediated by TYK2 kinase.

BACKGROUND OF INVENTION

Cytokine pathways mediate a broad range of biological functions, including many aspects of inflammation and immunity Janus kinases (JAK), including JAK1, JAK2, JAK3 and TYK2 are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets. JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence.

JAK1 is functionally and physically associated with the type I interferon (e.g., IFNalpha), type II interferon (e.g., IFNgamma), IL-2 and IL-6 cytokine receptor complexes. JAK1 knockout mice die perinatally due to defects in LIF receptor signaling. Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis.

Biochemical and genetic studies have shown an association between JAK2 and single-chain (e.g., EPO), IL-3 and interferon gamma cytokine receptor families. Consistent with this, JAK2 knockout mice die of anemia. Kinase activating mutations in JAK2 (e.g., JAK2 V617F) are associated with myeloproliferative disorders (MPDs) in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID). Based on its role in regulating lymphocytes, JAK3 and JAK3-mediated pathways have been targeted for immunosuppressive indications (e.g., transplantation rejection and rheumatoid arthritis).

TYK2 associates with the type I interferon (e.g., IFNalpha), IL-6, IL-10, IL-12 and IL-23 cytokine receptor complexes. Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and IL-23 cytokines (Ustekinumab) was recently approved by the European Commission for the treatment of moderate-to-severe plaque psoriasis. In addition, an antibody targeting the IL-12 and IL-23 pathways underwent clinical trials for treating Crohn's Disease.

SUMMARY OF INVENTION

One embodiment includes a compound of Formula I:

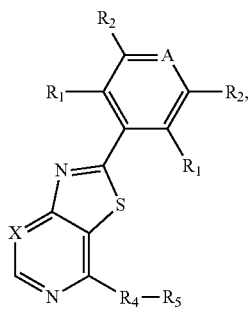

and stereoisomers, tautomers, solvates, prodrugs and pharmaceutically acceptable salts thereof, wherein A, X, $R^1$, $R^2$, $R^4$ and $R^5$ are defined herein.

Another embodiment includes a pharmaceutical composition that includes a compound of Formula I, stereoisomers, tautomers, solvates, prodrugs or pharmaceutically acceptable salts thereof, and a pharmaceutically acceptable carrier, adjuvant or vehicle.

Another embodiment includes a method of inhibiting TYK2 kinase activity in a cell, comprising introducing into said cell an amount effective to inhibit said kinase of a compound of Formula I, stereoisomers, tautomers, solvates, prodrugs or pharmaceutically acceptable salts thereof.

Another embodiment includes a method of treating or lessening the severity of a disease or condition responsive to the inhibition of TYK2 kinase activity in a patient. The method includes administering to the patient a therapeutically effective amount of a compound of Formula I, stereoisomers, tautomers, solvates, prodrugs or pharmaceutically acceptable salts thereof.

Another embodiment includes use of a compound of Formula I, stereoisomers, tautomers, solvates, prodrugs or pharmaceutically acceptable salts thereof, in therapy.

Another embodiment includes use of a compound of Formula I, stereoisomers, tautomers, solvates, prodrugs or pharmaceutically acceptable salts thereof, in the treatment of an immunological or inflammatory disease.

Another embodiment includes use of a compound of Formula I, stereoisomers, tautomers, solvates, prodrugs or pharmaceutically acceptable salts thereof, in manufacturing a medicament for treating a disease responsive to the inhibition of TYK2 kinase.

Another embodiment includes methods of preparing a compound of Formula I, stereoisomers, tautomers, solvates, prodrugs or pharmaceutically acceptable salts thereof.

Another embodiment includes a kit for treating a disease or disorder responsive to the inhibition of TYK2 kinase. The kit includes a first pharmaceutical composition comprising a compound of Formula I, stereoisomers, tautomers, solvates, prodrugs or pharmaceutically acceptable salts thereof and instructions for use.

DETAILED DESCRIPTION OF THE INVENTION

Reference will now be made in detail to certain embodiments, examples of which are illustrated in the accompanying structures and formulas. While the invention will be described in conjunction with the enumerated embodiments, the invention is intended to cover all alternatives, modifications, and equivalents, which may be included within the scope of the present invention as defined by the claims. One skilled in the art will recognize methods and materials similar or equivalent to those described herein, which could be used in the practice of the present invention.

DEFINITIONS

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl and 1-octyl.

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). $C_0$ refers to a bond. In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. Example alkylene groups include methylene (—$CH_2$—), 1,1-ethyl (—CH($CH_3$)—), (1,2-ethyl (—$CH_2CH_2$—), 1,1-propyl (—CH($CH_2CH_3$)—), 2,2-propyl (—C($CH_3$)$_2$—), 1,2-propyl (—CH($CH_3$)$CH_2$—), 1,3-propyl (—$CH_2CH_2CH_2$—), 1,1-dimethyleth-1,2-yl (—C($CH_3$)$_2CH_2$—), 1,4-butyl (—$CH_2CH_2CH_2CH_2$—), and the like.

"Alkenylene" refers to an unsaturated, branched or straight chain hydrocarbon group having two monovalent radical centers derived by the removal of two hydrogen atoms from the same or two different carbon atoms of a parent alkene. In one example, the alkenylene group is two to eighteen carbon atoms ($C_2$-$C_{18}$). In other examples, the alkenylene group is $C_2$-$C_{12}$, $C_2$-$C_{10}$, $C_2$-$C_8$, $C_2$-$C_6$ or $C_2$-$C_3$. Example alkenylene groups include: 1,2-ethylene (—CH=CH—).

"Alkynylene" refers to an unsaturated, branched or straight chain hydrocarbon group having two monovalent radical centers derived by the removal of two hydrogen atoms from the same or two different carbon atoms of a parent alkyne. In one example, the alkynylene radical is two to eighteen carbon atoms ($C_2$-$C_{18}$). In other examples, the alkynylene radical is $C_2$-$C_{12}$, $C_2$-$C_{10}$, $C_2$-$C_8$, $C_2$-$C_6$ or $C_2$-$C_3$. Example alkynylene radicals include: acetylene (—C≡C—), propargyl (—$CH_2$C≡C—), and 4-pentynyl (—$CH_2CH_2CH_2$C≡C—).

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_4$, $C_3$-$C_6$ or $C_5$-$C_6$. In another example, the cycloalkyl group, as a bicycle, is $C_7$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. In another example, the cycloalkyl, as a spiro, is $C_5$-$C_{12}$. Examples of spiro cycloalkyl include, but are not limited to, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane and spiro[4.5]decane.

"Aryl" refers to a cyclic aromatic hydrocarbon group optionally substituted independently with one or more substituents described herein. In one example, the aryl group is 6-20 carbon atoms ($C_6$-$C_{20}$). In another example, the aryl group is $C_6$-$C_{10}$. In another example, the aryl group is a $C_6$ aryl group. Aryl includes bicyclic groups comprising an aromatic ring with a fused non-aromatic or partially saturated ring. Example aryl groups include, but are not limited to, phenyl, naphthalenyl, anthracenyl, indenyl, indanyl, 1,2-dihydronapthalenyl and 1,2,3,4-tetrahydronapthyl. In one example, aryl includes phenyl. Substituted phenyl or substituted aryl means a phenyl group or aryl group substituted with one, two, three, four or five, for example 1-2, 1-3 or 1-4 substituents chosen from groups specified herein. In one example, optional substituents on aryl are selected from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylamino alkyl, arylsulfonylamino, arylsulfonylamino alkyl, heterocyclylsulfonylamino, heterocyclylsulfonylaminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Halo" or "halogen" refer to F, Cl, Br or I.

The terms "heterocycle," "heterocyclyl" and "heterocyclic ring" are used interchangeably herein and refer to: (i) a saturated or partially unsaturated cyclic group (i.e., having one or more double and/or triple bonds within the ring) ("heterocycloalkyl"), or (ii) an aromatic cyclic group ("heteroaryl"), and in each case, which at least one ring atom is a heteroatom independently selected from nitrogen, oxygen, phosphorus and sulfur, the remaining ring atoms being carbon. The heterocyclyl group may be optionally substituted with one or more substituents described below. In one embodiment, heterocyclyl includes monocycles or bicycles having 1 to 9 carbon ring members ($C_1$-$C_9$) with the remaining ring atoms being heteroatoms selected from N, O, S and P. In other examples, heterocyclyl includes monocycles or bicycles having $C_1$-$C_5$, $C_3$-$C_5$ or $C_4$-$C_5$, with the remaining ring atoms being heteroatoms selected from N, O, S and P. In another embodiment, heterocyclyl includes 3-10 membered rings, 3-7-membered rings or 3-6 membered rings, containing one or more heteroatoms independently selected from N, O, S and P. In other examples, heterocyclyl includes monocyclic 3-, 4-, 5-, 6- or 7-membered rings, containing one or more heteroatoms independently selected from N, O, S and P. In another embodiment, heterocyclyl includes bi- or polycyclic, spiro or bridged 4-, 5-, 6-, 7-, 8- and 9-membered ring systems, containing one or more heteroatoms independently selected from N, O, S and P. Examples of bicycle systems include, but are not limited to, [3,5], [4,5], [5,5], [3,6], [4,6], [5,6], or [6,6] systems. Examples of bridged ring systems include, but are not limited to [2.2.1], [2.2.2], [3.2.2] and [4.1.0] arrangements, and having 1 to 3 heteroatoms selected from N, O, S and P. In another embodiment, heterocyclyl includes spiro groups having 1 to 4 heteroatoms selected from N, O, S and P. The heterocyclyl group may be a carbon-linked group or heteroatom-linked group. "Heterocyclyl" includes a heterocyclyl group fused to a cycloalkyl group.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, oxazepanyl, diazepanyl, 1,4-diazepanyl, diazepinyl, thiazepinyl, thiazepanyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl and azabicyclo[2.2.2]hexanyl. Examples of a heterocyclyl group wherein a ring atom is substituted with oxo (=O) are pyrimidinonyl and 1,1-dioxo-thiomorpholinyl. The heterocyclyl groups herein are optionally substituted independently with one or more substituents described herein. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

The term "heteroaryl" refers to an aromatic carbocyclic radical in which at least one ring atom is a heteroatom independently selected from nitrogen, oxygen and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include 5-6-membered rings, or monocyclic aromatic 5-, 6- and 7-membered rings containing one or more heteroatoms independently selected from nitrogen, oxygen, and sulfur. In another embodiment, exemplary heteroaryl groups include fused ring systems of up to 9 carbon atoms wherein at least one aromatic ring contains one or more heteroatoms independently selected from nitrogen, oxygen, and sulfur. "Heteroaryl" includes heteroaryl groups fused with an aryl, cycloalkyl or other heterocyclyl group. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, thiazolopyridinyl, and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine (2-pyridyl, 3-pyridyl, 4-pyridyl, 5-pyridyl, 6-pyridyl), position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Leaving group" refers to a portion of a first reactant in a chemical reaction that is displaced from the first reactant in the chemical reaction. Examples of leaving groups include, but are not limited to, halogen atoms, hydroxyl, alkoxy (for example —OR, wherein R is independently alkyl, alkenyl, alkynyl, cycloalkyl, phenyl or heterocyclyl and R is independently optionally substituted) and sulfonyloxy (for example —OS(O)$_{1-2}$R, wherein R is independently alkyl, alkenyl, alkynyl, cycloalkyl, phenyl or heterocyclyl and R is independently optionally substituted) groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

"Treat" and "treatment" includes both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable, sustaining remission and suppressing reoccurrence. "Treatment" can also mean prolonging survival as compared to expected survival if not receiving treatment. Those in need of treatment include those already with the condition or disorder as well as those prone to have the condition or disorder, (for example, through a genetic mutation) or those in which the condition or disorder is to be prevented.

The phrase "therapeutically effective amount" means an amount of a compound of the present invention that (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and alternatively stop) cancer cell infiltration into peripheral organs; inhibit (i.e., slow to some extent and alternatively stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of B-cells.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase A$_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" and "cancerous" refer to or describe the physiological condition in patients that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is an agent useful in the treatment of a given disorder, for example, cancer or inflammatory disorders. Examples of chemotherapeutic agents include NSAIDs; hormones such as glucocorticoids; corticosteroids such as hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomide, methotrexate (MTX), minocycline, sulfasalazine, cyclophosphamide, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), monoclonal antibodies against B cells such as rituximab (RITUXAN®), T cell costimulation blockers such as abatacept (Orencia), Interleukin 6 (IL-6) blockers such as tocilizumab; hormone antagonists, such as tamoxifen, finasteride or LHRH antagonists; radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVEL- BINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as fenretinide, retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Additional chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretioic acid and fenretinide; onapristone; anti-progesterones; estrogen receptor down-regulators (ERDs); anti-androgens such as flutamide, nilutamide and bicalutamide.

Additional chemotherapeutic agents include therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659, 439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA™) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYK-ERB®, GSK572016 or N-[3-chloro-4-[(3 fluorophenyl)methoxy]phenyl]-6[5[[[2-methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC™, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC™); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include asthma treatment agents, including inhaled corticosteroids such as fluticasone, budesonide, mometasone, flunisolide and beclomethasone; leukotriene modifiers, such as montelukast, zafirlukast and zileuton; long-acting beta agonists, such as salmeterol and formoterol; combinations of the above such as combinations of fluticasone and salmeterol, and combinations of budesonide and formoterol; theophylline; short-acting beta agonists, such as albuterol, levalbuterol and pirbuterol; ipratropium; oral and intravenous corticosteroids, such as prednisone and methylprednisolone; omalizumab; lebrikizumab; antihistamines; and decongestants; cromolyn; and ipratropium.

"Optionally substituted" unless otherwise specified means that a group may be unsubstituted or substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

The term "prodrug" as used in this application refers to a precursor or derivative form of a pharmaceutically active substance that is less efficacious to the patient or cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "package insert" is used to refer to instructions customarily included in commercial packages of therapeutic products, that contain information about the indications, usage, dosage, administration, contraindications and/or warnings concerning the use of such therapeutic products.

The term "stereoisomers" refers to compounds which have identical chemical constitution, but differ with regard to the arrangement of the atoms or groups in space. Stereoisomers include diastereomers, enantiomers, conformers and the like.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt," as used herein, refers to pharmaceutically acceptable organic or inorganic salts of a compound of Formula I. "Pharmaceutically acceptable salts" include both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion, for example a dihydrochloride or diformate salt.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

A "solvate" refers to an association or complex of one or more solvent molecules and a compound of Formula I. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "patient" includes human patients and animal patients. The term "animal" includes companion animals (e.g., dogs, cats and horses), food-source animals, zoo animals, marine animals, birds and other similar animal species. In one example, patient is a human.

The phrase "pharmaceutically acceptable" indicates that the substance or composition must be compatible chemically and/or toxicologically, with the other ingredients comprising a formulation, and/or the mammal being treated therewith.

The terms "compound of this invention," and "compounds of the present invention", unless otherwise indicated, include compounds of Formulas I, stereoisomers, tautomers, solvates, prodrugs and salts (e.g., pharmaceutically acceptable salts) thereof. Unless otherwise stated, structures depicted herein are also meant to include compounds that differ only in the presence of one or more isotopically enriched atoms. For example, compounds of Formula I, wherein one or more hydrogen atoms are replaced deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}$S sulfur atom, or one or more oxygen atoms are replaced by a $^{17}$O or $^{18}$O oxygen atom are within the scope of this invention.

TYK2 Inhibitor Compounds

In one embodiment, a compound of Formulas I, stereoisomers, tautomers, solvates, prodrugs and pharmaceutically acceptable salts thereof, and pharmaceutical formulations thereof, are provided that are useful in the treatment of diseases, conditions and/or disorders responsive to the inhibition of TYK2.

Another embodiment includes compounds of Formula I:

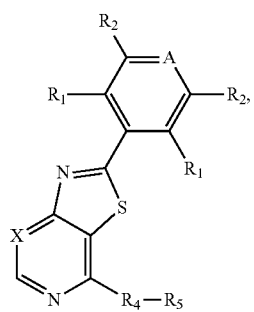

I stereoisomers, tautomers, solvates, prodrugs and pharmaceutically acceptable salts thereof, wherein:

A is $CR^3$ or N;

X is $CR^{15}$ or N;

$R^1$ is independently hydrogen, halogen, $C_1$-$C_6$ alkyl, $C_2$-$C_6$ alkenyl, $C_2$-$C_6$ alkynyl, $C_3$-$C_6$ cycloalkyl, —$CF_3$, —$OR^6$, —$SR^6$, —$OCF_3$, —CN, —$NO_2$, —$C(O)R^6$, —$C(O)OR^6$, —$C(O)NR^6R^7$, —$S(O)_{1-2}R^6$, —$S(O)_{1-2}NR^6R^7$, —$NR^6S(O)_{1-2}R^7$, —$NR^6SO_2NR^6R^7$, —$NR^6C(O)R^7$, —$NR^6C(O)OR^7$, —$NR^6C(O)NR^6R^7$, —$OC(O)NR^6R^7$ or —$NR^6R^7$, wherein both $R^1$ cannot be hydrogen at the same time, and wherein said alkyl, alkenyl, alkynyl and cycloalkyl are optionally substituted by halogen, oxo, —CN, $OR^6$, —$NR^6R^7$, $C_3$-$C_6$ cycloalkyl, 3-6 membered heterocyclyl or phenyl and said cycloalkyl, heterocyclyl and phenyl are independently optionally substituted by $R^{10}$;

$R^2$ and $R^3$ are each independently hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^8$, —($C_0$-$C_3$ alkylene)$SR^8$, —($C_0$-$C_3$ alkylene)$NR^8R^9$, —($C_0$-$C_3$ alkylene)$CF_3$, —O($C_0$-$C_3$ alkylene)$CF_3$, —($C_0$-$C_3$ alkylene)$NO_2$, —($C_0$-$C_3$ alkylene)$C(O)R^8$, —($C_0$-$C_3$ alkylene)$C(O)OR^8$, —($C_0$-$C_3$ alkylene)$C(O)NR^8R^9$, —($C_0$-$C_3$ alkylene)$NR^8C(O)R^9$, —($C_0$-$C_3$ alkylene)$S(O)_{1-2}R^8$, —($C_0$-$C_3$ alkylene)$NR^8S(O)_{1-2}R^9$, —($C_0$-$C_3$ alkylene)$S(O)_{1-2}NR^8R^9$, —($C_0$-$C_3$ alkylene)($C_3$-$C_6$ cycloalkyl), —($C_0$-$C_3$ alkylene) (3-10-membered heterocyclyl), —($C_0$-$C_3$ alkylene) (5-10-membered heteroaryl) or —($C_0$-$C_3$ alkylene)phenyl, wherein $R^2$ and $R^3$ are each independently optionally substituted by $R^{10}$;

$R^4$ is hydrogen, —$NR^6$—, —$NR^6R^7$, —$NR^6C(O)$—, —$NR^6C(O)O$—, —$NR^6C(O)NR^7$—, —$NR^6S(O)_{1-2}$— or —$NR^6S(O)_{1-2}NR^7$—;

$R^5$ is absent, hydrogen, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3-10-membered heterocyclyl or 5-10-membered heteroaryl, wherein $R^5$ is optionally substituted by $R^{10}$;

$R^6$ and $R^7$ are each independently hydrogen, $C_1$-$C_6$ alkyl, $C_2$-$C_6$ alkenyl, $C_2$-$C_6$ alkynyl or $C_3$-$C_6$ cycloalkyl, wherein said alkyl, alkenyl, alkynyl and cycloalkyl are independently optionally substituted by halogen, $C_1$-$C_6$ alkyl, oxo, —CN, —$OR^{11}$ or —$NR^{11}R^{12}$; or $R^6$ and $R^7$ are independently taken together with the atom to which they are attached to form a 3-6 membered heterocyclyl optionally substituted by halogen, oxo, —$OR^{11}$, —$NR^{11}R^{12}$ or $C_1$-$C_6$ alkyl optionally substituted by halogen;

$R^8$ and $R^9$ are each independently hydrogen, $C_1$-$C_6$ alkyl, $C_3$-$C_6$ cycloalkyl, phenyl, 3-6-membered heterocyclyl or 5-6-membered heteroaryl, wherein said alkyl, cycloalkyl, phenyl, heterocyclyl or heteroaryl are independently optionally substituted by $R^{10}$; or $R^8$ and $R^9$ are independently taken together with the atom to which they are attached to form a 3-6 membered heterocyclyl optionally substituted by halogen, oxo, —$NR^{11}R^{12}$ or $C_1$-$C_6$ alkyl;

$R^{10}$ is independently hydrogen, oxo, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^{11}$, —($C_0$-$C_3$ alkylene)$SR^{11}$, —($C_0$-$C_3$ alkylene)$NR^{11}R^{12}$, —($C_0$-$C_3$ alkylene)$CF_3$, —($C_0$-$C_3$ alkylene)$NO_2$, —C=NH($OR^{11}$), —($C_0$-$C_3$ alkylene)$C(O)R^{11}$, —($C_0$-$C_3$ alkylene)$C(O)OR^{11}$, —($C_0$-$C_3$ alkylene)$C(O)NR^{11}R^{12}$, —($C_0$-$C_3$ alkylene)$NR^{11}C(O)R^{12}$, —($C_0$-$C_3$ alkylene)$S(O)_{1-2}R^{11}$, —($C_0$-$C_3$ alkylene)$NR^{11}S(O)_{1-2}R^{12}$, —($C_0$-$C_3$ alkylene)$S(O)_{1-2}NR^{11}R^{12}$, —($C_0$-$C_3$ alkylene)($C_3$-$C_6$ cycloalkyl), —($C_0$-$C_3$ alkylene) (3-10-membered heterocyclyl), —($C_0$-$C_3$ alkylene)$C(O)$ (3-10-membered heterocyclyl), —($C_0$-$C_3$ alkylene) (5-10-membered heteroaryl) or —($C_0$-$C_3$ alkylene)phenyl, wherein $R^{10}$ is independently optionally substituted by halogen, oxo, —$CF_3$, —($C_0$-$C_3$ alkylene)$OR^{13}$, —($C_0$-$C_3$ alkylene)$NR^{13}R^{14}$, —($C_0$-$C_3$ alkylene)$C(O)R^{13}$, —($C_0$-$C_3$ alkylene)$S(O)_{1-2}R^{13}$ or $C_1$-$C_6$ alkyl optionally substituted by oxo, —CN or halogen;

$R^{11}$ and $R^{12}$ are each independently hydrogen, $C_1$-$C_6$ alkyl, $C_2$-$C_6$ alkenyl, $C_2$-$C_6$ alkynyl, $C_3$-$C_6$ cycloalkyl, phenyl, 5-6 membered heteroaryl or 3-6 membered heterocyclyl, wherein said alkyl, alkenyl, alkynyl, cycloalkyl, phenyl, heteroaryl and heterocyclyl are independently optionally substituted by halogen, oxo, —CN, —$OR^{16}$, —$NR^{16}R^{17}$ or $C_1$-$C_6$ alkyl optionally substituted by halogen, —CN or oxo; or $R^{11}$ and $R^{12}$ are taken together with the atom to which they attached to form a 3-6 membered heterocyclyl optionally substituted by halogen, oxo, —$OR^{16}$, —$NR^{16}R^{17}$ or $C_1$-$C_6$ alkyl optionally substituted by halogen, oxo or OH;

$R^{13}$ and $R^{14}$ are each independently hydrogen or $C_1$-$C_6$ alkyl optionally substituted by halogen or oxo; or $R^{13}$ and $R^{14}$ are taken together with the atom to which they attached to form a 3-6 membered heterocyclyl optionally substituted by halogen, oxo or $C_1$-$C_6$ alkyl optionally substituted by halogen or oxo;

$R^{15}$ is hydrogen, halogen, $C_1$-$C_6$ alkyl, $C_2$-$C_6$ alkenyl, $C_2$-$C_6$ alkynyl, —($C_0$-$C_3$ alkylene)CN, —($C_0$-$C_3$ alkylene)$OR^{18}$, —($C_0$-$C_3$ alkylene)$SR^{18}$, —($C_0$-$C_3$ alkylene)$NR^{18}R^{19}$, —($C_0$-$C_3$ alkylene)$CF_3$, —O($C_0$-$C_3$ alkylene)$CF_3$, —($C_0$-$C_3$ alkylene)$NO_2$, —($C_0$-$C_3$ alkylene)$C(O)R^{18}$, —($C_0$-$C_3$ alkylene)$C(O)OR^{18}$, —($C_0$-$C_3$ alkylene)$C(O)NR^{18}R^{19}$, —($C_0$-$C_3$ alkylene)$NR^{18}C(O)R^{19}$, —($C_0$-$C_3$ alkylene)$S(O)_{1-2}R^{18}$, —($C_0$-$C_3$ alkylene)$NR^{18}S(O)_{1-2}R^{19}$, —($C_0$-$C_3$ alkylene)$S(O)_{1-2}NR^{18}R^{19}$, —($C_0$-$C_3$ alkylene)($C_3$-$C_6$ cycloalkyl), —($C_0$-$C_3$ alkylene) (3-6-membered heterocyclyl), —($C_0$-$C_3$ alkylene) (5-6-membered heteroaryl) or —($C_0$-$C_3$ alkylene)phenyl;

$R^{16}$ and $R^{17}$ are each independently hydrogen or $C_1$-$C_6$ alkyl optionally substituted by halogen or oxo; or $R^{16}$ and $R^{17}$ are taken together with the atom to which they attached to form a 3-6 membered heterocyclyl optionally substituted by halogen, oxo or $C_1$-$C_6$ alkyl optionally substituted by oxo or halogen; and $R^{18}$ and $R^{19}$ are each independently hydrogen or $C_1$-$C_6$ alkyl optionally substituted by halogen or oxo.

Another embodiment includes compounds of Formula I, stereoisomers, tautomers, solvates, prodrugs and pharmaceutically acceptable salts thereof, wherein:

A is $CR^3$ or N;

X is $CR^{15}$ or N;

$R^1$ is independently hydrogen, halogen, $C_1$-$C_3$ alkyl, $C_2$-$C_3$ alkenyl, $C_2$-$C_3$ alkynyl, $C_3$-$C_4$ cycloalkyl, —$CF_3$, —$OR^6$, —$SR^6$, —$OCF_3$, —CN, —$NO_2$, —$NR^6SO_2R^7$, —$NR^6C(O)R^7$ or —$NR^6R^7$, wherein both $R^1$ cannot be hydrogen at the same time, and wherein said alkyl, alkenyl, alkynyl and cycloalkyl are optionally substituted by halogen, $OR^6$, —$NR^6R^7$ or phenyl;

$R^2$ and $R^3$ are each independently hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^8$, —($C_0$-$C_3$ alkylene)$SR^8$, —($C_0$-$C_3$ alkylene)$NR^8R^9$, —($C_0$-$C_3$ alkylene)$CF_3$, —O($C_0$-$C_3$ alkylene)$CF_3$, —($C_0$-$C_3$ alkylene)$NO_2$, —($C_0$-$C_3$ alkylene)C(O)$R^8$, —($C_0$-$C_3$ alkylene)C(O)$OR^8$, —($C_0$-$C_3$ alkylene)C(O)$NR^8R^9$, —($C_0$-$C_3$ alkylene)$NR^8C(O)R^9$, —($C_0$-$C_3$ alkylene)S(O)$_{1-2}R^8$, —($C_0$-$C_3$ alkylene)$NR^8S(O)_{1-2}R^9$, —($C_0$-$C_3$ alkylene)S(O)$_{1-2}NR^8R^9$, —($C_0$-$C_3$ alkylene)($C_3$-$C_6$ cycloalkylene), —($C_0$-$C_3$ alkylene) (3-6-membered heterocyclyl), —($C_0$-$C_3$ alkylene) (5-6-membered heteroaryl) or —($C_0$-$C_3$ alkylene)phenyl, wherein $R^2$ and $R^3$ are each independently optionally substituted by $R^{10}$;

$R^4$ is hydrogen, —$NH_2$, —NH—, —$NR^6R^7$, —$NR^6C(O)$—, —$NR^6C(O)O$—, —$NR^6C(O)NR^7$—, —$NR^6S(O)_{1-2}$— or —$NR^6S(O)_{1-2}NR^7$—;

$R^5$ is absent, hydrogen, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3-10-membered heterocyclyl or 5-10-membered heteroaryl, wherein $R^5$ is optionally substituted by $R^{10}$;

$R^6$ and $R^7$ are each independently hydrogen, $C_1$-$C_3$ alkyl, $C_2$-$C_6$ alkenyl, $C_2$-$C_6$ alkynyl or $C_3$-$C_4$ cycloalkyl, wherein said alkyl, alkenyl, alkynyl and cycloalkyl are independently optionally substituted by halogen, oxo, —$OR^{11}$ or —$NR^{11}R^{12}$; or $R^6$ and $R^7$ are independently taken together with the atom to which they are attached to form a 3-6 membered heterocyclyl optionally substituted by halogen, oxo, —$NR^{11}R^{12}$ or $C_1$-$C_3$ alkyl;

$R^8$ and $R^9$ are each independently hydrogen, $C_1$-$C_3$ alkyl, $C_3$-$C_6$ cycloalkyl, phenyl, 3-6-membered heterocyclyl or 5-6-membered heteroaryl, wherein said alkyl, cycloalkyl, phenyl, heterocyclyl or heteroaryl are independently optionally substituted by $R^{10}$; or $R^8$ and $R^9$ are independently taken together with the atom to which they are attached to form a 3-6 membered heterocyclyl optionally substituted by halogen, oxo, —$NR^{11}R^{12}$ or $C_1$-$C_3$ alkyl;

$R^{10}$ is independently hydrogen, oxo, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^{11}$, —($C_0$-$C_3$ alkylene)$SR^{11}$, —($C_0$-$C_3$ alkylene)$NR^{11}R^{12}$, —($C_0$-$C_3$ alkylene)$CF_3$, —($C_0$-$C_3$ alkylene)$NO_2$, —C=NH($OR^{11}$), —($C_0$-$C_3$ alkylene)C(O)$R^{11}$, —($C_0$-$C_3$ alkylene)C(O)$OR^{11}$, —($C_0$-$C_3$ alkylene)C(O)$NR^{11}R^{12}$, —($C_0$-$C_3$ alkylene)$NR^{11}C(O)R^{12}$, —($C_0$-$C_3$ alkylene)S(O)$_{1-2}R^{11}$, —($C_0$-$C_3$ alkylene)$NR^{11}S(O)_{1-2}R^{12}$, —($C_0$-$C_3$ alkylene)S(O)$_{1-2}NR^{11}R^{12}$, —($C_0$-$C_3$ alkylene)($C_3$-$C_6$ cycloalkylene), —($C_0$-$C_3$ alkylene) (3-6-membered heterocyclyl), —($C_0$-$C_3$ alkylene)C(O)(3-6-membered heterocyclyl), —($C_0$-$C_3$ alkylene) (5-6-membered heteroaryl) or —($C_0$-$C_3$ alkylene)phenyl, wherein $R^{10}$ is independently optionally substituted by halogen, oxo, —$CF_3$, —($C_0$-$C_3$ alkylene)$OR^{13}$, —($C_0$-$C_3$ alkylene)$NR^{13}R^{14}$, —($C_0$-$C_3$ alkylene)C(O)$R^{13}$, —($C_0$-$C_3$ alkylene)S(O)$_{1-2}R^{13}$ or $C_1$-$C_3$ alkyl optionally substituted by oxo or halogen;

$R^{11}$ and $R^{12}$ are each independently hydrogen, $C_1$-$C_6$ alkyl, $C_2$-$C_6$ alkenyl, $C_2$-$C_6$ alkynyl, $C_3$-$C_6$ cycloalkyl, phenyl, 5-6 membered heteroaryl or 3-6 membered heterocyclyl, wherein said alkyl, alkenyl, alkynyl, cycloalkyl, phenyl, heteroaryl and heterocyclyl are independently optionally substituted by halogen, oxo, —CN, —$OR^{16}$, —$NR^{16}R^{17}$ or $C_1$-$C_3$ alkyl optionally substituted by halogen or oxo; or $R^{11}$ and $R^{12}$ are taken together with the atom to which they attached to form a 3-6 membered heterocyclyl optionally substituted by halogen, oxo, —$OR^{16}$, —$NR^{16}R^{17}$ or $C_1$-$C_3$ alkyl optionally substituted by halogen, oxo or OH;

$R^{13}$ and $R^{14}$ are each independently hydrogen or $C_1$-$C_6$ alkyl optionally substituted by halogen or oxo; or $R^{13}$ and $R^{14}$ are taken together with the atom to which they attached to form a 3-6 membered heterocyclyl optionally substituted by halogen, oxo or $C_1$-$C_3$ alkyl optionally substituted by halogen or oxo;

$R^{15}$ is hydrogen, halogen, $C_1$-$C_6$ alkyl, $C_2$-$C_6$ alkenyl, $C_2$-$C_6$ alkynyl, —($C_0$-$C_3$ alkylene)CN, —($C_0$-$C_3$ alkylene)$OR^{18}$, —($C_0$-$C_3$ alkylene)$SR^{18}$, —($C_0$-$C_3$ alkylene)$NR^{18}R^{19}$, —($C_0$-$C_3$ alkylene)$CF_3$, —O($C_0$-$C_3$ alkylene)$CF_3$, —($C_0$-$C_3$ alkylene)$NO_2$, —($C_0$-$C_3$ alkylene)C(O)$R^{18}$, —($C_0$-$C_3$ alkylene)C(O)$OR^{18}$, —($C_0$-$C_3$ alkylene)C(O)$NR^{18}R^{19}$, —($C_0$-$C_3$ alkylene)$NR^{18}C(O)R^{19}$, —($C_0$-$C_3$ alkylene)S(O)$_{1-2}R^{18}$, —($C_0$-$C_3$ alkylene)$NR^{18}S(O)_{1-2}R^{19}$, —($C_0$-$C_3$ alkylene)S(O)$_{1-2}NR^{18}R^{19}$, —($C_0$-$C_3$ alkylene)($C_3$-$C_6$ cycloalkyl), —($C_0$-$C_3$ alkylene) (3-6-membered heterocyclyl), —($C_0$-$C_3$ alkylene) (5-6-membered heteroaryl) or —($C_0$-$C_3$ alkylene)phenyl;

$R^{16}$ and $R^{17}$ are each independently hydrogen or $C_1$-$C_6$ alkyl optionally substituted by halogen or oxo; or $R^{16}$ and $R^{17}$ are taken together with the atom to which they attached to form a 3-6 membered heterocyclyl optionally substituted by halogen, oxo or $C_1$-$C_3$ alkyl optionally substituted by halogen; and $R^{18}$ and $R^{19}$ are each independently hydrogen or $C_1$-$C_6$ alkyl optionally substituted by halogen or oxo.

In certain embodiments, compounds of Formula I, stereoisomers, tautomers, solvates, prodrugs and pharmaceutically acceptable salts thereof, includes compounds other than the compounds 2-(2-chlorophenyl)thiazolo[5,4-c]pyridine, 2-(thiazolo[5,4-c]pyridin-2-yl)aniline, 2-phenoxy-N-(2-thiazolo[5,4-c]pyridin-2-yl-phenyl)-propanamide, N-(2-thiazolo[5,4-c]pyridin-2-ylphenyl)-benzenepropanamide, 2-(2-methylphenyl)-thiazolo[5,4-c]pyridine, 2-[2-methoxy-4-(methylthio)phenyl]-thiazolo[5,4-c]pyridine and 2-(2,6-dichlorophenyl)thiazolo[5,4-c]pyridine.

In certain embodiments, A is $CR^3$.

In certain embodiments, A is $CR^3$ and X is $CR^{15}$.

In certain embodiments, A is $CR^3$ and X is N.

In certain embodiments, A is N.

In certain embodiments, A is N and X is $CR^{15}$.

In certain embodiments, A is N and X is N.

In certain embodiments, $R^1$ is independently halogen. In one embodiment, $R^1$ is independently F or Cl. In another embodiment, $R^1$ is Cl.

In certain embodiments, $R^1$ is independently halogen; and the group —$R^4$-$R^5$ is —$NHR^5$, —$NR^6C(O)R^5$, —$NR^6C(O)OR^5$ or —$NR^6C(O)NR^7R^5$, wherein $R^5$ is other than hydrogen.

In certain embodiments, $R^1$ is independently halogen or —CN; and the group —$R^4$-$R^5$ is —$NHR^5$, —$NR^6C(O)R^5$, —$NR^6C(O)OR^5$ or —$NR^6C(O)NR^7R^5$.

In certain embodiments, one $R^1$ is halogen and the other $R^1$ is hydrogen, halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl.

In certain embodiments, one $R^1$ is halogen and the other $R^1$ is hydrogen, halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^6$, —$NR^6R^7$ or phenyl.

In certain embodiments, one $R^1$ is halogen and the other $R^1$ is halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl.

In certain embodiments, one $R^1$ is halogen and the other $R^1$ is halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^6$, —$NR^6R^7$ or phenyl.

In certain embodiments, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl.

In certain embodiments, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^6$, —$NR^6R^7$ or phenyl.

In certain embodiments, $R^1$ is independently hydrogen, F, Cl, —$CF_3$, —$CH_3$, or —$OCF_3$, wherein both $R^1$ cannot be hydrogen at the same time.

In certain embodiments, $R^1$ is independently hydrogen, F, Cl or —CN, wherein both $R^1$ cannot be hydrogen at the same time.

In certain embodiments, $R^1$ is independently halogen or —CN. In certain embodiments, $R^1$ is independently F, Cl or —CN. In certain embodiments, one $R^1$ is halogen and the other $R^1$ is —CN.

In certain embodiments, $R^1$ is —CN.

In certain embodiments, $R^2$ is hydrogen or halogen.

In certain embodiments, $R^2$ is hydrogen.

In certain embodiments, $R^3$ is hydrogen, $C_1$-$C_6$ alkyl, $C_2$-$C_6$ alkenyl, $C_2$-$C_6$ alkynyl, halogen, —CN, —$C(O)R^8$ or —$S(O)_{1-2}(C_1$-$C_3$ alkyl), wherein said alkyl, alkenyl and alkynyl are independently optionally substituted by halogen, oxo, —$OR^8$ or —$NR^8R^9$. In one embodiment, $R^3$ is hydrogen, hydroxylmethyl, —C(O)H, ethenyl, —CN or —$S(O)_2CH_3$.

In one embodiment, $R^3$ is hydrogen, —C(O)H, ethenyl, —CN or hydroxymethyl. In one embodiment, $R^3$ is hydrogen. In one embodiment, $R^3$ is —CN.

In certain embodiments, $R^3$ is hydrogen, $C_1$-$C_6$ alkyl, $C_2$-$C_6$ alkenyl, $C_2$-$C_6$ alkynyl, halogen, —CN, —$C(O)R^8$ or —$S(O)_{1-2}(C_1$-$C_3$ alkyl), wherein said alkyl, alkenyl and alkynyl are independently optionally substituted by halogen, oxo, —$OR^{11}$ or —$NR^{11}R^{12}$.

In certain embodiments, $R^3$ is $C_1$-$C_6$ alkyl optionally substituted by halogen, oxo, —$OR^8$ or —$NR^8R^9$. In certain embodiments, $R^3$ is —$CH_2OH$ or —$CH_2NH_2$.

In certain embodiments, $R^3$ is $C_1$-$C_6$ alkyl optionally substituted by halogen, oxo, —$OR^{11}$ or —$NR^{11}R^{12}$.

In certain embodiments, $R^3$ is 3-10 membered heterocyclyl optionally substituted by halogen, oxo, —$OR^{11}$, —$NR^{11}R^{12}$ or $C_1$-$C_6$ alkyl optionally substituted by halogen or oxo. In certain embodiments, $R^3$ is aziridinyl.

In certain embodiments, $R^3$ is hydrogen, $C_1$-$C_6$ alkyl, $C_2$-$C_6$ alkenyl, $C_2$-$C_6$ alkynyl, halogen, —CN, —$NR^8R^9$, —$NR^8C(O)R^9$, —$C(O)R^8$ or —$S(O)_{1-2}(C_1$-$C_3$ alkyl), wherein said alkyl, alkenyl and alkynyl are independently optionally substituted by halogen, oxo, —$OR^{11}$ or —$NR^{11}R^{12}$. In one embodiment, $R^3$ is hydrogen, hydroxylmethyl, —$CH_2NH_2$, aziridinyl, cyclopropyl, —$C(O)NH_2$, —$NHC(O)CH_3$, —$OCH_3$, —C(O)H, ethenyl, —CN or —$S(O)_2CH_3$.

In certain embodiments, A is $CR^3$, $R^2$ is hydrogen and $R^3$ is hydrogen, —CN or hydroxymethyl.

In certain embodiments, A is $CR^3$, $R^2$ is hydrogen and $R^3$ is hydrogen, —CN, —$CH_2NH_2$, —$NHC(O)CH_3$ or hydroxymethyl. In certain embodiments, A is $CR^3$, $R^2$ is hydrogen and $R^3$ is hydrogen or —CN. In certain embodiments, $R^1$ is independently halogen or —CN, A is $CR^3$, $R^2$ is hydrogen and $R^3$ is hydrogen or —CN, In certain embodiments, the portion of Formula I having the structure:

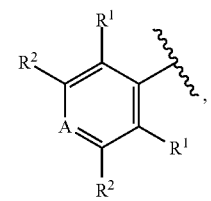

is selected from:

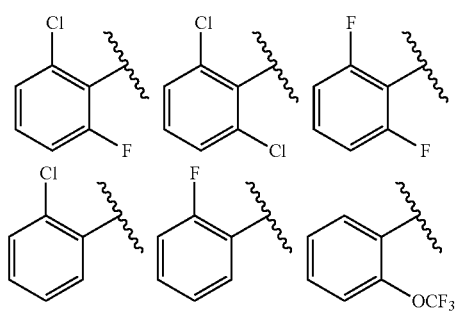

-continued

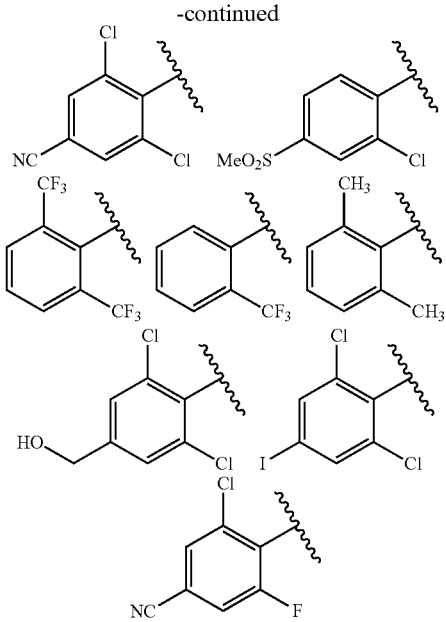

wherein the wavy lines represent the point of attachment in Formula I.

In certain embodiments, the portion of Formula I having the structure:

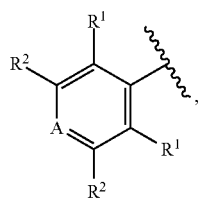

is selected from:

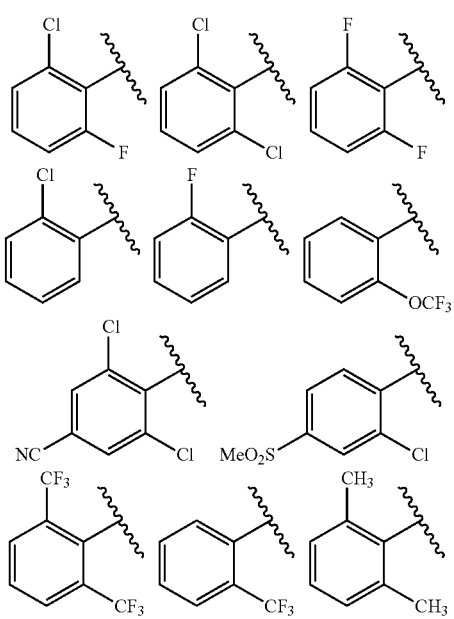

-continued

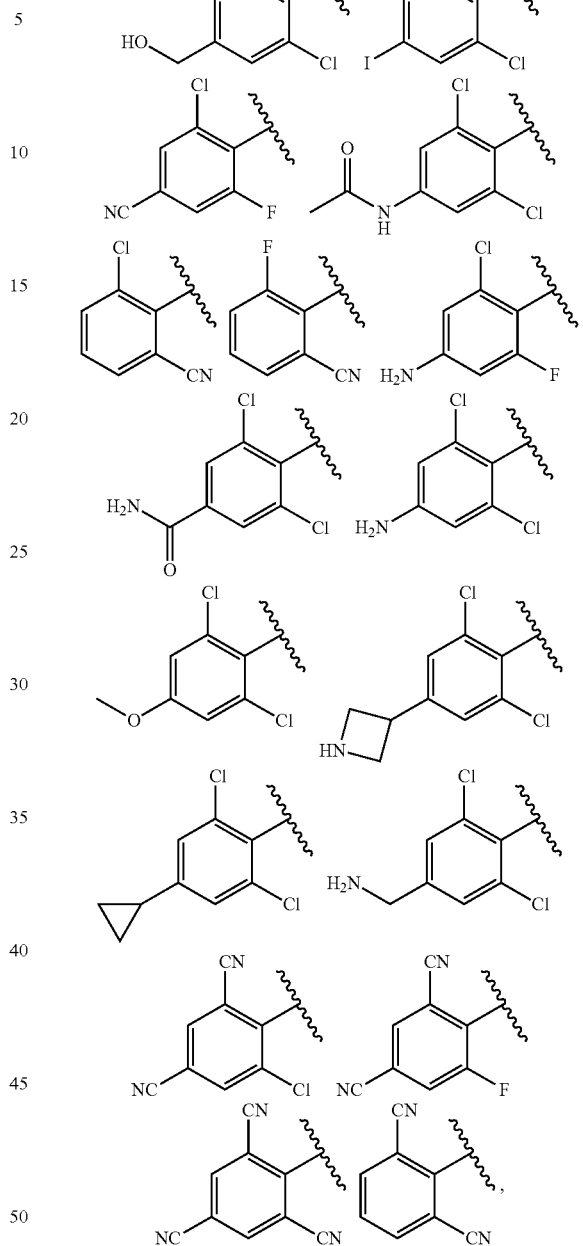

wherein the wavy lines represent the point of attachment in Formula I.

In certain embodiments, $R^4$ is hydrogen and $R^5$ is absent.

In certain embodiments, $R^1$ is independently hydrogen, halogen or —CN; $R^4$ is hydrogen and $R^5$ is absent. In certain embodiments, $R^1$ is independently halogen or —CN; $R^4$ is hydrogen and $R^5$ is absent.

In certain embodiments, $R^4$ is —$NR^6$—. In certain embodiments, $R^4$ is —$NR^6C(O)$—. In certain embodiments, $R^4$ is —$NR^6C(O)O$—. In certain embodiments, $R^4$ is —$NR^6C(O)NR^7$—. In certain embodiments, $R^4$ is —NH—. In certain embodiments, $R^4$ is —NHC(O)—. In certain embodiments, $R^4$ is —NHC(O)O—. In certain embodiments, $R^4$ is —NHC(O)NH—.

In certain embodiments, $R^4$ is —$NR^6$—, —$NR^6C(O)$—, —$NR^6C(O)O$— or —$NR^6C(O)NR^7$—.

In certain embodiments, the group —$R^4$-$R^5$ is —$NHR^5$, —$NHC(O)R^5$, —$NHC(O)OR^5$ or —$NHC(O)NHR^5$.

In certain embodiments, the group —$R^4$-$R^5$ is —$NHR^5$, —$NHC(O)R^5$, —$NHC(O)OR^5$ or —$NHC(O)NHR^5$, wherein $R^5$ is other than hydrogen.

In certain embodiments, X is $CR^{15}$ and the group —$R^4$-$R^5$ is —$NHR^5$, —$NHC(O)R^5$, —$NHC(O)OR^5$ or —$NHC(O)NR^7R^5$. In certain embodiments, X is $CR^{15}$; $R^{15}$ is hydrogen; and the group —$R^4$-$R^5$ is —$NHR^5$, —$NHC(O)R^5$, —$NHC(O)OR^5$ or —$NHC(O)NHR^5$, wherein $R^5$ is other than hydrogen. In certain embodiments, A is $CR^3$; X is $CR^{15}$; $R^{15}$ is hydrogen; and the group —$R^4$-$R^5$ is —$NHR^5$, —$NHC(O)R^5$, —$NHC(O)OR^5$ or —$NHC(O)NHR^5$, wherein $R^5$ is other than hydrogen.

In certain embodiments, X is $CR^{15}$; $R^{15}$ is hydrogen, halogen or —CN; and the group —$R^4$-$R^5$ is —$NHR^5$, —$NHC(O)R^5$, —$NHC(O)OR^5$ or —$NHC(O)NHR^5$, wherein $R^5$ is other than hydrogen. In certain embodiments, A is $CR^3$; X is $CR^{15}$; $R^{15}$ is hydrogen, halogen or —CN; and the group —$R^4$-$R^5$ is —$NHR^5$, —$NHC(O)R^5$, —$NHC(O)OR^5$ or —$NHC(O)NHR^5$, wherein $R^5$ is other than hydrogen. In certain embodiments, A is $CR^3$; $R^1$ is independently halogen or —CN; X is $CR^{15}$; $R^{15}$ is hydrogen, halogen or —CN; and the group —$R^4$-$R^5$ is —$NHR^5$, —$NHC(O)R^5$, —$NHC(O)OR^5$ or —$NHC(O)NHR^5$, wherein $R^5$ is other than hydrogen.

In certain embodiments, $R^4$ is —NH—, —NHC(O)— or —NHC(O)NH—.

In certain embodiments, $R^4$ is —$NH_2$ and $R^5$ absent.

In certain embodiments, $R^5$ is hydrogen.

In certain embodiments, $R^4$ is —$NR^6R^7$; $R^5$ is absent; and $R^6$ and $R^7$ are independently hydrogen, $C_1$-$C_3$ alkyl or $C_3$-$C_4$ cycloalkyl, wherein said alkyl and cycloalkyl are independently optionally substituted by halogen, oxo, —$OR^{11}$ or —$NR^{11}R^{12}$.

In certain embodiments, $R^5$ is $C_1$-$C_6$ alkyl optionally substituted by halogen, oxo, —$OR^{11}$, —$SR^{11}$, —CN, $C_3$-$C_{10}$ cycloalkyl, —$C(O)R^{11}$ or —$NR^{11}R^{12}$. In certain embodiments, $R^5$ is $C_1$-$C_6$ alkyl optionally substituted by halogen, oxo, —$OR^{11}$, —$SR^{11}$, —$C(O)R^{11}$ or —$NR^{11}R^{12}$. In certain embodiments, $R^5$ is methyl, ethyl, isopropyl, tert-butyl, —$CH_2OH$, —$CH_2NH_2$, —$CH_2N(CH_3)_2$ or —$CH_2CH_2NH_2$. In certain embodiments, $R^5$ is methyl, ethyl, isopropyl, tert-butyl, —$CH_2OH$, —$CH_2CH_2OH$, —$CH_2CN$, —$CH_2NH_2$, —$CH_2N(CH_3)_2$ or —$CH_2CH_2NH_2$.

In certain embodiments, $R^5$ is $C_3$-$C_{10}$ cycloalkyl optionally substituted by $R^{10}$. In certain embodiments, $R^5$ is $C_3$-$C_6$ cycloalkyl optionally substituted by halogen. In certain embodiments, $R^5$ is cyclopropyl optionally substituted by halogen. In certain embodiments, $R^5$ is cyclopropyl. In certain embodiments, $R^5$ is selected from:

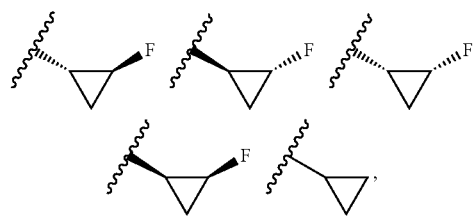

wherein the wavy line represents the point of attachment in Formula I.

In certain embodiments, $R^5$ is cyclopropyl. In certain embodiments, $R^5$ is selected from:

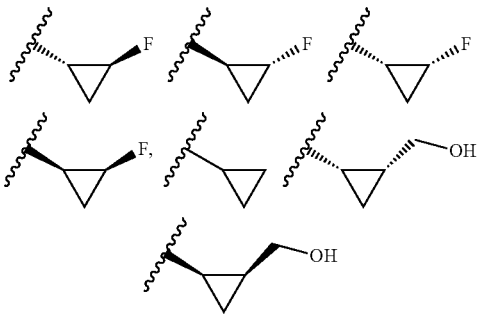

wherein the wavy line represents the point of attachment in Formula I.

In certain embodiments, $R^5$ is $C_6$-$C_{10}$ aryl optionally substituted by $R^{10}$. In certain embodiments, $R^5$ is selected from phenyl, naphthalenyl, dihydroindenyl and tetrahydronaphthalenyl, wherein $R^5$ is optionally substituted by $R^{10}$.

In certain embodiments, $R^5$ is phenyl optionally substituted by $R^{10}$. In certain embodiments, $R^5$ is phenyl. In certain embodiments, $R^5$ is phenyl optionally substituted by —$O(CH_2)_2$pyrrolidinyl.

In certain embodiments, $R^5$ is 3-10-membered heterocyclyl optionally substituted by $R^{10}$.

In certain embodiments, $R^5$ is 3-7-membered heterocyclyl optionally substituted by $R^{10}$.

In certain embodiments, $R^5$ is 5-10-membered heteroaryl optionally substituted by $R^{10}$. In certain embodiments, $R^5$ is pyridinyl, pyrimidinyl, pyrazolyl, thiazolyl, pyrazinyl, pyridazinyl, oxazolyl or isoxazolyl, wherein said $R^5$ is optionally substituted by $R^{10}$.

In certain embodiments, $R^5$ is pyridinyl, pyrimidinyl, pyrazolyl, thiazolyl, pyrazinyl, pyridazinyl, oxazolyl or isoxazolyl optionally substituted by $C_1$-$C_6$ alkyl, halogen, —CN, —$O(C_0$-$C_3$ alkyl), —$CF_3$, —$NR^{11}R^{12}$, $C=NH(OR^{11})$, —$C(O)OR^{11}$, 3-6-membered heterocyclyl, wherein said alkyl is optionally substituted by halogen or $OR^{11}$ and said heterocyclyl is optionally substituted by oxo, halogen or $C_1$-$C_3$ alkyl optionally substituted by halogen or $OR^{11}$.

In certain embodiments, $R^5$ is pyridinyl, pyrimidinyl, pyrazolyl, thiazolyl, pyrazinyl, pyridazinyl, oxazolyl or isoxazolyl optionally substituted by $C_1$-$C_6$ alkyl, halogen, —CN, —$O(C_1$-$C_3$ alkyl), —$CF_3$, —$NR^{11}R^{12}$, $C=NH(OR^{11})$, —$C(O)OR^{11}$, 3-6-membered heterocyclyl, wherein said alkyl is optionally substituted by halogen or $OR^{13}$ and said heterocyclyl is optionally substituted by oxo, halogen or $C_1$-$C_3$ alkyl optionally substituted by halogen or $OR^{13}$.

In certain embodiments, $R^5$ is 5-6-membered heteroaryl, wherein $R^5$ is optionally substituted by $R^{10}$, wherein $R^{10}$ is $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O) (3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$. In an example, $R^5$ is pyridinyl, pyrimidinyl, pyridazinyl, pyrazinyl, triazinyl, thienyl, pyrazolyl, pyranyl, triazolyl, isoxazolyl, oxazolyl, imidazolyl, thiazolyl or thiadiazolyl, wherein $R^5$ is optionally substituted by 1, 2 or 3 $R^{10}$.

In certain embodiments, $R^5$ is pyridinyl optionally substituted by $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^{11}$, —($C_0$-$C_3$ alkylene)$SR^{11}$, —($C_0$-$C_3$ alkylene)$NR^{11}R^{12}$, —($C_0$-$C_3$ alkylene)$CF_3$, —($C_0$-$C_3$ alkylene)$NO_2$, —C=NH($OR^{11}$), —($C_0$-$C_3$ alkylene)C(O)$R^{11}$, —($C_0$-$C_3$ alkylene)C(O)$OR^{11}$, —($C_0$-$C_3$ alkylene)C(O)$NR^{11}R^{12}$, —($C_0$-$C_3$ alkylene)$NR^{11}$C(O)$R^{12}$, —($C_0$-$C_3$ alkylene)S(O)$_{1-2}R^{11}$, —($C_0$-$C_3$ alkylene)$NR^{11}$S(O)$_{1-2}R^{12}$, —($C_0$-$C_3$ alkylene) S(O)$_{1-2}NR^{11}R^{12}$, —($C_0$-$C_3$ alkylene)($C_3$-$C_6$ cycloalkyl), —($C_0$-$C_3$ alkylene) (3-6-membered heterocyclyl), —($C_0$-$C_3$ alkylene)C(O)(3-6-membered heterocyclyl), —($C_0$-$C_3$ alkylene) (5-6-membered heteroaryl) or —($C_0$-$C_3$ alkylene)phenyl, wherein $R^{10}$ is independently optionally substituted by halogen, $C_1$-$C_3$ alkyl, oxo, —$CF_3$, —($C_0$-$C_3$ alkylene)$OR^{13}$, —($C_0$-$C_3$ alkylene)$NR^{13}R^{14}$, —($C_0$-$C_3$ alkylene)C(O)$R^{13}$ or —($C_0$-$C_3$ alkylene)S(O)$_{1-2}R^{13}$.

In certain embodiments, $R^5$ is selected from:

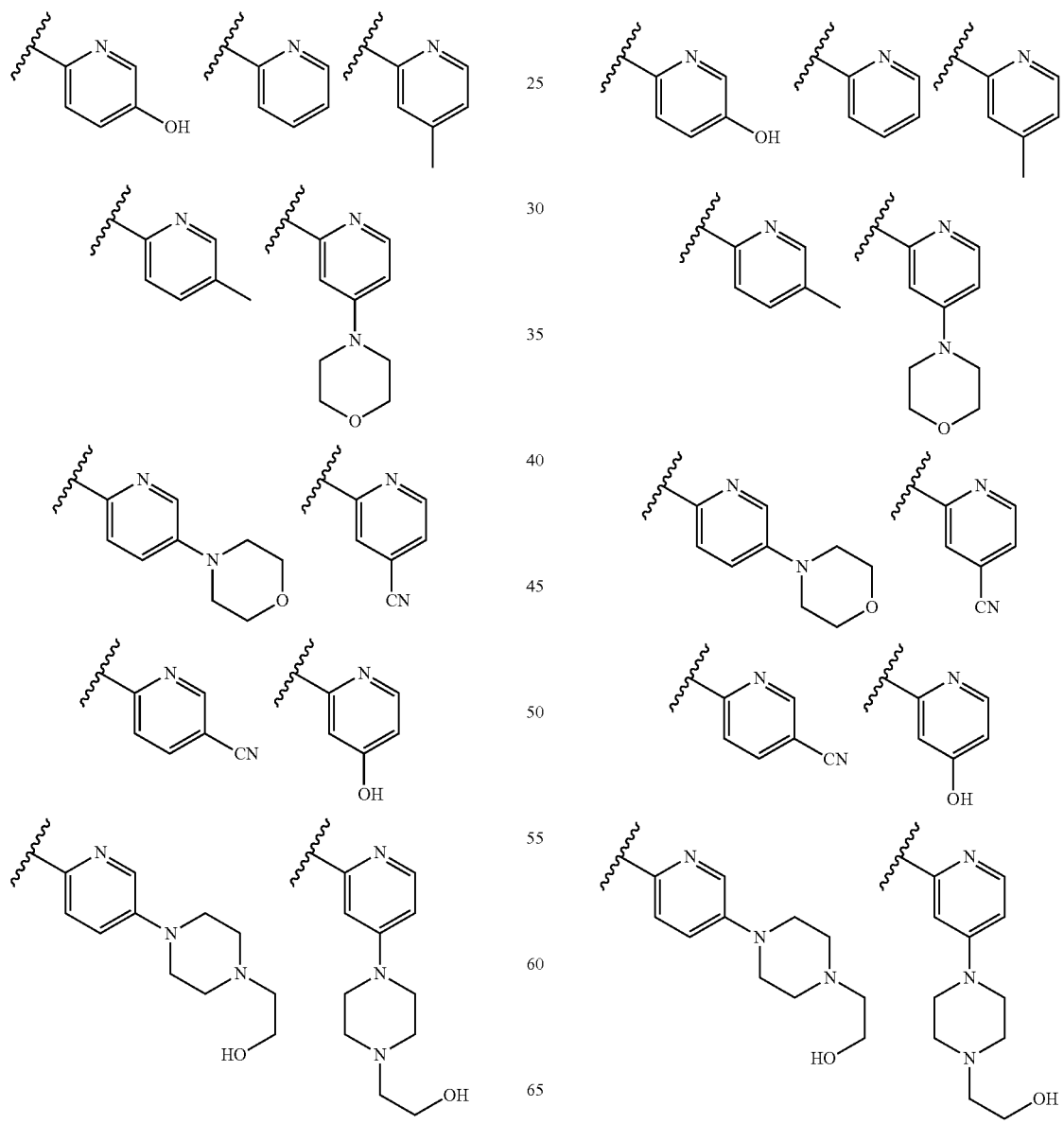

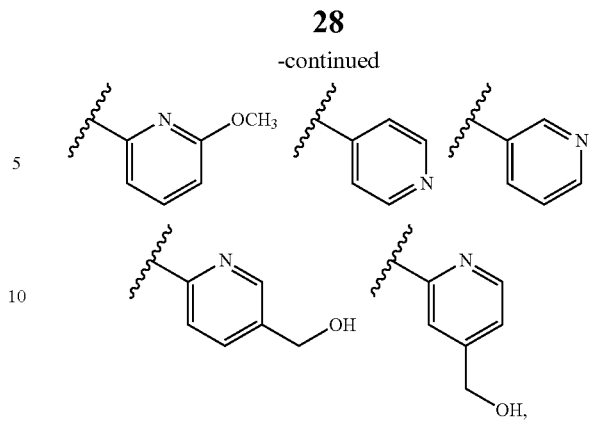

wherein the wavy lines represent the point of attachment in Formula I.

In certain embodiments, $R^5$ is selected from:

-continued

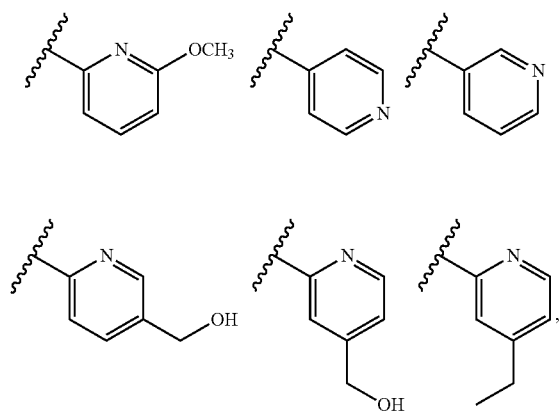

wherein the wavy lines represent the point of attachment in Formula I.

In certain embodiments, $R^5$ is selected from:

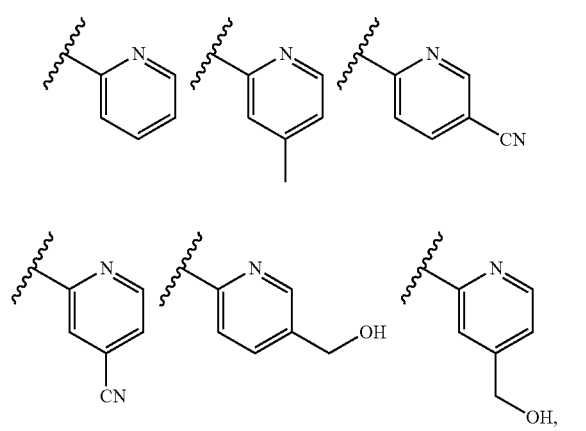

wherein the wavy lines represent the point of attachment in Formula I.

In certain embodiments, $R^5$ is pyrimidinyl, pyridazinyl, or pyrazinyl, optionally substituted by $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^{11}$, —($C_0$-$C_3$ alkylene)$SR^{11}$, —($C_0$-$C_3$ alkylene)$NR^{11}R^{12}$, —($C_0$-$C_3$ alkylene)$CF_3$, —($C_0$-$C_3$ alkylene)$NO_2$, —C=NH($OR^{11}$), —($C_0$-$C_3$ alkylene)C(O)$R^{11}$, —($C_0$-$C_3$ alkylene)C(O)$OR^{11}$, —($C_0$-$C_3$ alkylene)C(O)$NR^{11}R^{12}$, —($C_0$-$C_3$ alkylene)$NR^{11}$C(O)$R^{12}$, —($C_0$-$C_3$ alkylene)S(O)$_{1-2}R^{11}$, —($C_0$-$C_3$ alkylene)$NR^{11}$S(O)$_{1-2}R^{12}$, —($C_0$-$C_3$ alkylene)S(O)$_{1-2}NR^{11}R^{12}$, —($C_0$-$C_3$ alkylene)($C_3$-$C_6$ cycloalkyl), —($C_0$-$C_3$ alkylene) (3-6-membered heterocyclyl), —($C_0$-$C_3$ alkylene)C(O)(3-6-membered heterocyclyl), —($C_0$-$C_3$ alkylene) (5-6-membered heteroaryl) or —($C_0$-$C_3$ alkylene)phenyl, wherein $R^{10}$ is independently optionally substituted by halogen, $C_1$-$C_3$ alkyl, oxo, —$CF_3$, —($C_0$-$C_3$ alkylene)$OR^{13}$, —($C_0$-$C_3$ alkylene)$NR^{13}R^{14}$, —($C_0$-$C_3$ alkylene)C(O)$R^{13}$ or —($C_0$-$C_3$ alkylene)S(O)$_{1-2}R^{13}$.

In certain embodiments, $R^5$ is selected from:

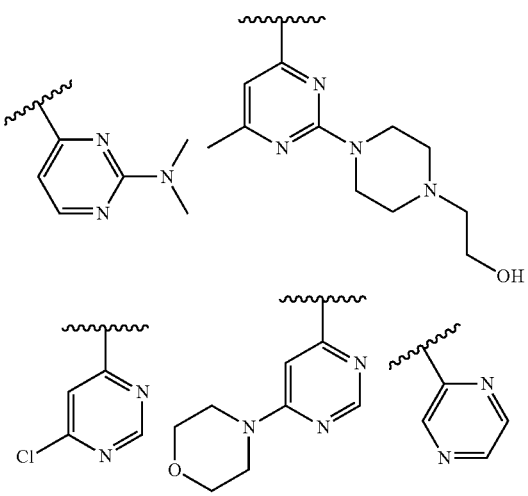

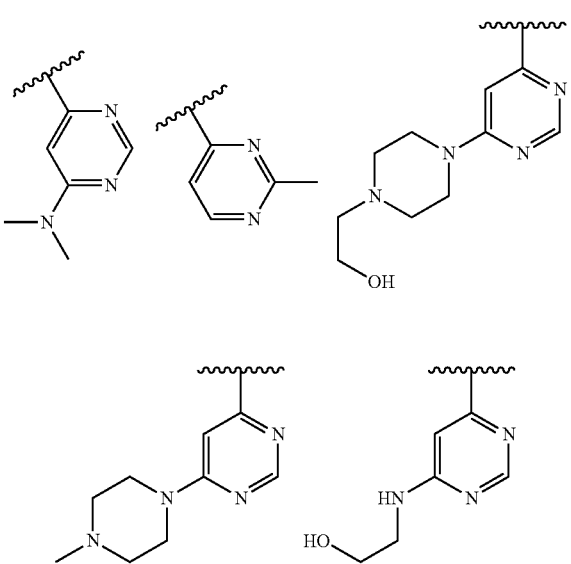

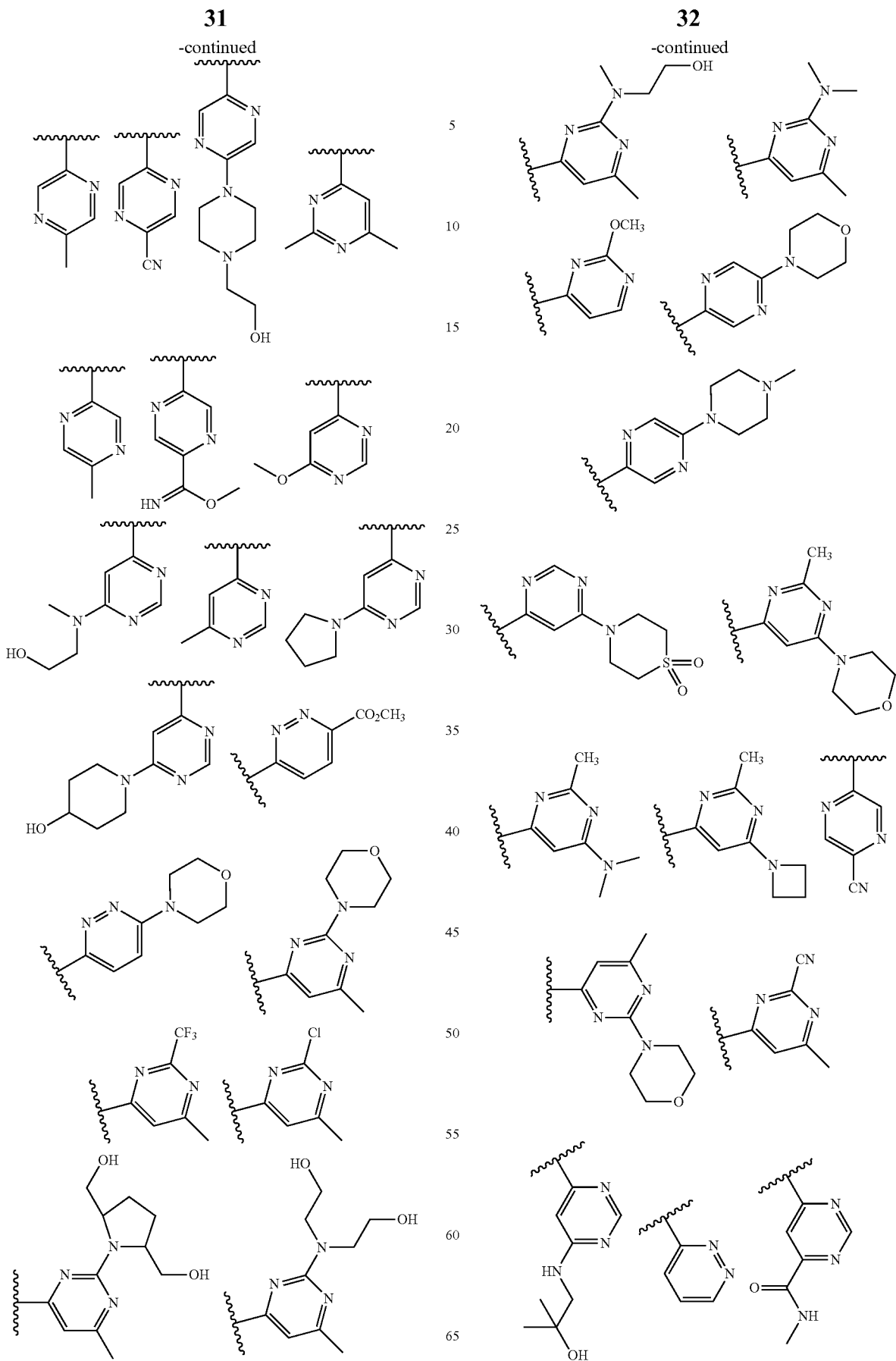

-continued
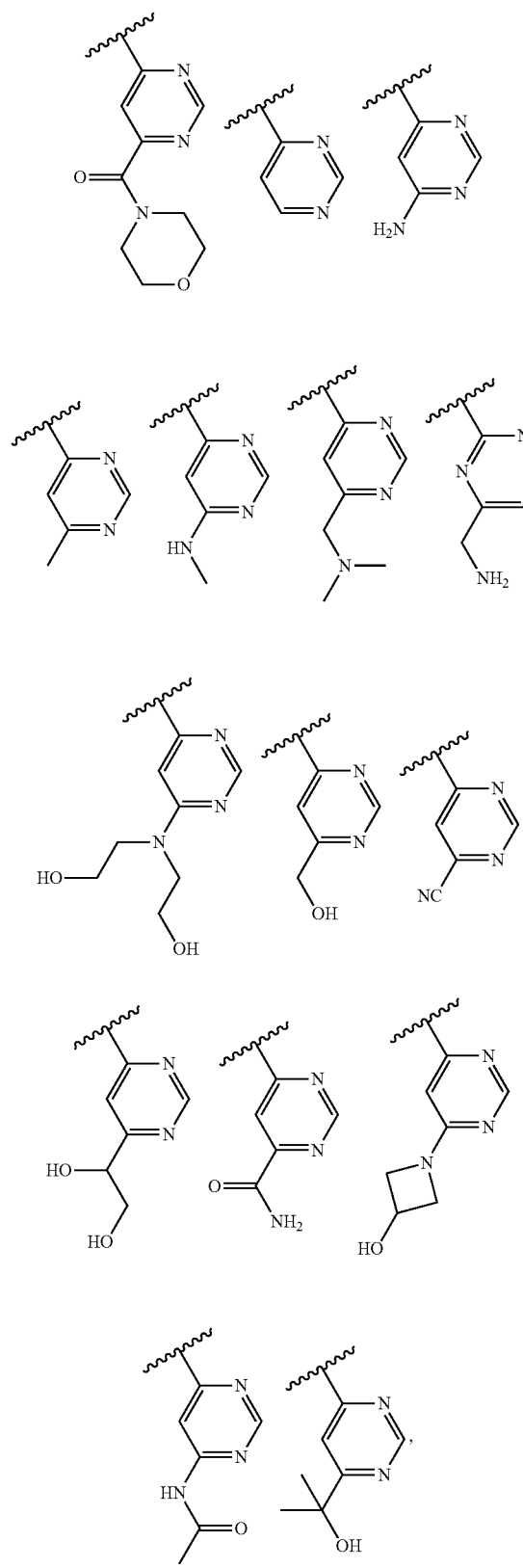
wherein the wavy lines represent the point of attachment in Formula I.
In certain embodiments, $R^5$ is selected from:
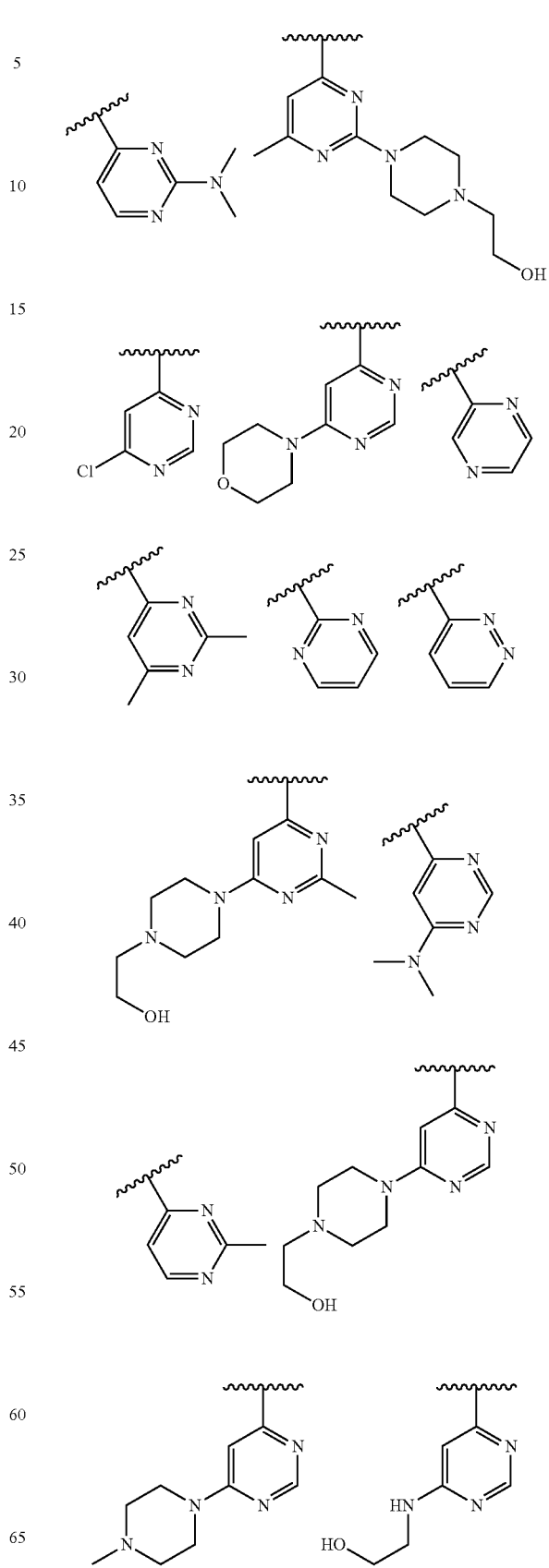

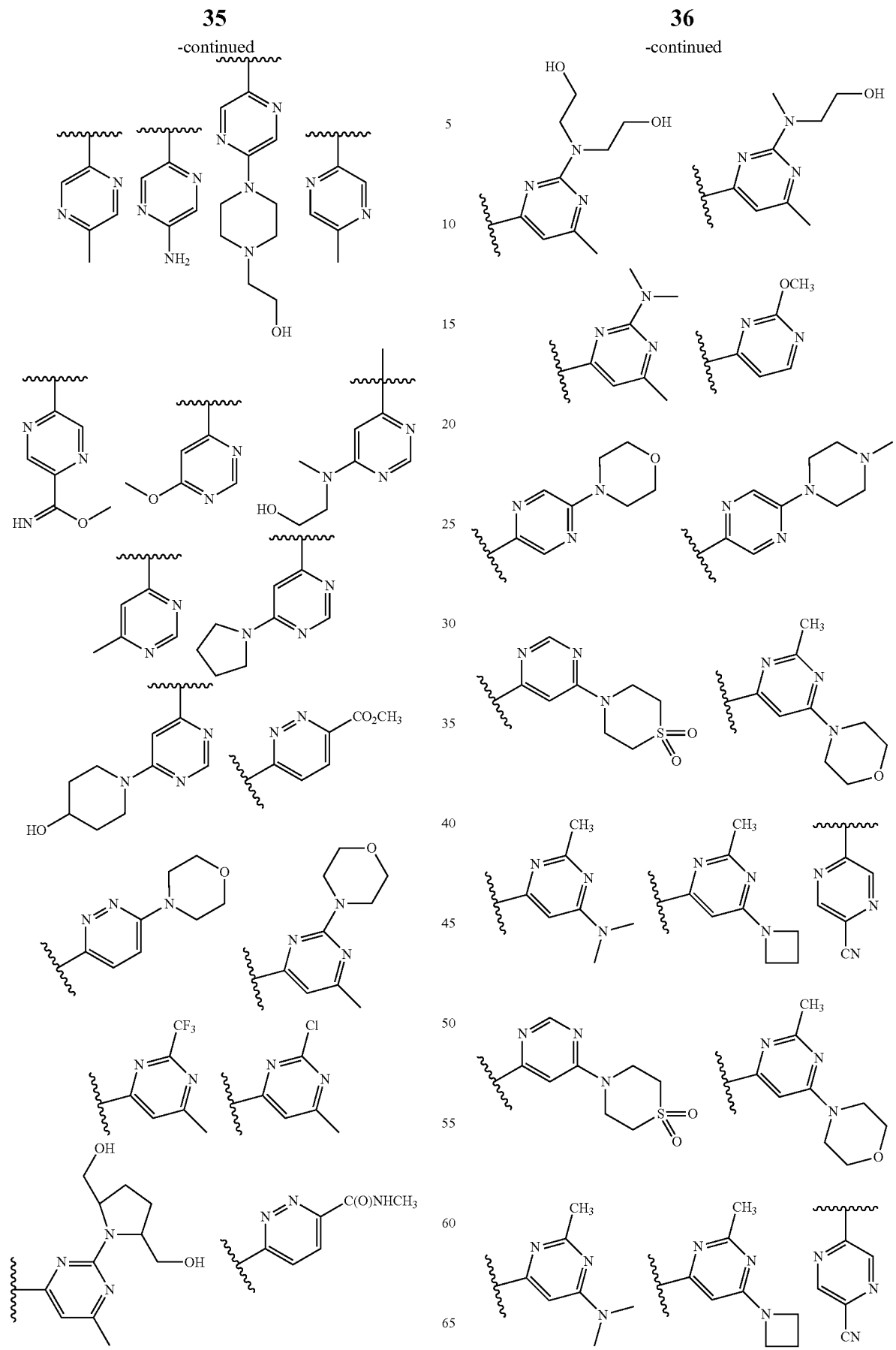

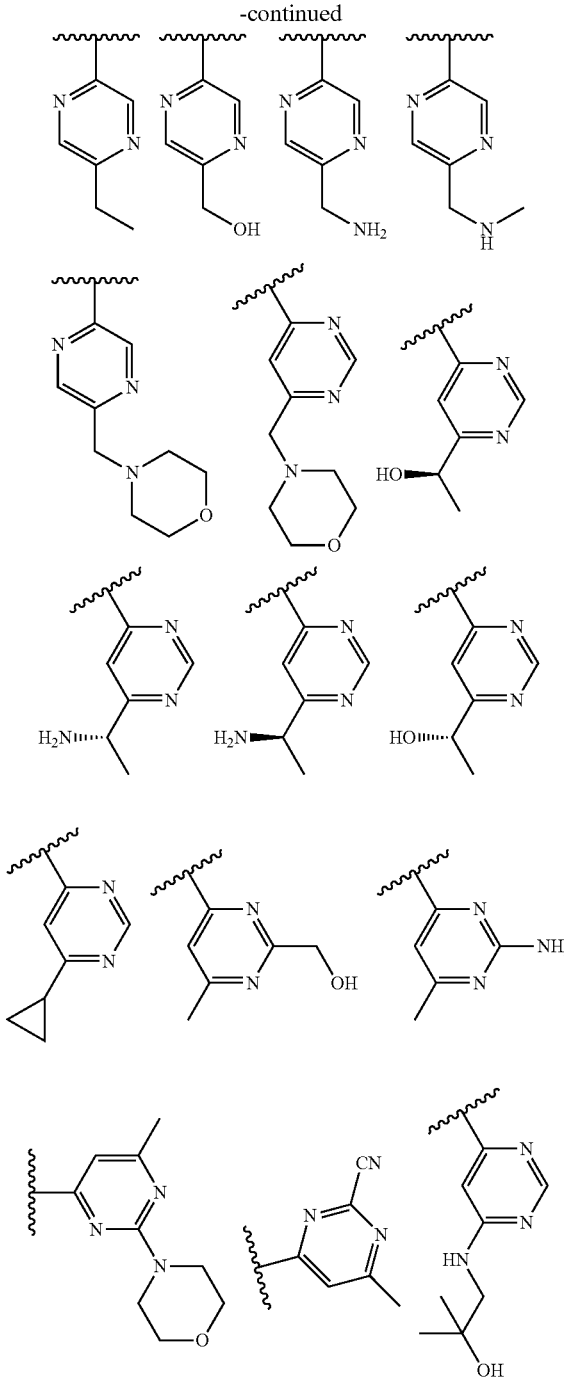
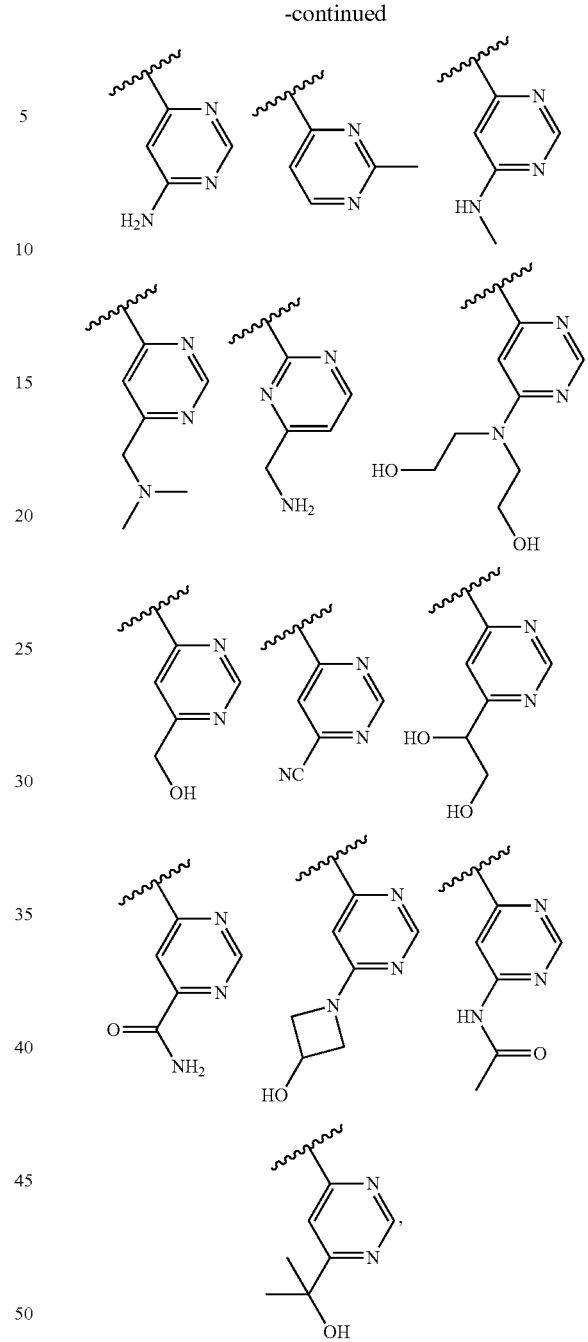
wherein the wavy lines represent the point of attachment in Formula I.
In certain embodiments, $R^5$ is selected from:
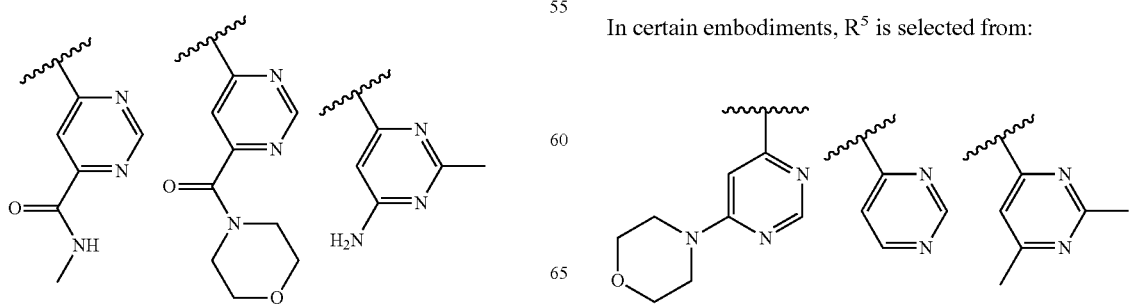

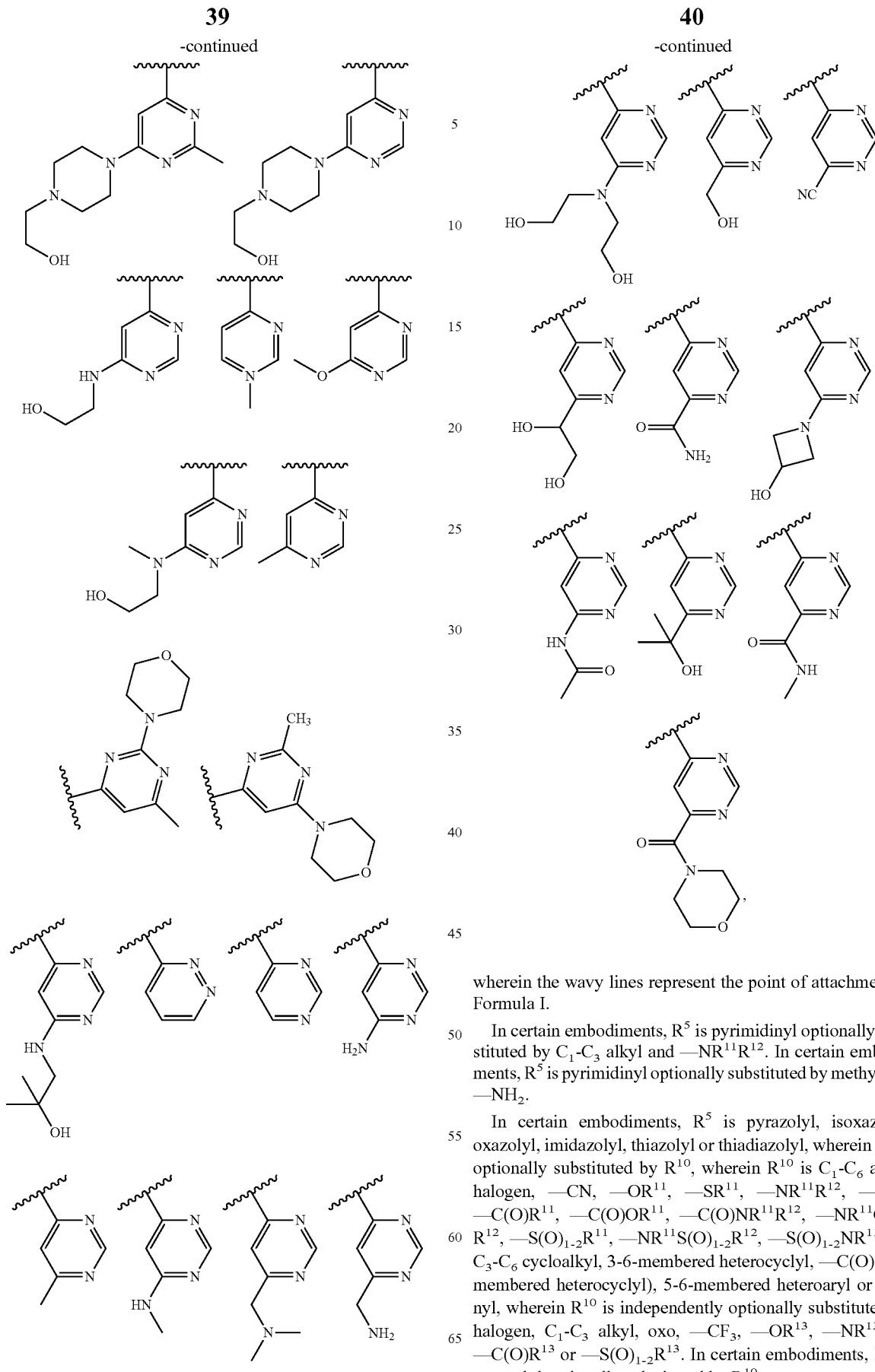

wherein the wavy lines represent the point of attachment in Formula I.

In certain embodiments, $R^5$ is pyrimidinyl optionally substituted by $C_1$-$C_3$ alkyl and —$NR^{11}R^{12}$. In certain embodiments, $R^5$ is pyrimidinyl optionally substituted by methyl and —$NH_2$.

In certain embodiments, $R^5$ is pyrazolyl, isoxazolyl, oxazolyl, imidazolyl, thiazolyl or thiadiazolyl, wherein $R^5$ is optionally substituted by $R^{10}$, wherein $R^{10}$ is $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$. In certain embodiments, $R^5$ is pyrazolyl optionally substituted by $R^{10}$.

In certain embodiments, $R^5$ is selected from:

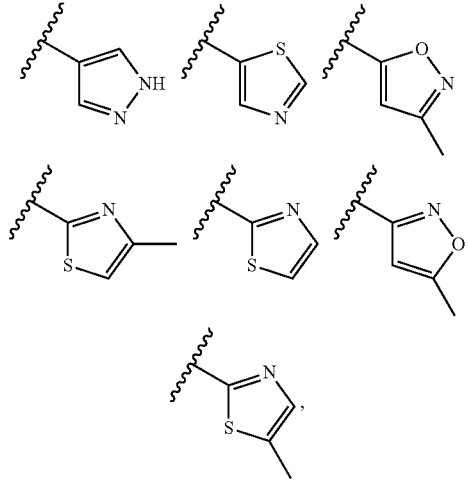

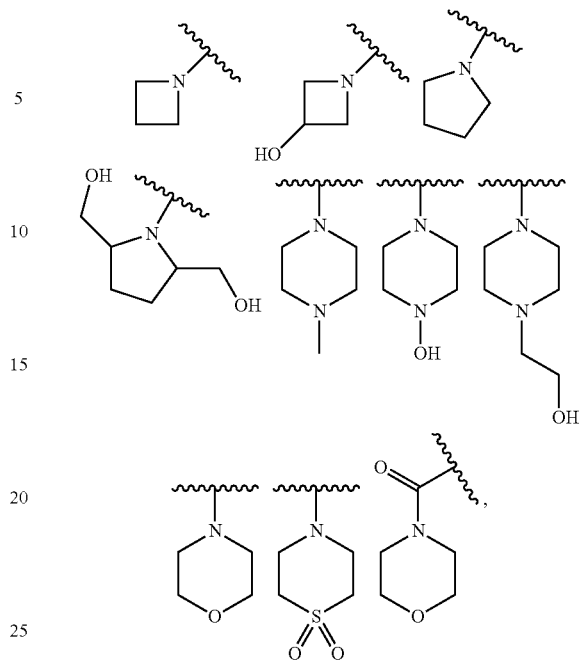

wherein the wavy lines represent the point of attachment in Formula I.

In certain embodiments, $R^{10}$ is independently halogen. In certain embodiments, $R^{10}$ is independently F.

In certain embodiments, $R^{10}$ is independently —CN.

In certain embodiments, $R^{10}$ is independently $C_1$-$C_6$ alkyl, $C_2$-$C_6$ alkenyl or $C_2$-$C_6$ alkynyl, wherein said alkyl, alkenyl and alkynyl are independently optionally substituted by halogen, oxo, —$OR^{13}$ or —$NR^{13}R^{14}$. In certain embodiments, $R^{10}$ is methyl, ethyl, isopropy, —CH$_2$OH, —CH$_2$CH$_2$OH, —CH(OH)CH$_2$OH, —C(CH$_3$)$_2$OH, —CH$_2$NH$_2$, —CH$_2$N(CH$_3$)$_2$, —CF$_3$, —C(O)NH$_2$, —C(O)NHCH$_3$, —C(O)N(CH$_3$)$_2$ or —C(O)morpholinyl. In certain embodiments, $R^{10}$ is methyl.

In certain embodiments, $R^{10}$ is independently $C_1$-$C_6$ alkyl, $C_2$-$C_6$ alkenyl or $C_2$-$C_6$ alkynyl, wherein said alkyl, alkenyl and alkynyl are independently optionally substituted by halogen, oxo, —$OR^{13}$ or —$NR^{13}R^{14}$. In certain embodiments, $R^{10}$ is methyl, ethyl, isopropy, —CH$_2$OH, —CH$_2$CH$_2$OH, —CH(OH)CH$_2$OH, —C(CH$_3$)$_2$OH, —CH$_2$NH$_2$, —CH$_2$NHCH$_3$, —CH$_2$N(CH$_3$)$_2$, —CF$_3$, —C(O)NH$_2$, —C(O)NHCH$_3$, —C(O)N(CH$_3$)$_2$, —CH$_2$thiomorpholinyl dioxide, —CH$_2$morpholinyl, (R)—CH(OH)CH$_3$, (R)—CH(NH$_2$)CH$_3$, (S)—CH(OH)CH$_3$, (S)—CH(NH$_2$)CH$_3$ or —C(O)morpholinyl. In certain embodiments, $R^{10}$ is methyl.

In certain embodiments, $R^{10}$ is independently $C_3$-$C_6$ cycloalkyl optionally substituted by halogen, oxo or $C_1$-$C_3$ alkyl. In certain embodiments, $R^{10}$ is independently cyclopropyl.

In certain embodiments, $R^{10}$ is independently 3-6 membered heterocyclyl or —C(O)(3-6 membered heterocyclyl), wherein said heterocyclyl is independently optionally substituted by —(C$_0$-C$_3$ alkylene)OR$^{13}$, —(C$_0$-C$_3$ alkylene)NR$^{13}$R$^{14}$, halogen, —CN, oxo or $C_1$-$C_6$ alkyl optionally substituted by oxo or halogen. In certain embodiments, said heterocyclyl is morpholinyl, thiomorpholinyl, piperizinyl, piperidinyl or aziridinyl, wherein said heterocyclyl is independently optionally substituted by oxo, —CH$_2$OH, —CH$_2$CH$_2$OH, —OH, methyl or —CF$_3$. In certain embodiments, $R^{10}$ is independently selected from:

wherein the wavy line represents the point of attachment in Formula I.

In certain embodiments, $R^{10}$ is independently —(C$_0$-C$_3$ alkylene)OR$^{11}$ or —(C$_0$-C$_3$ alkylene)SR$^{11}$. In certain embodiments, $R^{10}$ is —OH, —OCH$_3$, —CH$_2$OH, —CH$_2$CH$_2$OH, —CH(OH)CH$_2$OH or —C(CH$_3$)$_2$OH. In certain embodiments, $R^{10}$ is —OH or —OCH$_3$. In certain embodiments, $R^{10}$ is —OH, —OCH$_3$, —CH$_2$OH, —CH$_2$CH$_2$OH, —CH(OH)CH$_2$OH, —C(CH$_3$)$_2$OH. (R)—CH(OH)CH$_3$ or (S)—CH(OH)CH$_3$.

In certain embodiments, $R^{10}$ is independently —(C$_0$-C$_3$ alkylene)NR$^{11}$R$^{12}$. In certain embodiments, $R^{10}$ is —NH$_2$, —NHCH$_3$, —NHC(O)CH$_3$, —N(CH$_3$)$_2$, —N(CH$_2$CH$_2$OH)$_2$, —NHCH$_2$CH$_2$OH, —N(CH$_3$)CH$_2$CH$_2$OH, —NHCH$_2$C(CH$_3$)$_2$OH, —N(CH$_3$)CH$_2$C(CH$_3$)$_2$OH, 4-hydroxyaziridin-1-yl, morpholinyl, dioxothiomorpholinyl, piperidinyl, 4-hydroxypiperidinyl, 4-methylpiperazinyl, pyrrolidinyl or 4-(2-hydroxyethyl)piperazinyl. In certain embodiments, $R^{10}$ is —NH$_2$, —NHCH$_3$, —NHC(O)CH$_3$, —N(CH$_3$)$_2$, —N(CH$_2$CH$_2$OH)$_2$, —NHCH$_2$CH$_2$OH, —N(CH$_3$)CH$_2$CH$_2$OH, —NHCH$_2$C(CH$_3$)$_2$OH, —N(CH$_3$)CH$_2$C(CH$_3$)$_2$OH, 4-hydroxyaziridin-1-yl, morpholinyl, dioxothiomorpholinyl, piperidinyl, 4-hydroxypiperidinyl, 4-methylpiperazinyl, pyrrolidinyl, —CH$_2$thiomorpholinyl dioxide, —CH$_2$morpholinyl, (R)—CH(NH$_2$)CH$_3$, (S)—CH(NH$_2$)CH$_3$ or 4-(2-hydroxyethyl)piperazinyl.

In certain embodiments, $R^{10}$ is independently —C(O)NR$^{11}$R$^{12}$. In certain embodiments, $R^{10}$ is —C(O)NH$_2$, —C(O)NHCH$_3$, —C(O)N(CH$_3$)$_2$ or —C(O)morpholinyl.

In certain embodiments, $R^{10}$ is independently $C_1$-$C_6$ alkyl, halogen, —CN, —OR$^{11}$, —SR$^{11}$, —NR$^{11}$R$^{12}$, —CF$_3$, —C=NH(OR$^{11}$), —C(O)OR$^{11}$, $C_3$-$C_6$ cycloalkyl, 3-6-membered heterocyclyl, 5-6-membered heteroaryl or phenyl, wherein $R^{10}$ is independently optionally substituted by halogen, oxo, —CF$_3$, —OR$^{13}$, —NR$^{13}$R$^{14}$, —C(O)R$^{13}$, —S(O)$_{1-2}$R$^{13}$ or $C_1$-$C_3$ alkyl optionally substituted by oxo or halogen.

In certain embodiments, $R^{10}$ is independently selected from F, —CN, methyl, ethyl, isopropy, —CH$_2$OH, —CH$_2$CH$_2$OH, —CH(OH)CH$_2$OH, —C(CH$_3$)$_2$OH, —CH$_2$NH$_2$, —CH$_2$N(CH$_3$)$_2$, —CF$_3$, —OH, —OCH$_3$, —NH$_2$, —NHCH$_3$, —NHC(O)CH$_3$, —N(CH$_3$)$_2$, —N(CH$_2$CH$_2$OH)$_2$, —NHCH$_2$CH$_2$OH, —N(CH$_3$)CH$_2$CH$_2$OH, —NHCH$_2$C(CH$_3$)$_2$OH, —N(CH$_3$)CH$_2$C(CH$_3$)$_2$OH, —C(O)NH$_2$, —C(O)NHCH$_3$, —C(O)N(CH$_3$)$_2$,

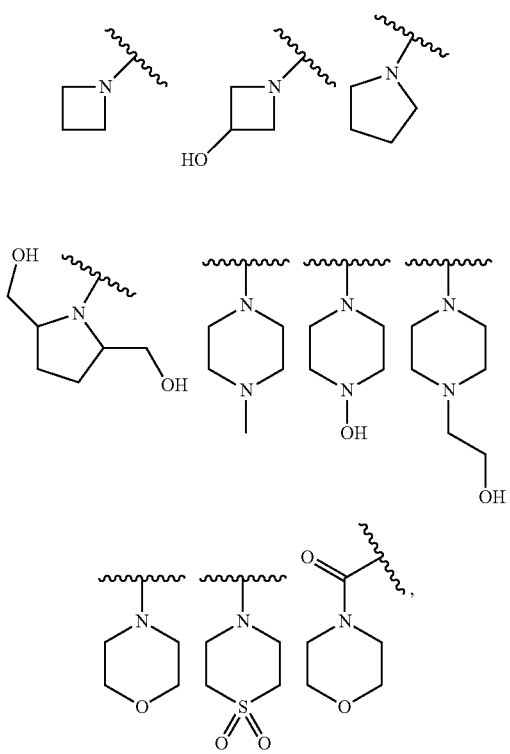

wherein the wavy line represents the point of attachment in Formula I.

In certain embodiments, $R^{10}$ is independently selected from F, —CN, methyl, ethyl, isopropy, —CH$_2$OH, —CH$_2$CH$_2$OH, —CH(OH)CH$_2$OH, —C(CH$_3$)$_2$OH, —CH$_2$NH$_2$, —CH$_2$NHCH$_3$, —CH$_2$N(CH$_3$)$_2$, —CF$_3$, —OH, —OCH$_3$, —NH$_2$, —NHCH$_3$, —NHC(O)CH$_3$, —N(CH$_3$)$_2$, —N(CH$_2$CH$_2$OH)$_2$, —NHCH$_2$CH$_2$OH, —N(CH$_3$)CH$_2$CH$_2$OH, —NHCH$_2$C(CH$_3$)$_2$OH, —N(CH$_3$)CH$_2$C(CH$_3$)$_2$OH, —C(O)NH$_2$, —C(O)NHCH$_3$, —C(O)N(CH$_3$)$_2$, —CH$_2$thiomorpholinyl dioxide, —CH$_2$morpholinyl, —CH$_2$cyclopropyl, —CH(OH)CH$_3$, —CH(NH$_2$)CH$_3$, (R)—CH(OH)CH$_3$, (R)—CH(NH$_2$)CH$_3$, (S)—CH(OH)CH$_3$, (S)—CH(NH$_2$)CH$_3$,

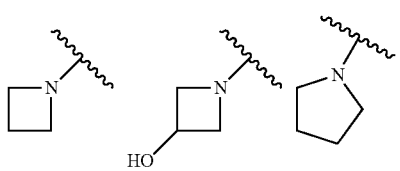

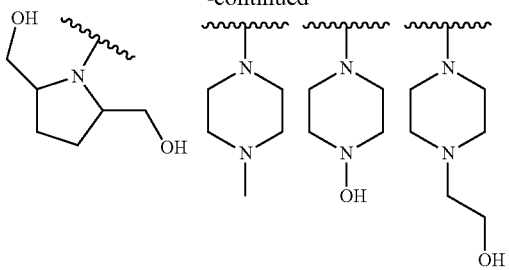

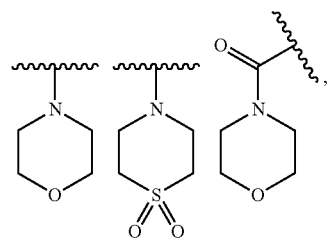

wherein the wavy line represents the point of attachment in Formula I.

In certain embodiments, $R^{11}$ and $R^{12}$ are independently hydrogen or C$_1$-C$_6$ alkyl optionally substituted by halogen, oxo, —CN, —OR$^{16}$ or —NR$^{16}$R$^{17}$, or are taken together with the atom to which they attached to form a 3-6 membered heterocyclyl optionally substituted by halogen, oxo, —OR$^{16}$, —NR$^{16}$R$^{17}$ or C$_1$-C$_3$ alkyl optionally substituted by halogen, oxo or OH.

In certain embodiments, $R^{11}$ and $R^{12}$ are independently hydrogen, methyl, —C(O)CH$_3$, 2-hydroxy-2-methylpropyl or 2-hydroxyethyl, or are taken together with the atom to which they attached to form a azetidinyl, pyrrolidinyl, morpholinyl, dioxothiomorpholinyl, piperazinyl or piperidinyl ring optionally substituted by halogen, oxo or C$_1$-C$_3$ alkyl optionally substituted by oxo, halogen or OH.

In certain embodiments, $R^{11}$ and $R^{12}$ are independently hydrogen, methyl, —C(O)CH$_3$, 2-hydroxy-2-methylpropyl or 2-hydroxyethyl.

In certain embodiments, $R^{13}$ and $R^{14}$ are independently hydrogen or C$_1$-C$_3$ alkyl. In certain embodiments, $R^{13}$ and $R^{14}$ are independently hydrogen or methyl.

In certain embodiments, $R^{15}$ is hydrogen, halogen, C$_1$-C$_6$ alkyl, C$_2$-C$_6$ alkenyl, C$_2$-C$_6$ alkynyl, —CN, —OR$^{18}$, —SR$^{18}$, —NR$^{18}$R$^{19}$, —CF$_3$, —OCF$_3$, —NO$_2$, —C(O)R$^{18}$, —C(O)OR$^{18}$, —C(O)NR$^{18}$R$^{19}$, —NR$^{18}$C(O)R$^{19}$, —S(O)$_{1-2}$R$^{18}$, —NR$^{18}$S(O)$_{1-2}$R$^{19}$, —S(O)$_{1-2}$NR$^{18}$R$^{19}$, —(C$_3$-C$_6$ cycloalkyl), -(3-6-membered heterocyclyl), -(5-6-membered heteroaryl) or -phenyl.

In certain embodiments, $R^{15}$ is hydrogen, halogen, —CF$_3$ or C$_1$-C$_3$ alkyl. In certain embodiments, $R^{15}$ is methyl. In certain embodiments, $R^{15}$ is halogen. In certain embodiments, $R^{15}$ is F.

In certain embodiments, $R^{15}$ is —(C$_0$-C$_3$ alkylene)OR$^{18}$. In certain embodiments, $R^{15}$ is —CH$_2$OR$^{18}$. In certain embodiments, $R^{15}$ is —CH$_2$OH.

In certain embodiments, $R^{15}$ is hydrogen, halogen, —CN, —CH$_2$OH, —CF$_3$ or C$_1$-C$_3$ alkyl. In certain embodiments, $R^{15}$ is methyl. In certain embodiments, $R^{15}$ is halogen. In certain embodiments, $R^{15}$ is F or Br. In certain embodiments, $R^{15}$ is F, Br, CN or CH$_2$OH.

In certain embodiments, $R^{16}$ and $R^{17}$ are each independently hydrogen or C$_1$-C$_3$ alkyl. In certain embodiments, $R^{16}$ and $R^{17}$ are each independently hydrogen or methyl.

In certain embodiments, $R^{18}$ and $R^{19}$ are independently hydrogen or methyl.

In certain embodiments, A is $CR^3$; X is CH; $R^1$ is independently hydrogen, —$OCH_3$, —$CF_3$, —$OCF_3$, —$CH_3$, Cl or F, wherein both $R^1$ cannot be hydrogen at the same time; $R^2$ is hydrogen; $R^3$ is hydrogen or —CN; $R^4$ is —NH—, —NHC(O)—, —NHC(O)NH— or —NHC(O)O—; and $R^5$ is $C_3$-$C_6$ cycloalkyl optionally substituted by $R^{10}$.

In certain embodiments, A is $CR^3$; X is CH; $R^1$ is independently hydrogen, —$OCH_3$, —$CF_3$, —$OCF_3$, —$CH_3$, Cl or F, wherein both $R^1$ cannot be hydrogen at the same time; $R^2$ is hydrogen; $R^3$ is hydrogen or —CN; $R^4$ is —NH—, —NHC(O)—, —NHC(O)NH— or —NHC(O)O—; and $R^5$ is pyrimidinyl, pyridinyl, pyridazinyl or pyrazinyl optionally substituted by $R^{10}$.

In certain embodiments, A is $CR^3$; X is $CR^{15}$; $R^1$ is independently hydrogen, —CN, Cl or F, wherein both $R^1$ cannot be hydrogen at the same time; $R^2$ is hydrogen; $R^3$ is hydrogen or —CN; $R^4$ is —NH—; $R^5$ is pyrimidinyl or pyridinyl optionally substituted by $R^{10}$; and $R^{15}$ is hydrogen, —CN or halogen.

In certain embodiments, A is $CR^3$; X is $CR^{15}$; $R^1$ is independently hydrogen, —CN, Cl or F, wherein both $R^1$ cannot be hydrogen at the same time; $R^2$ is hydrogen; $R^3$ is hydrogen or —CN; $R^4$ is —NHC(O)—; $R^5$ is $C_3$-$C_6$ cycloalkyl optionally substituted by $R^{10}$; and $R^{15}$ is hydrogen, —CN or halogen.

In certain embodiments, A is N; X is $CR^{15}$; $R^1$ is independently hydrogen, —CN, Cl or F, wherein both $R^1$ cannot be hydrogen at the same time; $R^2$ is hydrogen; $R^4$ is —NHC(O)—; $R^5$ is $C_3$-$C_6$ cycloalkyl optionally substituted by $R^{10}$; and $R^{15}$ is hydrogen, —CN or halogen.

In certain embodiments, A is N; X is $CR^{15}$; $R^1$ is independently hydrogen, —CN, Cl or F, wherein both $R^1$ cannot be hydrogen at the same time; $R^2$ is hydrogen; $R^4$ is —NH—; $R^5$ is pyrimidinyl or pyridinyl optionally substituted by $R^{10}$; and $R^{15}$ is hydrogen, —CN or halogen.

In certain embodiments, $R^1$ is independently hydrogen or halogen, wherein both $R^1$ cannot be hydrogen at the same time and $R^4$ is —NH—, —$NR^6C(O)$—, —$NR^6C(O)O$— or —$NR^6C(O)NR^7$—.

Another embodiment includes a compound of Formula I, stereoisomers or pharmaceutically acceptable salts thereof, selected from:

2-(2,6-Dichlorophenyl)-N-(6-methyl-2-morpholinopyrimidin-4-yl)thiazolo[5,4-c]pyridin-4-amine;
2-(2,6-Dichlorophenyl)-N-(2,6-dimethylpyrimidin-4-yl)thiazolo[5,4-c]pyridin-4-amine;
N-(2-(2,6-Dichlorophenyl)thiazolo[5,4-c]pyridin-4-yl)cyclopropanecarboxamide;
N-(6-(aminomethyl)pyrimidin-4-yl)-2-(2,6-dichlorophenyl)thiazolo[5,4-c]pyridin-4-amine;
4-[4-(2-Amino-6-methyl-pyrimidin-4-ylamino)-thiazolo[5,4-c]pyridin-2-yl]-3,5-dichloro-benzonitrile;
3-(6-(2-(2,6-dichlorophenyl)thiazolo[4,5-d]pyrimidin-7-ylamino)pyrimidin-4-yl)cyclobutanol;
N-(2-(2,6-dichlorophenyl)thiazolo[4,5-d]pyrimidin-7-yl)cyclopropanecarboxamide;
3-Chloro-5-fluoro-4-[4-(6-methyl-pyrimidin-4-ylamino)-thiazolo[5,4-c]pyridin-2-yl]-benzonitrile;
{3,5-Dichloro-4-[4-(6-methyl-pyrimidin-4-ylamino)-thiazolo[5,4-c]pyridin-2-yl]-phenyl}-methanol;
3,5-Dichloro-4-{4-[6-(2-hydroxy-ethylamino)-pyrimidin-4-ylamino]-thiazolo[5,4-c]pyridin-2-yl}-benzonitrile;
3,5-Dichloro-4-{4-[5-(3-hydroxy-azetidin-1-yl)-pyrimidin-4-ylamino]-thiazolo[5,4-c]pyridine-2-yl}-benzonitrile;
2-[2-(2,6-Dichloro-4-cyano-phenyl)-thiazolo[5,4-c]pyridine-4-ylamino]-isonicotinonitrile;
(2-(2-(2,6-dichlorophenyl)thiazolo[5,4-c]pyridin-4-ylamino)pyridin-4-yl)methanol;
N-(6-(2-(2-Chloro-6-fluorophenyl)thiazolo[5,4-c]pyridin-4-ylamino)pyrimidin-4-yl)acetamide;
1-(2-(2-Chloro-6-fluorophenyl)thiazolo[5,4-c]pyridin-4-yl)-3-cyclopropylurea;
1-(6-(2-(2-Chloro-6-fluorophenyl)thiazolo[5,4-c]pyridin-4-ylamino)pyrimidin-4-yl)ethane-1,2-diol;
2-(2-Chloro-6-fluorophenyl)-N-(2-methyl-6-morpholinopyrimidin-4-yl)thiazolo[5,4-c]pyridin-4-amine;
N-(2-(2-Chloro-6-fluorophenyl)thiazolo[5,4-c]pyridin-4-yl)cyclopropanecarboxamide;
6-(2-(2,6-Dichlorophenyl)thiazolo[5,4-c]pyridin-4-ylamino)pyrimidine-4-carbonitrile;
N-(2-(2,6-Dichlorophenyl)thiazolo[5,4-c]pyridin-4-yl)-2-(dimethylamino)acetamide;
N-(2-(2,6-Dichlorophenyl)thiazolo[5,4-c]pyridin-4-yl)-2-hydroxyacetamide;
2-(2,6-Dichlorophenyl)thiazolo[5,4-c]pyridin-4-ylcarbamate;
(6-(2-(2,6-Dichlorophenyl)thiazolo[5,4-c]pyridin-4-ylamino)pyrimidin-4-yl)methanol;
2-(4-(6-(2-(2,6-Dichlorophenyl)thiazolo[5,4-c]pyridin-4-ylamino)-2-methylpyrimidin-4-yl)piperazin-1-yl)ethanol;
2-(2,6-Dichlorophenyl)-N-(1H-pyrazol-4-yl)thiazolo[5,4-c]pyridin-4-amine;
N-(2-(2,6-Dichlorophenyl)thiazolo[5,4-c]pyridin-4-yl)acetamide;
2-(2,6-dichlorophenyl)-N-(2-methyl-6-morpholinopyrimidin-4-yl)thiazolo[5,4-c]pyridin-4-amine;
2-(2,6-dichlorophenyl)-N-(6-morpholinopyrimidin-4-yl)thiazolo[5,4-c]pyridin-4-amine;
2-(4-(6-(2-(2,6-dichlorophenyl)thiazolo[5,4-c]pyridin-4-ylamino)pyrimidin-4-yl)piperazin-1-yl)ethanol;
1-(6-(2-(2,6-dichlorophenyl)thiazolo[5,4-c]pyridin-4-ylamino)pyrimidin-4-yl)azetidin-3-ol;
2-((6-(2-(2,6-dichlorophenyl)thiazolo[5,4-c]pyridin-4-ylamino)pyrimidin-4-yl)(methyl)amino)ethanol;
2,2'-(6-(2-(2,6-dichlorophenyl)thiazolo[5,4-c]pyridin-4-ylamino)pyrimidin-4-ylazanediyl)diethanol;
2-(2,6-dichlorophenyl)-N-(pyridin-2-yl)thiazolo[5,4-c]pyridin-4-amine;
2-(2,6-dichlorophenyl)-N-(pyrimidin-4-yl)thiazolo[5,4-c]pyridin-4-amine;
2-(6-(2-(2,6-dichlorophenyl)thiazolo[5,4-c]pyridin-4-ylamino)pyrimidin-4-ylamino)ethanol;
N-4-(2-(2,6-dichlorophenyl)thiazolo[5,4-c]pyridin-4-yl)pyrimidine-4,6-diamine;
2-(2-chloro-6-fluorophenyl)-N-(2,6-dimethylpyrimidin-4-yl)thiazolo[5,4-c]pyridin-4-amine;
2-(2-chloro-6-fluorophenyl)-N-(6-methyl-2-morpholinopyrimidin-4-yl)thiazolo[5,4-c]pyridin-4-amine;
2-(2-chloro-6-fluorophenyl)-N-(6-morpholinopyrimidin-4-yl)thiazolo[5,4-c]pyridin-4-amine;
2-(4-(6-(2-(2-chloro-6-fluorophenyl)thiazolo[5,4-c]pyridin-4-ylamino)-2-methylpyrimidin-4-yl)piperazin-1-yl)ethanol;
2-(4-(6-(2-(2-chloro-6-fluorophenyl)thiazolo[5,4-c]pyridin-4-ylamino)pyrimidin-4-yl)piperazin-1-yl)ethanol;
2-((6-(2-(2-chloro-6-fluorophenyl)thiazolo[5,4-c]pyridin-4-ylamino)pyrimidin-4-yl)(methyl)amino)ethanol;
2,2'-(6-(2-(2-chloro-6-fluorophenyl)thiazolo[5,4-c]pyridin-4-ylamino)pyrimidin-4-ylazanediyl)diethanol;
(6-(2-(2-chloro-6-fluorophenyl)thiazolo[5,4-c]pyridin-4-ylamino)pyrimidin-4-yl)methanol;

1-(6-(2-(2,6-dichlorophenyl)thiazolo[5,4-c]pyridin-4-ylamino)pyrimidin-4-yl)ethane-1,2-diol;

2-(6-(2-(2-chloro-6-fluorophenyl)thiazolo[5,4-c]pyridin-4-ylamino)pyrimidin-4-ylamino)ethanol;

N-(2-(2-chlorophenyl)thiazolo[5,4-c]pyridin-4-yl)cyclopropanecarboxamide;

2-(2-chloro-6-fluorophenyl)-N-(6-methylpyrimidin-4-yl)thiazolo[5,4-c]pyridin-4-amine;

methyl 2-(2,6-dichlorophenyl)thiazolo[5,4-c]pyridin-4-ylcarbamate;

methyl 2-(2-chloro-6-fluorophenyl)thiazolo[5,4-c]pyridin-4-ylcarbamate;

N-(2-(2-chloro-6-fluorophenyl)thiazolo[5,4-c]pyridin-4-yl)-2-hydroxyacetamide;

2-(2,6-dichlorophenyl)-N-(6-methylpyrimidin-4-yl)thiazolo[5,4-c]pyridin-4-amine;

N-4-(2-(2-chloro-6-fluorophenyl)thiazolo[5,4-c]pyridin-4-yl)pyrimidine-4,6-diamine;

1-cyclopropyl-3-(2-(2,6-dichlorophenyl)thiazolo[5,4-c]pyridin-4-yl)urea;

2-(2-chlorophenyl)-N-(2,6-dimethylpyrimidin-4-yl)thiazolo[5,4-c]pyridin-4-amine;

1-(2-(2-chloro-6-fluorophenyl)thiazolo[5,4-c]pyridin-4-yl)-3-methylurea;

N-4-(2-(2,6-dichlorophenyl)thiazolo[5,4-c]pyridin-4-yl)-N6-methylpyrimidine-4,6-diamine;

N-4-(2-(2-chloro-6-fluorophenyl)thiazolo[5,4-c]pyridin-4-yl)-N6-methylpyrimidine-4,6-diamine;

2-(2,6-dichlorophenyl)-N-(6-((dimethylamino)methyl)pyrimidin-4-yl)thiazolo[5,4-c]pyridin-4-amine;

2-(2-chloro-6-fluorophenyl)-N-(6-((dimethylamino)methyl)pyrimidin-4-yl)thiazolo[5,4-c]pyridin-4-amine;

N-(2-(2-chloro-6-fluorophenyl)thiazolo[5,4-c]pyridin-4-yl)-2-(dimethylamino)acetamide;

6-(2-(2-chloro-6-fluorophenyl)thiazolo[5,4-c]pyridin-4-ylamino)pyrimidine-4-carbonitrile;

N-(6-(2-(2,6-dichlorophenyl)thiazolo[5,4-c]pyridin-4-ylamino)pyrimidin-4-yl)acetamide;

2-amino-N-(2-(2,6-dichlorophenyl)thiazolo[5,4-c]pyridin-4-yl)acetamide;

2-amino-N-(2-(2-chloro-6-fluorophenyl)thiazolo[5,4-c]pyridin-4-yl)acetamide;

2-(6-(2-(2,6-dichlorophenyl)thiazolo[5,4-c]pyridin-4-ylamino)pyrimidin-4-yl)propan-2-ol;

2-(6-(2-(2-chloro-6-fluorophenyl)thiazolo[5,4-c]pyridin-4-ylamino)pyrimidin-4-yl)propan-2-ol;

3-amino-N-(2-(2,6-dichlorophenyl)thiazolo[5,4-c]pyridin-4-yl)propanamide;

1-(2-(2,6-dichlorophenyl)thiazolo[5,4-c]pyridin-4-yl)-3-methylurea;

3-amino-N-(2-(2-chloro-6-fluorophenyl)thiazolo[5,4-c]pyridin-4-yl)propanamide;

6-(2-(2,6-dichlorophenyl)thiazolo[5,4-c]pyridin-4-ylamino)-N-methylpyrimidine-4-carboxamide;

(6-(2-(2,6-dichlorophenyl)thiazolo[5,4-c]pyridin-4-ylamino)pyrimidin-4-yl)(morpholino)methanone;

6-(2-(2-chloro-6-fluorophenyl)thiazolo[5,4-c]pyridin-4-ylamino)-N-methylpyrimidine-4-carboxamide;

(2-(2-(2-chloro-6-fluorophenyl)thiazolo[5,4-c]pyridin-4-ylamino)pyridin-4-yl)methanol;

2-(2,6-dichlorophenyl)-N-(4-methylpyridin-2-yl)thiazolo[5,4-c]pyridin-4-amine;

N-(4-(aminomethyl)pyrimidin-2-yl)-2-(2,6-dichlorophenyl)thiazolo[5,4-c]pyridin-4-amine;

N-(4-(aminomethyl)pyrimidin-2-yl)-2-(2-chloro-6-fluorophenyl)thiazolo[5,4-c]pyridin-4-amine;

6-[2-(2,6-Dichloro-4-cyano-phenyl)-thiazolo[5,4-c]pyridine-4-ylamino]-nicotinonitrile;

3,5-Dichloro-4-[4-(2,6-dimethyl-pyrimidin-4-ylamino)-thiazolo[5,4-c]pyridine-2-yl]-benzonitrile; Cyclopropanecarboxylic acid [2-(2,6-dichloro-4-cyano-phenyl)-thiazolo[5,4-c]pyridin-4-yl]-amide;

3,5-Dichloro-4-[4-(pyrimidin-4-ylamino)-thiazolo[5,4-c]pyridin-2-yl]-benzonitrile;

3,5-Dichloro-4-[4-(6-methyl-pyrimidin-4-ylamino)-thiazolo[5,4-c]pyridin-2-yl]-benzonitrile;

1-[2-(2,6-Dichloro-4-cyano-phenyl)-thiazolo[5,4-c]pyridine-4-yl]-3-methyl-urea;

3,5-Dichloro-4-[4-(6-morpholin-4-yl-pyrimidin-4-ylamino)-thiazolo[5,4-c]pyridine-2-yl]-benzonitrile;

3,5-Dichloro-4-(4-{6-[2-(2-hydroxy-ethyl)-piperazin-1-yl]-pyrimidin-4-ylamino}-thiazolo[5,4-c]pyridine-2-yl)-benzonitrile;

3,5-Dichloro-4-[4-(5-hydroxymethyl-pyrimidin-4-ylamino)-thiazolo[5,4-c]pyridine-2-yl}-benzonitrile;

3,5-Dichloro-4-[4-(4-hydroxymethyl-pyridin-2-ylamino)-thiazolo[5,4-c]pyridin-2-yl]-benzonitrile;

3,5-Dichloro-4-[4-(6-dimethylaminomethyl-pyrimidin-4-ylamino)-thiazolo[5,4-c]pyridin-2-yl]-benzonitrile;

6-[2-(2,6-Dichloro-4-cyano-phenyl)-thiazolo[5,4-c]pyridin-4-ylamino]-pyrimidine-4-carboxylic acid amide;

N-{6-[2-(2,6-Dichloro-4-cyano-phenyl)-thiazolo[5,4-c]pyridin-4-ylamino]-pyrimidin-4-yl}-acetamide;

3,5-Dichloro-4-[4-(5-hydroxymethyl-pyridin-2-ylamino)-thiazolo[5,4-c]pyridin-2-yl]-benzonitrile;

3,5-Dichloro-4-[4-(6-methoxy-pyrimidin-4-ylamino)-thiazolo[5,4-c]pyridin-2-yl]-benzonitrile;

3,5-Dichloro-4-[4-(5-methyl-pyrazin-2-ylamino)-thiazolo[5,4-c]pyridin-2-yl]-benzonitrile;

3,5-Dichloro-4-[4-(6-methyl-pyridazin-3-ylamino)-thiazolo[5,4-c]pyridin-2-yl]-benzonitrile;

[2-(2,6-Dichloro-4-cyano-phenyl)-thiazolo[5,4-c]pyridin-4-yl]-carbamic acid methyl ester;

3,5-Dichloro-4-[4-(6-methylamino-pyrimidin-4-ylamino)-thiazolo[5,4-c]pyridin-2-yl]-benzonitrile;

4-[4-(6-Amino-pyrimidin-4-ylamino)-thiazolo[5,4-c]pyridin-2-yl]-3,5-dichloro-benzonitrile;

3,5-Dichloro-4-{4-[6-(2-hydroxy-2-methyl-propylamino)-pyrimidin-4-ylamino]-thiazolo[5,4-c]pyridin-2-yl}-benzonitrile;

3-Chloro-4-[4-(2,6-dimethyl-pyrimidin-4-ylamino)-thiazolo[5,4-c]pyridin-2-yl]-5-fluoro-benzonitrile;

1-[2-(2-Chloro-4-cyano-6-fluoro-phenyl)-thiazolo[5,4-c]pyridin-4-yl]-3-methyl-urea;

2-(2,6-dichlorophenyl)-N-(pyrimidin-4-yl)thiazolo[4,5-d]pyrimidin-7-amine;

2-(2,6-dichlorophenyl)-N-(2,6-dimethylpyrimidin-4-yl)thiazolo[4,5-d]pyrimidin-7-amine;

[2-(2,6-dichlorophenyl)-N-(6-methylpyrimidin-4-yl)thiazolo[4,5-d]pyrimidin-7-amine;

2-(4-(6-(2-(2,6-dichlorophenyl)thiazolo[4,5-d]pyrimidin-7-ylamino)pyrimidin-4-yl)piperazin-1-yl)ethanol;

3-Chloro-5-fluoro-4-[4-(6-hydroxymethyl-pyrimidin-4-ylamino)-thiazolo[5,4-c]pyridin-2-yl]-benzonitrile;

(6-(2-(2-chloro-6-fluorophenyl)thiazolo[5,4-c]pyridin-4-ylamino)pyrimidin-4-yl)(morpholino)methanone;

2-(2-chloro-6-fluorophenyl)-N-(pyridin-2-yl)thiazolo[5,4-c]pyridin-4-amine;

2-(2-chloro-6-fluorophenyl)-N-(4-methylpyridin-2-yl)thiazolo[5,4-c]pyridin-4-amine;

2-(2,6-dichlorophenyl)-N-(pyridazin-3-yl)thiazolo[5,4-c]pyridin-4-amine;

6-(2-(2,6-dichlorophenyl)thiazolo[5,4-c]pyridin-4-ylamino) pyrimidine-4-carboxamide;

2-(2-chloro-6-fluorophenyl)-N-(pyridazin-3-yl)thiazolo[5,4-c]pyridin-4-amine;

2-(2-(2,6-dichlorophenyl)thiazolo[5,4-c]pyridin-4-ylamino) isonicotinonitrile;

6-(2-(2,6-dichlorophenyl)thiazolo[5,4-c]pyridin-4-ylamino) pyridazine-3-carboxamide;

(6-(2-(2,6-dichlorophenyl)thiazolo[5,4-c]pyridin-4-ylamino)pyridazin-3-yl)(morpholino)methanone;

(6-(2-(2-chloro-6-fluorophenyl)thiazolo[5,4-c]pyridin-4-ylamino)pyridazin-3-yl)(morpholino)methanone;

6-(2-(2,6-dichlorophenyl)thiazolo[5,4-c]pyridin-4-ylamino)-N,N-dimethylpyridazine-3-carboxamide;

6-(2-(2-chloro-6-fluorophenyl)thiazolo[5,4-c]pyridin-4-ylamino)-N,N-dimethylpyridazine-3-carboxamide;

2-(2,6-dichlorophenyl)-N-(pyrazin-2-yl)thiazolo[5,4-c]pyridin-4-amine;

2-(2-(2,6-dichlorophenyl)thiazolo[5,4-c]pyridin-4-ylamino) isonicotinamide;

6-(2-(2-chloro-6-fluorophenyl)thiazolo[5,4-c]pyridin-4-ylamino)pyridazine-3-carboxamide;

N-(6-(aminomethyl)pyrimidin-4-yl)-2-(2-chloro-6-fluorophenyl)thiazolo[5,4-c]pyridin-4-amine;

2-(2-chloro-6-fluorophenyl)-N-(pyrazin-2-yl)thiazolo[5,4-c]pyridin-4-amine;

5-(2-(2,6-dichlorophenyl)thiazolo[5,4-c]pyridin-4-ylamino) pyrazine-2-carboxamide; isopropyl 2-(2,6-dichlorophenyl)thiazolo[5,4-c]pyridin-4-ylcarbamate; and 1-(2-(2,6-dichlorophenyl)thiazolo[5,4-c]pyridin-4-yl)-3-(2-hydroxyethyl)urea.

Another embodiment includes a compound of Formula I, stereoisomers or pharmaceutically acceptable salts thereof, selected from:

2-(2,6-Dichlorophenyl)-N-(6-methyl-2-morpholinopyrimidin-4-yl)thiazolo[5,4-c]pyridin-4-amine;

2-(2,6-Dichlorophenyl)-N-(2,6-dimethylpyrimidin-4-yl) thiazolo[5,4-c]pyridin-4-amine;

N-(2-(2,6-Dichlorophenyl)thiazolo[5,4-c]pyridin-4-yl)cyclopropanecarboxamide;

N-(6-(aminomethyl)pyrimidin-4-yl)-2-(2,6-dichlorophenyl) thiazolo[5,4-c]pyridin-4-amine;

4-[4-(2-Amino-6-methyl-pyrimidin-4-ylamino)-thiazolo[5,4-c]pyridin-2-yl]-3,5-dichloro-benzonitrile;

3-(6-(2-(2,6-dichlorophenyl)thiazolo[4,5-d]pyrimidin-7-ylamino)pyrimidin-4-yl)cyclobutanol;

N-(2-(2,6-dichlorophenyl)thiazolo[4,5-d]pyrimidin-7-yl)cyclopropanecarboxamide;

3-Chloro-5-fluoro-4-[4-(6-methyl-pyrimidin-4-ylamino)-thiazolo[5,4-c]pyridin-2-yl]-benzonitrile;

{3,5-Dichloro-4-[4-(6-methyl-pyrimidin-4-ylamino)-thiazolo[5,4-c]pyridin-2-yl]-phenyl}-methanol;

3,5-Dichloro-4-{4-[6-(2-hydroxy-ethylamino)-pyrimidin-4-ylamino]-thiazolo[5,4-c]pyridin-2-yl}-benzonitrile;

3,5-Dichloro-4-{4-[5-(3-hydroxy-azetidin-1-yl)-pyrimidin-4-ylamino]-thiazolo[5,4-c]pyridine-2-yl}-benzonitrile;

2-[2-(2,6-Dichloro-4-cyano-phenyl)-thiazolo[5,4-c]pyridine-4-ylamino]-isonicotinonitrile;

(2-(2-(2,6-dichlorophenyl)thiazolo[5,4-c]pyridin-4-ylamino)pyridin-4-yl)methanol;

N-(6-(2-(2-Chloro-6-fluorophenyl)thiazolo[5,4-c]pyridin-4-ylamino)pyrimidin-4-yl)acetamide;

1-(2-(2-Chloro-6-fluorophenyl)thiazolo[5,4-c]pyridin-4-yl)-3-cyclopropylurea;

1-(6-(2-(2-Chloro-6-fluorophenyl)thiazolo[5,4-c]pyridin-4-ylamino)pyrimidin-4-yl)ethane-1,2-diol;

2-(2-Chloro-6-fluorophenyl)-N-(2-methyl-6-morpholinopyrimidin-4-yl)thiazolo[5,4-c]pyridin-4-amine;

N-(2-(2-Chloro-6-fluorophenyl)thiazolo[5,4-c]pyridin-4-yl) cyclopropanecarboxamide;

6-(2-(2,6-Dichlorophenyl)thiazolo[5,4-c]pyridin-4-ylamino)pyrimidine-4-carbonitrile;

N-(2-(2,6-Dichlorophenyl)thiazolo[5,4-c]pyridin-4-yl)-2-(dimethylamino)acetamide;

N-(2-(2,6-Dichlorophenyl)thiazolo[5,4-c]pyridin-4-yl)-2-hydroxyacetamide;

2-(2,6-Dichlorophenyl)thiazolo[5,4-c]pyridin-4-ylcarbamate;

(6-(2-(2,6-Dichlorophenyl)thiazolo[5,4-c]pyridin-4-ylamino)pyrimidin-4-yl)methanol;

2-(4-(6-(2-(2,6-Dichlorophenyl)thiazolo[5,4-c]pyridin-4-ylamino)-2-methylpyrimidin-4-yl)piperazin-1-yl)ethanol;

2-(2,6-Dichlorophenyl)-N-(1H-pyrazol-4-yl)thiazolo[5,4-c] pyridin-4-amine;

N-(2-(2,6-Dichlorophenyl)thiazolo[5,4-c]pyridin-4-yl)acetamide;

2-(2,6-dichlorophenyl)-N-(2-methyl-6-morpholinopyrimidin-4-yl)thiazolo[5,4-c]pyridin-4-amine;

2-(2,6-dichlorophenyl)-N-(6-morpholinopyrimidin-4-yl) thiazolo[5,4-c]pyridin-4-amine;

2-(4-(6-(2-(2,6-dichlorophenyl)thiazolo[5,4-c]pyridin-4-ylamino)pyrimidin-4-yl)piperazin-1-yl)ethanol;

1-(6-(2-(2,6-dichlorophenyl)thiazolo[5,4-c]pyridin-4-ylamino)pyrimidin-4-yl)azetidin-3-ol;

2-((6-(2-(2,6-dichlorophenyl)thiazolo[5,4-c]pyridin-4-ylamino)pyrimidin-4-yl)(methyl)amino)ethanol;

2,2'-(6-(2-(2,6-dichlorophenyl)thiazolo[5,4-c]pyridin-4-ylamino)pyrimidin-4-ylazanediyl)diethanol;

2-(2,6-dichlorophenyl)-N-(pyridin-2-yl)thiazolo[5,4-c]pyridin-4-amine;

2-(2,6-dichlorophenyl)-N-(pyrimidin-4-yl)thiazolo[5,4-c] pyridin-4-amine;

2-(6-(2-(2,6-dichlorophenyl)thiazolo[5,4-c]pyridin-4-ylamino)pyrimidin-4-ylamino)ethanol;

N-4-(2-(2,6-dichlorophenyl)thiazolo[5,4-c]pyridin-4-yl)pyrimidine-4,6-diamine;

2-(2-chloro-6-fluorophenyl)-N-(2,6-dimethylpyrimidin-4-yl)thiazolo[5,4-c]pyridin-4-amine;

2-(2-chloro-6-fluorophenyl)-N-(6-methyl-2-morpholinopyrimidin-4-yl)thiazolo[5,4-c]pyridin-4-amine;

2-(2-chloro-6-fluorophenyl)-N-(6-morpholinopyrimidin-4-yl)thiazolo[5,4-c]pyridin-4-amine;

2-(4-(6-(2-(2-chloro-6-fluorophenyl)thiazolo[5,4-c]pyridin-4-ylamino)-2-methylpyrimidin-4-yl)piperazin-1-yl)ethanol;

2-(4-(6-(2-(2-chloro-6-fluorophenyl)thiazolo[5,4-c]pyridin-4-ylamino)pyrimidin-4-yl)piperazin-1-yl)ethanol;

2-((6-(2-(2-chloro-6-fluorophenyl)thiazolo[5,4-c]pyridin-4-ylamino)pyrimidin-4-yl)(methyl)amino)ethanol;

2,2'-(6-(2-(2-chloro-6-fluorophenyl)thiazolo[5,4-c]pyridin-4-ylamino)pyrimidin-4-ylazanediyl)diethanol;

(6-(2-(2-chloro-6-fluorophenyl)thiazolo[5,4-c]pyridin-4-ylamino)pyrimidin-4-yl)methanol;

1-(6-(2-(2,6-dichlorophenyl)thiazolo[5,4-c]pyridin-4-ylamino)pyrimidin-4-yl)ethane-1,2-diol;

2-(6-(2-(2-chloro-6-fluorophenyl)thiazolo[5,4-c]pyridin-4-ylamino)pyrimidin-4-ylamino)ethanol;

N-(2-(2-chlorophenyl)thiazolo[5,4-c]pyridin-4-yl)cyclopropanecarboxamide;

2-chloro-6-fluorophenyl)-N-(6-methylpyrimidin-4-yl) thiazolo[5,4-c]pyridin-4-amine;

methyl 2-(2,6-dichlorophenyl)thiazolo[5,4-c]pyridin-4-ylcarbamate;

methyl 2-(2-chloro-6-fluorophenyl)thiazolo[5,4-c]pyridin-4-ylcarbamate;
N-(2-(2-chloro-6-fluorophenyl)thiazolo[5,4-c]pyridin-4-yl)-2-hydroxyacetamide;
2-(2,6-dichlorophenyl)-N-(6-methylpyrimidin-4-yl)thiazolo[5,4-c]pyridin-4-amine;
N-4-(2-(2-chloro-6-fluorophenyl)thiazolo[5,4-c]pyridin-4-yl)pyrimidine-4,6-diamine;
1-cyclopropyl-3-(2-(2,6-dichlorophenyl)thiazolo[5,4-c]pyridin-4-yl)urea;
2-(2-chlorophenyl)-N-(2,6-dimethylpyrimidin-4-yl)thiazolo[5,4-c]pyridin-4-amine;
1-(2-(2-chloro-6-fluorophenyl)thiazolo[5,4-c]pyridin-4-yl)-3-methylurea;
N-4-(2-(2,6-dichlorophenyl)thiazolo[5,4-c]pyridin-4-yl)-N6-methylpyrimidine-4,6-diamine;
N-4-(2-(2-chloro-6-fluorophenyl)thiazolo[5,4-c]pyridin-4-yl)-N6-methylpyrimidine-4,6-diamine;
2-(2,6-dichlorophenyl)-N-(6-((dimethylamino)methyl)pyrimidin-4-yl)thiazolo[5,4-c]pyridin-4-amine;
2-(2-chloro-6-fluorophenyl)-N-(6-((dimethylamino)methyl)pyrimidin-4-yl)thiazolo[5,4-c]pyridin-4-amine;
N-(2-(2-chloro-6-fluorophenyl)thiazolo[5,4-c]pyridin-4-yl)-2-(dimethylamino)acetamide;
6-(2-(2-chloro-6-fluorophenyl)thiazolo[5,4-c]pyridin-4-ylamino)pyrimidine-4-carbonitrile;
N-(6-(2-(2,6-dichlorophenyl)thiazolo[5,4-c]pyridin-4-ylamino)pyrimidin-4-yl)acetamide;
2-amino-N-(2-(2,6-dichlorophenyl)thiazolo[5,4-c]pyridin-4-yl)acetamide;
2-amino-N-(2-(2-chloro-6-fluorophenyl)thiazolo[5,4-c]pyridin-4-yl)acetamide;
2-(6-(2-(2,6-dichlorophenyl)thiazolo[5,4-c]pyridin-4-ylamino)pyrimidin-4-yl)propan-2-ol;
2-(6-(2-(2-chloro-6-fluorophenyl)thiazolo[5,4-c]pyridin-4-ylamino)pyrimidin-4-yl)propan-2-ol;
3-amino-N-(2-(2,6-dichlorophenyl)thiazolo[5,4-c]pyridin-4-yl)propanamide;
1-(2-(2,6-dichlorophenyl)thiazolo[5,4-c]pyridin-4-yl)-3-methylurea;
3-amino-N-(2-(2-chloro-6-fluorophenyl)thiazolo[5,4-c]pyridin-4-yl)propanamide;
6-(2-(2,6-dichlorophenyl)thiazolo[5,4-c]pyridin-4-ylamino)-N-methylpyrimidine-4-carboxamide;
(6-(2-(2,6-dichlorophenyl)thiazolo[5,4-c]pyridin-4-ylamino)pyrimidin-4-yl)(morpholino)methanone;
6-(2-(2-chloro-6-fluorophenyl)thiazolo[5,4-c]pyridin-4-ylamino)-N-methylpyrimidine-4-carboxamide;
(2-(2-(2-chloro-6-fluorophenyl)thiazolo[5,4-c]pyridin-4-ylamino)pyridin-4-yl)methanol;
2-(2,6-dichlorophenyl)-N-(4-methylpyridin-2-yl)thiazolo[5,4-c]pyridin-4-amine;
N-(4-(aminomethyl)pyrimidin-2-yl)-2-(2,6-dichlorophenyl)thiazolo[5,4-c]pyridin-4-amine;
N-(4-(aminomethyl)pyrimidin-2-yl)-2-(2-chloro-6-fluorophenyl)thiazolo[5,4-c]pyridin-4-amine;
6-[2-(2,6-Dichloro-4-cyano-phenyl)-thiazolo[5,4-c]pyridine-4-ylamino]-nicotinonitrile;
3,5-Dichloro-4-[4-(2,6-dimethyl-pyrimidin-4-ylamino)-thiazolo[5,4-c]pyridine-2-yl]-benzonitrile;
Cyclopropanecarboxylic acid [2-(2,6-dichloro-4-cyano-phenyl)-thiazolo[5,4-c]pyridin-4-yl]-amide;
3,5-Dichloro-4-[4-(pyrimidin-4-ylamino)-thiazolo[5,4-c]pyridin-2-yl]-benzonitrile;
3,5-Dichloro-4-[4-(6-methyl-pyrimidin-4-ylamino)-thiazolo[5,4-c]pyridin-2-yl]-benzonitrile;
1-[2-(2,6-Dichloro-4-cyano-phenyl)-thiazolo[5,4-c]pyridine-4-yl]-3-methyl-urea;
3,5-Dichloro-4-[4-(6-morpholin-4-yl-pyrimidin-4-ylamino)-thiazolo[5,4-c]pyridine-2-yl]-benzonitrile;
3,5-Dichloro-4-(4-{6-[2-(2-hydroxy-ethyl)-piperazin-1-yl]-pyrimidin-4-ylamino}-thiazolo[5,4-c]pyridine-2-yl)-benzonitrile;
3,5-Dichloro-4-[4-(5-hydroxymethyl-pyrimidin-4-ylamino)-thiazolo[5,4-c]pyridine-2-yl}-benzonitrile;
3,5-Dichloro-4-[4-(4-hydroxymethyl-pyridin-2-ylamino)-thiazolo[5,4-c]pyridin-2-yl]-benzonitrile;
3,5-Dichloro-4-[4-(6-dimethylaminomethyl-pyrimidin-4-ylamino)-thiazolo[5,4-c]pyridin-2-yl]-benzonitrile;
6-[2-(2,6-Dichloro-4-cyano-phenyl)-thiazolo[5,4-c]pyridin-4-ylamino]-pyrimidine-4-carboxylic acid amide;
N-{6-[2-(2,6-Dichloro-4-cyano-phenyl)-thiazolo[5,4-c]pyridin-4-ylamino]-pyrimidin-4-yl}-acetamide;
3,5-Dichloro-4-[4-(5-hydroxymethyl-pyridin-2-ylamino)-thiazolo[5,4-c]pyridin-2-yl]-benzonitrile;
3,5-Dichloro-4-[4-(6-methoxy-pyrimidin-4-ylamino)-thiazolo[5,4-c]pyridin-2-yl]-benzonitrile;
3,5-Dichloro-4-[4-(5-methyl-pyrazin-2-ylamino)-thiazolo[5,4-c]pyridin-2-yl]-benzonitrile;
3,5-Dichloro-4-[4-(6-methyl-pyridazin-3-ylamino)-thiazolo[5,4-c]pyridin-2-yl]-benzonitrile;
[2-(2,6-Dichloro-4-cyano-phenyl)-thiazolo[5,4-c]pyridin-4-yl]-carbamic acid methyl ester;
3,5-Dichloro-4-[4-(6-methylamino-pyrimidin-4-ylamino)-thiazolo[5,4-c]pyridin-2-yl]-benzonitrile;
4-[4-(6-Amino-pyrimidin-4-ylamino)-thiazolo[5,4-c]pyridin-2-yl]-3,5-dichloro-benzonitrile;
3,5-Dichloro-4-{4-[6-(2-hydroxy-2-methyl-propylamino)-pyrimidin-4-ylamino]-thiazolo[5,4-c]pyridin-2-yl}-benzonitrile;
3-Chloro-4-[4-(2,6-dimethyl-pyrimidin-4-ylamino)-thiazolo[5,4-c]pyridin-2-yl]-5-fluoro-benzonitrile;
1-[2-(2-Chloro-4-cyano-6-fluoro-phenyl)-thiazolo[5,4-c]pyridin-4-yl]-3-methyl-urea;
2-(2,6-dichlorophenyl)-N-(pyrimidin-4-yl)thiazolo[4,5-d]pyrimidin-7-amine;
2-(2,6-dichlorophenyl)-N-(2,6-dimethylpyrimidin-4-yl)thiazolo[4,5-d]pyrimidin-7-amine;
[2-(2,6-dichlorophenyl)-N-(6-methylpyrimidin-4-yl)thiazolo[4,5-d]pyrimidin-7-amine;
2-(4-(6-(2-(2,6-dichlorophenyl)thiazolo[4,5-d]pyrimidin-7-ylamino)pyrimidin-4-yl)piperazin-1-yl)ethanol;
3-Chloro-5-fluoro-4-[4-(6-hydroxymethyl-pyrimidin-4-ylamino)-thiazolo[5,4-c]pyridin-2-yl]-benzonitrile;
(6-(2-(2-chloro-6-fluorophenyl)thiazolo[5,4-c]pyridin-4-ylamino)pyrimidin-4-yl)(morpholino)methanone;
2-(2-chloro-6-fluorophenyl)-N-(pyridin-2-yl)thiazolo[5,4-c]pyridin-4-amine;
2-(2-chloro-6-fluorophenyl)-N-(4-methylpyridin-2-yl)thiazolo[5,4-c]pyridin-4-amine;
2-(2,6-dichlorophenyl)-N-(pyridazin-3-yl)thiazolo[5,4-c]pyridin-4-amine;
6-(2-(2,6-dichlorophenyl)thiazolo[5,4-c]pyridin-4-ylamino)pyrimidine-4-carboxamide;
2-(2-chloro-6-fluorophenyl)-N-(pyridazin-3-yl)thiazolo[5,4-c]pyridin-4-amine;
2-(2-(2,6-dichlorophenyl)thiazolo[5,4-c]pyridin-4-ylamino)isonicotinonitrile;
6-(2-(2,6-dichlorophenyl)thiazolo[5,4-c]pyridin-4-ylamino)pyridazine-3-carboxamide;
(6-(2-(2,6-dichlorophenyl)thiazolo[5,4-c]pyridin-4-ylamino)pyridazin-3-yl)(morpholino)methanone;

(6-(2-(2-chloro-6-fluorophenyl)thiazolo[5,4-c]pyridin-4-ylamino)pyridazin-3-yl)(morpholino)methanone;
6-(2-(2,6-dichlorophenyl)thiazolo[5,4-c]pyridin-4-ylamino)-N,N-dimethylpyridazine-3-carboxamide;
6-(2-(2-chloro-6-fluorophenyl)thiazolo[5,4-c]pyridin-4-ylamino)-N,N-dimethylpyridazine-3-carboxamide;
2-(2,6-dichlorophenyl)-N-(pyrazin-2-yl)thiazolo[5,4-c]pyridin-4-amine;
2-(2-(2,6-dichlorophenyl)thiazolo[5,4-c]pyridin-4-ylamino)isonicotinamide;
6-(2-(2-chloro-6-fluorophenyl)thiazolo[5,4-c]pyridin-4-ylamino)pyridazine-3-carboxamide;
N-(6-(aminomethyl)pyrimidin-4-yl)-2-(2-chloro-6-fluorophenyl)thiazolo[5,4-c]pyridin-4-amine;
2-(2-chloro-6-fluorophenyl)-N-(pyrazin-2-yl)thiazolo[5,4-c]pyridin-4-amine;
5-(2-(2,6-dichlorophenyl)thiazolo[5,4-c]pyridin-4-ylamino)pyrazine-2-carboxamide;
isopropyl 2-(2,6-dichlorophenyl)thiazolo[5,4-c]pyridin-4-ylcarbamate;
1-(2-(2,6-dichlorophenyl)thiazolo[5,4-c]pyridin-4-yl)-3-(2-hydroxyethyl)urea;
4-[4-(6-Amino-2-methylpyrimidin-4-ylamino)thiazolo[5,4-c]pyridin-2-yl]-3,5-dichloro-benzonitrile;
3,5-Dichloro-4-[4-(6-ethylpyrimidin-4-ylamino)thiazolo[5,4-c]pyridin-2-yl]-benzonitrile;
3,5-Dichloro-4-[4-(6-ethylpyrimidin-4-ylamino)thiazolo[5,4-c]pyridin-2-yl]-benzamide;
4-[4-(6-Aminopyrimidin-4-ylamino)thiazolo[5,4-c]pyridin-2-yl]-3-chloro-5-fluorobenzonitrile;
N-[2-(4-Amino-2,6-dichlorophenyl)thiazolo[5,4-c]pyridin-4-yl]-pyrimidine-4,6-diamine;
[2-(4-Amino-2,6-dichlorophenyl)thiazolo[5,4-c]pyridin-4-yl]-(6-methylpyrimidin-4-yl)-amine;
{4-[4-(6-Aminopyrimidin-4-ylamino)thiazolo[5,4-c]pyridin-2-yl]-3,5-dichlorophenyl}-methanol;
N-[2-(4-Aminomethyl-2,6-dichlorophenyl)thiazolo[5,4-c]pyridin-4-yl]-pyrimidine-4,6-diamine;
[2-(4-Aminomethyl-2,6-dichlorophenyl)thiazolo[5,4-c]pyridin-4-yl]-(6-methylpyrimidin-4-yl)-amine;
[2-(2,6-Dichloro-4-methoxyphenyl)thiazolo[5,4-c]pyridin-4-yl]-(6-methylpyrimidin-4-yl)-amine;
[2-(4-Azetidin-3-yl-2,6-dichlorophenyl)thiazolo[5,4-c]pyridin-4-yl]-(6-methylpyrimidin-4-yl)-amine;
[2-(2,6-Dichloro-4-cyclopropylphenyl)thiazolo[5,4-c]pyridin-4-yl]-(6-methylpyrimidin-4-yl)-amine;
1-{3,5-Dichloro-4-[4-(6-methylpyrimidin-4-ylamino)thiazolo[5,4-c]pyridin-2-yl]-phenyl}-acetamide;
[2-(2-Chloro-6-fluorophenyl)-7-fluorothiazolo[5,4-c]pyridin-4-yl]-(6-methylpyrimidin-4-yl)-amine;
N-[2-(2-Chloro-6-fluorophenyl)-7-fluorothiazolo[5,4-c]pyridin-4-yl]-pyrimidine-4,6-diamine;
[2-(2,6-Dichlorophenyl)-7-fluorothiazolo[5,4-c]pyridin-4-yl]-(6-methylpyrimidin-4-yl)-amine;
[2-(2,6-Dichlorophenyl)-7-fluorothiazolo[5,4-c]pyridin-4-yl]-carbamic acid methyl ester;
3,5-Dichloro-4-[7-fluoro-4-(6-methylpyrimidin-4-ylamino)thiazolo[5,4-c]pyridin-2-yl]-benzonitrile;
2-[4-(6-Aminopyrimidin-4-ylamino)thiazolo[5,4-c]pyridin-2-yl]-3-chlorobenzonitrile;
3-Chloro-2-[4-(6-hydroxymethylpyrimidin-4-ylamino)thiazolo[5,4-c]pyridin-2-yl]-benzonitrile;
2-[4-(6-Amino-2-methylpyrimidin-4-ylamino)-thiazolo[5,4-c]pyridin-2-yl]-3-chlorobenzonitrile;
3-Chloro-2-[7-fluoro-4-(6-methylpyrimidin-4-ylamino)thiazolo[5,4-c]pyridin-2-yl]-benzonitrile;
3-Chloro-2-[7-fluoro-4-(6-hydroxymethyl-pyrimidin-4-ylamino)-thiazolo[5,4-c]pyridin-2-yl]-benzonitrile;
3-Fluoro-2-[7-fluoro-4-(6-methylpyrimidin-4-ylamino)-thiazolo[5,4-c]pyridin-2-yl]-benzonitrile;
7-bromo-2-(2-chloro-6-fluorophenyl)-N-(6-methylpyrimidin-4-yl)thiazolo[5,4-c]pyridin-4-amine;
2-(2-chloro-6-fluorophenyl)-4-(6-methylpyrimidin-4-ylamino)thiazolo[5,4-c]pyridine-7-carbonitrile;
2-(2-cyano-6-fluorophenyl)-4-(6-methylpyrimidin-4-ylamino)thiazolo[5,4-c]pyridine-7-carbonitrile;
(2-(2-chloro-6-fluorophenyl)-4-(6-methylpyrimidin-4-ylamino)thiazolo[5,4-c]pyridin-7-yl)methanol;
(1S,2S)—N-(2-(2,6-dichlorophenyl)thiazolo[5,4-c]pyridin-4-yl)-2-fluorocyclopropanecarboxamide;
(1R,2R)—N-(2-(2,6-dichlorophenyl)thiazolo[5,4-c]pyridin-4-yl)-2-fluoro-cyclopropane-carboxamide;
(1R,2S)—N-(2-(2,6-dichlorophenyl)thiazolo[5,4-c]pyridin-4-yl)-2-(hydroxymethyl)cyclopropane-carboxamide;
(1S,2R)—N-(2-(2,6-dichlorophenyl)thiazolo[5,4-c]pyridin-4-yl)-2-(hydroxymethyl)cyclopropane-carboxamide;
2-(4-amino-2-chloro-6-fluorophenyl)-N-(6-methylpyrimidin-4-yl)thiazolo[5,4-c]pyridin-4-amine;
Cyclopropylmethyl 2-(2,6-dichlorophenyl)thiazolo[5,4-c]pyridin-4-ylcarbamate;
2-(2,6-Dichlorophenyl)-N-(5-methylpyrazin-2-yl)thiazolo[5,4-c]pyridin-4-amine;
2-(2-Chloro-6-fluorophenyl)-N-(5-methylpyrazin-2-yl)thiazolo[5,4-c]pyridin-4-amine;
5-(2-(2,6-Dichlorophenyl)thiazolo[5,4-c]pyridin-4-ylamino)pyrazine-2-carbonitrile;
(5-(2-(2,6-Dichlorophenyl)thiazolo[5,4-c]pyridin-4-ylamino)pyrazin-2-yl)methanol;
2-(2,6-Dichlorophenyl)-N-(6-methylpyrimidin-4-yl)thiazolo[5,4-c]pyridin-4-amine;
Cyclopropylmethyl 2-(2-chloro-6-fluorophenyl)thiazolo[5,4-c]pyridin-4-ylcarbamate;
2-(2,6-Dichlorophenyl)-N-(6-(morpholinomethyl)pyrimidin-4-yl)thiazolo[5,4-c]pyridin-4-amine;
2-(2-Chloro-6-fluorophenyl)-N-(6-(morpholinomethyl)pyrimidin-4-yl)thiazolo[5,4-c]pyridin-4-amine;
(R)-1-(6-(2-(2-Chloro-6-fluorophenyl)thiazolo[5,4-c]pyridin-4-ylamino)pyrimidin-4-yl)ethanol;
(S)-1-(6-(2-(2-Chloro-6-fluorophenyl)thiazolo[5,4-c]pyridin-4-ylamino)pyrimidin-4-yl)ethanol;
(R)-1-(6-(2-(2,6-Dichlorophenyl)thiazolo[5,4-c]pyridin-4-ylamino)pyrimidin-4-yl)ethanol;
(S)-1-(6-(2-(2,6-Dichlorophenyl)thiazolo[5,4-c]pyridin-4-ylamino)pyrimidin-4-yl)ethanol;
(R)—N-(6-(1-Aminoethyl)pyrimidin-4-yl)-2-(2,6-dichlorophenyl)thiazolo[5,4-c]pyridin-4-amine;
(S)—N-(6-(1-Aminoethyl)pyrimidin-4-yl)-2-(2,6-dichlorophenyl)thiazolo[5,4-c]pyridin-4-amine;
5-(2-(2-Chloro-6-fluorophenyl)thiazolo[5,4-c]pyridin-4-ylamino)pyrazine-2-carbonitrile;
N-(5-(Aminomethyl)pyrazin-2-yl)-2-(2,6-dichlorophenyl)thiazolo[5,4-c]pyridin-4-amine;
2-(2,6-Dichlorophenyl)-N-(5-((methylamino)methyl)pyrazin-2-yl)thiazolo[5,4-c]pyridin-4-amine;
(5-(2-(2-Chloro-6-fluorophenyl)thiazolo[5,4-c]pyridin-4-ylamino)pyrazin-2-yl)methanol;
N-(5-(Aminomethyl)pyrazin-2-yl)-2-(2-chloro-6-fluorophenyl)thiazolo[5,4-c]pyridin-4-amine;
2-(2-Chloro-6-fluorophenyl)-N-(5-((methylamino)methyl)pyrazin-2-yl)thiazolo[5,4-c]pyridin-4-amine;
6-(2-(2,6-Dichlorophenyl)thiazolo[5,4-c]pyridin-4-ylamino)-N-methylpyridazine-3-carboxamide;

Ethyl 2-(2,6-dichlorophenyl)thiazolo[5,4-c]pyridin-4-ylcarbamate;
Ethyl 2-(2-chloro-6-fluorophenyl)thiazolo[5,4-c]pyridin-4-ylcarbamate;
Isopropyl 2-(2-chloro-6-fluorophenyl)thiazolo[5,4-c]pyridin-4-ylcarbamate;
1-(2-(2-Chloro-6-fluorophenyl)thiazolo[5,4-c]pyridin-4-yl)-3-(2-hydroxyethyl)urea;
N2-(2-(2,6-Dichlorophenyl)thiazolo[5,4-c]pyridin-4-yl)pyrazine-2,5-diamine;
N2-(2-(2-Chloro-6-fluorophenyl)thiazolo[5,4-c]pyridin-4-yl)pyrazine-2,5-diamine;
2-Cyano-N-(2-(2,6-dichlorophenyl)thiazolo[5,4-c]pyridin-4-yl)acetamide;
N-(2-(2-Chloro-6-fluorophenyl)thiazolo[5,4-c]pyridin-4-yl)-2-cyanoacetamide;
N-(6-Cyclopropylpyrimidin-4-yl)-2-(2,6-dichlorophenyl)thiazolo[5,4-c]pyridin-4-amine;
2-(2,6-Dichlorophenyl)-N-(5-ethylpyrazin-2-yl)thiazolo[5,4-c]pyridin-4-amine;
4-[(5-{[2-(2-Chloro-6-fluorophenyl)-[1,3]thiazolo[5,4-c]pyridin-4-yl]amino}pyrazin-2-yl)methyl]-1λ6,4-thiomorpholine-1,1-dione;
2-(2,6-Dichlorophenyl)-N-(5-methylpyridin-2-yl)thiazolo[5,4-c]pyridin-4-amine;
2-(2,6-Dichlorophenyl)-N-(5-ethylpyridin-2-yl)thiazolo[5,4-c]pyridin-4-amine;
2-(2-Chloro-6-fluorophenyl)-N-(5-ethylpyrazin-2-yl)thiazolo[5,4-c]pyridin-4-amine;
2-(2-Chloro-6-fluorophenyl)-N-(5-(morpholinomethyl)pyrazin-2-yl)thiazolo[5,4-c]pyridin-4-amine;
N-(6-(1-Aminoethyl)pyrimidin-4-yl)-2-(2-chloro-6-fluorophenyl)thiazolo[5,4-c]pyridin-4-amine;
3-Fluoro-2-(4-(6-methylpyrimidin-4-ylamino)thiazolo[5,4-c]pyridin-2-yl)benzonitrile;
2-(4-(6-Aminopyrimidin-4-ylamino)thiazolo[5,4-c]pyridin-2-yl)-3-fluorobenzonitrile;
3-Fluoro-2-(4-(6-(hydroxymethyl)pyrimidin-4-ylamino)thiazolo[5,4-c]pyridin-2-yl)benzonitrile;
3-Fluoro-2-(4-(6-(methylamino)pyrimidin-4-ylamino)thiazolo[5,4-c]pyridin-2-yl)benzonitrile;
N-(2-(2-Cyano-6-fluorophenyl)thiazolo[5,4-c]pyridin-4-yl)cyclopropanecarboxamide;
(1S,2R)—N-(2-(2,6-Dichlorophenyl)thiazolo[5,4-c]pyridin-4-yl)-2-fluorocyclopropanecarboxamide;
(1R,2S)—N-(2-(2,6-Dichlorophenyl)thiazolo[5,4-c]pyridin-4-yl)-2-fluorocyclopropanecarboxamide;
N-[2-(4-Aminomethyl-2,6-dichlorophenyl)-thiazolo[5,4-c]pyridin-4-yl]-2-methylpyrimidine-4,6-diamine;
Cyclopropanecarboxylic acid [2-(4-amino-2,6-dichlorophenyl)-thiazolo[5,4-c]pyridin-4-yl]-amide;
{6-[2-(2-Chloro-6-fluorophenyl)-7-fluorothiazolo[5,4-c]pyridin-4-ylamino]-pyrimidin-4-yl}-methanol;
N-[2-(2-Chloro-6-fluorophenyl)-7-fluorothiazolo[5,4-c]pyridin-4-yl]-2-methylpyrimidine-4,6-diamine;
N-[2-(2,6-Dichlorophenyl)-7-fluorothiazolo[5,4-c]pyridin-4-yl]-pyrimidine-4,6-diamine;
{6-[2-(2,6-Dichlorophenyl)-7-fluorothiazolo[5,4-c]pyridin-4-ylamino]-pyrimidin-4-yl}-methanol;
1-[2-(2,6-Dichlorophenyl)-7-fluorothiazolo[5,4-c]pyridin-4-yl]-3-methyl-urea;
N-[2-(2,6-Dichlorophenyl)-7-fluorothiazolo[5,4-c]pyridin-4-yl]-2-methylpyrimidine-4,6-diamine;
Cyclopropanecarboxylic acid [2-(2,6-dichloro-4-cyano-phenyl)-7-fluorothiazolo[5,4-c]pyridin-4-yl]-amide;
3,5-Dichloro-4-[7-fluoro-4-(6-hydroxymethylpyrimidin-4-ylamino)-thiazolo[5,4-c]pyridin-2-yl]-benzonitrile;
4-[4-(6-Aminopyrimidin-4-ylamino)-7-fluorothiazolo[5,4-c]pyridin-2-yl]-3,5-dichlorobenzonitrile;
3-Chloro-2-[4-(6-methylpyrimidin-4-ylamino)-thiazolo[5,4-c]pyridin-2-yl]benzonitrile;
Cyclopropanecarboxylic acid [2-(2-chloro-6-cyanophenyl)-thiazolo[5,4-c]pyridin-4-yl]-amide;
2-[4-(6-Aminopyrimidin-4-ylamino)-7-fluorothiazolo[5,4-c]pyridin-2-yl]-3-chlorobenzonitrile;
2-[4-(6-Amino-2-methyl-pyrimidin-4-ylamino)-7-fluorothiazolo[5,4-c]pyridin-2-yl]-3-chlorobenzonitrile;
Cyclopropanecarboxylic acid [2-(2-chloro-6-cyanophenyl)-7-fluorothiazolo[5,4-c]pyridin-4-yl]-amide;
2-[4-(6-Aminopyrimidin-4-ylamino)-7-fluorothiazolo[5,4-c]pyridin-2-yl]-3-fluorobenzonitrile;
3-Fluoro-2-[7-fluoro-4-(6-hydroxymethylpyrimidin-4-ylamino)thiazolo[5,4-c]pyridin-2-yl]-benzonitrile;
4-(6-aminopyrimidin-4-ylamino)-2-(2-chloro-6-fluorophenyl)thiazolo[5,4-c]pyridine-7-carbonitrile;
4-(6-aminopyrimidin-4-ylamino)-2-(2-cyano-6-fluorophenyl)thiazolo[5,4-c]pyridine-7-carbonitrile;
5-chloro-4-(4-(2,6-dimethylpyrimidin-4-ylamino)thiazolo[5,4-c]pyridin-2-yl)isophthalonitrile;
4-(4-(6-aminopyrimidin-4-ylamino)thiazolo[5,4-c]pyridin-2-yl)-5-chloroisophthalonitrile;
2-(4-(2,6-dimethylpyrimidin-4-ylamino)thiazolo[5,4-c]pyridin-2-yl)benzene-1,3,5-tricarbonitrile;
2-[4-(2-Amino-6-methylpyrimidin-4-ylamino)-7-fluorothiazolo[5,4-c]pyridin-2-yl]-3-chlorobenzonitrile;
3-Chloro-2-[7-fluoro-4-(2-hydroxymethyl-6-methylpyrimidin-4-ylamino)-thiazolo[5,4-c]pyridin-2-yl]-benzonitrile;
2-[4-(6-Amino-2-methylpyrimidin-4-ylamino)-7-fluorothiazolo[5,4-c]pyridin-2-yl]-3-fluorobenzonitrile;
3-Chloro-2-[7-fluoro-4-(6-hydroxymethyl-2-methylpyrimidin-4-ylamino)-thiazolo[5,4-c]pyridin-2-yl]benzonitrile;
{6-[2-(4-Amino-2,6-dichlorophenyl)-7-fluorothiazolo[5,4-c]pyridin-4-ylamino]-pyrimidin-4-yl}-methanol;
4-[4-(6-Methylpyrimidin-4-ylamino)-thiazolo[5,4-c]pyridin-2-yl]-3,5-dichlorobenzamidine;
3-Chloro-5-fluoro-2-[4-(6-hydroxymethylpyrimidin-4-ylamino)-thiazolo[5,4-c]pyridin-2-yl]benzonitrile;
2-[4-(2-Amino-6-methylpyrimidin-4-ylamino)-thiazolo[5,4-c]pyridin-2-yl]-3-chlorobenzonitrile;
3-Chloro-2-[4-(6-hydroxymethyl-2-methylpyrimidin-4-ylamino)-thiazolo[5,4-c]pyridin-2-yl]-benzonitrile;
3-Chloro-2-[4-(2-hydroxymethyl-6-methylpyrimidin-4-ylamino)-thiazolo[5,4-c]pyridin-2-yl]-benzonitrile;
[2-(4-Amino-2,6-dichlorophenyl)-7-fluorothiazolo[5,4-c]pyridin-4-yl]-(6-methylpyrimidin-4-yl)-amine;
3-Chloro-5-fluoro-2-[4-(6-methylpyrimidin-4-ylamino)-thiazolo[5,4-c]pyridin-2-yl]benzonitrile; and
2-[4-(6-Amino-2-methylpyrimidin-4-ylamino)-thiazolo[5,4-c]pyridin-2-yl]-3-chloro-5-fluorobenzonitrile.

The compounds of Formula I may contain asymmetric or chiral centers, and, therefore, exist in different stereoisomeric forms. It is intended that all stereoisomeric forms of the compounds of Formula I, including but not limited to: diastereomers, enantiomers, and atropisomers as well as mixtures thereof such as racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidinyl and pyrrozolyl rings, or the E and Z forms of compounds of Formula I (for example oxime moieties), are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention, as defined by the claims, embrace both solvated and unsolvated forms.

In an embodiment, compounds of Formula I may exist in different tautomeric forms, and all such forms are embraced within the scope of the invention, as defined by the claims. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of Formula I, which are identical to those recited herein, but for the fact that one or more atoms are replaced by an atom having an atomic mass or mass number different from the atomic mass or mass number usually found in nature. All isotopes of any particular atom or element as specified are contemplated within the scope of the invention. Exemplary isotopes that can be incorporated into compounds of Formula I include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of Formula I (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). Positron emitting isotopes such as $^{15}$O, $^{13}$N, $^{11}$C, and $^{18}$F are useful for positron emission tomography (PET) studies to examine substrate receptor occupancy. Isotopically labeled compounds of Formula I can generally be prepared by following procedures analogous to those disclosed in the Schemes and/or in the Examples herein below, by substituting an isotopically labeled reagent for a non-isotopically labeled reagent.

Synthesis of TYK2 Inhibitor Compounds

Compounds of Formula I may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry*, Editors Katrizky and Rees, Pergamon Press, 1984.

Compounds of Formula I may be prepared singly or as compound libraries comprising at least 2, for example 5 to 1,000 compounds, or 10 to 100 compounds of Formula I. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, enantiomers, diastereomers or pharmaceutically acceptable salts thereof.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from commercially available starting materials using the general methods illustrated herein.

For illustrative purposes, reaction Schemes 1-4 depicted below provide routes for synthesizing the compounds of Formula I, as well as key intermediates. For a more detailed description of the individual reaction steps, see the Examples section below. Those skilled in the art will appreciate that other synthetic routes may be available and used. Although specific starting materials and reagents are depicted in the Schemes and discussed below, other starting materials and reagents may be available for substitution to provide a variety of derivatives and/or reaction conditions. In addition, many of the compounds prepared by the methods described below can be further modified in light of this disclosure using conventional chemistry well known to those skilled in the art.

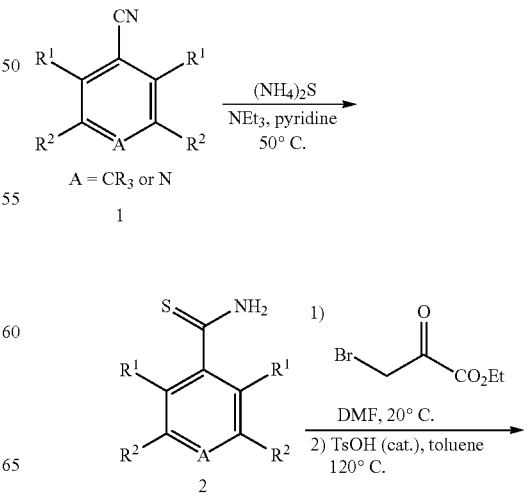

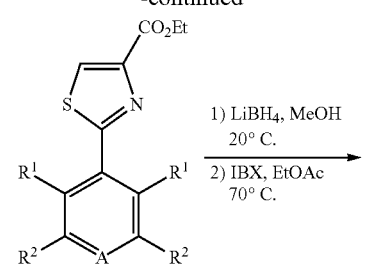

3

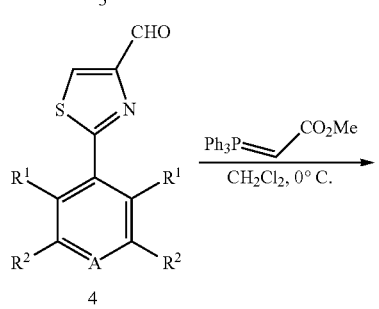

4

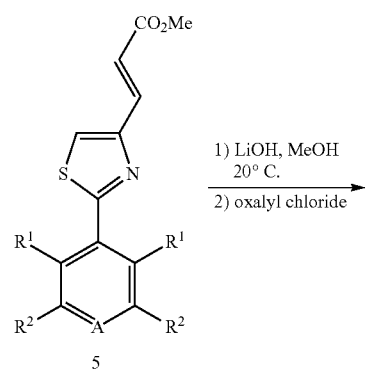

5

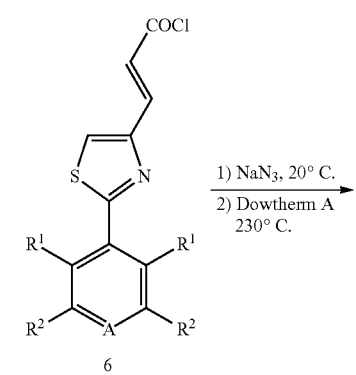

6

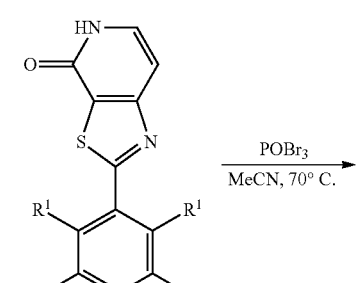

7

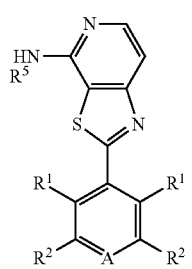

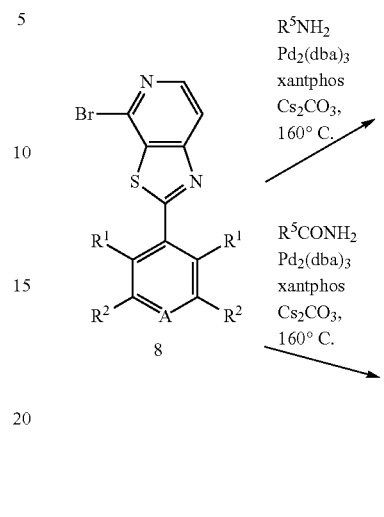

8

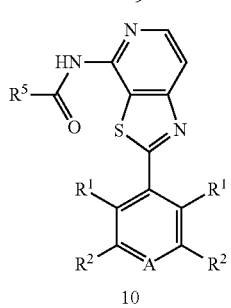

9

10

Scheme 1 shows methods of preparing compounds of formulas 9 and 10, wherein $R^1$, $R^2$, $R^5$ and A are as defined in Formula I. An aryl nitrile 1 can be treated with ammonium sulfide to give thioamide 2. Thioamide 2 can be reacted with methyl 3-bromo-2-oxopropanoate, followed by heating in toluene with a catalytic amount of p-toluene sulfonic acid, to yield thiazole ethyl ester 3. Ethyl ester 3 can be subsequently converted to thiazole aldehyde 4 through a two-step process. Wittig reaction of aldehyde 4 with triphenyl phosphonium glide provides α,β-unsaturated methyl ester 5. Hydrolysis, followed by treatment with oxalyl chloride provides acid chloride 6, which reacts with sodium azide to give an acyl azide intermediate. This acyl azide intermediate can undergo Curtis rearrangement upon heating in Dowtherm A at 230° C., and subsequent ring closure to arrive at pyridone 7. When treated with POBr₃, pyridone 7 can be converted to pyridine 2-bromide intermediate 8, which could be coupled to an amine or amide under palladium-catalyzed conditions, to furnish final products such as 9 or 10.

Scheme 2

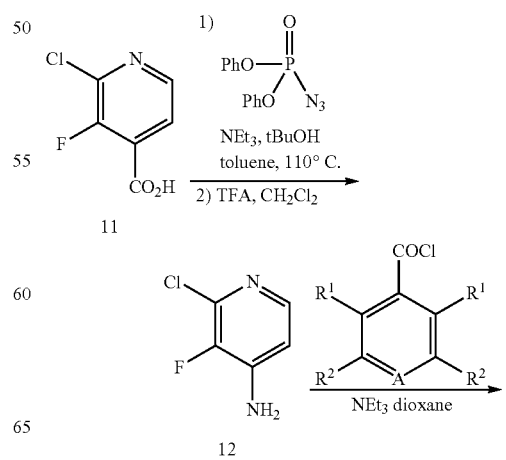

11

12

-continued

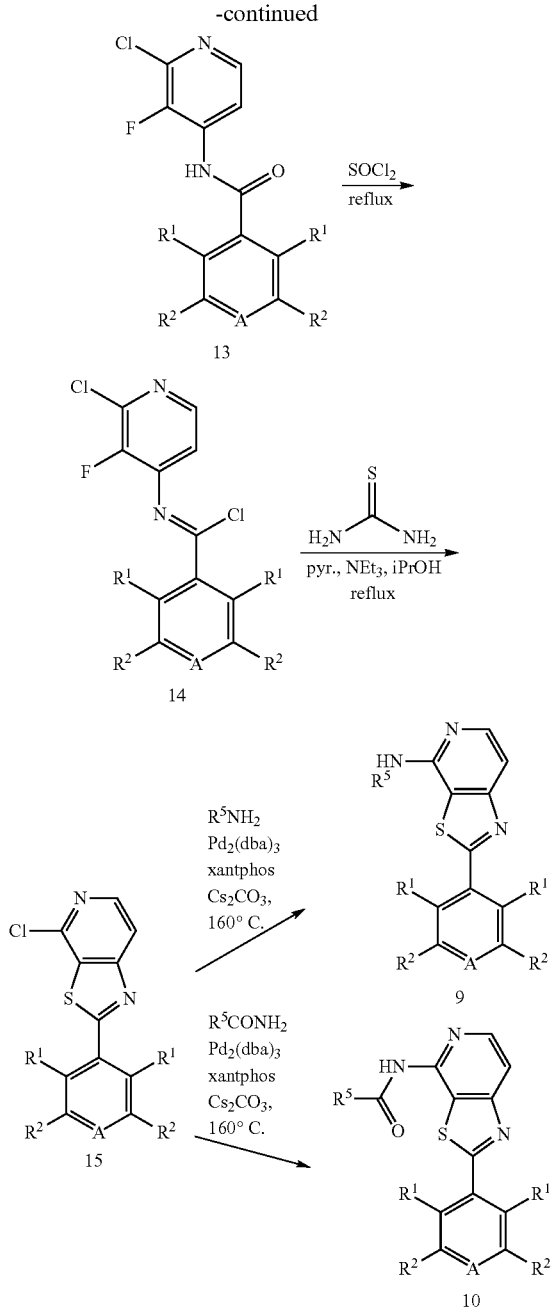

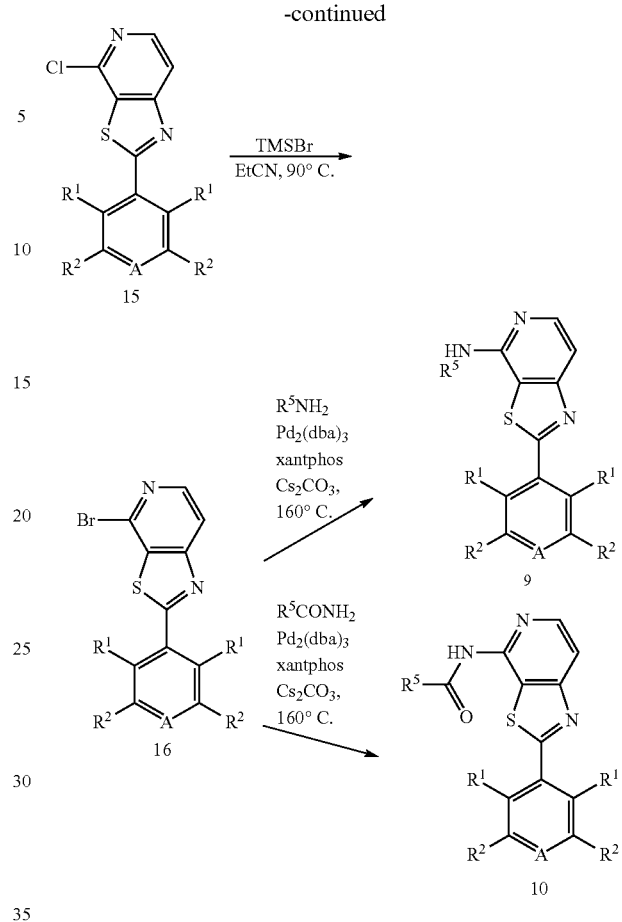

Scheme 2 shows an alternative method of preparing compounds of formulas 9 and 10, wherein $R^1$, $R^2$, $R^5$ and A are as defined in Formula I. The 2-chloro-3-fluoroisonicotinic acid 11, can be converted to 4-amino pyridine 12 via a 2-step process. Amide coupling of 12 with an aryl acid chloride gives rise to amide 13. Amide 13 can then be transformed to chloroimidate intermediate 14 upon refluxing with thionyl chloride. Chloroimidate 14 can be treated with thio-urea, followed by heating in isopropanol, to generate thiazole 15. Thiazole 15 can be coupled with an amine or amide following the same palladium-catalyzed conditions as in Scheme 1, to give 9 or 10. Furthermore, as shown in Scheme 2, it was also found that the 2-Cl pyridine intermediate 15 could be converted to the 2-Br analog 16, which also can react with an amine or amide under palladium-catalyzed conditions to give final products such as 9 or 10.

Scheme 3

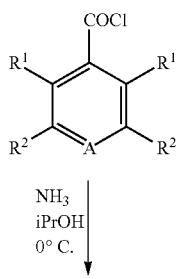

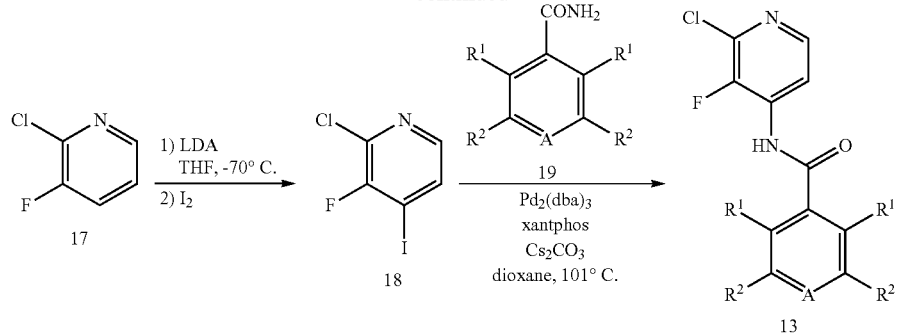

Scheme 3 shows an alternative general method for the preparation of compounds of formula 13, wherein $R^1$, $R^2$ and A are as defined in Formula I. The 2-chloro-3-fluoropyridine 17 can be treated with lithium diisopropylamide in THF at −70° C., followed by reaction with iodine to give 2-chloro-3-fluoro-4-iodopyridine 18. Iodide 18 can be coupled with a primary amide 19 through a palladium-catalyzed reaction to provide compounds of formula 13.

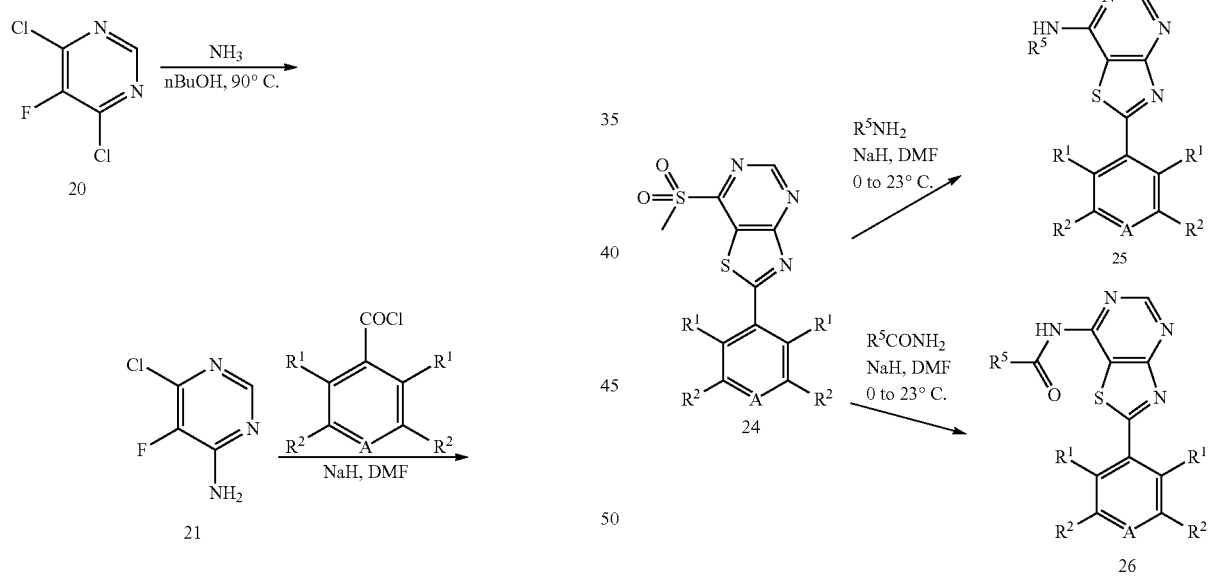

Scheme 4 shows general methods of preparing pyrimidine analogs 25 and 26, wherein $R^1$, $R^2$, $R^5$ and A are as defined in Formula I. 4,6-Dichloro-5-fluoropyrimidine 20 can be converted to amino intermediate 21 by heating with ammonia in n-butanol. Coupling amino intermediate 21 with an aryl acid chloride, in the presence of sodium hydride, can give rise to amide 22. Reaction of 22 with $P_2S_5$ can give thiol 23, which can be methylated and then oxidized with mCPBA to give sulfone 24. When treated with an amine or an amide in the presence of sodium hydride in DMF, sulfone 24 can be transformed to final products 25 and 26.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In each of the exemplary Schemes it may be advantageous to separate reaction products from one another and/or from starting materials. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g. an enantiomer, substantially free of its stereoisomer may be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.*, 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of Formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends on the particular use and the concentration of compound, and can range anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit TYK2 kinase activity. For example, such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, aerosols, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In one embodiment, the pharmaceutical composition also includes an additional chemotherapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Another embodiment includes a pharmaceutical composition comprising a compound of Formula I, or a stereoisomer or pharmaceutically acceptable salt thereof, for use in the treatment of an immunological or inflammatory disease. Another embodiment includes a pharmaceutical composition comprising a compound of Formula I, or a stereoisomer or pharmaceutically acceptable salt thereof for use in the treatment of psoriasis or inflammatory bowel disease.

Indications and Methods of Treatment

The compounds of the invention inhibit TYK2 kinase activity. Accordingly, the compounds of the invention are useful for reducing inflammation in particular patient tissue and cells. Compounds of the invention are useful for inhibiting TYK2 kinase activity in cells that overexpress TYK2 kinase. Alternatively, compounds of the invention are useful for inhibiting TYK2 kinase activity in cells in which, for example, the type I interferon, IL-6, IL-10, IL-12 and IL-23 signaling pathway is disruptive or abnormal, for example by binding to TYK2 kinase and inhibiting its activity. Alternatively, the compounds of the invention can be used for the treatment of immunological or inflammatory disorders.

Another embodiment includes a method of treating or lessening the severity of a disease or condition responsive to the inhibition of TYK2 kinase activity in a patient. The method includes the step of administering to a patient a therapeutically effective amount of a compound of Formula I, stereoisomers, tautomers or salts thereof.

In one embodiment, a compound of Formula I is administered to a patient in a therapeutically effective amount to treat or lessen the severity of a disease or condition responsive to the inhibition of TYK2 kinase activity, and said compound is at least 15 fold, alternatively 10 fold, alternatively 5 fold or more selective in inhibiting TYK2 kinase activity over inhibiting each of the other Janus kinase activities.

Another embodiment includes a compound of Formula I, stereoisomers, tautomers or salts thereof for use in therapy.

Another embodiment includes a compound of Formula I, stereoisomers, tautomers or salts thereof for use in treating an immunological or inflammatory disease.

Another embodiment includes a compound of Formula I, stereoisomers, tautomers or salts thereof for use in treating psoriasis or inflammatory bowel disease.

Another embodiment includes the use of a compound of Formula I, stereoisomers, tautomers or salts thereof for treating an immunological or inflammatory disease.

Another embodiment includes the use of a compound of Formula I, stereoisomers, tautomers or salts thereof for treating psoriasis or inflammatory bowel disease.

Another embodiment includes the use of a compound of Formula I, stereoisomers, tautomers or salts thereof in the preparation of a medicament for the treatment of an immunological or inflammatory disease.

Another embodiment includes the use of a compound of Formula I, stereoisomers, tautomers or salts thereof in the preparation of a medicament for the treatment of psoriasis or inflammatory bowel disease.

In one embodiment, the disease or condition is cancer, stroke, diabetes, hepatomegaly, cardiovascular disease, multiple sclerosis, Alzheimer's disease, cystic fibrosis, viral disease, autoimmune diseases, immunological disease, atherosclerosis, restenosis, psoriasis, allergic disorders, inflammatory disease, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.

In one embodiment, the disease or condition is an immunological disorder.

In one embodiment, the disease is a myeloproliferative disorder.

In one embodiment, the myeloproliferative disorder is polycythemia vera, essential thrombocytosis, myelofibrosis or chronic myelogenous leukemia (CML).

In one embodiment, the disease is asthma.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia (including T-cell leukemia).

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory disease is inflammatory bowel disease, Crohn's disease, ulcerative colitis, rheumatoid arthritis, psoriasis, contact dermatitis or delayed hypersensitivity reactions.

In one embodiment, the inflammatory disease is asthma, inflammatory bowel disease, Crohn's disease, ulcerative colitis, rheumatoid arthritis, psoriasis, allergic rhinitis, atopic dermatitis, contact dermatitis or delayed hypersensitivity reactions.

In one embodiment, the autoimmune disease is lupus or multiple sclerosis.

In one embodiment, the disease is asthma, inflammatory bowel disease, Crohn's disease, pouchitis, microscopic colitis, ulcerative colitis, rheumatoid arthritis, psoriasis, allergic rhinitis, atopic dermatitis, contact dermatitis, delayed hypersensitivity reactions, lupus or multiple sclerosis.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology, Vol.* 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through one or more of the Janus kinase pathways in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-induced arthritis (CIA) is an animal model of human rheumatoid arthritis (RA). Joint inflammation, which develops in animals with CIA, strongly resembles inflammation observed in patients with rheumatoid arthritis (RA). Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

The T-cell Dependent Antibody Response (TDAR) is An assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR is an assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M.P. Holsapple In: G. R. Burleson, J. H. Dean and A. E. Munson, Editors, *Modern Methods in Immunotoxicology, Volume* 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol.

181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

A compound of Formula I may be administered by any route appropriate to the disease or condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the route may vary with, for example, the condition of the recipient. Where the compound of Formula I is administered orally, it may be formulated as a pill, capsule, tablet, etc. with a pharmaceutically acceptable carrier or excipient. Where the compound of Formula I is administered parenterally, it may be formulated with a pharmaceutically acceptable parenteral vehicle and in a unit dosage injectable form, as detailed below.

A dose to treat human patients may range from about 5 mg to about 1000 mg of a compound of Formula I. A typical dose may be about 5 mg to about 300 mg of a compound of Formula I. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Combination Therapy

The compounds of Formula I may be employed alone or in combination with other therapeutic agents for the treatment of a disease or disorder described herein, such as an immunologic disorder (e.g. psoriasis or inflammation) or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be a NSAID or other anti-inflammatory agent. The second therapeutic agent may be a chemotherapeutic agent. The second therapeutic agent of the pharmaceutical combination formulation or dosing regimen can have complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

Another embodiment, therefore, includes a method of treating or lessening the severity of a disease or condition responsive to the inhibition of TYK2 kinase in a patient, comprising administering to said patient a therapeutically effective amount of a compound of Formula I, and further comprising, administering a second therapeutic agent.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

In a particular embodiment of therapy, a compound of Formula I, or a stereoisomer, geometric isomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method, or immunological disorder method. The amounts of the compound(s) of Formula I and the other pharmaceutically active immunologic or chemotherapeutic agent(s) and the relative timings of administration will be selected in order to achieve the desired combined therapeutic effect.

In one embodiment, compounds of the present invention are coadministered with any of anti-IBD agents, including but not limited to anti-inflammatory drugs, such as sulfasalazine, mesalamine or corticosteroids, such as budesonide, prednisone, cortisone or hydrocortisone, immune suppressing agents, such as azathioprine, mercaptopurine, infliximab, adalimumab, certolizumab pegol, methotrexate, cyclosporine or natalizumab, antibiotics, such as metronidazole or ciprofloxacin, anti-diarrheals, such as psyllium powder, loperamide or methylcellulose, laxatives, pain relievers, such as NSAIDs or acetaminophen, iron supplements, vitamin B supplements, vitamin D supplements and any combination of the above. In another example, compounds of the present invention are administered with (e.g. before, during or after) other anti-IBD therapies, such as surgery.

In one embodiment, compounds of the present invention are coadministered with any of anti-psoriasis agents, including but not limited to topical corticosteroids, vitamin D analogues, such as calcipotriene or calcitriol, anthralin, topical retinoids, such as tazarotene, calcineurin inhibitors, such as tacrolimus or pimecrolimus, salicylic acid, coal tar, NSAIDs, moisturizing creams and ointments, oral or injectible retinoids, such as acitretin, methotrexate, cyclosporine, hydroxyurea immunomodulator drugs, such as alefacept, etanercept, infliximab or ustekinumab, thioguanine, and any combinations of the above. In another example, compounds of the present invention are administered with (e.g. before, during or after) other anti-psoriasis therapies, such as light therapy, sunlight therapy, UVB therapy, narrow-band UVB therapy, Goeckerman therapy, photochemotherapy, such as psoralen plus ultraviolet A (PUVA), excimer and pulsed dye laser therapy, or in any combination of antipsoriasis agents and anti-psoriasis therapies.

In one embodiment, compounds of the present invention are coadministered with any of anti-asthmtic agents, including but not limited to beta2-adrenergic agonists, inhaled and oral corticosteroids, leukotriene receptor antagonist, and omalizumab. In another embodiment, compounds of the present invention are coadministered with an anti-asthmtic agent selected from a NSAID, combinations of fluticasone and salmeterol, combinations of budesonide and formoterol, omalizumab, lebrikizumad and corticosteroid selected from fluticasone, budesonide, mometasone, flunisolide and beclomethasone.

Methods and Articles of Manufacture

Another embodiment includes a method of manufacturing a compound of Formula I. The method includes: (a) reacting a compound of formula (i):

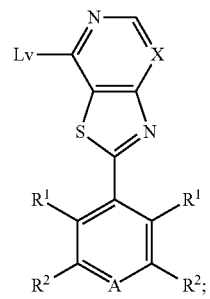

(i)

wherein Lv is a leaving group, for example a halogen, and X, A, $R^1$ and $R^2$ are as defined for Formula I, with a compound of the formula H—$R^4$-$R^5$ under conditions sufficient to form a compound of Formula I; and (b) optionally further functionalizing said above compound.

Certain embodiments include a compound of formula (i), stereoisomers or pharmaceutically acceptable salts thereof. Certain embodiments include a compound of formula (i), stereoisomers or pharmaceutically acceptable salts thereof, wherein X, A, $R^1$ and $R^2$ are as defined for Formula I and the group -Lv is a halogen, —OR or —OS(O)$_{1-2}$R, wherein R is independently hydrogen, alkyl, alkenyl, alkynyl, cycloalkyl, phenyl or heterocyclyl and R is independently optionally substituted. In certain embodiments, the group -Lv is halogen. Certain embodiments include a compound of formula (i) wherein the group -Lv is —Br or —I. Certain embodiments include a compound of formula (i) other than 4-chloro-2-(2,3-difluorophenyl)thiazolo[5,4-c]pyridine, 4-chloro-2-(2,3-dimethylphenyl)thiazolo[5,4-c]pyridine, 4-chloro-2-(2-methoxyphenyl)thiazolo[5,4-c]pyridine, 4-chloro-2-o-tolylthiazolo[5,4-c]pyridine, 4-chloro-2-(2-(difluoromethoxy)phenyl)thiazolo[5,4-c]pyridine, 4-chloro-2-(2-fluorophenyl)thiazolo[5,4-c]pyridine, 4-chloro-2-(2,3-dichlorophenyl)thiazolo[5,4-c]pyridine, 4-chloro-2-(2,4-dichlorophenyl)thiazolo[5,4-c]pyridine, 4-chloro-2-(2,4-dimethylphenyl)thiazolo[5,4-c]pyridine, 4-chloro-2-(2,6-dichlorophenyl)thiazolo[5,4-c]pyridine, 4-chloro-2-(2-chlorophenyl)thiazolo[5,4-c]pyridine, 4-chloro-2-(2,6-dimethylphenyl)thiazolo[5,4-c]pyridine, 4-chloro-2-(2,5-dichlorophenyl)thiazolo[5,4-c]pyridine, 4-chloro-2-(2-chloro-6-fluorophenyl)thiazolo[5,4-c]pyridine, 2-(2-bromophenyl)-4-chlorothiazolo[5,4-c]pyridine, 4-chloro-2-(2,6-difluorophenyl)thiazolo[5,4-c]pyridine, 4-chloro-2-(2,5-difluorophenyl)thiazolo[5,4-c]pyridine, 4-chloro-2-(2,4-difluorophenyl)thiazolo[5,4-c]pyridine or 4-chloro-2-(2,5-dimethyl)thiazolo[5,4-c]pyridine.

In certain embodiments, the conditions for reacting a compound of formula (i) with a compound of the formula H—$R^4$-$R^5$ include transition metal catalyzed reaction conditions. In one embodiment, the transition metal catalyst is selected from a platinum, palladium or copper catalyst. In one embodiment, the catalyst is a Pd(0) catalyst. Pd(0) catalysts for use in the method include tetrakis(tri-optionally substituted phenyl) phosphine palladium(0) catalyst, wherein said optional substituents on phenyl are selected from —OMe, —CF$_3$, —OCF$_3$, -Me and -Et and dipalladium(0) catalysts, such as tris(dibenzylideneacetone)dipalladium(0). In certain embodiments, the conditions include heating the reactants under basic conditions, for example, in the presence of an inorganic base, for example, a cesium, potassium, ammonium, or sodium carbonate or bicarbonate base, for example Cs$_2$CO$_3$. In certain embodiments, the conditions further include ligands to the transition metal catalyst. In one embodiment, a bidentate ligand is included, for example, the bidentate ligand xantphos is added.

In certain embodiments, methods of manufacturing a compound of Formula I optionally include reacting a compound of formula (ii):

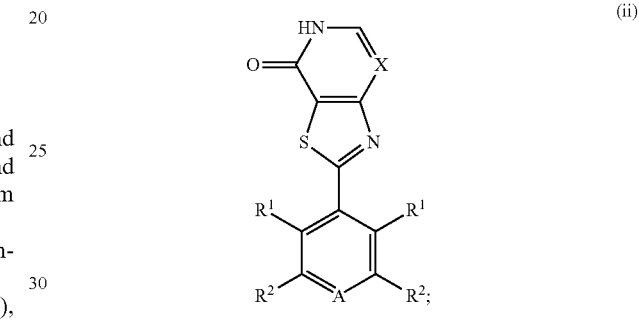

(ii)

wherein X, $R^1$ and $R^2$ are as defined for Formula I, with a halogenating reagent, for example a phosphorous oxyhalide, such as POBr$_3$ or POCl$_3$, to form a compound of formula (i), wherein Lv is a halogen. The halogenation reaction can optionally be performed in the presence of a base, such as an inorganic base, for example, a cesium, potassium, ammonium, or sodium carbonate, bicarbonate or hydroxide base.

Certain embodiments include a compound of formula (ii), stereoisomers or pharmaceutically acceptable salts thereof.

Another embodiment includes a kit for treating a disease or disorder responsive to the inhibition of a TYK2 kinase. The kit includes:

(a) a first pharmaceutical composition comprising a compound of Formula I; and (b) instructions for use.

In another embodiment, the kit further includes:

(c) a second pharmaceutical composition, which includes a chemotherapeutic agent.

In one embodiment, the instructions include instructions for the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of Formula I or formulation thereof which is effective for treating the condition and may have a sterile access port (for example the container may be an intravenous solution bag or a vial having a stopper pierceable by a hypodermic injection needle). The container includes a composition comprising at least one compound of Formula I.

The label or package insert indicates that the composition is used for treating the condition of choice, such as cancer. In one embodiment, the label or package inserts indicates that the composition comprising the compound of Formula I can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of Formula I contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of Formula I, and alternative methods for preparing the compounds of Formula I are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

BIOLOGICAL EXAMPLES

Compounds of Formula I may be assayed for the ability to modulate the activity of protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of Formula I to bind to kinases and may be measured either by radiolabelling the compound of Formula I prior to binding, isolating the compound of Formula I/kinase complex and determining the amount of radiolabel bound, or by running a competition experiment where a compound of Formula I is incubated with known radiolabeled ligands. These and other useful in vitro assays are well known to those of skill in the art.

In an embodiment, the compounds of Formula I can be used to control, modulate or inhibit tyrosine kinase activity, for example TYK2 kinase activity, additional serine/threonine kinases, and/or dual specificity kinases. Thus, they are useful as pharmacological standards for use in the development of new biological tests, assays and in the search for new pharmacological agents.

Example A

JAK1, JAK2 and TYK2 Inhibition Assay Protocol

The activity of the isolated JAK1, JAK2 or TYK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants (Ki) of Examples 1-240, compounds were diluted serially in DMSO and added to 50 µL kinase reactions containing 1.5 nM JAK1, 0.2 nM purified JAK2 or 1 nM purified TYK2 enzyme, 100 mM Hepes pH7.2, 0.015% Brij-35, 1.5 µM peptide substrate, 25 µM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 µL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example B

JAK3 Inhibition Assay Protocol

The activity of the isolated JAK3 kinase domain was measured by monitoring phosphorylation of a peptide derived from JAK3 (Leu-Pro-Leu-Asp-Lys-Asp-Tyr-Tyr-Val-Val-Arg) fluorescently labeled on the N-terminus with 5-carboxyfluorescein using the Caliper LabChip technology (Caliper Life Sciences, Hopkinton, Mass.). To determine the inhibition constants (Ki) of Examples 1-240, compounds were diluted serially in DMSO and added to 50 µL kinase reactions containing 5 nM purified JAK3 enzyme, 100 mM Hepes pH7.2, 0.015% Brij-35, 1.5 µM peptide substrate, 5 µM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 µL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example C

Cell-Based Pharmacology Assays

The activities of compounds 1-240 were determined in cell-based assays that are designed to measure Janus kinase dependent signaling. Compounds were serially diluted in DMSO and incubated with NK92 cells (American Type Culture Collection (ATCC); Manassas, Va.) in 384-well microtiter plates in RPMI medium at a final cell density of 50,000 cells per well and a final DMSO concentration of 0.2%. Human recombinant IL-12 (R&D systems; Minneapolis, Minn.) was then added at a final concentration of 30 ng/ml to the microtiter plates containing the NK92 cells and compound and the plates were incubated for 45 min at 37° C. Alternatively, compounds were serially diluted in DMSO and incubated with TF-1 cells (American Type Culture Collection (ATCC); Manassas, Va.) in 384-well microtiter plates in Opti-MEM medium without phenol red, 1% Charcoal/Dextran stripped FBS, 0.1 mM NEAA, 1 mM sodium pyruvate (Invitrogen Corp.; Carlsbad, Calif.) at a final cell density of 100,000 cells per well and a final DMSO concentration of 0.2%. Human recombinant EPO (Invitrogen Corp.; Carlsbad, Calif.) was then added at a final concentration of 10 Units/ml to the microtiter plates containing the TF-1 cells and compound and the plates were incubated for 30 min at 37° C. Compound-mediated effects on STAT4 or STAT5 phosphorylation were then measured in the lysates of incubated cells using the Meso Scale Discovery (MSD) technology (Gaithersburg, Md.) according to the manufacturer's protocol and $EC_{50}$ values were determined.

The compounds of Examples 1-126 were tested in the above assays and found to have $K_i$ values for TYK2 inhibition (Example A) of less than about 500 nM. The compounds of Examples 1-240 were tested in the above assays and found to have $K_i$ values for TYK2 inhibition (Example A) of less than about 500 nM. Table 0 below shows example $K_i$ values for TYK2 inhibition (Example A).

TABLE 0

| Example no. | TYK2 Ki (nM) |
| --- | --- |
| 2 | 0.5 |
| 9 | 1.4 |
| 10 | 23 |
| 16 | 1.4 |
| 18 | 0.3 |
| 22 | 1.0 |
| 24 | 6.2 |
| 25 | 87 |
| 56 | 8.6 |
| 129 | 1.6 |
| 138 | 4.1 |
| 213 | 1.5 |
| 223 | 0.4 |
| 224 | 0.3 |
| 227 | 0.8 |
| 236 | 0.5 |

PREPARATIVE EXAMPLES

| Abbreviations | |
| --- | --- |
| $NH_4HCO_3$ | Ammonium hydrogen carbonate |
| n-BuLi | n-Butyllithium |
| t-BuOH | tert-Butanol |
| $CDCl_3$ | Deuterochloroform |
| $CH_3CN$ | Acetonitrile |
| $Cs_2CO_3$ | Cesium carbonate |
| DCE | Dichloroethane |
| DCM | Dichloromethane |
| DIPEA | Diisopropylethylamine |
| DME | Ethyleneglycol dimethyl ether |
| DMF | N,N-Dimethylformamide |
| DMSO | Dimethylsulfoxide |
| EtOAc | Ethyl acetate |
| HATU | O-(7-Azabenzotriazol-1-yl)-N,N,N',N'-tetramethyluronium hexafluorophosphate |

-continued

| Abbreviations | |
| --- | --- |
| HCl | Hydrochloric acid |
| HPLC | High Pressure Liquid Chromatography |
| IMS | Industrial methylated spirits |
| LCMS | Liquid Chromatography Mass Spectrometry |
| MeOH | Methanol |
| MeOH-$d_4$ | Deuteromethanol |
| $MgSO_4$ | Anhydrous magnesium sulfate |
| $NaHCO_3$ | Sodium hydrogen carbonate |
| NaOH | Sodium hydroxide |
| $Na_2SO_4$ | Anhydrous sodium sulfate |
| $NH_2$ cartridge | Isolute ® silica-based sorbent with a chemically bonded aminopropyl functional group |
| $POBr_3$ | Phosphorus oxybromide |
| RPHPLC | Reverse phase high pressure liquid chromatography |
| RT | Retention time |
| SCX-2 | Isolute ® silica-based sorbent with a chemically bonded propylsulfonic acid functional group |
| p-TsOH | p-Toluenesulfonic acid |
| TFA | Trifluoroacetic acid |
| THF | Tetrahydrofuran |
| $Pd_2(dba)_3$ | Tris(dibenzylideneacetone)dipalladium(0) |
| $Pd(dppf)Cl_2$ | (1,1'-Bis(diphenylphosphino)ferrocene) palladium(II) dichloride |
| $Pd(PPh_3)_4$ | tetrakis(triphenylphosphine)palladium(0) |
| Xantphos | 4,5-Bis(diphenylphosphino)-9,9-dimethylxanthene |

General Experimental Conditions

Compounds of this invention may be prepared from commercially available starting materials using the general methods illustrated herein. Specifically, 2,6-dichlorobenzoic acid, 2,6-dichlorobenzoyl chloride, 2-chloro-6-fluorobenzoic acid, 2,6-dichlorobenzonitrile, 2-chloro-6-fluorobenzonitrile, 2-chloro-3-fluoropyridine-4-carboxylic acid, 2-chloro-3-fluoropyridine, were purchased from Aldrich (St. Louis, Mo.). 4,6-dichloro-5-fluoropyrimidine and 6-methylpyrimidine-4-amine were purchased from Ark Pharm Inc. (Libertyville, Ill.). 4,6-diaminopyrimidine was purchased from Allichem (Baltimore, Md.). 6-chloropyrimidin-4-ylamine was purchased from Toronto Research Chemicals (North York, Ontario). 4-amino-2,6-dimethylpyrimidine and cyclopropanecarboxamide were purchased from Alfa Aesar (Ward Hill, Mass.). All commercial chemicals, including reagents and solvents, were used as received.

High Pressure Liquid Chromatography—Mass Spectrometry (LCMS) experiments to determine retention times (RT) and associated mass ions were performed using one of the following methods, with UV detector monitoring at 220 nm and 254 nm, and mass spectrometry scanning 110-800 amu in ESI+ ionization mode.

LCMS Analytical Methods

Final compounds were analyzed using a couple of LC/MS conditions, with UV detector monitoring at 220 nm and 254 nm, and mass spectrometry scanning 110-800 amu in ESI+ ionization mode.

LC/MS Method A: column: XBridge C18, 4.6×50 mm, 3.5 um; mobile phase: A water (0.01% ammonia), B $CH_3CN$; gradient: 5%-95% B in 8.0 min; flow rate: 1.2 mL/min; oven temperature 40° C.

LC/MS Method B: column: XBridge C18, 4.6×50 mm, 3.5 um; mobile phase: A water (10 mM ammonium hydrogen carbonate), B $CH_3CN$; gradient: 5%-95% B in 8.0 min; flow rate: 1.2 mL/min; oven temperature 40° C.

LC/MS Method C: Experiments performed on a Waters Micromass ZQ2000 quadrupole mass spectrometer linked to a Waters Acquity HPLC system with a PDA UV detector. The spectrometer has an electrospray source operating in positive and negative ion mode. This system uses an Acquity BEH C18 1.7 um 100×2.1 mm column, maintained at 40° C. or an Acquity BEH Shield RP18 1.7 μm 100×2.1 mm column, maintained at 40° C. and a 0.4 ml/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95% solvent A and 5% solvent B over the next 1.2 minutes. Total run time was 8 minutes.

LC/MS Method D: Experiments performed on a Waters Platform LC quadrupole mass spectrometer linked to a Hewlett Packard HP1100 LC system with a diode array and a Sedex 85 evaporative light scattering detector. The spectrometer has an electrospray source operating in positive and negative ion mode. This system uses a Phenomenex Luna 3 micron C18(2) 30×4.6 mm column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4.0 minutes. This was maintained for 1 minute before returning to 95% solvent A and 5% solvent B over the next 0.5 minute. Total run time was 6 minutes.

Method E: Experiments performed on a Waters ZMD quadrupole mass spectrometer linked to a Waters 1525 LC system with a Waters 996 diode array detector and a Sedex 85 evaporative light scattering detector. The spectrometer has an electrospray source operating in positive and negative ion mode. This system uses a Luna 3 micron C18(2) 30×4.6 mm column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4.0 minutes. This was maintained for 1 minute before returning to 95% solvent A and 5% solvent B over the next 0.5 minute. Total run time was 6 minutes.

$^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a Biotage Initiator 60™ which uses a single-mode resonator and dynamic field tuning Temperature from 40-250° C. can be achieved, and pressures of up to 30 bar can be reached.

Example 1

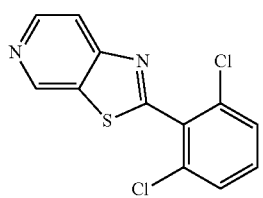 [SMILES: Clc1cccc(Cl)c1-c1nc2ccncc2s1]

2-(2,6-Dichlorophenyl)thiazolo[5,4-c]pyridine

Step 1. N-(Pyridin-4-yl)pivalamide

A solution of pivaloyl chloride (13.4 g, 111 mmol) in DCM (20 mL) was slowly added to a cooled (0° C.) solution of pyridin-4-amine (10 g, 106 mmol) and triethylamine (26.7 g, 265 mmol) in DCM (80 mL). After addition, the icebath was removed and the resulting mixture was stirred at 20° C. for 6 hours. The mixture was poured into water (100 mL) and extracted with DCM (3×100 mL). The combined organic extract was washed with saturated NaHCO$_3$ solution (100 mL) and brine (100 mL), dried over MgSO$_4$, and concentrated under reduced pressure. The residue was re-crystallized from EtOAc/petroleum ether to give the desired product as white crystals (7.9 g, 40% yield). LCMS (ESI) m/z: 179.1 [M+H$^+$].

Step 2. 4-Pivalamidopyridin-3-yl diisopropylcarbamodithioate

To a cooled (−78° C.) solution of N-(pyridin-4-yl)pivalamide (2.50 g, 14.0 mmol) in anhydrous THF (100 mL) was added n-BuLi (2.5 M in hexanes, 12 mL, 29.4 mmol). The mixture was allowed to warm rapidly to 0° C. and stirred at this temperature for 1.5 hours. The resulting mixture was cooled to −78° C. again and a solution of tetraisopropylthiuram disulfide (4.93 g, 14.0 mmol) in anhydrous THF (20 mL) was slowly added. After addition, the mixture was allowed to warm to room temperature, and then water (200 mL) and EtOAc (200 mL) were added sequentially. The organic layer was separated, washed with water (2×200 mL), dried over Na$_2$SO$_4$, and concentrated under reduced pressure. The mixture was purified by silica gel column chromatography, eluting with EtOAc/petroleum ether (1:8) to give the desired product as a yellow solid (2.46 g, 50% yield). $^1$H NMR (500 MHz, CDCl$_3$): δ 8.60 (d, J=7.5 Hz, 1H), 8.50-8.45 (m, 2H), 8.40 (d, J=6.5 Hz, 1H), 1.60-1.11 (m, 14H), 1.29 (s, 9H). LCMS (ESI) m/z: 354.2 [M+H$^+$].

Step 3. 4-Aminopyridin-3-yl diisopropylcarbamodithioate

A mixture of 4-pivalamidopyridin-3-yl diisopropylcarbamodithioate (5.0 g, 14 mmol) and NaOH (1.1 g, 28 mmol) in MeOH (100 mL) was stirred at 20° C. for 20 hours. The reaction was concentrated under reduced pressure and the residue was purified by silica gel column chromatography, eluting with EtOAc/petroleum ether (1:8) to give the desired product as a white solid (3.8 g, 93% yield). $^1$H NMR (500 MHz, CDCl$_3$): δ 8.24 (t, J=2.0 Hz, 1H), 6.69 (d, J=5.5 Hz, 1H), 4.90 (s, 2H), 1.64-1.30 (m, 14H). LCMS (ESI) m/z: 270.1 [M+H$^+$].

Step 4. 4-(2,6-Dichlorobenzamido)pyridin-3-yl diisopropylcarbamodithioate

A solution of 2,6-dichlorobenzoyl chloride (62 mg, 0.30 mmol) in DCM (4 mL) was slowly added to a cooled (0° C.) solution of 4-aminopyridin-3-yl diisopropylcarbamodithioate (100 mg, 0.37 mmol) in DCM (15 mL). The solution was stirred at 20° C. for 30 minutes. The mixture was concentrated under reduced pressure and the residue was purified by silica gel column chromatography, eluting with EtOAc/petroleum ether (1:4) to give the desired product as a yellow solid (20 mg, 15% yield). LCMS (ESI) m/z: 442.1 [M+H$^+$].

Step 5.
2-(2,6-Dichlorophenyl)thiazolo[5,4-c]pyridine

A solution of 4-(2,6-dichlorobenzamido)pyridin-3-yl diisopropylcarbamodithioate (50 mg, 0.11 mmol) in 5 M HCl (10 mL) was stirred at 100° C. for 4 hours. The pH of the mixture was adjusted to 7 by the addition of 2N sodium hydroxide solution and the aqueous phase extracted with EtOAc (3×100 mL). The combined organic extract was washed with water (2×50 mL) and brine (100 ml), dried over Na$_2$SO$_4$ and evaporated. The crude product was re-crystallized from EtOAc/DCM/petroleum ether (1:10:10) to give the product as a white solid (24 mg, 76% yield). $^1$H NMR (500 MHz, MeOH-d$_4$): δ 9.30 (s, 1H), 8.60 (d, J=5.5 Hz, 1H), 8.03 (d, J=5.5 Hz, 1H), 7.54-7.50 (m, 3H). LCMS (Method A): RT=4.84 min, m/z: 281.0 [M+H$^+$].

Example 2

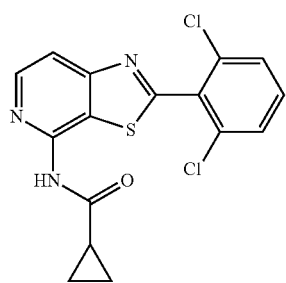 [SMILES: O=C(Nc1nccc2nc(-c3c(Cl)cccc3Cl)sc12)C1CC1]

N-(2-(2,6-Dichlorophenyl)thiazolo[5,4-c]pyridin-4-yl)cyclopropanecarboxamide

Step 1. 2,6-Dichlorobenzothioamide

A mixture of 2,6-dichlorobenzonitrile (100 g, 581 mmol), triethylamine (64.5 g, 640 mmol) and (NH$_4$)$_2$S (20% aqueous solution, 217 mL, 640 mmol) in pyridine (500 mL) was stirred at 50° C. for 4 hours. The mixture was concentrated under reduced pressure. The residue was dissolved in water (400 mL) and extracted with EtOAc (3×300 mL). The combined organic extract was washed with brine (100 mL), dried over Na$_2$SO$_4$, and concentrated under reduced pressure. The residue was re-crystallized with EtOAc/petroleum ether to afford the desired intermediate as a pale yellow solid (105 g, 88% yield). LCMS (ESI) m/z: 206.0 [M+H$^+$].

Step 2. Ethyl 2-(2,6-dichlorophenyl)thiazole-4-carboxylate

A mixture of 2,6-dichlorobenzothioamide (15 g, 73 mmol) and 3-bromo-2-oxopropanoate (28.4 g, 146 mmol) in DMF (200 mL) was stirred at 20° C. for 14 hours. The resulting mixture was then poured into water (100 mL), and extracted with EtOAc (3×100 mL). The combined organic extract was washed with brine (100 mL), dried over Na$_2$SO$_4$ and concentrated under reduced pressure. The residue was dissolved in toluene (800 mL), p-TsOH (2.0 g) was added and the resulting mixture was heated at 120° C. for 4 hours. The mixture was concentrated under reduced pressure and the residue was purified via silica gel column chromatography, eluting with EtOAc/petroleum ether (1:9) to give the desired product as a brown solid (18 g, 82% yield). $^1$H NMR (500 MHz, DMSO-d$_6$): δ 8.83 (s, 1H), 7.71-7.64 (m, 3H), 4.34 (q, J=9.0 Hz, 7.5 Hz, 2H), 1.33 (t, J=9 Hz, 3H). LCMS (ESI) m/z: 301.1 [M+H$^+$].

Step 3. (2-(2,6-Dichlorophenyl)thiazol-4-yl)methanol

To a cooled (0° C.) solution of ethyl 2-(2,6-dichlorophenyl)thiazole-4-carboxylate (7.0 g, 23 mmol) in MeOH (100 mL) was added lithium borohydride (0.98 g, 47 mmol) in four portions. After addition, the mixture was stirred at 0° C. for 1 hour. The reaction mixture was quenched with water (100 mL) and extracted with EtOAc (3×100 mL). The combined organic extract was washed with brine (100 mL), dried over Na$_2$SO$_4$ and concentrated under reduced pressure. The residue was purified via silica gel column chromatography eluting with EtOAc/petroleum ether (1:5) to give the desired product as a white solid (6.2 g, 97% yield). $^1$H NMR (DMSO-d$_6$, 500 MHz): δ 7.74 (s, 1H), 7.66-7.64 (m, 2H), 7.60-7.56 (m, 1H), 5.52 (t, J=5.5 Hz, 1H), 4.70 (m, 2H). LCMS (ESI) m/z: 260.1 [M+H$^+$].

Step 4. 2-(2,6-Dichlorophenyl)thiazole-4-carbaldehyde

To a stirred solution of (2-(2,6-dichlorophenyl)thiazol-4-yl)methanol (5.8 g, 22 mmol) in EtOAc (200 mL) at room temperature was added 2-iodoxybenzoic acid (12.5 g, 44.6 mmol). The resulting mixture was warmed to 70° C. and stirred for 18 hours. The solid was removed via filtration, and the filtrate concentrated under reduced pressure to afford the desired product as a white solid (5.8 g, ~100% yield), which was used in the next step without further purification.

Step 5. (E)-Methyl 3-(2-(2,6-dichlorophenyl)thiazol-4-yl)acrylate

To a cooled (0° C.) solution of Ph$_3$PCHCOOMe (7.5 g, 22 mmol) in DCM (200 mL) was added a solution of 2-(2,6-dichlorophenyl)thiazole-4-carbaldehyde (5.8 g, 22 mmol) in DCM (20 mL) dropwise. After addition, the resulting mixture was slowly warmed to room temperature and stirred for 4 hours. The mixture was concentrated under reduced pressure and the residue was suspended in petroleum ether (250 mL). The solid was removed by filtration and the filtrate was concentrated under reduced pressure. The residue was purified via silica gel column chromatography eluting with EtOAc/petroleum ether (1:8) to afford the desired product as a white solid (6.3 g, 90% yield). LCMS (ESI) m/z: 314.1 [M+H$^+$].

Step 6. (E)-3-(2-(2,6-Dichlorophenyl)thiazol-4-yl)acrylic acid

To a stirred solution of (E)-methyl 3-(2-(2,6-dichlorophenyl)thiazol-4-yl)acrylate (6.3 g, 20 mmol) in MeOH (100 mL) and H$_2$O (20 mL) was added lithium hydroxide (1.5 g, 61 mmol). The resulting mixture was stirred for 24 hours and then partially concentrated under reduced pressure. The pH of the residual aqueous mixture was adjusted to 5 by addition of 2N HCl and extracted with EtOAc (3×100 mL). The combined organic extract was washed with brine (100 mL), dried over Na$_2$SO$_4$ and concentrated under reduced pressure. The residue was purified by silica gel column chromatography, eluting with a 0-20% gradient of MeOH in DCM to give the desired product as a white solid (5.4 g, 94% yield). LCMS (ESI) m/z: 300.0 [M+H$^+$].

Step 7. (E)-3-(2-(2,6-Dichlorophenyl)thiazol-4-yl)acryloyl chloride

To a suspension of (E)-3-(2-(2,6-dichlorophenyl)thiazol-4-yl)acrylic acid (5.7 g, 19 mmol) in DCM (20 mL) was added oxalyl chloride (4.8 g, 38 mmol) and 2 drops of DMF. The resulting mixture was stirred for 2 hours at room temperature and then concentrated under reduced pressure to give the crude desired product (6.0 g, 99% yield), which was used in the next step without purification.

Step 8. (E)-3-(2-(2,6-Dichlorophenyl)thiazol-4-yl)acryloyl azide

To a cooled (0° C.) solution of sodium azide (6.2 g, 95 mmol) in water (100 mL) and acetone (100 mL) was added a solution of (E)-3-(2-(2,6-dichlorophenyl)thiazol-4-yl)acryloyl chloride (6.0 g, 19 mmol) in dioxane (100 mL) dropwise. After addition, the resulting mixture was stirred for 1 hour at 0° C. The reaction was quenched with water (50 mL) and extracted with EtOAc (3×80 mL). The combined organic extract was washed with brine (100 mL), dried over $Na_2SO_4$ and concentrated under reduced pressure. The resultant residue was purified via silica gel column chromatography eluting with EtOAc/petroleum ether (1:8) to afford the desired product as a yellow solid (6.0 g, 98% yield). LCMS (ESI) m/z: 325.0 [M+H$^+$].

Step 9. 2-(2,6-Dichlorophenyl)thiazolo[5,4-c]pyridin-4(5H)-one

To a stirred solution of Dowtherm A® (20 mL) at 230° C. was added a solution of the (E)-3-(2-(2,6-dichlorophenyl)thiazol-4-yl)acryloyl azide (0.33 g, 1.0 mmol) in dioxane (1.0 mL) dropwise over 15 minutes. After addition, the resulting mixture was stirred for 1 hour at 230° C., and then cooled to room temperature. The mixture was purified on a short silica gel column, eluting with petroleum ether then EtOAc/petroleum ether (1:1) to give the desired product as a yellow solid (0.10 g, 31% yield). LCMS (ESI) m/z: 297.0 [M+H$^+$].

Step 10. 4-Bromo-2-(2,6-dichlorophenyl)thiazolo[5,4-c]pyridine

To a stirred solution of 2-(2,6-dichlorophenyl)thiazolo[5,4-c]pyridin-4(5H)-one (0.32 g, 1.1 mmol) in $CH_3CN$ (50 ml) was added POBr$_3$ (0.918 g, 3.21 mmol). The mixture was heated at 100° C. for 2 hours. The mixture was cooled to room temperature, quenched with ice (200 mL) and extracted with EtOAc (3×20 mL). The combined organic extract was washed with saturated NaHCO$_3$ (100 mL) and brine (100 mL), dried over Na$_2$SO$_4$, and concentrated under reduced pressure. The resultant residue was purified by silica gel column chromatography eluting with a 0-10% gradient of EtOAc/petroleum ether to give the desired product as a white solid (0.22 g, 56% yield). $^1$H NMR (500 MHz DMSO-d$_6$): δ 8.59 (d, J=5.5 Hz, 1H), 8.26 (d, J=6.0 Hz, 1H), 7.76-7.74 (m, 2H), 7.71-7.68 (m, 1H). LCMS (ESI) m/z: 359.1 [M+H$^+$].

Step 11. N-(2-(2,6-Dichlorophenyl)thiazolo[5,4-c]pyridin-4-yl)cyclopropane-carboxamide To a microwave tube was added 4-bromo-2-(2,6-dichlorophenyl)thiazolo[5,4-c]pyridine (60 mg, 0.17 mmol), cyclopropanecarboxamide (0.019 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified by reverse phase column chromatography eluting with a 0-60% gradient of CH$_3$CN in 0.5% NH$_4$HCO$_3$ to give the desired product as a white solid (13 mg, 21% yield). $^1$H NMR (500 MHz, DMSO-d$_6$): δ 11.44 (s, 1H), 8.46 (d, J=6.0 Hz, 1H), 7.92 (d, J=6.0 Hz, 1H), 7.72-7.67 (m, 3H), 2.09-2.06 (m, 1H), 0.9-0.87 (m, 4H). LCMS (Method A): RT=5.84 min, m/z: 371.0 [M+H$^+$].

Example 3

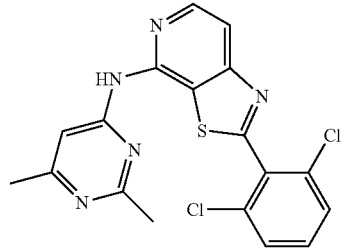 [SMILES: Cc1cc(Nc2nccc3nc(-c4c(Cl)cccc4Cl)sc23)nc(C)n1]

2-(2,6-Dichlorophenyl)-N-(2,6-dimethylpyrimidin-4-yl)thiazolo[5,4-c]pyridin-4-amine To a microwave tube was added 4-bromo-2-(2,6-dichlorophenyl)thiazolo[5,4-c]pyridine (60 mg, 0.17 mmol), 2,6-dimethylpyrimidin-4-amine (0.027 g, 0.22 mmol), Pd$_2$(dba)$_3$ (0.013 g, 0.017 mmol), XantPhos ((0.017 g, 0.034 mmol) and Cs$_2$CO$_3$ (0.111 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography eluting with a 0-60% gradient of CH$_3$CN in 0.5% NH$_4$HCO$_3$ to give the desired product as a white solid (14 mg, 21% yield). $^1$H NMR (500 MHz, CH$_3$OH-d$_4$): δ 8.44 (d, J=5.5 Hz, 1H), 7.71 (d, J=5.5 Hz, 1H), 7.56-7.51 (m, 4H), 7.31 (s, 1H), 2.44 (s, 3H), 2.35 (s, 3H). LCMS (Method A): RT=5.75 min, m/z: 402.0 [M+H$^+$].

Example 4

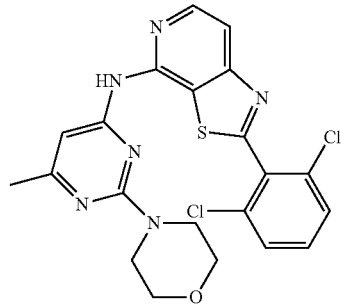 [SMILES: Cc1cc(Nc2nccc3nc(-c4c(Cl)cccc4Cl)sc23)nc(N2CCOCC2)n1]

2-(2,6-Dichlorophenyl)-N-(6-methyl-2-morpholinopyrimidin-4-yl)thiazolo[5,4-c]pyridin-4-amine To a microwave tube was added 4-bromo-2-(2,6-dichlorophenyl)thiazolo[5,4-c]pyridine (60 mg, 0.17 mmol), 6-methyl-2-morpholinopyrimidin-4-amine (0.043 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography eluting with a 0-60% gradient of CH$_3$CN in 0.5% NH$_4$HCO$_3$ to give the desired product as a white solid (25 mg, 31% yield). $^1$H NMR (500 MHz, DMSO-d$_6$): δ 10.31 (s, 1H), 8.44 (d, J=5.5 Hz, 1H), 7.41 (d, J=5.5 Hz, 1H), 7.44-7.28 (m, 2H), 7.68-7.67 (m, 1H), 6.40 (s, 1H), 3.55-3.54 (m, 8H), 2.21 (s, 3H). LCMS (Method A): RT=6.53 min, m/z: 473.1 [M+H$^+$].

Example 5

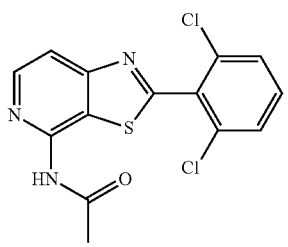 [SMILES: CC(=O)Nc1nccc2nc(-c3c(Cl)cccc3Cl)sc12]

N-(2-(2,6-Dichlorophenyl)thiazolo[5,4-c]pyridin-4-yl)acetamide

To a microwave tube was added 4-bromo-2-(2,6-dichlorophenyl)thiazolo[5,4-c]pyridine (60 mg, 0.17 mmol), acetamide (0.013 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography, eluting with a 0-60% gradient of CH$_3$CN in 0.5% NH$_4$HCO$_3$ to give the desired product as a white solid (25 mg, 44% yield). $^1$H NMR (500 MHz, DMSO-d$_6$): δ 11.14 (s, 1H), 8.49 (d, J=5.5 Hz, 1H), 7.93 (d, J=5.5 Hz, 1H), 7.74-7.20 (m, 2H), 7.67-7.65 (m, 1H), 2.18 (s, 3H). LCMS (Method B): RT=5.02 min, m/z: 338.0 [M+H$^+$].

Example 6

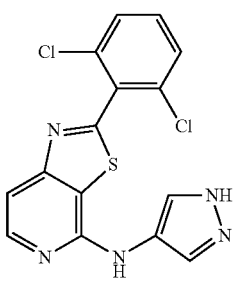 [SMILES: Clc1cccc(Cl)c1-c1nc2ccnc(Nc3cn[nH]c3)c2s1]

2-(2,6-Dichlorophenyl)-N-(1H-pyrazol-4-yl)thiazolo[5,4-c]pyridin-4-amine

To a microwave tube was added 4-bromo-2-(2,6-dichlorophenyl)thiazolo[5,4-c]pyridine (60 mg, 0.17 mmol), 1H-pyrazol-4-amine (0.018 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography eluting with a 0-60% gradient of CH$_3$CN in 0.5% NH$_4$HCO$_3$ to give the desired product as a white solid (12 mg, 20% yield). $^1$H NMR (500 MHz, CH$_3$OH-d$_4$): δ 8.27 (d, J=5.5 Hz, 1H), 8.12 (br, 1H), 7.74 (br, 1H), 7.64-7.58 (m, 3H), 7.41-7.40 (d, J=5.5 Hz, 1H). LCMS (Method A): RT=4.94 min, m/z: 362.0 [M+H$^+$].

Example 7

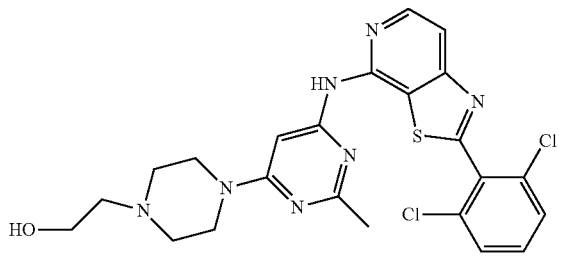 [SMILES: Cc1nc(Nc2nccc3nc(-c4c(Cl)cccc4Cl)sc23)cc(N2CCN(CCO)CC2)n1]

2-(4-(6-(2-(2,6-Dichlorophenyl)thiazolo[5,4-c]pyridin-4-ylamino)-2-methylpyrimidin-4-yl)piperazin-1-yl)ethanol To a microwave tube was added 4-bromo-2-(2,6-dichlorophenyl)thiazolo[5,4-c]pyridine (60 mg, 0.17 mmol), 2-(4-(6-amino-2-methylpyrimidin-4-yl)piperazin-1-yl)ethanol (0.052 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography, eluting with a 0-60% gradient of CH$_3$CN in 0.5% NH$_4$HCO$_3$ to give the desired product as a white solid (15 mg, 18% yield). $^1$H NMR (500 MHz, DMSO-d$_6$): δ 10.16 (s, 1H), 8.38 (d, J=5.5 Hz, 1H), 7.74-7.70 (m, 4H), 6.70 (s, 1H), 4.46 (t, J=5.5 Hz, 1H), 3.54-3.52 (m, 6H), 2.51-2.47 (m, 4H), 2.44-2.41 (m, 2H), 2.32 (s, 3H). LCMS (Method A): RT=5.52 min, m/z: 516.1 [M+H$^+$].

Example 8

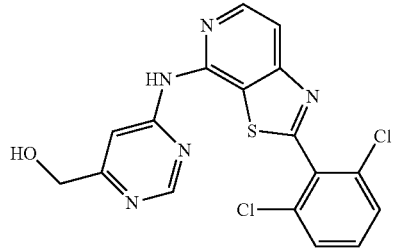 [SMILES: OCc1cc(Nc2nccc3nc(-c4c(Cl)cccc4Cl)sc23)ncn1]

(6-(2-(2,6-Dichlorophenyl)thiazolo[5,4-c]pyridin-4-ylamino)pyrimidin-4-yl)methanol Step 1. 6-Chloropyrimidin-4-amine A mixture of 4,6-dichloropyrimidine (20 g, 0.14 mol) and NH$_4$OH (200 mL) was heated at 30° C. for 15 hours with stirring. The resulting precipitate was collected via filtration, and the filter cake was washed with water (100 mL). The resultant solid was purified by silica gel column chromatography, eluting with EtOAc to give the desired product as a white solid (14 g, 81% yield). LCMS (ESI) m/z: 130.1 [M+H$^+$].

Step 2. 6-Vinylpyrimidin-4-amine

A mixture of 6-chloropyrimidin-4-amine (6.5 g, 0.050 mol), 4,4,5,5-tetramethyl-2-vinyl-1,3,2-dioxaborolane (9.24 g, 0.060 mol), tetrakis(triphenylphosphine)-palladium(0) (3.9 g, 0.0030 mol) and sodium carbonate (21 g, 0.20 mol) in dioxane (300 mL) and H$_2$O (30 mL) was stirred at 90° C. under nitrogen for 15 hours. The mixture was concentrated under reduced pressure and the residue was partitioned between EtOAc (400 mL) and water (150 mL). The organic layer was separated, dried over Na$_2$SO$_4$, and concentrated under reduced pressure. The resultant residue was purified by silica gel column chromatography eluting with DCM/MeOH (20:1) to give the desired product as a white solid (4.8 g, 80% yield). LCMS (ESI) m/z: 122.1 [M+H$^+$].

Step 3. tert-Butyl 6-vinylpyrimidin-4-ylcarbamate

6-Vinylpyrimidin-4-amine (3.6 g, 0.030 mol) was dissolved in anhydrous THF (50 mL) and a solution of sodium hexamethyldisilazide in THF (2M, 24 mL) was added dropwise over 5 minutes. The reaction was stirred for 10 minutes at room temperature, and then a solution of di-tert-butoxydicarbonate (10 g, 0.045 mol) in THF (20 mL) was added dropwise over 10 minutes). The reaction was stirred for 3 hours and then diluted with water (200 mL) and extracted with EtOAc (2×100 mL). The combined organic phase was washed with brine (200 mL), dried over MgSO$_4$ and concentrated under reduced pressure. The resultant residue was purified by silica gel column chromatography, eluting with DCM/MeOH (50:1) to afford the desired product (5.9 g, 90% yield). LCMS (ESI) m/z: 222.1 [M+H$^+$].

Step 4. tert-Butyl 6-formylpyrimidin-4-ylcarbamate

To a stirred solution of tert-butyl 6-vinylpyrimidin-4-ylcarbamate (4.4 g, 0.020 mol) in MeOH (200 mL) at −78° C. was bubbled O$_3$ for 1 hour. N$_2$ was bubbled through the mixture for 10 minutes and then dimethylsulfide (1.24 g, 0.020 mol) was added dropwise. After addition, the solvent was removed under reduced pressure to give the crude desired product (4.6 g, over 100% yield) which was used in the next step without purification. LCMS (ESI) m/z: 224.1 [M+H$^+$].

Step 5. tert-Butyl 6-(hydroxymethyl)pyrimidin-4-ylcarbamate

To a stirred solution of the crude tert-butyl 6-formylpyrimidin-4-ylcarbamate (4.6 g, 0.020 mol) in MeOH (100 mL) was added sodium borohydride (0.74 g, 0.020 mol) in four portions at room temperature. After addition, the resulting mixture was stirred for 1 hour and then water (50 mL) was added. The solvent was removed under reduced pressure and the resulting aqueous residue was extracted with EtOAc (3×100 mL). The combined organic extract was washed with water (30 mL) and brine (30 mL), dried over Na$_2$SO$_4$ and concentrated under reduced pressure. The residue was purified via silica gel column chromatography, eluting with DCM/MeOH (30:1) to give the desired product (1.4 g, 30% yield). LCMS (ESI) m/z: 226.0 [M+H$^+$].

Step 6. (6-Aminopyrimidin-4-yl)methanol hydrochloric salt

Concentrated hydrochloric acid (0.80 mL) was added to a solution of tert-butyl-6-(hydroxymethyl)pyrimidin-4-ylcarbamate (0.50 g, 2.2 mmol) in MeOH (10 mL). The reaction was stirred at 25° C. for 1 hour and then concentrated under reduced pressure to give the desired compound (0.50 g) as a pale yellow solid, which was used in the next step without further purification. LCMS (ESI) m/z: 126.0 [M+H$^+$].

Step 7. (6-(2-(2,6-Dichlorophenyl)thiazolo[5,4-c]pyridin-4-ylamino)pyrimidin-4-yl)methanol To a microwave tube was added 4-bromo-2-(2,6-dichlorophenyl)thiazolo[5,4-c]pyridine (60 mg, 0.17 mmol), (6-aminopyrimidin-4-yl)methanol hydrochloride salt (0.052 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography, eluting with a 0-60% gradient of CH$_3$CN in 0.5% NH$_4$HCO$_3$ to give the desired product as a white solid (20 mg, 24% yield). $^1$H NMR (500 MHz, DMSO-d$_6$): δ 10.71 (s, 1H), 8.63 (s, 1H), 8.45 (d, J=5.5 Hz, 1H), 7.85-7.66 (m, 5H), 5.58 (m, 1H), 4.49 (d, J=5.5 Hz, 2H). LCMS (Method B): RT=4.84 min, m/z: 404.0 [M+H$^+$].

Example 9

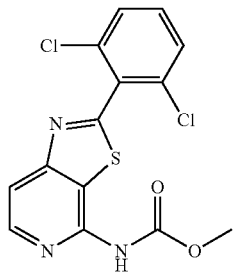 [SMILES: COC(=O)Nc1nccc2nc(-c3c(Cl)cccc3Cl)sc12]

2-(2,6-Dichlorophenyl)thiazolo[5,4-c]pyridin-4-yl-carbamate

To a microwave tube was added 4-bromo-2-(2,6-dichlorophenyl)thiazolo[5,4-c]pyridine (60 mg, 0.17 mmol), methyl carbamate (0.017 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 160° C. for 2 hours. After cooling to room temperature the solid was removed via filtration. The filtrate was concentrated under reduced pressure and the residue was purified by reverse phase column chromatography, eluting with a 0-60% gradient of $CH_3CN$ in 0.5% $NH_4HCO_3$ to give the desired product as a white solid (12 mg, 20% yield). $^1H$ NMR (500 MHz, DMSO-$d_6$): δ 10.74 (br, 1H), 8.44 (d, J=6.5 Hz, 1H), 7.92 (d, J=6.5 Hz, 1H), 7.75-7.69 (m, 3H), 3.7 (s, 3H). LCMS (Method A): RT=5.60 min, m/z: 354.0 [M+H$^+$].

Example 10

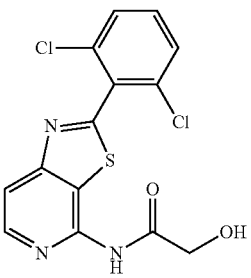 [SMILES: O=C(CO)Nc1nccc2nc(-c3c(Cl)cccc3Cl)sc12]

N-(2-(2,6-Dichlorophenyl)thiazolo[5,4-c]pyridin-4-yl)-2-hydroxyacetamide

To a microwave tube was added 4-bromo-2-(2,6-dichlorophenyl)thiazolo[5,4-c]pyridine (60 mg, 0.17 mmol), 2-hydroxyacetamide (0.017 g, 0.22 mmol), $Pd_2(dba)_3$ (0.013 g, 0.017 mmol), XantPhos (0.017 g, 0.034 mmol) and $Cs_2CO_3$ (0.11 g, 0.34 mmol) in dioxane (3.0 mL). The mixture was degassed with $N_2$ for 10 minutes and then irradiated in a microwave reactor at 160° C. for 2 hours. After cooling to room temperature the solid was removed via filtration. The filtrate was concentrated under reduced pressure and the residue was purified by reverse phase column chromatography, eluting with a 0-60% gradient of $CH_3CN$ in 0.5% $NH_4HCO_3$ to give the desired product as a white solid (16 mg, 27% yield). $^1H$ NMR (DMSO-$d_6$, 500 MHz): δ 8.48 (d, J=7.0 Hz, 1H), 7.97 (d, J=7.0 Hz, 1H), 7.75-7.65 (m, 3H), 5.75 (t, J=7.0 Hz, 1H), 4.16 (d, J=7.0 Hz, 2H). LCMS (Method B): RT=4.73 min, m/z: 354.0 [M+H$^+$].

Example 11

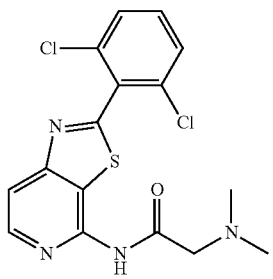

N-(2-(2,6-Dichlorophenyl)thiazolo[5,4-c]pyridin-4-yl)-2-(dimethylamino)acetamide To a microwave tube was added 4-bromo-2-(2,6-dichlorophenyl)thiazolo[5,4-c]pyridine (60 mg, 0.17 mmol), 2-(dimethylamino)acetamide (0.023 g, 0.22 mmol), $Pd_2(dba)_3$ (0.013 g, 0.017 mmol), XantPhos (0.017 g, 0.034 mmol) and $Cs_2CO_3$ (0.11 g, 0.34 mmol) in dioxane (3.0 mL). The mixture was degassed with $N_2$ for 10 minutes and then irradiated in a microwave reactor at 160° C. for 2 hours. After cooling to room temperature the solid was removed via filtration. The filtrate was concentrated under reduced pressure and the residue was purified by reverse phase column chromatography, eluting with a 0-60% gradient of $CH_3CN$ in 0.5% $NH_4HCO_3$ to give the desired product as a white solid (15 mg, 25% yield). $^1H$ NMR (500 MHz, DMSO-$d_6$): δ 10.62 (s, 1H), 8.46 (d, J=6.0 Hz, 1H), 7.96 (d, J=6.0 Hz, 1H), 7.74-7.65 (m, 3H), 3.24 (s, 2H), 2.49 (s, 6H). LCMS (Method B): RT=6.01 min, m/z: 381.1 [M+H$^+$].

Example 12

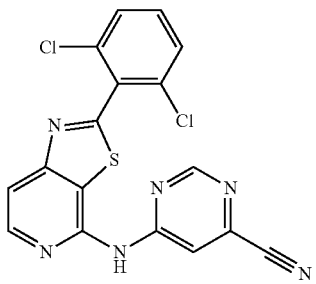 [SMILES: N#Cc1cc(Nc2nccc3nc(-c4c(Cl)cccc4Cl)sc23)ncn1]

6-(2-(2,6-Dichlorophenyl)thiazolo[5,4-c]pyridin-4-ylamino)pyrimidine-4-carbonitrile Step 1. 6-Aminopyrimidine-4-carbonitrile A mixture of 6-chloropyrimidin-4-amine (3.0 g, 23 mmol), zinc (II) cyanide (5.4 g, 46 mmol) and tetrakis(triphenylphosphine)palladium(0) (1.3 g, 1.2 mmol) in dry DMF (50 mL) was heated to 120° C. under nitrogen atmosphere for 15 hours. EtOAc (100 mL) was added and the insoluble precipitate was removed by filtration. The filtrate was diluted with water (100 mL), and extracted with EtOAc (3×50 mL). The combined organic extract was washed with brine, dried over $Na_2SO_4$, and concentrated under reduced pressure. The residue was purified by reverse phase column chromatography, eluting with a 0-60% gradient of $CH_3CN$ in 0.5% $NH_4HCO_3$ to give the desired product as a pale yellow solid (0.6 g, 21% yield). LCMS (ESI) m/z: 121.2 [M+H$^+$].

Step 2. 6-(2-(2,6-Dichlorophenyl)thiazolo[5,4-c]pyridin-4-ylamino)pyrimidine-4-carbonitrile To a microwave tube was added 4-bromo-2-(2,6-dichlorophenyl)thiazolo[5,4-c]pyridine (60 mg, 0.17 mmol), 6-aminopyrimidine-4-carbonitrile (0.029 g, 0.22 mmol), $Pd_2(dba)_3$ (0.013 g, 0.017 mmol), XantPhos (0.017 g, 0.034 mmol) and $Cs_2CO_3$ (0.11 g, 0.34 mmol) in dioxane (3.0 mL). The mixture was degassed with $N_2$ for 10 minutes and then irradiated in a microwave reactor at 160° C. for 2 hours. After cooling to room temperature the solid was removed via filtration. The filtrate was concentrated under reduced pressure and the residue was purified with reverse phase column chromatography, eluting with a 0-60% gradient of $CH_3CN$ in 0.5% $NH_4HCO_3$ to give the desired product as a white solid (21 mg, 35% yield). $^1H$ NMR (500 MHz, DMSO-$d_6$): δ 11.43

(s, 1H), 8.91 (s, 1H), 8.54 (d, J=5.0 Hz, 1H), 8.31 (s, 1H), 8.00 (d, J=5.0 Hz, 1H), 7.76-7.67 (m, 3H). LCMS (Method B): RT=6.30 min, m/z: 399.0 [M+H⁺].

Example 13

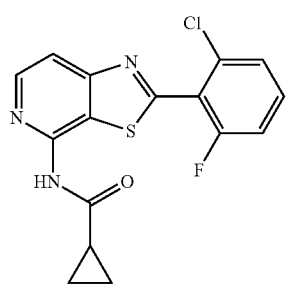 [SMILES: O=C(Nc1nccc2nc(-c3c(F)cccc3Cl)sc12)C1CC1]

N-(2-(2-Chloro-6-fluorophenyl)thiazolo[5,4-c]pyridin-4-yl)cyclopropanecarboxamide Procedure A:

Step 1. 2-Chloro-6-fluorobenzothioamide

A mixture of 2-chloro-6-fluorobenzonitrile (100 g, 643 mmol), triethylamine (71.5 g, 707 mmol) and (NH$_4$)$_2$S (20% aqueous solution, 240 ml, 707 mmol) in pyridine (500 mL) was stirred at 50° C. for 4 hours. After cooling to room temperature, the mixture was concentrated under reduced pressure. The residue was dissolved in water (400 mL) and extracted with EtOAc (3×300 mL). The combined organic extract was washed with brine (100 mL), dried over Na$_2$SO$_4$, and concentrated under reduced pressure. The resultant residue was re-crystallized from EtOAc and petroleum ether to give the desired product as a pale yellow solid (101 g, 78% yield). LCMS (ESI) m/z: 190.1 [M+H⁺].

Step 2. Ethyl 2-(2-chloro-6-fluorophenyl)thiazole-4-carboxylate

A mixture of 2-chloro-6-fluorobenzothioamide (15 g, 79 mmol) and 3-bromo-2-oxopropanoate (30.8 g, 158 mmol) in DMF (200 mL) was stirred at 20° C. for 18 hours. The reaction mixture was poured into water (100 mL) and extracted with EtOAc (3×100 mL). The combined organic extract was washed with brine (100 mL), dried over Na$_2$SO$_4$ and concentrated under reduced pressure. The residue was dissolved in toluene (800 mL) and p-TsOH (2.0 g) was added. The mixture was heated at 120° C. for 4 hours and then cooled to room temperature. The mixture was concentrated under reduced pressure and the residue was purified via silica gel column chromatography, eluting with EtOAc/petroleum ether (1:10) to give the desired product as a brown solid (17 g, 90% yield). ¹H NMR (500 MHz, DMSO-d$_6$): δ 7.70 (s, 1H), 7.35-7.07 (m, 3H), 4.52 (q, J=14.0 Hz, 7.5 Hz, 2H), 1.35 (t, J=7.5 Hz, 3H). LCMS (ESI) m/z: 286.1 [M+H⁺].

Step 3. (2-(2-Chloro-6-fluorophenyl)thiazol-4-yl)methanol

To a cooled (0° C.) solution of ethyl 2-(2-chloro-6-fluorophenyl)thiazole-4-carboxylate (7.0 g, 25 mmol) in MeOH (100 mL) was added lithium borohydride (1.62 g, 73.8 mmol) in four portions. After addition, the resulting mixture was stirred at 0° C. for 1 hour. The mixture was quenched with water (100 mL), and extracted with EtOAc (3×100 mL). The combined organic extract was washed with brine (100 mL), dried over Na$_2$SO$_4$, and concentrated under reduced pressure. The residue was purified via silica gel column chromatography, eluting with EtOAc/petroleum ether (1:5) to give the desired product as a white solid (5.8 g, 98% yield). ¹H NMR (500 MHz, DMSO-d$_6$): δ 7.74 (s, 1H), 7.35-7.41 (m, 1H) NOT ENOUGH AR PROTONS, 5.47 (s, 1H), 4.67 (m, 2H). LCMS (ESI) m/z: 244.1 [M+H⁺].

Step 4. 2-(2-Chloro-6-fluorophenyl)thiazole-4-carbaldehyde

To a stirred solution of (2-(2-chloro-6-fluorophenyl)thiazol-4-yl)methanol (5.8 g, 24 mmol) in EtOAc (200 mL) at room temperature was added 2-iodoxybenzoic acid (12.5 g, 44.6 mmol). The resulting mixture was heated at 70° C. for 18 hours. After cooling to room temperature, the residual solid was removed via filtration and the filtrate was concentrated under reduced pressure to give the crude desired product as a white solid (5.4 g, 93% yield) which was used in the next step without further purification.

Step 5. (E)-methyl 3-(2-(2-chloro-6-fluorophenyl) thiazol-4-yl)acrylate

To a cooled (0° C.) solution of Ph$_3$PCHCOOMe (7.5 g, 22 mmol) in anhydrous DCM (200 mL) was added a solution of 2-(2-chloro-6-fluorophenyl)thiazole-4-carbaldehyde (5.4 g, 22 mmol) in DCM (20 mL) dropwise over 15 minutes. After addition, the resulting mixture was slowly warmed to room temperature and stirred for another 4 hours. The mixture was concentrated under reduced pressure and the residue was taken up in petroleum ether (250 mL). The resulting precipitate was removed by filtration and the filtrate was concentrated under reduced pressure. The residue was purified via silica gel column chromatography, eluting with EtOAc/petroleum ether (1:8) to give the desired product as a white solid (6.0 g, 90% yield). LCMS (ESI) m/z: 298.1 [M+H⁺].

Step 6. (E)-3-(2-(2-Chloro-6-fluorophenyl)thiazol-4-yl)acrylic acid

To a stirred solution of (E)-methyl 3-(2-(2-chloro-6-fluorophenyl)thiazol-4-yl)acrylate (6.0 g, 20 mmol) in MeOH (100 mL) and H$_2$O (20 mL) was added lithium hydroxide (1.5 g, 61 mmol). The resulting mixture was stirred at room temperature for 24 hours and then partially concentrated under reduced pressure. The pH of the residue was adjusted to 5 by the addition of 2N HCl and the aqueous phase extracted with EtOAc (3×100 mL). The combined organic extract was washed with brine (100 mL), dried over Na$_2$SO$_4$, and concentrated under reduced pressure. The residue was purified by silica gel column chromatography, eluting with a 0-20% gradient of MeOH in DCM to give the desired product as a white solid (5.4 g, 94% yield). LCMS (ESI) m/z: 284.0 [M+H⁺].

Step 7. (E)-3-(2-(2-Chloro-6-fluorophenyl)thiazol-4-yl)acryloyl chloride

To a suspension of (E)-3-(2-(2-chloro-6-fluorophenyl) thiazol-4-yl)acrylic acid (5.4 g, 19 mmol) in DCM (20 mL) was added oxalyl chloride (4.8 g, 38 mmol) and 2 drops of DMF. The resulting mixture was stirred at room temperature for 2 hours and then concentrated under reduced pressure to give the crude product (5.7 g, 100% yield), which was used in the next step without purification.

Step 8. (E)-3-(2-(2-Chloro-6-fluorophenyl)thiazol-4-yl)acryloyl azide

To a cooled (0° C.) solution of NaN$_3$ (6.2 g, 95 mmol) in water (100 mL) and acetone (100 mL) was added a solution of (E)-3-(2-(2-chloro-6-fluorophenyl)thiazol-4-yl)acryloyl chloride (5.7 g, 19 mmol) in dioxane (100 mL) dropwise over 15 minutes. After addition, the resulting mixture was stirred for another 1 hour at 0° C. The reaction was quenched with water (50 mL) and extracted with EtOAc (3×100 mL). The combined organic extract was washed brine (100 mL), dried over Na$_2$SO$_4$, and concentrated under reduced pressure. The residue was purified with silica gel column chromatography, eluting with EtOAc/petroleum ether (1:8) to give the desired product as a yellow solid (5.3 g, 90% yield). LCMS (ESI) m/z: 309.0 [M+H$^+$].

Step 9. 2-(2-Chloro-6-fluorophenyl)thiazolo[5,4-c]pyridin-4(5H)-one

To a stirred solution of Dowthem A® (20 ml) at 230° C. was added a solution of (E)-3-(2-(2-chloro-6-fluorophenyl)thiazol-4-yl)acryloyl azide (0.30 g, 1.0 mmol) in dioxane (1.0 mL) dropwise over 15 minutes. After addition, the resulting mixture was stirred at 230° C. for 1 hour and then cooled to room temperature. The mixture was purified on a short silica gel column, eluting first with petroleum ether and then with EtOAc/petroleum ether (1:1) to give the desired product as a yellow solid (0.10 g, 35% yield). LCMS (ESI) m/z: 281.0 [M+H$^+$].

Step 10. 4-Bromo-2-(2-chloro-6-fluorophenyl)thiazolo[5,4-c]pyridine

To a stirred solution of 2-(2-chloro-6-fluorophenyl)thiazolo[5,4-c]pyridin-4(5H)-one (0.30 g, 1.1 mmol) in MeCN (50 mL), was added POBr$_3$ (0.92 g, 3.2 mmol). The mixture was heated at 100° C. for 2 hours and then cooled to room temperature. The reaction was quenched with ice and extracted with EtOAc (3×20 mL). The combined organic extract was washed with saturated NaHCO$_3$ solution (100 mL) and brine (100 mL), dried over Na$_2$SO$_4$ and concentrated under reduced pressure. The residue was purified by silica gel column chromatography eluting with a 0-10% gradient of EtOAc in petroleum ether to give the desired product as a white solid (0.22 g, 60% yield). $^1$H NMR (500 MHz, DMSO-d$_6$): δ 8.59 (d, J=5.5 Hz, 1H), 8.27 (d, J=5.5 Hz, 1H), 7.76-7.68 (m, 3H). LCMS (ESI) m/z: 342.9 [M+H$^+$].

Step 11. N-(2-(2-Chloro-6-fluorophenyl)thiazolo[5,4-c]pyridin-4-yl)cyclopropanecarboxamide To a microwave tube was added 4-bromo-2-(2-chloro-6-fluorophenyl)thiazolo[5,4-c]pyridine (0.050 g, 1.5 mmol), cyclopropanecarboxamide (0.019 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (2.0 mL). The mixture was degassed with N$_2$ for 10 minutes and then irradiated in a microwave reactor at 160° C. for 2 hours. After cooling to room temperature, the solid was removed via filtration and the filtrate was concentrated under reduced pressure. The residue was purified with reverse phase column chromatography, eluting with a 0-60% gradient of CH$_3$CN in 0.5% NH$_4$HCO$_3$ to give the desired product as a white solid (0.030 g, 59% yield). $^1$H NMR (500 MHz, DMSO-d$_6$): δ 11.43 (s, 1H), 8.46 (d, J=6.0 Hz, 1H), 7.92 (d, J=6.0 Hz, 1H), 7.72-7.68 (m, 1H), 7.67-7.59 (m, 1H), 7.52-7.49 (m, 1H), 2.09-2.06 (m, 1H), 0.92-0.86 (m, 4H). LCMS (Method A): RT=6.30 min, m/z: 348.0 [M+H$^+$].

Procedure B:

Step 1. 2-Chloro-N-(2-chloro-3-fluoro-pyridine-4-yl)-6-fluorobenzamide

A mixture of 2-chloro-3-fluoropyridin-4-ylamine (293 mg, 2.0 mmol), 2-chloro-6-fluoro-benzoyl chloride (400 mg, 2.07 mmol) and triethylamine (300 μL, 218 mg, 2.15 mmol) in dioxane (6 mL) was heated at 50° C. for 4 hours. After cooling to ambient temperature, triethylamine (60 μL) and 2-chloro-6-fluorobenzoyl chloride (40 μL) were added. The resultant mixture was heated under reflux for a further 2 hours. The reaction mixture was cooled and concentrated under reduced pressure. The residue was purified by silica gel flash chromatography eluting with DCM and the resultant solid was triturated in diethyl ether, filtered, and dried to give the desired compound as a white solid (380 mg, 63% yield). $^1$H NMR (400 MHz, DMSO-d$_6$): δ 11.46 (br s, 1H), 8.27-8.23 (m, 2H), 7.59 (td, J=8.3, 6.2 Hz, 1H), 7.47 (d, J=8.1 Hz, 1H), 7.42-7.37 (m, 1H). LCMS (Method C): RT=3.34 min, m/z: 303 [M+H$^+$].

Step 2. 2-Chloro-N-(2-chloro-3-fluoro-pyridin-4-yl)-6-fluorobenzimidoyl chloride A mixture of 2-chloro-N-(2-chloro-3-fluoro-pyridine-4-yl)-6-fluorobenzamide (600 mg, 2 mmol) and thionyl chloride (5 mL) was heated under reflux for 16 hours then cooled to ambient temperature. The reaction mixture was diluted with toluene (6 mL) and concentrated to dryness under reduced pressure to give the desired compound as a brown oil (650 mg, quant. yield). $^1$H NMR (400 MHz, CDCl$_3$): δ 8.23 (d, J=5.1 Hz, 1H), 7.44 (td, J=8.3, 5.6 Hz, 1H), 7.33 (d, J=8.2 Hz, 1H), 7.16 (t, J=8.7 Hz, 1H), 6.97 (t, J=5.1 Hz, 1H).

Step 3. 4-Chloro-2-(2-chloro-6-fluoro-phenyl)-thiazolo[5,4-c]pyridine

A mixture of 2-chloro-N-(2-chloro-3-fluoro-pyridin-4-yl)-6-fluorobenzimidoyl chloride (80 mg, 0.25 mmol), thiourea (76 mg, 1.0 mmol) and pyridine (82 μL, 1.0 mmol) in anhydrous isopropanol (1.5 mL) was heated under reflux, under nitrogen, for 3.5 hours. The reaction mixture was allowed to cool to ambient temperature and then triethylamine (1 mL) was added. The resultant mixture was heated under reflux for a further 1 hour then cooled to ambient temperature. The mixture was concentrated to dryness under reduced pressure and the residue was triturated with DCM, filtered and left to air dry. The crude product was purified by silica gel flash chromatography (0-10% EtOAc in cyclohexane) to give the desired compound as a white solid (65 mg, 86% yield). $^1$H NMR (400 MHz, CDCl$_3$): δ 8.52 (d, J=5.6 Hz, 1H), 7.99 (d, J=5.6 Hz, 1H), 7.50 (td, J=8.3, 5.8 Hz, 1H), 7.41 (dt, J=8.2, 1.1 Hz, 1H), 7.21 (ddd, J=9.0, 8.4, 1.1 Hz, 1H). LCMS (Method C): RT=3.90 min, m/z: 299 [M+H$^+$].

Step 4. Cyclopropanecarboxylic acid [2-(2-chloro-6-fluoro-phenyl)-thiazolo[5,4-c]pyridin-4-yl]-amide A mixture of 4-chloro-2-(2-chloro-6-fluoro-phenyl)-thiazolo[5,4-c]pyridine (0.050 g, 0.17 mmol), cyclopropanecarboxamide (0.016 g, 0.18 mmol), Pd$_2$(dba)$_3$ (0.008 g, 0.009 mmol), XantPhos (0.010 g, 0.017 mmol) and cesium carbonate (0.139 g, 0.43 mmol) in dioxane (1.7 mL) was degassed with nitrogen then subjected to microwave irradiation at 170° C. for 60 minutes. Further cyclopropanecarboxamide (0.006 g, 0.08 mmol), Pd$_2$(dba)$_3$ (0.010 g, 0.010 mmol) and XantPhos (0.012 g, 0.021 mmol) were added. The mixture was degassed with nitrogen then subjected to microwave irradiation at 200° C. for 90 minutes. Water and DCM were added and the resulting mixture was filtered through Celite®. The layers of the filtrate were separated via a phase separator and the organic phase concentrated under reduced pressure. The residue was loaded onto an Isolute® SCX-2 cartridge that was washed with MeOH and the product eluted with 2M ammonia in MeOH. The relevant fractions were combined, concentrated under reduced pressure and the resultant residue was purified by silica gel flash chromatography (0-30% EtOAc in DCM) to give the desired compound as an off-white solid (0.018 g, 30% yield). $^1$H NMR (300 MHz, DMSO-d$_6$): δ 11.40 (s, 1H), 8.45 (d, J=5.6 Hz, 1H), 7.92 (d, J=5.6 Hz, 1H), 7.69 (dd, J=8.3, 6.1 Hz, 1H), 7.59-7.58 (m, 1H), 7.52-7.49 (m, 1H), 2.13-2.03 (s, 1H), 0.91-0.90 (m, 4H). LCMS (Method D): RT=3.36 min, m/z: 348 [M+H$^+$].

Example 14

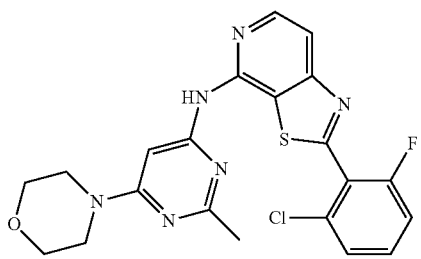 [SMILES: Cc1nc(Nc2nccc3nc(-c4c(F)cccc4Cl)sc23)cc(N2CCOCC2)n1]

2-(2-Chloro-6-fluorophenyl)-N-(2-methyl-6-morpholinopyrimidin-4-yl)thiazolo[5,4-c]pyridin-4-amine To a microwave tube was added 4-bromo-2-(2-chloro-6-fluorophenyl)thiazolo[5,4-c]pyridine (0.050 g, 1.5 mmol), 2-methyl-6-morpholinopyrimidin-4-amine (0.043 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (2.0 mL). The mixture was degassed with N$_2$ for 10 minutes and then irradiated in a microwave reactor at 160° C. for 2 hours. After cooling to room temperature, the solid was removed via filtration and the filtrate was concentrated under reduced pressure. The residue was purified with reverse phase column chromatography, eluting with a 0-60% gradient of CH$_3$CN in 0.5% NH$_4$HCO$_3$ to give the desired product as a yellow solid (0.016 g, 24% yield). $^1$H NMR (500 MHz, DMSO-d$_6$): δ 10.22 (s, 1H), 8.38 (d, J=5.5 Hz, 1H), 7.75 (d, J=5.5 Hz, 1H), 7.73-7.68 (m, 1H), 7.62-7.60 (m, 1H), 7.54-7.50 (m, 1H), 6.75 (s, 1H), 3.69-3.67 (m, 4H), 3.52-3.50 (m, 4H), 2.33 (s, 3H). LCMS (Method A): RT=6.16 min, m/z: 457.1 [M+H$^+$].

Example 15

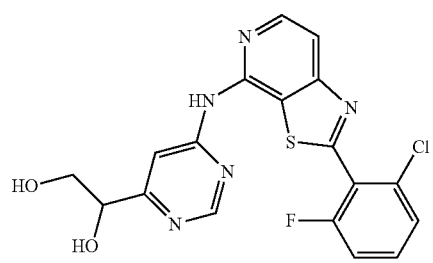 [SMILES: OCC(O)c1cc(Nc2nccc3nc(-c4c(F)cccc4Cl)sc23)ncn1]

1-(6-(2-(2-Chloro-6-fluorophenyl)thiazolo[5,4-c]pyridin-4-ylamino)pyrimidin-4-yl)ethane-1,2-diol Step 1. 1-(6-Aminopyrimidin-4-yl)ethane-1,2-diol To a stirred suspension of 6-vinylpyrimidin-4-amine (700 mg, 5.78 mmol) in t-BuOH (25 mL) at room temperature was added a solution of OsO$_4$ (2% in t-BuOH, 3 mL). The resulting mixture was stirred at room temperature for 15 hours. The reaction was diluted with water (50 mL) and then extracted with EtOAc (2×20 mL). The aqueous layer was lyophilized and the residue was purified via prep-HPLC (Gilson GX 281, Shim-pack PRC-ODS 250 mm×20 mm×2, gradient: CH$_3$CN/10 mm/L NH$_4$HCO$_3$, 17 min) to give the desired diol (160 mg, 18% yield) as a white solid. $^1$H NMR (500 MHz, D$_2$O): δ 8.16 (s, 1H), 6.59 (s, 1H), 4.52 (m, 1H), 3.78 (m, 1H), 3.64 (m, 1H). LCMS (ESI) m/z: 138.0 [M+H$^+$].

Step 2. 1-(6-(2-(2-Chloro-6-fluorophenyl)thiazolo[5,4-c]pyridin-4-ylamino)pyrimidin-4-yl)ethane-1,2-diol To a microwave tube was added 4-bromo-2-(2-chloro-6-fluorophenyl)thiazolo[5,4-c]pyridine (0.050 g, 1.5 mmol), 2-methyl-6-morpholinopyrimidin-4-amine (0.043 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (2.0 mL). The mixture was degassed with N$_2$ for 10 minutes and then irradiated in a microwave reactor at 160° C. for 2 hours. After cooling to room temperature, the solid was removed via filtration and the filtrate was concentrated under reduced pressure. The residue was purified with reverse phase column chromatography eluting with a 0-60% gradient of CH$_3$CN in 0.5% NH$_4$HCO$_3$ to give the desired product as a yellow solid (0.040 g, 60% yield). $^1$H NMR (500 MHz, DMSO-d$_6$): δ 10.72 (s, 1H), 8.64 (s, 1H), 8.46 (d, J=5.5 Hz, 1H), 7.85 (d, J=5.5 Hz, 1H), 7.76-7.70 (m, 2H), 7.61-7.60 (m, 1H), 7.54-7.52 (m, 1H), 5.57-5.56 (m, 1H), 4.76-4.74 (m, 1H), 4.50-

4.47 (m, 1H), 3.75-3.71 (m, 1H), 3.54-3.50 (m, 1H). LCMS (Method B): RT=4.33 min, m/z: 418.1 [M+H$^+$].

Example 16

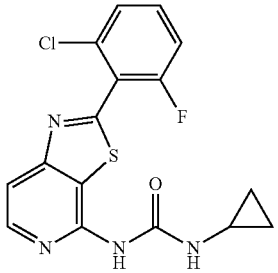 [SMILES: O=C(Nc1nccc2nc(-c3c(F)cccc3Cl)sc12)NC1CC1]

1-(2-(2-Chloro-6-fluorophenyl)thiazolo[5,4-c]pyridin-4-yl)-3-cyclopropylurea

Step 1. 1-cyclopropylurea

To a cooled (0° C.) mixture of cyclopropylamine (8.0 g, 0.14 mol) in 5N HCl (28 mL) was added potassium cyanate (11.3 g, 0.139 mol). The solution was stirred at 70° C. for 4 hours, cooled to room temperature and then concentrated under reduced pressure. The residue was diluted with petroleum ether (100 mL). The resulting precipitate was collected via filtration and washed with petroleum ether (2×50 mL) to give the desired product as a white solid (2.0 g, 10% yield).

Step 2. 1-(2-(2-chloro-6-fluorophenyl)thiazolo[5,4-c]pyridin-4-yl)-3-cyclopropylurea To a microwave tube was added 4-bromo-2-(2-chloro-6-fluorophenyl)thiazolo[5,4-c]pyridine (0.050 g, 1.5 mmol), 1-cyclopropylurea (0.043 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (2.0 mL). The mixture was degassed with N$_2$ for 10 minutes and then irradiated in a microwave reactor at 160° C. for 2 hours. After cooling to room temperature, solid was removed via filtration and the filtrate was concentrated under reduced pressure. The residue was purified with reverse phase column chromatography eluting with a 0-60% gradient of CH$_3$CN in 0.5% NH$_4$HCO$_3$ to give the desired product as a yellow solid (0.017 g, 26% yield). $^1$H NMR (500 MHz, DMSO-d$_6$): δ 9.64 (s, 1H), 8.32 (d, J=7.5 Hz, 1H), 7.99 (br, 1H), 7.75-7.49 (m, 4H), 2.63 (m, 1H), 0.72-0.66 (m, 2H), 0.52-0.46 (m, 2H). LCMS (Method A): RT=5.63 min, m/z: 363.0 [M+H$^+$].

Example 17

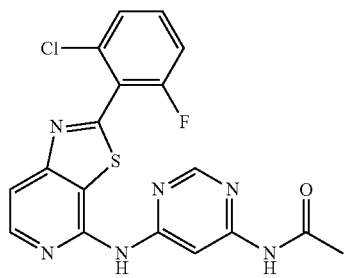 [SMILES: CC(=O)Nc1cc(Nc2nccc3nc(-c4c(F)cccc4Cl)sc23)ncn1]

N-(6-(2-(2-Chloro-6-fluorophenyl)thiazolo[5,4-c]pyridin-4-ylamino)pyrimidin-4-yl)acetamide Step 1. N-(6-aminopyrimidin-4-yl)acetamide To a stirred suspension of pyrimidine-4,6-diamine (500 mg, 4.55 mmol) in dioxane (20 mL) was added acetic anhydride (465 mg, 4.55 mmol) and the resulting mixture was heated under reflux for 15 hours. The reaction was cooled to room temperature and the resulting precipitate was collected by filtration. The filtercake was dissolved in 1N HCl and the pH of the aqueous phase adjusted to 7 by the addition of 1N NaOH. The resulting white precipitate was collected by filtration and dried to afford the desired product as a white solid (420 mg, 61% yield). LCMS (ESI) m/z: 152.0 [M+H$^+$].

Step 2. N-(6-(2-(2-Chloro-6-fluorophenyl)thiazolo[5,4-c]pyridin-4-ylamino)pyrimidin-4-yl)acetamide To a microwave tube was added 4-bromo-2-(2-chloro-6-fluorophenyl)thiazolo[5,4-c]pyridine (0.050 g, 1.5 mmol), N-(6-aminopyrimidin-4-yl)acetamide (0.034 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (2.0 mL). The mixture was degassed with N$_2$ for 10 minutes and then irradiated in a microwave reactor at 160° C. for 2 hours. After cooling to room temperature the solid was removed via filtration and the filtrate was concentrated under reduced pressure. The residue was purified with reverse phase column chromatography eluting with a 0-60% gradient of CH$_3$CN in 0.5% NH$_4$HCO$_3$ to give the desired product as a yellow solid (0.018 g, 27% yield). $^1$H NMR (500 MHz, DMSO-d$_6$): δ 10.67 (s, 1H), 8.48-8.25 (m, 3H), 7.85-7.51 (m, 4H), 2.12 (s, 3H). LCMS (Method A): RT=5.04 min, m/z: 415.0 [M+H$^+$].

Example 18

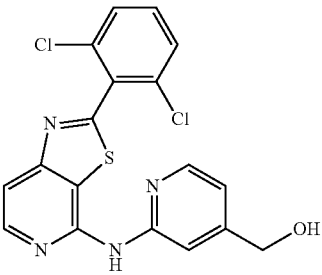 [SMILES: OCc1ccnc(Nc2nccc3nc(-c4c(Cl)cccc4Cl)sc23)c1]

(2-(2-(2,6-dichlorophenyl)thiazolo[5,4-c]pyridin-4-ylamino)pyridin-4-yl)methanol Step 1. (2-Chloro-3-fluoropyridin-4-yl)carbamic acid tert-butyl ester To a mixture of 2-chloro-3-fluoroisonicotinic acid (3.55 g, 20.2 mmol) and triethylamine (8.4 mL, 6.13 g, 60.6 mmol) in dry toluene (40 mL) and dry t-BuOH (40 mL) under nitrogen, was added diphenylphosphoryl azide (6.51 mL, 8.27 g, 30.1 mmol). The reaction was heated at 110° C. for 3 hours then cooled to ambient temperature. The reaction mixture was concentrated under reduced pressure. The residue was dissolved in DCM (50 mL) and washed with water (40 mL). The aqueous phase was extracted with DCM (2×40 mL) and the combined organic extract was dried over MgSO$_4$, and concentrated under reduced pressure. The residue was purified by silica gel flash chromatography (0-20% EtOAc in DCM) to give the title compound as a yellow oil (3.8 g, 71% yield). $^1$H NMR (400 MHz, CDCl$_3$): δ 8.09-8.07 (m, 2H), 6.98 (br s, 1H), 1.54 (s, 9H).

Step 2. 2-Chloro-3-fluoropyridin-4-ylamine

TFA (5 mL) was added to a solution of (2-chloro-3-fluoropyridin-4-yl)carbamic acid tert-butyl ester (1.9 g, 7.7 mmol) in DCM (10 mL). The solution was stirred at ambient temperature for 5 hours and concentrated under reduced pressure. The resultant residue was dissolved in DCM and purified by column chromatography on a NH$_2$ cartridge (0-10% MeOH in DCM) to afford the title compound as a beige solid (0.96 g, 94% yield). $^1$H NMR (400 MHz, CDCl$_3$): δ 7.82 (d, J=5.4 Hz, 1H), 6.60 (t, J=5.8 Hz, 1H), 4.38 (br s, 2H).

Step 3. 2,6-Dichloro-N-(2-chloro-3-fluoropyridin-4-yl)benzamide

A mixture of 2-chloro-3-fluoropyridin-4-ylamine (660 mg, 4.5 mmol), 2,6-dichlorobenzoyl chloride (1.43 mL, 2.10 g, 10.0 mmol) and triethylamine (1.53 mL, 1.11 g, 11.0 mmol) in dioxane (12 mL) was heated under reflux for 18 hours then cooled to ambient temperature. The resultant mixture was partitioned between EtOAc (50 mL) and water (50 mL). The organic layer was separated, washed with brine, dried over Na$_2$SO$_4$ and concentrated under reduced pressure. The residue was triturated with diethyl ether, filtered, dried and further purified by silica gel flash chromatography (0-25% EtOAc in pentane) to afford the title compound as a pink solid (1.17 g, 81% yield). $^1$H NMR (300 MHz, CDCl$_3$): δ 8.50 (t, J=5.3 Hz, 1H), 8.22 (d, J=5.5 Hz, 1H), 7.83 (br s, 1H), 7.40-7.39 (m, 3H).

Step 4. 2,6-Dichloro-N-(2-chloro-3-fluoropyridin-4-yl)benzimidoyl chloride

A mixture of 2,6-dichloro-N-(2-chloro-3-fluoropyridin-4-yl)benzamide (1.12 g, 3.5 mmol) and thionyl chloride (10 mL) was heated under reflux for 18 hours then cooled to ambient temperature. The reaction mixture was diluted with toluene (10 mL) and concentrated under reduced pressure to afford the title compound as a pale brown solid (1.23 g, quant. yield). $^1$H NMR (400 MHz, CDCl$_3$): δ 8.23 (d, J=5.1 Hz, 1H), 7.45-7.44 (m, 2H), 7.38 (dd, J=9.4, 6.5 Hz, 1H), 6.98 (t, J=5.1 Hz, 1H).

Step 5. 4-Chloro-2-(2,6-dichlorophenyl)thiazolo[5,4-c]pyridine

A mixture of 2,6-dichloro-N-(2-chloro-3-fluoropyridin-4-yl)benzimidoyl chloride (400 mg, 1.15 mmol), thiourea (305 mg, 4.0 mmol) and pyridine (325 µL, 4.0 mmol) in anhydrous isopropanol (6 mL) was heated under reflux under nitrogen for 3.5 hours. Triethylamine (1 mL) was added and heating was continued for a further 2 hours. The mixture was cooled to ambient temperature and concentrated under reduced pressure. The resultant residue was partitioned between DCM (15 mL) and water (15 mL). The aqueous phase was extracted with DCM (2×10 mL), the combined organic extract was dried over MgSO$_4$ and concentrated under reduced pressure. The residue was purified by silica gel flash chromatography (0-10% EtOAc in pentane) to give the title compound as a beige solid (270 mg, 74% yield). $^1$H NMR (400 MHz, CDCl$_3$): δ 8.52 (d, J=5.6 Hz, 1H), 7.98 (d, J=5.6 Hz, 1H), 7.52-7.48 (m, 2H), 7.45 (dd, J=9.6, 6.2 Hz, 1H).

Step 6. (2-(2-(2,6-dichlorophenyl)thiazolo[5,4-c]pyridin-4-ylamino)pyridin-4-yl)methanol To a microwave tube was added 4-chloro-2-(2,6-dichlorophenyl)thiazolo[5,4-c]pyridine (70 mg, 0.22 mmol), methyl carbamate (0.017 g, 0.22 mmol), Pd$_2$(dba)$_3$ (0.013 g, 0.017 mmol), XantPhos (0.017 g, 0.034 mmol) and Cs$_2$CO$_3$ (0.11 g, 0.34 mmol) in dioxane (3.0 mL). The mixture was degassed with N$_2$ for 10 minutes and then irradiated in a microwave reactor at 140° C. for 2 hours. After cooling to room temperature, the solid was removed via filtration and the filtrate was concentrated under reduced pressure. The residue was purified with reverse phase column chromatography eluting with a 0-60% gradient of CH$_3$CN in 0.5% NH$_4$HCO$_3$ to give the desired product as a white solid (45 mg, 50% yield). $^1$H NMR (500 MHz, DMSO-d$_6$): δ 10.17 (s, 1H), 8.34 (d, J=5.5 Hz, 1H), 8.16 (d, J=5.5 Hz, 1H), 7.73-7.59 (m, 5H), 6.90 (d, J=5.0 Hz, 1H), 5.43 (t, J=5.0 Hz, 1H), 4.53 (d, J=5.5 Hz, 2H). LCMS (Method C): RT=5.36 min, m/z: 403.0 [M+H$^+$].

Example 19

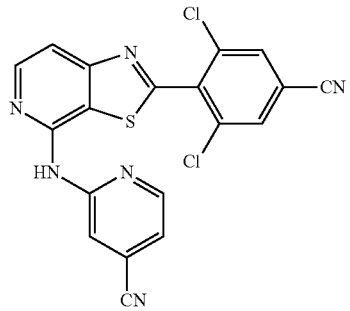 [SMILES: N#Cc1ccnc(Nc2nccc3nc(-c4c(Cl)cc(C#N)cc4Cl)sc23)c1]

2-[2-(2,6-Dichloro-4-cyano-phenyl)-thiazolo[5,4-c]pyridine-4-ylamino]-isonicotinonitrile

Step 1. 2,6-Dichloro-N-(2-chloro-3-fluoro-pyridin-4-yl)-4-cyano-benzamide

2-Chloro-3-fluoropyridin-4-ylamine (146 mg, 10 mmol) was added to a suspension of sodium hydride (60% dispersed in mineral oil, 80 mg, 2.0 mmol) in DMF (5 mL). The mixture was stirred for 30 minutes then 2,6-dichloro-4-cyano-benzoyl chloride (250 mg, 1.1 mmol) was added and stirring continued for 18 hours. Water (10 mL) and DCM (20 mL) were added to the reaction, and the resultant mixture was acidified with 1M HCl. The organic phase was separated, washed with brine (10 mL), dried over MgSO$_4$, and concentrated to dryness under reduced pressure. The residue was purified by silica gel flash chromatography eluting with DCM. The crude product was triturated with diethyl ether to give the desired compound as a white solid (230 mg, 67% yield). $^1$H NMR (400 MHz, CDCl$_3$): δ 8.46 (t, J=5.3 Hz, 1H), 8.25 (d, J=5.5 Hz, 1H), 7.88 (br s, 1H), 7.72 (s, 2H).

Step 2. 2,6-Dichloro-N-(2-chloro-3-fluoro-pyridin-4-yl)-4-cyano-benzimidoyl chloride A mixture of 2,6-dichloro-N-(2-chloro-3-fluoro-pyridin-4-yl)-4-cyano-benzamide (1.2 g, 3.4 mmol) and thionyl chloride (12.5 mL) was heated under reflux for 18 hours then cooled to ambient temperature. The reaction mixture was diluted with toluene (10 mL) and concentrated to dryness under reduced pressure to afford the title compound as a white solid (1.23 g, 97% yield). $^1$H NMR (400 MHz, CDCl$_3$): δ 8.25 (d, J=5.1 Hz, 1H), 7.75 (s, 2H), 6.97 (t, J=5.1 Hz, 1H).

Step 3. 3,5-Dichloro-4-(4-chloro-thiazolo[5,4-c]pyridine-2-yl)-benzonitrile

A mixture of 2,6-dichloro-N-(2-chloro-3-fluoro-pyridin-4-yl)-4-cyano-benzimidoyl chloride (454 mg, 1.25 mmol), thiourea (380 mg, 5.0 mmol) and pyridine (325 μL, 4.0 mmol) in anhydrous isopropanol (4 mL) was heated under reflux, under nitrogen, for 16 hours. Triethylamine (1.05 mL, 7.5 mmol) was added and the resultant mixture was heated under reflux for a further 6.5 hours. The mixture was cooled to ambient temperature and concentrated to dryness under reduced pressure. The residue was partitioned between DCM (15 mL) and water (15 mL). The aqueous phase was extracted with DCM (2×10 mL) and the combined organic extract was dried over MgSO$_4$ and concentrated to dryness under reduced pressure. The residue was purified by silica gel flash chromatography eluting with 0-20% EtOAc in DCM. The resultant solid was triturated with cyclohexane and dried under reduced pressure to give the desired compound as a white solid (275 mg, 65% yield). $^1$H NMR (400 MHz, CDCl$_3$): δ 8.55 (d, J=5.6 Hz, 1H), 8.00 (d, J=5.6 Hz, 1H), 7.79 (s, 2H).

Step 4. 4-(4-Bromo-thiazolo[5,4-c]pyridine-2-yl)-3,5-dichloro-benzonitrile

Trimethylsilylbromide (0.23 mL, 1.74 mmol) was added to a stirred solution of 3,5-dichloro-4-(4-chloro-thiazolo[5,4-c]pyridine-2-yl)-benzonitrile (295 mg, 0.87 mmol) in propionitrile (11 mL) and the mixture heated at 90° C. for 48 hours. The reaction mixture was allowed to cool and poured onto a mixture of saturated aqueous potassium carbonate solution and ice. DCM was added and the organic phase was separated, dried over Na$_2$SO$_4$ and concentrated to dryness under reduced pressure to give the desired compound as a white solid (322 mg, 96% yield). $^1$H NMR (300 MHz, CDCl$_3$): δ 8.53 (d, J=5.5 Hz, 1H), 8.03-8.00 (m, 1H), 7.80 (s, 2H). LCMS (Method D): RT=4.04 min, m/z: 386 [M+H$^+$].

Step 5. 2-[2-(2,6-Dichloro-4-cyano-phenyl)-thiazolo[5,4-c]pyridine-4-ylamino]-isonicotinonitrile Argon was bubbled through a suspension of 4-(4-bromo-thiazolo[5,4-c]pyridine-2-yl)-3,5-dichloro-benzonitrile (92 mg, 0.24 mmol), 2-amino-isonicotinonitrile (26 mg, 0.22 mmol), XantPhos (14 mg, 0.024 mmol) and cesium carbonate (195 mg, 0.6 mmol) in dioxane (2.5 ml) for 5 minutes then Pd$_2$(dba)$_3$ (11 mg, 0.012 mmol) was added. The reaction was heated at 70° C. for 8 hours and then cooled to room temperature. The reaction was partitioned between water (10 mL) and DCM (20 mL). The organic layer was separated, dried over Na$_2$SO$_4$ and concentrated to dryness under reduced pressure. The resultant residue was purified by silica gel flash chromatography eluting with 0-60% EtOAc in DCM. The resultant solid was triturated with diethyl ether, filtered, and left to air dry to give the desired compound as a yellow solid (64 mg, 63% yield). $^1$H NMR (400 MHz, DMSO-d$_6$): δ 10.74 (br s, 1H), 8.50 (dd, J=5.1, 0.9 Hz, 1H), 8.44 (d, J=5.6 Hz, 1H), 8.39 (s, 2H), 8.23 (s, 1H), 7.79 (d, J=5.6 Hz, 1H), 7.38 (dd, J=5.1, 1.4 Hz, 1H). LCMS (Method C): RT=4.70 min, m/z: 423 [M+H$^+$].

Example 20

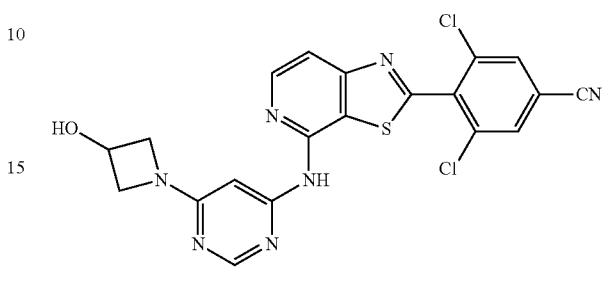

3,5-Dichloro-4-{4-[5-(3-hydroxy-azetidin-1-yl)-pyrimidin-4-ylamino]-thiazolo[5,4-c]pyridine-2-yl}-benzonitrile Step 1. 1-(6-Amino-pyrimidin-4-yl)-azetidin-3-ol A solution of 3-azetidinol hydrochloride (454 mg, 4.1 mmol) in MeOH and water was loaded onto an Isolute® SCX-2 cartridge that was washed with MeOH and the product eluted with 2M ammonia in MeOH. The relevant fractions were concentrated to dryness under reduced pressure. The resultant residue was then added to a solution of 6-chloro-pyrimidin-4-ylamine (151 mg, 1.16 mmol) in IMS (10 mL) under argon and heated under reflux for 18 hours. The reaction mixture was cooled and then loaded onto an Isolute® SCX-2 column. The column was then washed with MeOH and eluted with 2 M ammonia in MeOH. The relevant fractions were concentrated to dryness under reduced pressure and the resulting residue was purified by flash chromatography (NH$_2$ cartridge, 0-5% MeOH in DCM) to give the desired compound as a white solid (163 mg, 85% yield). $^1$H NMR (400 MHz, DMSO-d$_6$): δ 7.90 (d, J=1.0 Hz, 1H), 6.18 (s, 2H), 5.65 (d, J=6.5 Hz, 1H), 5.21 (d, J=1.1 Hz, 1H), 4.54-4.53 (m, 1H), 4.07 (dd, J=8.7, 6.7 Hz, 2H), 3.59 (dd, J=8.8, 4.6 Hz, 2H).

Step 2. 3,5-Dichloro-4-{4-[5-(3-hydroxy-azetidin-1-yl)-pyrimidin-4-ylamino]-thiazolo[5,4-c]pyridine-2-yl}-benzonitrile Following the procedure described for 2-[2-(2,6-dichloro-4-cyano-phenyl)-thiazolo[5,4-c]pyridine-4-ylamino]-isonicotinonitrile (Example 19), 4-(4-bromo-thiazolo[5,4-c]pyridine-2-yl)-3,5-dichloro-benzonitrile and 1-(6-amino-pyrimidin-4-yl)-azetidin-3-ol were reacted to give the desired compound as a yellow solid (56 mg, 52% yield). $^1$H NMR (400 MHz, DMSO-d$_6$): δ 10.24 (s, 1H), 8.39 (d, J=5.5 Hz, 1H), 8.37 (s, 2H), 8.20 (d, J=1.0 Hz, 1H), 7.74 (d, J=5.6 Hz, 1H), 6.58 (s, 1H), 5.72-5.69 (m, 1H), 4.63-4.56 (m, 1H), 4.20 (t, J=7.8 Hz, 2H), 3.73 (dd, J=9.1, 4.5 Hz, 2H). LCMS (Method C): RT=3.21, m/z: 470 [M+H$^+$].

Example 21

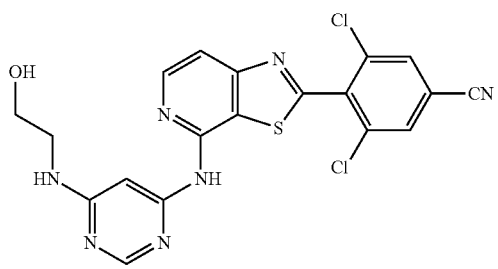 [SMILES: N#Cc1cc(Cl)c(-c2nc3ccnc(Nc4cc(NCCO)ncn4)c3s2)c(Cl)c1]

3,5-Dichloro-4-{4-[6-(2-hydroxy-ethylamino)-pyrimidin-4-ylamino]-thiazolo[5,4-c]pyridin-2-yl}-benzonitrile

Step 1. 3,5-Dichloro-4-[4-(6-chloropyrimidin-4-ylamino)-thiazolo[5,4-c]pyridin-2-yl]-benzonitrile A mixture of 4-(4-bromothiazolo[5,4-c]pyridin-2-yl)-3,5-dichlorobenzonitrile (0.250 g, 0.65 mmol), 4-amino-6-chloropyridine (0.080 g, 0.62 mmol), $Pd_2(dba)_3$ (0.030 g, 0.033 mmol), XantPhos (0.038 g, 0.065 mmol) and cesium carbonate (0.530 g, 1.60 mmol) in dioxane (6.5 mL) was degassed with nitrogen then heated at 70° C. for 4 hours. The resulting mixture was diluted with DCM and water, and then filtered through Celite®. The layers of the filtrate were separated and the organic layer, dried over $Na_2SO_4$ and concentrated under reduced pressure. The residue was purified by silica gel flash chromatography eluting with 0-25% EtOAc in pentane and 0-10% EtOAc in DCM to give the desired compound as a yellow solid (0.215 g, 76% yield). $^1$H NMR (300 MHz, DMSO-$d_6$): δ 11.16 (s, 1H), 8.65 (s, 1H), 8.52 (d, J=5.6 Hz, 1H), 8.39 (s, 2H), 7.97 (s, 1H), 7.91 (d, J=5.6 Hz, 1H). LCMS (Method E): RT=3.83 min, m/z: 433 [M+H$^+$].

Step 2. 3,5-Dichloro-4-{4-[6-(2-hydroxyethylamino)-pyrimidin-4-ylamino]-thiazolo[5,4-c]pyridin-2-yl}-benzonitrile A mixture of 3,5-dichloro-4-[4-(6-chloropyrimidin-4-ylamino)-thiazolo[5,4-c]pyridin-2-yl]-benzonitrile (0.030 g, 0.07 mmol) and ethanolamine (12.6 μL, 0.21 mmol) in NMP (0.7 mL) was subjected to microwave irradiation at 150° C. for 75 minutes. Further ethanolamine (5.0 μL, 0.08 mmol) was added and the mixture subjected to microwave irradiation at 160° C. for 45 minutes then 190° C. for 45 minutes. The reaction mixture was loaded onto an Isolute® SCX-2 cartridge that was washed with MeOH and the product eluted with 2M ammonia in MeOH. The relevant fractions were combined and concentrated under reduced pressure. The residue was purified by silica gel flash chromatography (0-5% MeOH in DCM) to give the desired compound as an off-white solid (0.014 g, 45% yield). $^1$H NMR (400 MHz, DMSO-$d_6$): δ 10.13 (s, 1H), 8.40-8.34 (m, 3H), 8.16 (s, 1H), 7.73 (d, J=5.6 Hz, 1H), 7.22 (br s, 1H), 6.85 (br s, 1H), 4.72 (t, J=5.4 Hz, 1H), 3.52 (q, J=5.9 Hz, 3H). LCMS (Method C): RT=3.10 min, m/z: 458 [M+H$^+$].

Example 22

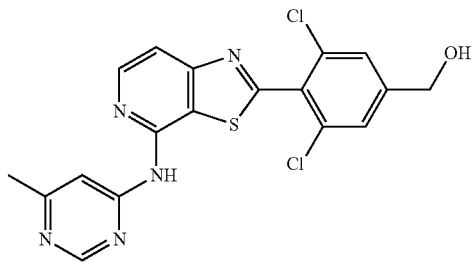 [SMILES: Cc1cc(Nc2nccc3nc(-c4c(Cl)cc(CO)cc4Cl)sc23)ncn1]

{3,5-Dichloro-4-[4-(6-methyl-pyrimidin-4-ylamino)-thiazolo[5,4-c]pyridin-2-yl]-phenyl}-methanol

Step 1. 2,6-Dichloro-4-iodobenzoyl chloride

A solution of 2,6-dichloro-4-iodobenzoic acid (5.50 g, 17.4 mmol) in thionyl chloride (52 mL) was heated under reflux for 2 hours then diluted with toluene and concentrated under reduced pressure. The resultant residue was partitioned between EtOAc and saturated aqueous sodium bicarbonate solution. The organic layer was dried over $Na_2SO_4$ and concentrated under reduced pressure to give the desired compound as a yellow oil (5.75 g, 99% yield). $^1$H NMR (400 MHz, CDCl$_3$) δ 7.75 (s, 2H).

Step 2. 2,6-Dichloro-N-(2-chloro-3-fluoro-pyridin-4-yl)-4-iodobenzamide

A mixture of 2-chloro-3-fluoropyridin-4-ylamine (1.73 g, 11.8 mmol), 2,6-dichloro-4-iodobenzoyl chloride (5.90 g, 17.65 mmol) and triethylamine (3.1 mL, 22.4 mmol) in dioxane (35 mL) was heated to 100° C. for 18 hours. The reaction mixture was partitioned between EtOAc and water. The organic layer washed with brine, dried over $Na_2SO_4$ and concentrated under reduced pressure. The resultant residue was triturated with diethyl ether and dried under reduced pressure to give the desired compound as a pink solid (2.83 g, 54% yield). $^1$H NMR (300 MHz, CDCl$_3$): δ 8.49-8.43 (m, 1H), 8.22 (d, J=5.5 Hz, 1H), 7.82-7.73 (m, 2H).

Step 3. 2,6-Dichloro-N-(2-chloro-3-fluoro-pyridin-4-yl)-4-iodobenzimidoyl chloride A solution of 2,6-dichloro-N-(2-chloro-3-fluoro-pyridin-4-yl)-4-iodobenzamide (2.83 g, 6.4 mmol) in thionyl chloride (23 mL) was heated to 90° C. for 56 hours then diluted with toluene and concentrated under reduced pressure to give the desired compound (2.94 g, 99% yield). $^1$H NMR (300 MHz, CDCl$_3$): δ 8.22 (d, J=5.1 Hz, 1H), 7.84-7.76 (m, 2H), 6.95 (t, J=5.1 Hz, 1H).

Step 4. 4-Chloro-2-(2,6-dichloro-4-iodo-phenyl)-thiazolo[5,4-c]pyridine

A mixture of 2,6-dichloro-N-(2-chloro-3-fluoropyridin-4-yl)-4-iodobenzimidoyl chloride (2.94 g, 6.30 mmol), thiourea (1.93 g, 25.3 mmol) and pyridine (1.73 mL, 21.4 mmol) in isopropanol (25 mL) was heated to 90° C. for 3.5 hours. Triethylamine (5.3 mL, 37.8 mmol) was added and the resulting mixture was heated to 90° C. for a further 1.5 h. The reaction was cooled to room temperature and then concentrated under reduced pressure. The resultant residue was partitioned between DCM and water. The organic layer was separated, dried over $Na_2SO_4$ and concentrated under reduced pressure. The residue was triturated with MeOH and dried under reduced pressure to give the desired compound (2.33 g, 84% yield). $^1$H NMR (300 MHz, $CDCl_3$): δ 8.52 (d, J=5.6 Hz, 1H), 7.98 (d, J=5.6 Hz, 1H), 7.90-7.81 (s, 2H).

Step 5. 4-Chloro-2-(2,6-dichloro-4-vinyl-phenyl)-thiazolo[5,4-c]pyridine

A mixture of 4-chloro-2-(2,6-dichloro-4-iodo-phenyl)-thiazolo[5,4-c]pyridine (0.30 g, 0.68 mmol), vinyl borane pinacol ester (0.105 g, 0.68 mmol), $PdCl_2(PPh_3)_2$ (0.029 g, 0.04 mmol) and sodium carbonate (0.288 g, 2.70 mmol) in water (0.4 mL) and dioxane (4 mL) was degassed with nitrogen and heated at 100° C. for 2 hours. The reaction mixture was cooled to room temperature and then partitioned between EtOAc and water. The organic layer was separated, dried over $Na_2SO_4$ and concentrated under reduced pressure. The residue was purified by silica gel flash chromatography eluting with 0-8% EtOAc in pentane to give the desired compound as an off-white solid (0.168 g, 72% yield). $^1$H NMR (300 MHz, $CDCl_3$): δ 8.51 (d, J=5.6 Hz, 1H), 7.98 (d, J=5.6 Hz, 1H), 7.53-7.45 (m, 2H), 6.69-6.62 (m, 1H), 5.91 (d, J=17.5 Hz, 1H), 5.52 (d, J=10.9 Hz, 1H).

Step 6. 3,5-Dichloro-4-(4-chloro-thiazolo[5,4-c]pyridin-2-yl)-benzaldehyde

A solution of 4-chloro-2-(2,6-dichloro-4-vinyl-phenyl)-thiazolo[5,4-c]pyridine (0.168 g, 0.48 mmol) in DCM (3.8 mL) and MeOH (1 mL) was cooled to −78° C. and degassed with nitrogen then compressed air before the ozone generator was turned on. After 10 minutes, a persistent grey colour remained so the ozone generator was turned off and the reaction mixture was degassed with nitrogen. Triphenylphosphine (0.125 g, 0.48 mmol) was added and the mixture warmed to ambient temperature and stirred for 1 hour. The reaction mixture was partitioned between DCM and water. The organic layer dried over $Na_2SO_4$ and concentrated under reduced pressure. The residue was purified by silica gel flash chromatography eluting with 0-12% EtOAc in pentane to give the desired compound as an off-white solid (0.138 g, 84% yield). $^1$H NMR (300 MHz, $CDCl_3$): δ 10.04 (s, 1H), 8.55 (d, J=5.6 Hz, 1H), 7.99-7.98 (m, 3H).

Step 7. [3,5-Dichloro-4-(4-chloro-thiazolo[5,4-c]pyridin-2-yl)-phenyl]-methanol

A solution of 3,5-dichloro-4-(4-chloro-thiazolo[5,4-c]pyridin-2-yl)-benzaldehyde (0.065 g, 0.19 mmol) in DCM (0.5 mL), MeOH (0.5 mL) and acetic acid (0.5 mL) was treated with sodium cyanoborohydride (0.013 g, 0.21 mmol) and the resultant mixture was stirred for 2 hours. The reaction mixture was quenched with saturated aqueous sodium bicarbonate solution and partitioned between DCM and water. The organic layer was dried over $Na_2SO_4$ and concentrated under reduced pressure to give the desired compound as an off-white solid (0.066 g, quant. yield). $^1$H NMR (300 MHz, $CDCl_3$): δ 8.52 (d, J=5.6 Hz, 1H), 7.99 (d, J=5.6 Hz, 1H), 7.49 (s, 2H), 4.79 (s, 2H).

Step 8. {3,5-Dichloro-4-[4-(6-methyl-pyrimidin-4-ylamino)-thiazolo[5,4-c]pyridin-2-yl]-phenyl}-methanol A mixture of [3,5-dichloro-4-(4-chloro-thiazolo[5,4-c]pyridin-2-yl)-phenyl]-methanol (0.063 g, 0.18 mmol), 4-amino-6-methylpyrimidine (0.022 g, 0.20 mmol), $Pd_2(dba)_3$ (0.003 g, 3.6 mmol), XantPhos (0.003 g, 5.0 pmol) and cesium carbonate (0.117 g, 0.36 mmol) in dioxane (1.1 mL) was degassed with nitrogen and subjected to microwave irradiation at 150° C. for 30 minutes. Further 4-amino-6-methylpyrimidine (0.011 g, 0.10 mmol), $Pd_2(dba)_3$ (0.006 g, 7.2 pmol), and XantPhos (0.006 g, 10.0 pmol) were added and the mixture subjected to further microwave irradiation at 150° C. for 60 minutes. The reaction mixture was diluted with MeOH and passed through a nylon filter. The filtrate was concentrated under reduced pressure then loaded onto an Isolute® SCX-2 cartridge which was washed with MeOH and the product eluted with 2M ammonia in MeOH. The eluent was concentrated under reduced pressure and the resultant residue was purified by silica gel flash chromatography eluting with 0-100% EtOAc in DCM to give the desired compound as a yellow solid (0.030 g, 40% yield). $^1$H NMR (300 MHz, $CDCl_3$): δ 8.68 (s, 1H), 8.42 (br s, 1H), 8.18-8.04 (m, 1H), 7.77 (d, J=5.7 Hz, 1H), 7.50 (s, 2H), 4.72 (s, 2H), 2.55 (s, 3H). LCMS (Method C): RT=2.90 min, m/z: 418 [M+H$^+$].

Example 23

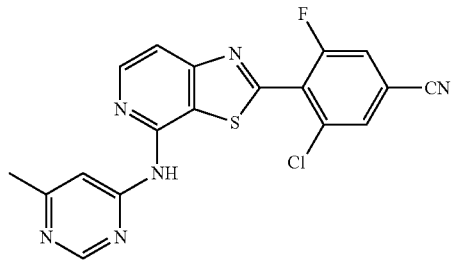 [SMILES: Cc1cc(Nc2nccc3nc(-c4c(F)cc(C#N)cc4Cl)sc23)ncn1]

3-Chloro-5-fluoro-4-[4-(6-methyl-pyrimidin-4-ylamino)-thiazolo[5,4-c]pyridin-2-yl]-benzonitrile Procedure A:

Step 1. 2-Chloro-N-(2-chloro-4-cyano-6-fluoro-benzoyl)-N-(2-chloro-3-fluoropyridin-4-yl)-4-cyano-6-fluorobenzamide To a solution of 2-chloro-3-fluoropyridin-4-ylamine (1.05 g, 7.1 mmol) in DMF (25 mL) at 0° C. was added sodium hydride (0.343 g, 14.3 mmol). The resulting violet mixture stirred for 20 minutes before a solution of 2-chloro-4-cyano-6-fluoro-benzoyl chloride (1.87 g, 8.6 mmol) in DMF (10 mL) was added. The mixture was warmed to room temperature stirred for 16 hours, then quenched with water and 1M HCl. The mixture was filtered through Celite®, washing with EtOAc. The organic filtrate was dried over $Na_2SO_4$ and concentrated under reduced pressure. The resultant residue was purified by silica gel flash chromatography eluting with DCM to give the desired compound as an off-white foam (0.869 g, 25% yield). $^1$H NMR (300 MHz, $CDCl_3$): δ 8.24 (d, J=5.1 Hz, 1H), 7.55 (s, 2H), 7.36 (d, J=8.0 Hz, 2H), 7.32-7.23 (m, 1H).

Step 2. 2-Chloro-N-(2-chloro-3-fluoro-pyridin-4-yl)-4-cyano-6-fluorobenzamide To a solution of 2-chloro-N-(2-chloro-4-cyano-6-fluorobenzoyl)-N-(2-chloro-3-fluoro-pyridin-4-yl)-4-cyano-6-fluoro-benzamide (0.865 g, 1.7 mmol) in MeOH (8.5 mL) and dioxane (8.5 mL) was added sodium hydroxide (0.102 g, 2.5 mmol). The resulting mixture stirred at room temperature for 2.5 hours and then concentrated under reduced pressure. The residue was partitioned between DCM and saturated aqueous sodium hydrogen carbonate solution. The organic layer was dried over $Na_2SO_4$ and concentrated under reduced pressure. The residue was purified by silica gel flash chromatography eluting with 0-100% DCM in pentane to give the desired compound as an off-white solid (0.308 g, 55% yield). $^1$H NMR (300 MHz, $CDCl_3$): δ 8.49-8.40 (m, 1H), 8.25 (d, J=5.4 Hz, 1H), 7.98 (br s, 1H), 7.64 (t, J=1.3 Hz, 1H), 7.47 (dd, J=7.9, 1.5 Hz, 1H). LCMS (Method D): RT=3.33 min, m/z: 328 [M+H$^+$].

Step 3. 2-Chloro-N-(2-chloro-3-fluoropyridin-4-yl)-4-cyano-6-fluorobenzimidoyl chloride A solution of 2-chloro-N-(2-chloro-3-fluoro-pyridin-4-yl)-4-cyano-6-fluorobenzamide (0.805 g, 2.5 mmol) in thionyl chloride (7.5 mL) was heated under reflux for 65 h then cooled to ambient temperature. The reaction mixture was diluted with toluene and concentrated under reduced pressure to give the desired compound as a yellow solid (0.814 g, 96% yield). $^1$H NMR (300 MHz, $CDCl_3$): δ 8.25 (d, J=5.1 Hz, 1H), 7.70-7.63 (m, 1H), 7.49 (dd, J=8.0, 1.0 Hz, 1H), 6.97 (t, J=5.0 Hz, 1H). LCMS (Method D): RT=4.09 min, m/z: 346 [M+H$^+$].

Step 4. 3-Chloro-4-(4-chlorothiazolo[5,4-c]pyridin-2-yl)-5-fluorobenzonitrile A mixture of 2-chloro-N-(2-chloro-3-fluoropyridin-4-yl)-4-cyano-6-fluorobenzimidoyl chloride (0.713 g, 2.05 mmol), thiourea (0.623 g, 8.2 mmol) and pyridine (538 μL, 6.66 mmol) in isopropanol (7 mL) was heated under reflux for 3 hours. The reaction mixture was allowed to cool to ambient temperature before adding triethylamine (1.7 mL, 12.3 mmol). The resulting mixture was heated under reflux for a further 3 hours and allowed to cool. The mixture was concentrated under reduced pressure and the residue was partitioned between DCM and water. The organic layer was dried over $Na_2SO_4$ and concentrated under reduced pressure. The crude residue was purified by silica gel flash chromatography (0-10% EtOAc in pentane) to give the desired compound as an off-white solid (0.356 g, 53% yield). $^1$H NMR (300 MHz, $CDCl_3$): δ 8.55 (d, J=5.6 Hz, 1H), 8.01 (d, J=5.6 Hz, 1H), 7.72 (t, J=1.4 Hz, 1H), 7.52 (dd, J=8.3, 1.5 Hz, 1H). LCMS (Method D): RT=3.86 min, m/z: 324 [M+H$^+$].

Step 5. 4-(4-Bromothiazolo[5,4-c]pyridin-2-yl)-3-chloro-5-fluorobenzonitrile A suspension of 3-chloro-4-(4-chlorothiazolo[5,4-c]pyridin-2-yl)-5-fluorobenzonitrile (0.077 g, 0.24 mmol) and trimethylsilyl bromide (63 μL 0.48 mmol) in propionitrile (2.4 mL) was heated under reflux for 5 hours before further trimethylsilyl bromide (30 μL, 0.24 mmol) was added. The resulting mixture was heated under reflux for a further 16 hours then partitioned between DCM and water. The organic layer was dried over $Na_2SO_4$ and concentrated under reduced pressure to give the desired compound as an off-white solid (0.090 g, quant. yield). $^1$H NMR (300 MHz, $CDCl_3$): δ 8.53 (d, J=5.6 Hz, 1H), 8.03 (d, J=5.6 Hz, 1H), 7.72 (t, J=1.4 Hz, 1H), 7.52 (dd, J=8.3; 1.5 Hz, 1H). LCMS (Method D): RT=3.89 min, m/z: 368 [M+H$^+$].

Step 6. 3-Chloro-5-fluoro-4-[4-(6-methyl-pyrimidin-4-ylamino)-thiazolo[5,4-c]pyridin-2-yl]-benzonitrile A mixture of 4-(4-bromo-thiazolo[5,4-c]pyridin-2-yl)-3-chloro-5-fluoro-benzonitrile (0.087 g, 0.24 mmol), 4-amino-6-methylpyrimidine (0.024 g, 0.22 mmol), $Pd_2(dba)_3$ (0.011 g, 0.01 mmol), XantPhos (0.014 g, 0.02 mmol) and cesium carbonate (0.192 g, 0.59 mmol) in dioxane (2.4 mL) was degassed with nitrogen and heated to 70° C. for 16 hours. The reaction mixture was diluted with DCM and water, and then filtered through Celite®. The layers of the filtrate were separated and the organic layer dried over $Na_2SO_4$ and concentrated under reduced pressure. The residue was purified by silica gel flash chromatography eluting with 0-5% MeOH in DCM and triturated with acetonitrile to give the desired compound as a yellow solid (0.033 g, 35% yield). $^1$H NMR (300 MHz, DMSO-$d_6$): δ 10.70 (s, 1H), 8.63 (d, J=1.2 Hz, 1H), 8.46 (d, J=5.6 Hz, 1H), 8.27 (t, J=1.3 Hz, 1H), 8.22 (dd, J=9.0, 1.4 Hz, 1H), 7.85 (d, J=5.6 Hz, 1H), 7.56 (s, 1H), 2.39 (s, 3H). LCMS (Method C): RT=3.30 min, m/z: 397 [M+H$^+$].

Procedure B:

Step 1. 2-Chloro-3-fluoro-4-iodopyridine

A solution of lithium diisopropylamide (2M in tetrahydrofuran/ethylbenzene/heptane, 155 mL, 0.31 mol) was added dropwise over 40 minutes to solution of 2-chloro-3-fluoropyridine (31 g, 0.235 mol) in tetrahydrofuran (200 mL) at –70° C. and the resulting mixture stirred for 4 hours. A solution of iodine (69 g, 0.2 mol) in tetrahydrofuran (100 mL) was added dropwise over 30 minutes and the resultant mixture was stirred for 30 minutes at –70° C. then allowed to warm to room temperature over 1 hour. The reaction mixture was poured onto aqueous sodium metabisulphite solution (20% w/v, 2 L) and extracted with diethyl ether (3×300 mL). The combined organic extract was washed with aqueous sodium metabisulphite solution (20% w/v, 2 L) and water (200 mL), dried over $Na_2SO_4$ and evaporated under reduced pressure to give a colorless oil. The resultant oil was triturated with diethyl ether to give the desired compound as a red/brown solid (28 g, 46% yield). $^1$H NMR (400 MHz, $CDCl_3$): δ 7.87 (d, J=5.0 Hz, 1H), 7.66 (ddd, J=5.0, 4.0, 0.4 Hz, 1H).

Step 2. 2-chloro-4-cyano-6-fluoro-benzamide

A suspension of 2-chloro-4-cyano-6-fluoro-benzoic acid (8.5 g, 42.6 mmol) and thionyl chloride (50 mL) was heated under reflux for 2 hours. The reaction mixture was allowed to cool to ambient temperature, evaporated to dryness and azeotroped with toluene (2×50 mL). The resultant pale brown solid was dissolved in tetrahydrofuran (150 mL), cooled to 0° C. and a 2M solution of ammonia in isopropanol (600 mL) was added. After addition, the suspension was stirred for 1 hour then concentrated under reduced pressure to afford a white solid. The residue was triturated with water (100 mL), the solid collected by filtration and left to air dry to give the desired compound as a pale brown solid (7.5 g, 89% yield). $^1$H NMR (400 MHz, DMSO-$d_6$): δ 8.27 (s, 1H), 8.06-7.99 (m, 3H).

Step 3. 2,6-Dichloro-N-(2-chloro-3-fluoro-pyridin-4-yl)-4-cyano-benzamide

A mixture of 2-chloro-3-fluoro-4-iodopyridine (6.4 g, 24.8 mmol), 2-chloro-4-cyano-6-fluoro-benzamide (6.0 g, 28.0 mmol), cesium carbonate (16.3 g, 49.6 mmol), XantPhos (1.45 g, 2.5 mmol) and Pd$_2$(dba)$_3$ (1.13 g, 1.23 mmol) in dioxane (180 mL) was degassed with nitrogen then heated under reflux for 4 hours. The pale green suspension was allowed to cool to ambient temperature, poured into water (1200 mL) and extracted with EtOAc (2×500 mL). The combined organic layer was washed with water (500 mL), dried over Na$_2$SO$_4$ and concentrated under reduced pressure to afford a yellow oil. The resultant oil was purified by silica gel flash chromatography eluting with 10-20% EtOAc in pentane to afford the title compound as a white solid (5.2 g, 64% yield). $^1$H NMR (400 MHz, CDCl$_3$): δ 8.45 (t, J=5.3 Hz, 1H), 8.24 (d, J=5.5 Hz, 1H), 8.03 (s, 1H), 7.63 (t, J=1.3 Hz, 1H), 7.46 (dd, J=8.0, 1.4 Hz, 1H). LCMS: RT=4.01 min, m/z: 328 [M+H$^+$].

Example 24

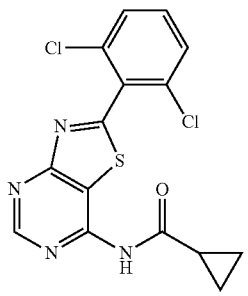 [SMILES: O=C(Nc1ncnc2nc(-c3c(Cl)cccc3Cl)sc12)C1CC1]

N-(2-(2,6-dichlorophenyl)thiazolo[4,5-d]pyrimidin-7-yl)cyclopropanecarboxamide

Step 1. 6-chloro-5-fluoropyrimidin-4-amine

A mixture of 4,6-dichloro-5-fluoro-pyrimidine (1.67 g, 10.0 mmol), n-butanol (6 mL) and 28% ammonium hydroxide (12 mL) in a sealed tube was heated at 90° C. for 2 hours. The precipitated white crystals were collected by filtration to give the desired compound (1.31 g, 89% yield). LCMS (ESI) m/z: 147.9 [M+H$^+$].

Step 2. 2,6-dichloro-N-(6-chloro-5-fluoropyrimidin-4-yl)benzamide

To a solution of 6-chloro-5-fluoropyrimidin-4-amine (1.21 g, 8.2 mmol) in DMF (25 mL) at 0° C. was added NaH (60% in mineral oil, 0.46 g, 11.5 mmol). The reaction mixture was stirred at 0° C. for 20 minutes. 2,6-dichlorobenzoyl chloride (2.06 g, 9.8 mmol) was then added dropwise over 5 minutes. The reaction mixture was warmed to room temperature and stirred under nitrogen overnight. The reaction was quenched with saturated NH$_4$Cl solution (100 mL), and extracted with EtOAc (3×100 mL). The combined organics layer was dried over Na$_2$SO$_4$ and concentrated under reduced pressure. The crude product was purified by silica gel column chromatography eluting with 0-25% EtOAc in hexane gradient to give the desired compound as a white solid (1.32 g, 50% yield). $^1$H NMR (400 MHz, CDCl$_3$) δ 8.39 (s, 1H), 8.10 (s, 1H), 7.39-7.35 (m, 3H). LCMS (ESI) m/z: 320.0 [M+H$^+$].

Step 3. 2-(2,6-dichlorophenyl)thiazolo[4,5-d]pyrimidine-7-thiol

The mixture of 2,6-dichloro-N-(6-chloro-5-fluoropyrimidin-4-yl)benzamide (1.32 g, 4.1 mmol) and P$_2$S$_5$ (2.75 g, 12.4 mmol) in pyridine (8 mL) and xylene (32 mL) was heated at 120° C. for 7 hours. The mixture was concentrated under reduced pressure to give crude desired product, which was used in the next step without purification. LCMS (ESI) m/z: 313.9 [M+H$^+$].

Step 4. 2-(2,6-dichlorophenyl)-7-(methylthio)thiazolo[4,5-d]pyrimidine

To a solution of 2-(2,6-dichlorophenyl)thiazolo[4,5-d]pyrimidine-7-thiol (1.29 g, 4.1 mmol) and triethylamine (1.66 g, 16.4 mmol) in ethanol (20 mL) was added methyl iodide (2.32 g, 16.4 mmol). The reaction mixture was stirred at room temperature for 1 hour and then concentrated under reduced pressure. The crude product was purified by silica gel column chromatography eluting with 0-20% EtOAc/hexane gradient to give the desired compound as a white solid (0.59 g, 44% yield). $^1$H NMR (500 MHz, CDCl$_3$) δ 9.12 (s, 1H), 7.49-7.47 (M, 2H), 7.45-7.40 (m, 1H), 2.81 (s, 3H). LCMS (ESI) m/z: 328.9 [M+H$^+$].

Step 5. 2-(2,6-dichlorophenyl)-7-(methylsulfonyl)thiazolo[4,5-d]pyrimidine

To a solution of 2-(2,6-dichlorophenyl)-7-(methylthio)thiazolo[4,5-d]pyrimidine (627 mg, 1.91 mmol) in DCM (10 mL) was added m-chloroperoxybenzoic acid (1.07 g, 4.78 mmol). The reaction mixture was stirred at room temperature overnight. The reaction was quenched with saturated aqueous sodium hydrogen carbonate solution (30 mL). The organic layer was separated and the aqueous layer was extracted with DCM (2×30 mL). The combined organic extract was dried over Na$_2$SO$_4$ and concentrated under reduced pressure. The crude product was purified by silica gel chromatography eluting with 0-70% EtOAc/hexane gradient to give the desired compound as a white solid (271 mg, 40%). LCMS (ESI) m/z: 360.0 [M+H$^+$].

Step 6. N-(2-(2,6-dichlorophenyl)thiazolo[4,5-d]pyrimidin-7-yl)cyclopropane-carboxamide To a solution of cyclopropylcarboxamide (19 mg, 0.22 mmol) in DMF (1.5 mL) at 0° C. was added NaH (9.8 mg, 0.24 mmol). The reaction mixture was stirred at 0° C. for 10 minutes. A solution of 2-(2,6-dichlorophenyl)-7-(methylsulfonyl)thiazolo[4,5-d]pyrimidine (940 mg, 0.11 mmol) in DMF (0.5 mL) was then added at 0° C. The reaction mixture was warmed to room temperature and stirred for 2 hours. The reaction was quenched with ice-water and extracted with EtOAc (3×25 mL). The combined organic extract was dried over Na$_2$SO$_4$ and concentrated under reduced pressure. The crude product was purified by reverse phase HPLC (Gemini-NX, 3×10 cm, gradient: 30-70% CH$_3$CN/H$_2$O, 0.1% NH$_4$OH/H$_2$O, flow rate 60 mL/min, 10 min) to give the desired compound as a yellow solid (12 mg, 31%). $^1$H NMR (400 MHz, DMSO-d$_6$) δ 11.89 (s, 1H), 8.98 (s, 1H), 7.75-7.70

(m, 2H), 7.66 (dd, J=9.4, 6.6 Hz, 1H), 2.19-2.10 (m, 1H), 0.95 (tt, J=7.6, 4.2 Hz, 4H). LCMS (Method B): RT=4.69 min, m/z: 365.0 [M+H⁺].

Example 25

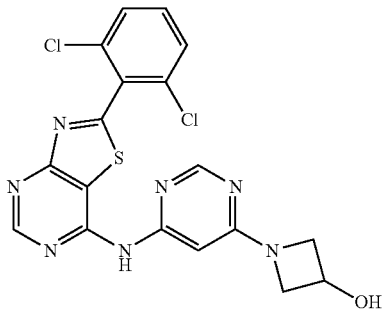 [SMILES: OC1CN(c2cc(Nc3ncnc4nc(-c5c(Cl)cccc5Cl)sc34)ncn2)C1]

3-(6-(2-(2,6-dichlorophenyl)thiazolo[4,5-d]pyrimidin-7-ylamino)pyrimidin-4-yl)cyclobutanol Step 1. N-(6-chloropyrimidin-4-yl)-2-(2,6-dichlorophenyl)thiazolo[4,5-d]pyrimidin-7-amine To a solution of 3-amino-6-chloropyrimidine (57 mg, 0.44 mmol) in DMF (2 mL) at 0° C. was added NaH (24 mg, 0.61 mmol). The reaction mixture was stirred at 0° C. for 10 minutes. A solution of 2-(2,6-dichlorophenyl)-7-(methylsulfonyl)thiazolo[4,5-d]pyrimidine (88 mg, 0.24 mmol) in DMF (1 mL) was then added at 0° C. The reaction mixture was warmed up to room temperature and stirred for 0.5 hour. The reaction was quenched with ice-water and extracted with EtOAc (3×25 mL). The combined organic extract was dried over Na₂SO₄, and concentrated under reduced pressure. The crude product was purified by silica gel chromatography eluting with 5-50% EtOAc/hexanes gradient to give the desired compound as a white solid (71 mg, 71%). $^1$H NMR (400 MHz, DMSO) δ 11.75 (s, 1H), 9.02 (s, 1H), 8.80 (s, 1H), 8.11 (s, 1H), 7.76 (d, J=8.3 Hz, 2H), 7.72-7.63 (m, 1H). LCMS (ESI) m/z: 490 [M+H⁺].

Step 2. 3-(6-(2-(2,6-dichlorophenyl)thiazolo[4,5-d]pyrimidin-7-ylamino)pyrimidin-4-yl)cyclobutanol The mixture of N-(6-chloropyrimidin-4-yl)-2-(2,6-dichlorophenyl)-thiazolo[4,5-d]pyrimidin-7-amine (45 mg, 0.11 mmol), azetidin-3-ol hydrochloride (24 mg, 0.22 mmol) and diisopropylamine (45 mg, 0.35 mmol) in ethanol (1 mL) was heated at 130° C. under microwave radiation for 30 minutes. The reaction mixture was concentrated under reduced pressure. The crude product was purified by reverse phase HPLC (Gemini-NX, 3×10 cm, gradient: 5-85% CH₃CN/H₂O, 0.1% formic acid/H₂O, flow rate 60 mL/min, 10 min) to give the desired compound as a white solid (25 mg, 51% yield). $^1$H NMR (400 MHz, DMSO-d₆) δ 10.94 (s, 1H), 8.85 (s, 1H), 8.31 (d, J=0.8 Hz, 1H), 7.78-7.71 (m, 2H), 7.67 (dd, J=9.4, 6.7 Hz, 1H), 6.54 (s, 1H), 5.79 (d, J=6.5 Hz, 1H), 4.69-4.55 (m, 1H), 4.29-4.18 (m, 2H), 3.76 (dd, J=9.4, 4.4 Hz, 2H). LCMS (Method B): RT=3.55 min, m/z: 446.2 [M+H⁺].

Example 26

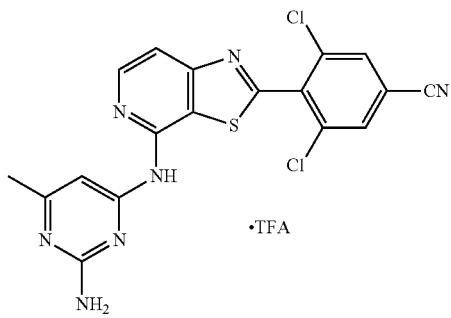 [SMILES: Cc1cc(Nc2nccc3nc(-c4c(Cl)cc(C#N)cc4Cl)sc23)nc(N)n1]

4-[4-(2-Amino-6-methyl-pyrimidin-4-ylamino)-thiazolo[5,4-c]pyridin-2-yl]-3,5-dichloro-benzonitrile trifluoroacetate salt Step 1. [2-(2,6-Dichloro-4-cyano-phenyl)-thiazolo[5,4-c]pyridin-4-yl]-carbamic acid tert-butyl ester A mixture of 4-(4-bromo-thiazolo[5,4-c]pyridin-2-yl)-3,5-dichloro-benzonitrile (0.578 g, 1.50 mmol), tert-butyl carbamate (1.76 g, 15.0 mmol), Pd₂(dba)₃ (0.069 g, 0.075 mmol), XantPhos (0.087 g, 0.15 mmol) and tribasic potassium phosphate (0.635 g, 3.0 mmol) in toluene (10 mL) and water (1.5 mL) was degassed with argon then heated at 80° C. for 3 hours. The reaction mixture was filtered through Celite® and washed with EtOAc. The filtrate was washed with water then brine, dried over Na₂SO₄ and concentrated under reduced pressure. The resultant residue was purified by silica gel flash chromatography (0-50% EtOAc in pentane) to give the desired compound as an off-white solid (0.48 g, 76% yield). $^1$H NMR (300 MHz, CDCl₃): δ 8.35 (d, J=5.6 Hz, 1H), 7.79 (d, J=5.6 Hz, 1H), 7.75 (s, 2H), 1.56 (s, 9H).

Step 2. 4-(4-Amino-thiazolo[5,4-c]pyridin-2-yl)-3,5-dichloro-benzonitrile

A mixture of [2-(2,6-dichloro-4-cyano-phenyl)-thiazolo[5,4-c]pyridin-4-yl]-carbamic acid tert-butyl ester (0.48 g, 1.14 mmol) and TFA (2 mL) in DCM (8 mL) was stirred at room temperature for 2 hours then concentrated to dryness under reduced pressure. The resultant residue was loaded onto an Isolute® SCX-2 cartridge which was washed with MeOH and the product eluted with 2M ammonia in isopropanol. The relevant fractions were combined and concentrated under reduced pressure to afford the title compound as a pale yellow solid (0.309 g, 82% yield). $^1$H NMR (300 MHz, CDCl₃): δ 8.21 (d, J=5.8 Hz, 1H), 7.77 (s, 2H), 7.50 (d, J=5.8 Hz, 1H), 4.94 (s, 2H). LCMS (Method D): RT=2.04 min, m/z: 321 [M+H⁺].

Step 3. {4-[2-(2,6-Dichloro-4-cyano-phenyl)-thiazolo[5,4-c]pyridin-4-ylamino]-6-methyl-pyrimidin-2-yl}-bis-carbamic acid tert-butyl ester A mixture of 4-(4-amino-thiazolo[5,4-c]pyridin-2-yl)-3,5-dichloro-benzonitrile (0.020 g, 0.06 mmol), (4-chloro-6-methyl-pyrimidin-2-yl)-bis-carbamic acid tert-butyl ester (0.041 g, 0.12 mmol), Pd$_2$(dba)$_3$ (0.003 g, 0.003 mmol), XantPhos (0.0035 g, 0.006 mmol) and cesium carbonate (0.049 g, 0.15 mmol) in dioxane (0.6 mL) was degassed with argon then heated at 80° C. for 1.5 hours. The reaction mixture allowed to cool to room temperature, the solid removed by filtration through Celite® and the filtrate concentrated under reduced pressure. The resultant residue was purified by silica gel flash chromatography eluting with 0-60% EtOAc in pentane to give the desired compound as a yellow glass (0.016 g, 42% yield). $^1$H NMR (300 MHz, CDCl$_3$): δ 8.48 (d, J=5.6 Hz, 1H), 8.11 (s, 1H), 7.81-7.75 (m, 2H), 7.65 (s, 1H), 2.57 (s, 3H), 1.46 (s, 18H). LCMS (Method D): RT=4.20 min, m/z: 628 [M+H$^+$].

Step 4. 4-[4-(2-Amino-6-methyl-pyrimidin-4-ylamino)-thiazolo[5,4-c]pyridin-2-yl]-3,5-dichloro-benzonitrile trifluoroacetate salt A mixture of {4-[2-(2,6-dichloro-4-cyano-phenyl)-thiazolo[5,4-c]pyridin-4-ylamino]-6-methyl-pyrimidin-2-yl}-bis-carbamic acid tert-butyl ester (0.016 g, 0.025 mmol) and TFA (0.5 mL) in DCM (1 mL) was stirred at room temperature for 2 hours then concentrated to dryness under reduced pressure. The resultant residue was purified by silica gel flash chromatography eluting with 0-5% MeOH in DCM to give the desired compound as a yellow solid (0.0096 g, 71% yield). $^1$H NMR (400 MHz, DMSO-d$_6$): δ 11.35 (br s, 1H), 8.58-8.51 (m, 2H), 8.39 (s, 2H), 8.05-7.98 (m, 2H), 7.68 (br s, 1H), 6.59 (s, 1H), 2.32 (s, 3H). LCMS (Method C): RT=3.16 min, m/z: 428 [M+H$^+$].

Example 27

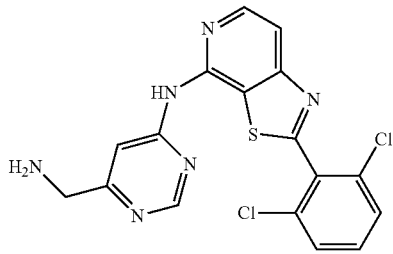

N-(6-(aminomethyl)pyrimidin-4-yl)-2-(2,6-dichlorophenyl)thiazolo[5,4-c]pyridin-4-amine Step 1. Methyl 6-aminopyrimidine-4-carboxylate A mixture of 6-chloropyrimidin-4-amine (10.0 g, 77.2 mmol), PdCl$_2$(dppf) (6.0 g, 8.2 mmol), Et$_3$N (30 mL), MeOH (30 mL) in DMF (100 mL) was heated 100° C. for 24 h under 20 atm CO (g) atmosphere. The solvents were removed under reduced pressure, and the residue was partitioned between water (100 mL) and ethyl acetate (100 mL). The aqueous layer was extracted with ethyl acetate (100 mL) three times. The combined organic phase was dried over Na$_2$SO$_4$ and concentrated. The resulting residue was purified by silica gel column chromatography (0-10% MeOH/DCM) to give the desired product as a gray solid (5.0 g, 42% yield). $^1$H-NMR (500 MHz, DMSO-d$_6$): δ 8.44 (d, J=0.5 Hz, 1H), 7.27 (s, 2H), 7.03 (d, J=1.5 Hz, 1H), 3.84 (s, 3H). LCMS (ESI) m/z: 154.1 [M+H$^+$].

Step 2. (6-aminopyrimidin-4-yl)-methanol

To a stirred solution of methyl 6-aminopyrimidine-4-carboxylate (2.0 g, 13 mmol) in MeOH (20 mL) at 25° C., was added LiBH$_4$ (0.85 g, 39 mmol). After addition, the resulting mixture was allowed to stir at 70° C. for 16 hours. TLC indicated the starting material was consumed completely at this point. Solvents were removed under reduced pressure and the residue was purified via chromatography column on silica gel eluting with a 5% gradient of methanol in dichloromethane to give the desired alcohol as pale yellow oil (1.0 g, 61% yield). LCMS (ESI) m/z: 126.1 [M+H$^+$].

Step 3. 2-((6-aminopyrimidin-4-yl)methyl)isoindoline-1,3-dione

To a stirred solution of (6-aminopyrimidin-4-yl)methanol (1.0 g, 8.0 mmol), isoindoline-1,3-dione (1.4 g, 9.6 mmol), n-Bu$_3$P (2.42 g, 12.0 mmol) in dry DMF (20 mL) at room temperature was added diisopropyl azodicarboxylate (2.42 g, 12.0 mmol) dropwise. After addition, the resulting mixture was allowed to stir at 80° C. for 48 hours. Solvents were removed under reduced pressure and the residue was purified via chromatography column on silica gel eluting with a 2% gradient of methanol in dichloromethane to give the desired target as a gray solid (0.60 g, 30% yield). $^1$H-NMR (500 MHz, DMSO-d$_6$): δ 8.22 (s, 1H), 7.95-7.88 (m, 4H), 6.85 (s, 2H), 6.28 (s, 1H), 4.63 (s, 2H). LCMS (ESI) Method B: RT=3.23 min, m/z 233.1 [M+H$^+$].

Step 4. 2-((6-(2-(2,6-dichlorophenyl)thiazolo[5,4-c]pyridin-4-ylamino)pyrimidin-4-yl)methyl)isoindoline-1,3-dione To a microwave tube was added 4-bromo-2-(2,6-dichlorophenyl)thiazolo[5,4-c]pyridine (100 mg, 0.280 mmol), 2-((6-aminopyrimidin-4-yl)methyl)isoindoline-1,3-dione (100 mg, 0.390 mmol), Pd$_2$(dba)$_3$ (32 mg, 0.035 mmol), XantPhos (30 mg, 0.052 mmol), Cs$_2$CO$_3$ (250 mg, 0.770 mmol) in dioxane (5.0 mL). The mixture was degassed with N$_2$ for 10 min. The resulting mixture was irradiated in a microwave reactor at 160° C. for 2 hours and then cooled to room temperature. Insoluble solid was removed via filtration, and the residue was purified with reverse phase column chromatography eluting with a 0-60% gradient of CH$_3$CN in 0.5% NH$_4$HCO$_3$ to give the desired product as a white solid (100 mg, 70% yield). LCMS: m/z: 533.1 [M+H$^+$].

Step 5. N-(6-(aminomethyl)pyrimidin-4-yl)-2-(2,6-dichlorophenyl)thiazolo[5,4-c]pyridin-4-amine To a stirred solution of N-(6-(aminomethyl)pyrimidin-4-yl)-2-(2,6-dichlorophenyl)thiazolo[5,4-c]pyridin-4-amine (100 mg, 0.190 mmol) in EtOH (2.0 mL) in 25° C., was added 85% hydrazine (0.10 mL). The resulting mixture was stirred at the same temperature for 30 min. TLC showed the starting material was consumed. Solvents were removed under reduced pressure and the residue was purified via prep-HPLC (Gilson GX 281, Shim-pack PRC-ODS 250 mm×20 mm×2, gradient: CH$_3$CN/10 mm/L NH$_4$HCO$_3$, 17 min) to give the desired product as a pale yellow solid (14 mg, 19% yield). $^1$H-NMR (500 MHz, DMSO-d$_6$): δ 8.64 (s, 1H), 8.46 (d, J=5.5 Hz, 1H), 7.84 (d, J=5.5 Hz, 1H), 7.74-7.67 (m, 4H), 3.73 (s, 2H). LCMS (ESI) Method B: RT=4.62 min, m/z: 403.1 [M+H$^+$].

Additional compounds shown in Table 1 were also made according to the above procedures.

TABLE 1

| Example | Structure | Name | Synth. Method | LCMS (ESI) m/z [M + H⁺] | LCMS Method | R$_T$ (min) | NMR |
|---|---|---|---|---|---|---|---|
| 28 | 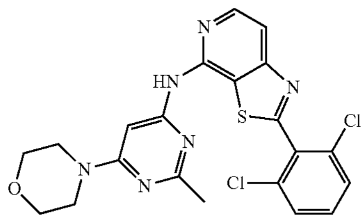 [SMILES: Cc1nc(Nc2nccc3nc(-c4c(Cl)cccc4Cl)sc23)cc(N2CCOCC2)n1] | 2-(2,6-dichlorophenyl)-N-(2-methyl-6-morpholino-pyrimidin-4-yl)thiazolo[5,4-c]pyridin-4-amine | 1 | 473.0 | A | 6.38 | ¹H NMR (500 MHz, DMSO-d₆): δ 10.22 (s, 1H), 8.38 (d, J = 6.0 Hz, 1H), 7.75-7.69 (m, 3H), 7.66-7.65 (m, 1H), 6.73 (s, 1H), 3.69-3.67 (m, 4H), 3.51-3.35 (m, 4H), 2.32 (s, 3H). |
| 29 | 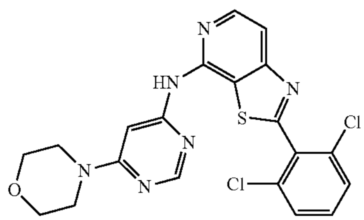 [SMILES: Clc1cccc(Cl)c1-c1nc2ccnc(Nc3cc(N4CCOCC4)ncn3)c2s1] | 2-(2,6-dichlorophenyl)-N-(6-morpholino-pyrimidin-4-yl)thiazolo[5,4-c]pyridin-4-amine | 1 | 459.0 | A | 5.93 | ¹H NMR (500 MHz, DMSO-d₆): δ 10.28 (s, 1H), 8.40 (d, J = 5.5 Hz, 1H), 8.28 (s, 1H), 7.76-7.25 (m, 3H), 7.68-7.66 (m, 1H), 7.06 (s, 1H), 3.70-3.68 (m, 4H), 3.54-3.52 (m, 4H). |
| 30 | 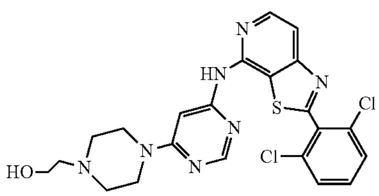 [SMILES: OCCN1CCN(c2cc(Nc3nccc4nc(-c5c(Cl)cccc5Cl)sc34)ncn2)CC1] | 2-(4-(6-(2-(2,6-dichlorophenyl)thiazolo[5,4-c]pyridin-4-ylamino)pyrimidin-4-yl)piperazin-1-yl)ethanol | 1 | 402.1 | A | 5.10 | ¹H NMR (500 MHz, DMSO-d₆): δ 10.31 (s, 1H), 8.40 (d, J = 6.0 Hz, 1H), 8.26 (s, 1H), 7.75-7.65 (m, 4H), 7.02 (s, 1H), 4.46 (t, J = 6.0 Hz, 1H), 3.56-3.52 (m, 6H), 2.50-2.48 (m, 4H), 2.45-2.42 (m, 2H). |
| 31 | 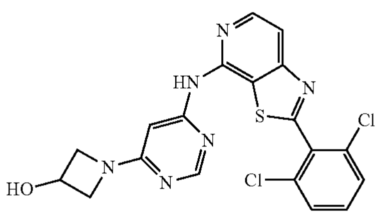 [SMILES: OC1CN(c2cc(Nc3nccc4nc(-c5c(Cl)cccc5Cl)sc34)ncn2)C1] | 1-(6-(2-(2,6-dichlorophenyl)thiazolo[5,4-c]pyridin-4-ylamino)pyrimidin-4-yl)azetidin-3-ol | 1 | 445.0 | A | 4.92 | ¹H NMR (500 MHz, DMSO-d₆): δ 10.22 (s, 1H), 8.91 (s, 1H), 6.0 Hz, 1H), 8.21 (s, 1H), 7.75-7.38 (m, 3H), 7.22-7.68 (m, 1H), 6.64 (s, 1H), 5.77 (d, J = 6.0 Hz, 1H), 4.62 (m, 1H), 4.22 (d, J = 6.0 Hz, 2H), 3.74 (d, J = 6.0 Hz, 2H). |
| 32 | 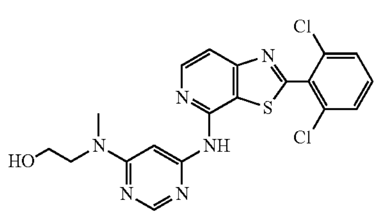 [SMILES: CN(CCO)c1cc(Nc2nccc3nc(-c4c(Cl)cccc4Cl)sc23)ncn1] | 2-((6-(2-(2,6-dichlorophenyl)thiazolo[5,4-c]pyridin-4-ylamino)pyrimidin-4-yl)(methyl)amino)ethanol | 1 | 447.1 | A | 5.20 | ¹H NMR (500 MHz, CH₃OH-d₄): δ 8.34 (d, J = 5.5 Hz, 1H), 8.24 (s, 1H), 7.72 (d, J = 5.5 Hz, 1H), 7.66-7.60 (m, 3H), 7.09 (s, 1H), 3.80-3.75 (m, 4H), 3.20 (s, 1H). |
| 33 | 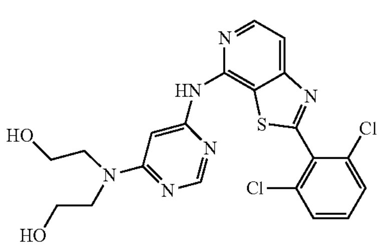 [SMILES: OCCN(CCO)c1cc(Nc2nccc3nc(-c4c(Cl)cccc4Cl)sc23)ncn1] | 2,2'-(6-(2-(2,6-dichlorophenyl)thiazolo[5,4-c]pyridin-4-ylamino)pyrimidin-4-ylazanediyl)diethanol | 1 | 477.1 | A | 4.80 | ¹H NMR (500 MHz, DMSO-d₆): δ 10.05 (s, 1H), 8.32 (d, J = 6.0 Hz, 1H), 8.14 (s, 1H), 7.66-7.64 (m, 3H), 7.60-7.57 (m, 1H), 6.82 (s, 1H), 4.77 (s, 2H), 3.52 (s, 8H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 34 | 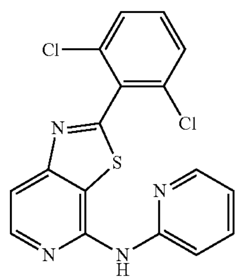 [SMILES: Clc1cccc(Cl)c1-c1nc2ccnc(Nc3ccccn3)c2s1] | 2-(2,6-dichlorophenyl)-N-(pyridin-2-yl)thiazolo[5,4-c]pyridin-4-amine | 1 | 373.0 | A | 6.45 | $^1$H NMR (500 MHz, DMSO-d$_6$): δ 10.23 (s, 1H), 8.36 (d, J = 5.5 Hz, 1H), 8.25 (d, J = 5.5 Hz, 1H), 7.74-7.66 (m, 6H), 6.97 (m, 1H). |
| 35 | 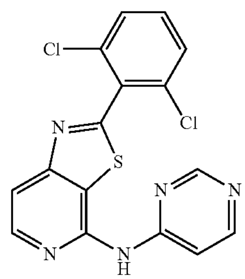 [SMILES: Clc1cccc(Cl)c1-c1nc2ccnc(Nc3ccncn3)c2s1] | 2-(2,6-dichlorophenyl)-N-(pyrimidin-4-yl)thiazolo[5,4-c]pyridin-4-amine | 1 | 374.0 | A | 5.37 | $^1$H NMR (500 MHz, DMSO-d$_6$): δ 10.80 (s, 1H), 8.76 (s, 1H), 8.51 (d, J = 6.0 Hz, 1H), 8.46 (d, J = 6.0 Hz, 1H), 7.86-7.68 (m, 5H). |
| 36 | 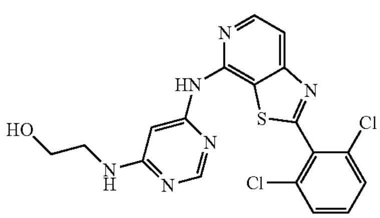 [SMILES: OCCNc1cc(Nc2nccc3nc(-c4c(Cl)cccc4Cl)sc23)ncn1] | 2-(6-(2-(2,6-dichlorophenyl)thiazolo[5,4-c]pyridin-4-ylamino)pyrimidin-4-ylamino)ethanol | 1 | 433.0 | A | 4.76 | $^1$H NMR (500 MHz, CH$_3$OH-d$_4$): δ 8.42 (d, J = 5.5 Hz, 1H), 8.18 (s, 1H), 7.70 (d, J = 5.5 Hz, 1H), 7.70-7.60 (m, 3H), 7.21 (s, 1H), 3.75-3.73 (m, 2H), 3.49 (m, 1H). |
| 37 | 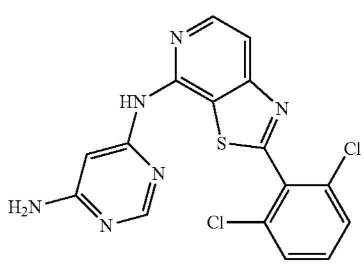 [SMILES: Nc1cc(Nc2nccc3nc(-c4c(Cl)cccc4Cl)sc23)ncn1] | N-4-(2-(2,6-dichlorophenyl)thiazolo[5,4-c]pyridin-4-yl)pyrimidine-4,6-diamine | 1 | 389.1 | A | 4.99 | $^1$H NMR (500 MHz, DMSO-d$_6$): δ 10.10 (s, 1H), 8.36 (d, J = 5.5 Hz, 1H), 8.10 (s, 1H), 7.74-7.65 (m, 4H), 6.85 (s, 1H), 6.64 (s, 1H). |
| 38 | 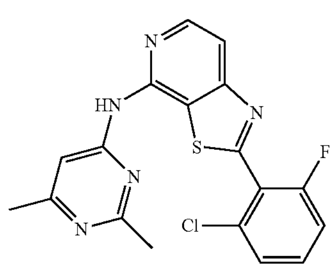 [SMILES: Cc1cc(Nc2nccc3nc(-c4c(F)cccc4Cl)sc23)nc(C)n1] | 2-(2-chloro-6-fluorophenyl)-N-(2,6-dimethylpyrimidin-4-yl)thiazolo[5,4-c]pyridin-4-amine | 1 | 386.1 | A | 5.51 | $^1$H NMR (500 MHz, DMSO-d$_6$): δ 10.62 (s, 1H), 8.44 (d, J = 5.5 Hz, 1H), 7.83 (d, J = 5.5 Hz, 1H), 7.72-7.69 (m, 1H), 7.62-7.61 (m, 1H), 7.55-7.51 (m, 1H), 7.30 (s, 1H), 2.44 (s, 3H), 2.34 (s, 3H). |

TABLE 1-continued

| Example | Structure | Name | Synth. Method | LCMS (ESI) m/z [M + H+] | LCMS Method | R_T (min) | NMR |
|---|---|---|---|---|---|---|---|
| 39 | 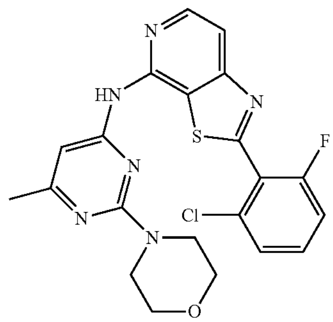 [SMILES: Cc1cc(Nc2nccc3nc(-c4c(F)cccc4Cl)sc23)nc(N2CCOCC2)n1] | 2-(2-chloro-6-fluorophenyl)-N-(6-methyl-2-morpholinopyrimidin-4-yl)thiazolo[5,4-c]pyridin-4-amine | 1 | 457.1 | A | 6.29 | $^1$H NMR (500 MHz, DMSO-d$_6$): δ 10.30 (s, 1H), 8.44 (d, J = 6.0 Hz, 1H), 7.72-7.69 (m, 1H), 7.62-7.60 (m, 1H), 7.55-7.51 (m, 1H), 6.45 (s, 1H), 3.55-3.54 (m, 8H), 2.22 (s, 3H). |
| 40 | 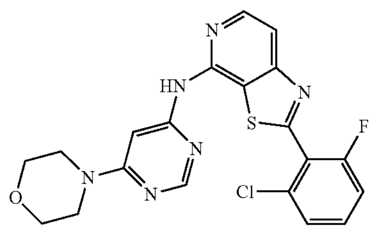 [SMILES: Fc1cccc(Cl)c1-c1nc2ccnc(Nc3cc(N4CCOCC4)ncn3)c2s1] | 2-(2-chloro-6-fluorophenyl)-N-(6-morpholinopyrimidin-4-yl)thiazolo[5,4-c]pyridin-4-amine | 1 | 443.1 | A | 5.70 | $^1$H NMR (500 MHz, DMSO-d$_6$): δ 10.28 (s, 1H), 8.34 (d, J = 5.5 Hz, 1H), 8.28 (s, 1H), 7.76 (d, J = 5.5 Hz, 1H), 7.72-7.69 (m, 1H), 7.62-7.60 (m, 1H), 7.54-7.50 (m, 1H), 7.04 (s, 1H), 3.70-3.68 (m, 4H), 3.54-3.52 (m, 4H). |
| 41 | 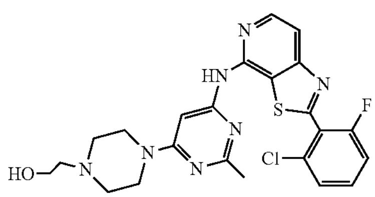 [SMILES: Cc1nc(Nc2nccc3nc(-c4c(F)cccc4Cl)sc23)cc(N2CCN(CCO)CC2)n1] | 2-(4-(6-(2-(2-chloro-6-fluorophenyl)thiazolo[5,4-c]pyridin-4-ylamino)-2-methylpyrimidin-4-yl)piperazin-1-yl)ethanol | 1 | 500.2 | A | 5.23 | $^1$H NMR (500 MHz, DMSO-d$_6$): δ 10.14 (s, 1H), 8.38 (d, J = 5.5 Hz, 1H), 7.74 (d, J = 5.5 Hz, 1H), 7.73-7.70 (m, 1H), 7.61-7.60 (m, 1H), 7.53-7.50 (m, 1H), 6.71 (s, 1H), 6.71 (s, 1H), 4.45 (t, J = 5.5 Hz, 1H), 3.55-3.52 (m, 6H), 2.51-2.47 (m, 4H), 2.44-2.41 (m, 2H), 2.32 (s, 3H) |
| 42 | 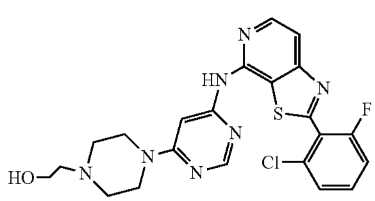 [SMILES: OCCN1CCN(c2cc(Nc3nccc4nc(-c5c(F)cccc5Cl)sc34)ncn2)CC1] | 2-(4-(6-(2-(2-chloro-6-fluorophenyl)thiazolo[5,4-c]pyridin-4-ylamino)pyrimidin-4-yl)piperazin-1-yl)ethanol | 1 | 486.1 | A | 4.90 | $^1$H NMR (500 MHz, DMSO-d$_6$): δ 10.21 (s, 1H), 8.90 (d, J = 5.5 Hz, 1H), 8.26 (s, 1H), 7.75 (d, J = 5.5 Hz, 1H), 7.72-7.69 (m, 1H), 7.61-7.60 (m, 1H), 7.53-7.50 (m, 1H), 7.00 (s, 1H), 4.46 (t, J = 5.5 Hz, 1H), 3.55-3.52 (m, 6H), 2.50-2.47 (m, 4H), 2.44-2.42 (m, 2H). |
| 43 | 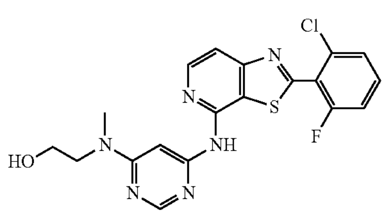 [SMILES: CN(CCO)c1cc(Nc2nccc3nc(-c4c(F)cccc4Cl)sc23)ncn1] | 2-((6-(2-(2-chloro-6-fluorophenyl)thiazolo[5,4-c]pyridin-4-ylamino)pyrimidin-4-yl)(methyl)amino)ethanol | 1 | 431.1 | A | 5.01 | $^1$H NMR (500 MHz, DMSO-d$_6$): δ 10.15 (s, 1H), 8.38 (d, J = 5.5 Hz, 1H), 8.22 (s, 1H), 7.74 (d, J = 5.5 Hz, 1H), 7.71-7.68 (m, 1H), 7.61-7.60 (m, 1H), 7.53-7.50 (m, 1H), 6.84 (s, 1H), 4.76 (s, 1H), 3.58 (s, 4H), 3.58 (s, 3H). |
| 44 | 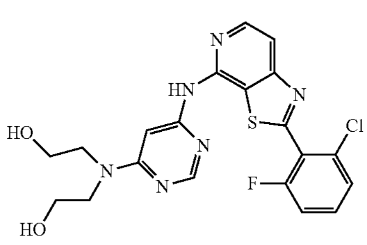 [SMILES: OCCN(CCO)c1cc(Nc2nccc3nc(-c4c(F)cccc4Cl)sc23)ncn1] | 2,2'-(6-(2-(2-chloro-6-fluorophenyl)thiazolo[5,4-c]pyridin-4-ylamino)pyrimidin-4-ylazanediyl)diethanol | 1 | 461.1 | A | 4.60 | $^1$H NMR (500 MHz, DMSO-d$_6$): δ 10.11 (s, 1H), 8.37 (d, J = 5.5 Hz, 1H), 8.21 (s, 1H), 7.73 (d, J = 5.5 Hz, 1H), 7.71-7.68 (m, 1H), 7.61-7.59 (m, 1H), 7.53-7.49 (m, 1H), 6.88 (s, 1H), 4.82 (s, 2H), 3.60 (s, 8H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 45 | 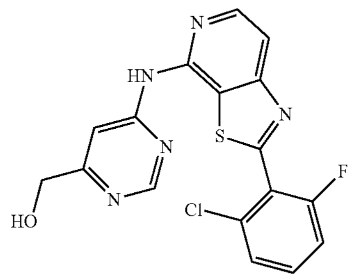 [SMILES: OCc1cc(Nc2nccc3nc(-c4c(F)cccc4Cl)sc23)ncn1] | (6-(2-(2-chloro-6-fluorophenyl)thiazolo[5,4-c]pyridin-4-ylamino)pyrimidin-4-yl)methanol | 1 | 388.0 | A | 4.57 | $^1$H NMR (500 MHz, DMSO-d$_6$): δ 10.74 (s, 1H), 8.63 (s, 1H), 8.46 (d, J = 5.5 Hz, 1H), 7.86 (d, J = 5.5 Hz, 1H), 7.76-7.70 (m, 2H), 7.62-7.60 (m, 1H), 7.54-7.51 (m, 1H), 4.58 (t, J = 6.0 Hz, 1H), 4.48 (d, J = 6.0 Hz, 2H) |
| 46 | 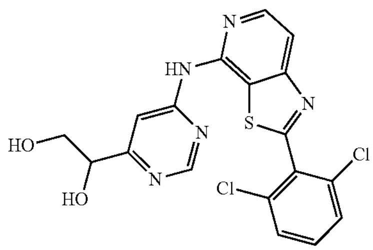 [SMILES: OCC(O)c1cc(Nc2nccc3nc(-c4c(Cl)cccc4Cl)sc23)ncn1] | 1-(6-(2-(2,6-dichlorophenyl)thiazolo[5,4-c]pyridin-4-ylamino)pyrimidin-4-yl)ethane-1,2-diol | 1 | 434.0 | A | 4.46 | $^1$H NMR (500 MHz, DMSO-d$_6$): δ 10.72 (s, 1H), 8.65 (s, 1H), 8.46 (d, J = 5.5 Hz, 1H), 7.85 (d, J = 5.5 Hz, 1H), 7.78 (s, 1H), 7.74-7.73 (m, 2H), 7.69-7.65 (m, 1H), 7.54-7.51 (m, 1H), 5.58-5.57 (m, 1H), 4.77-4.75 (m, 1H), 4.50-4.47 (m, 1H), 3.75-3.71 (m, 1H), 3.54-3.49 (m, 1H) |
| 47 | 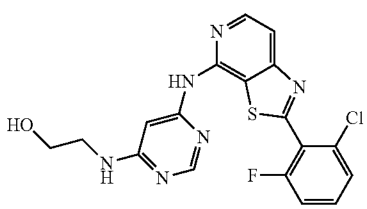 [SMILES: OCCNc1cc(Nc2nccc3nc(-c4c(F)cccc4Cl)sc23)ncn1] | 2-(6-(2-(2-chloro-6-fluorophenyl)thiazolo[5,4-c]pryidin-4-ylamino)pyrimidin-4-ylamino)ethanol | 1 | 417.0 | A | 4.63 | $^1$H NMR (500 MHz, DMSO-d$_6$): δ 10.10 (s, 1H), 8.37 (d, J = 5.5 Hz, 1H), 8.17 (s, 1H), 7.73-7.50 (m, 4H), 7.27 (br, 1H), 6.92 (br, 1H), 4.74 (s, 1H), 3.53 (m, 2H), 3.34 (m, 2H). |
| 48 | 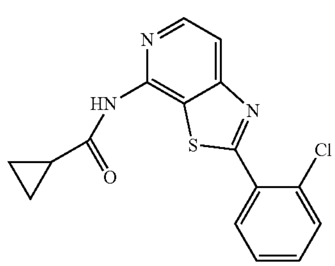 [SMILES: O=C(Nc1nccc2nc(-c3ccccc3Cl)sc12)C1CC1] | N-(2-(2-chlorophenyl)thiazolo[5,4-c]pyridin-4-yl)cyclopropanecarboxamide | 1 | 330.0 | A | 5.81 | $^1$H NMR (500 MHz, DMSO-d$_6$): δ 11.36 (s, 1H), 8.43 (d, J = 5.0 Hz, 1H), 8.22 (m, 1H), 7.90 (d, J = 5.0 Hz, 1H), 7.74-7.56 (m, 3H), 2.09 (m, 1H), 0.91 (m, 4H). |
| 49 | 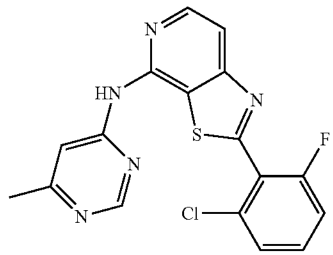 [SMILES: Cc1cc(Nc2nccc3nc(-c4c(F)cccc4Cl)sc23)ncn1] | 2-(2-chloro-6-fluorophenyl)-N-(6-methylpyrimidin-4-yl)thiazolo[5,4-c]pyridin-4-amine | 1 | 372.1 | A | 5.42 | $^1$H NMR (500 MHz, DMSO-d$_6$): δ 10.68 (s, 1H), 8.63 (s, 1H), 8.46 (d, J = 6.0 Hz, 1H), 7.85 (d, J = 6.0 Hz, 1H), 7.73-7.53 (m, 4H), 2.39 (s, 3H). |

TABLE 1-continued

| Example | Structure | Name | Synth. Method | LCMS (ESI) m/z [M + H⁺] | LCMS Method | R_T (min) | NMR |
|---|---|---|---|---|---|---|---|
| 50 | 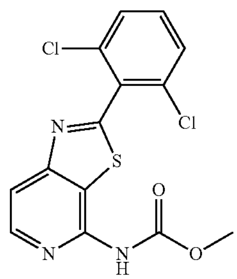 [SMILES: COC(=O)Nc1nccc2nc(-c3c(Cl)cccc3Cl)sc12] | methyl 2-(2,6-dichlorophenyl)thiazolo[5,4-c]pyridin-4-ylcarbamate | 1 | 354.0 | A | 5.60 | $^1$H NMR (500 MHz, DMSO-d$_6$): δ 10.75 (br, 1H), 8.44 (d, J = 6.5 Hz, 1H), 7.92 (d, J = 6.5 Hz, 1H), 7.75-7.69 (m, 3H), 3.73 (s, 3H). |
| 51 | 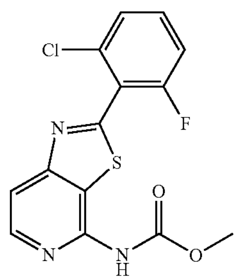 [SMILES: COC(=O)Nc1nccc2nc(-c3c(F)cccc3Cl)sc12] | methyl 2-(2-chloro-6-fluorophenyl)thiazolo[5,4-c]pyridin-4-ylcarbamate | 1 | 338.0 | A | 5.33 | $^1$H NMR (500 MHz, DMSO-d$_6$): δ 10.83 (br, 1H), 8.44 (d, J = 6.5 Hz, 1H), 7.93 (d, J = 6.5 Hz, 1H), 7.74-7.50 (m, 3H), 3.73 (s, 3H). |
| 52 | 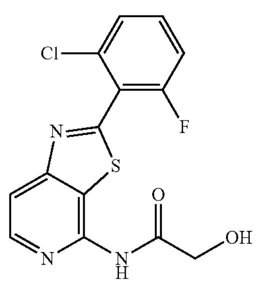 [SMILES: O=C(CO)Nc1nccc2nc(-c3c(F)cccc3Cl)sc12] | N-(2-(2-chloro-6-fluorophenyl)thiazolo[5,4-c]pyridin-4-yl)-2-hydroxyacetamide | 1 | 338.1 | A | 4.50 | $^1$H NMR (500 MHz, DMSO-d$_6$): δ 8.48 (d, J = 6.5 Hz, 1H), 7.97 (d, J = 6.5 Hz, 1H), 7.73-7.50 (m, 3H), 5.75 (br, 1H), 4.15 (s, 2H). |
| 53 | 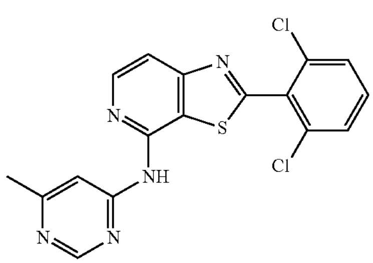 [SMILES: Cc1cc(Nc2nccc3nc(-c4c(Cl)cccc4Cl)sc23)ncn1] | 2-(2,6-dichlorophenyl)-N-(6-methylpyrimidin-4-yl)thiazolo[5,4-c]pyridin-4-amine | 1 | 338.0 | A | 5.70 | $^1$H NMR (500 MHz, DMSO-d$_6$): δ 10.67 (br, 1H), 8.83 (s, 1H), 8.46 (d, J = 5.5 Hz, 1H), 7.84 (d, J = 5.5 Hz, 1H), 7.75-7.61 (m, 4H), 2.39 (s, 3H). |
| 54 | 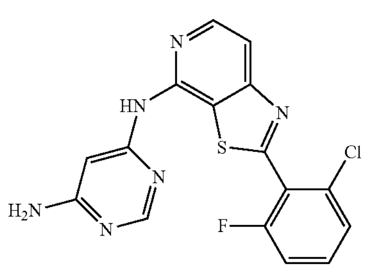 [SMILES: Nc1cc(Nc2nccc3nc(-c4c(F)cccc4Cl)sc23)ncn1] | N-4-(2-(2-chloro-6-fluorophenyl)thiazolo[5,4-c]pyridin-4-yl)pyrimidine-4,6-diamine | 1 | 373.1 | A | 4.76 | $^1$H-NMR (500 MHz, DMSO-d$_6$): δ 10.10 (br, 1H), 8.37 (d, J = 5.5 Hz, 1H), 8.11 (s, 1H), 7.73-7.521 (m, 4H), 6.81 (s, 1H), 6.66 (br, 2H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 55 | 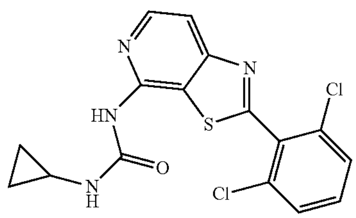 [SMILES: O=C(Nc1nccc2nc(-c3c(Cl)cccc3Cl)sc12)NC1CC1] | 1-cyclopropyl-3-(2-(2,6-dichlorophenyl)thiazolo[5,4-c]pyridin-4-yl)urea | 1 | 379.0 | A | 5.85 | ¹H NMR (500 MHz, DMSO-d₆): δ 9.64 (s, 1H), 8.32 (d, J = 6.0 Hz, 1H), 7.90 (m, 1H), 7.75-7.66 (m, 4H), 2.60 (m, 1H), 0.69 (m, 2H), 0.50 (m, 2H). |
| 56 | 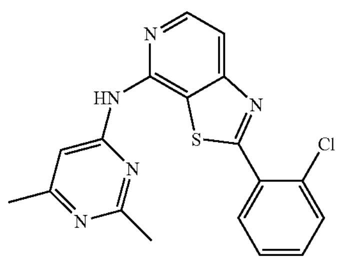 [SMILES: Cc1cc(Nc2nccc3nc(-c4ccccc4Cl)sc23)nc(C)n1] | 2-(2-chlorophenyl)-N-(2,6-dimethylpyrimidin-4-yl)thiazolo[5,4-c]pyridin-4-amine | 1 | 368.0 | A | 5.91 | ¹H NMR (500 MHz, DMSO-d₆): δ 10.55 (s, 1H), 8.41 (d, J = 5.5 Hz, 1H), 8.29 (m, 1H), 7.79-7.59 (m, 4H), 7.30 (s, 1H), 2.46 (s, 3H), 2.35 (s, 3H). |
| 57 | 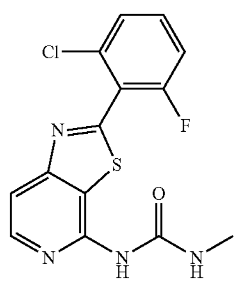 [SMILES: CNC(=O)Nc1nccc2nc(-c3c(F)cccc3Cl)sc12] | 1-(2-(2-chloro-6-fluorophenyl)thiazolo[5,4-c]pyridin-4-yl)-3-methylurea | 1 | 337.1 | A | 5.15 | ¹H NMR (500 MHz, DMSO-d₆): δ 9.84 (s, 1H), 8.32 (d, J = 5.5 Hz, 1H), 7.95 (s, 1H), 7.74-7.51 (m, 4H), 2.78 (s, 3H). |
| 58 | 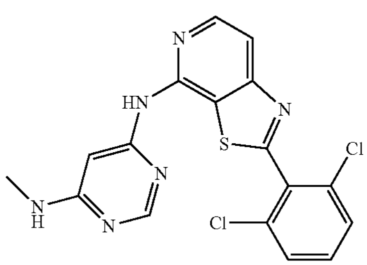 [SMILES: CNc1cc(Nc2nccc3nc(-c4c(Cl)cccc4Cl)sc23)ncn1] | N-4-(2-(2,6-dichlorophenyl)thiazolo[5,4-c]pyridin-4-yl)-N6-methylpyrimidine-4,6-diamine | 1 | 403.0 | A | 5.44 | ¹H NMR (500 MHz, DMSO-d₆): δ 10.11 (s, 1H), 8.37 (d, J = 5.0 Hz, 1H), 8.17 (s, 1H), 7.74-7.65 (m, 4H), 7.18 (br, 1H), 6.89 (br, 1H), 2.78 (d, J = 4.5 Hz, 3H). |
| 59 | 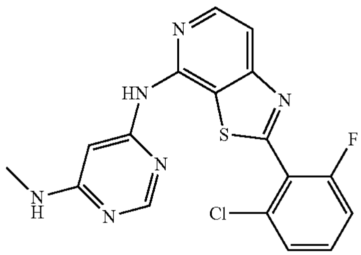 [SMILES: CNc1cc(Nc2nccc3nc(-c4c(F)cccc4Cl)sc23)ncn1] | N-4-(2-(2-chloro-6-fluorophenyl)thiazolo[5,4-c]pyridin-4-yl)-N6-methylpyrimidine-4,6-diamine | 1 | 387.1 | A | 5.22 | ¹H NMR (500 MHz, DMSO-d₆): δ 10.11 (s, 1H), 8.37 (d, J = 5.0 Hz, 1H), 8.17 (s, 1H), 7.73-7.50 (m, 4H), 7.17 (br, 1H), 6.84 (br, 1H), 2.78 (d, J = 5.0 Hz, 3H). |

TABLE 1-continued

| Example | Name | Synth. Method | LCMS (ESI) m/z [M + H⁺] | LCMS Method | R$_T$ (min) | NMR |
|---|---|---|---|---|---|---|
| 60 | 2-(2,6-dichlorophenyl)-N-(6-((dimethylamino)methyl)pyrimidin-4-yl)thiazolo[5,4-c]pyridin-4-amine | 1 | 431.0 | A | 5.50 | ¹H NMR (500 MHz, DMSO-d₆): δ 10.73 (br, 1H), 8.68 (s, 1H), 8.48 (d, J = 6.0 Hz, 1H), 7.87 (d, J = 6.0 Hz, 1H), 7.76-7.69 (m, 4H), 3.40 (s, 2H), 2.26 (s, 6H). |
| 61 | 2-(2-chloro-6-fluorophenyl)-N-(6-((dimethylamino)methyl)pyrimidin-4-yl)thiazolo[5,4-c]pyridin-4-amine | 1 | 415.1 | A | 5.29 | ¹H NMR (500 MHz, DMSO-d₆): δ 10.74 (s, 1H), 8.68 (s, 1H), 8.48 (d, J = 5.5 Hz, 1H), 7.88 (d, J = 5.5 Hz, 1H), 7.47-7.53 (m, 4H), 3.40 (s, 2H), 2.26 (s, 6H). |
| 62 | N-(2-(2-chloro-6-fluorophenyl)thiazolo[5,4-c]pyridin-4-yl)-2-(dimethylamino)acetamide | 1 | 365.0 | A | 5.67 | ¹H NMR (500 MHz, DMSO-d₆): δ 10.64 (s, 1H), 8.48 (d, J = 5.5 Hz, 1H), 7.98 (d, J = 5.5 Hz, 1H), 7.75-7.51 (m, 3H), 3.26 (s, 2H), 2.35 (s, 6H). |
| 63 | 6-(2-(2-chloro-6-fluorophenyl)thiazolo[5,4-c]pyridin-4-ylamino)pyrimidine-4-carbonitrile | 1 | 383.1 | A | 6.06 | ¹H NMR (500 MHz, DMSO-d₆): δ 11.43 (s, 1H), 8.90 (s, 1H), 8.54 (d, J = 5.0 Hz, 1H), 8.28 (s, 1H), 7.96 (d, J = 5.0 Hz, 1H), 7.75-7.52 (m, 3H). |
| 64 | N-(6-(2-(2,6-dichlorophenyl)thiazolo[5,4-c]pyridin-4-ylamino)pyrimidin-4-yl)acetamide | 1 | 431.1 | A | 5.30 | ¹H NMR (500 MHz, DMSO-d₆): δ 10.67 (s, 1H), 8.50 (s, 1H), 8.45 (d, J = 6.0 Hz, 1H), 8.29 (s, 1H), 7.86 (d, J = 6.0 Hz, 1H), 7.76-7.67 (m, 3H), 2.14 (s, 3H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 65 | 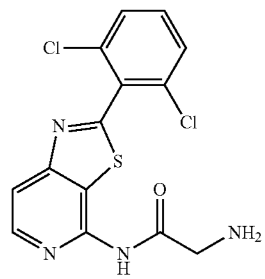 [SMILES: NCC(=O)Nc1nccc2nc(-c3c(Cl)cccc3Cl)sc12] | 2-amino-N-(2-(2,6-dichlorophenyl)thiazolo[5,4-c]pyridin-4-yl)acetamide | 1 | 353.0 | A | 4.51 | ¹H NMR (500 MHz, DMSO-d$_6$): δ 8.45 (d, J = 6.0 Hz, 1H), 7.93 (d, J = 6.0 Hz, 1H), 7.74-7.66 (m, 3H), 5.13 (br, 2H), 3.39 (s, 2H). |
| 66 | 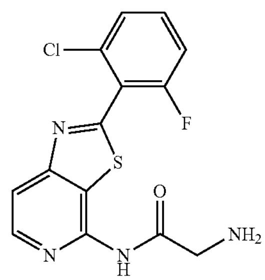 [SMILES: NCC(=O)Nc1nccc2nc(-c3c(F)cccc3Cl)sc12] | 2-amino-N-(2-(2-chloro-6-fluorophenyl)thiazolo[5,4-c]pyridin-4-yl)acetamide | 1 | 337.1 | A | 4.24 | ¹H NMR (500 MHz, DMSO-d$_6$): δ 8.45 (d, J = 6.0 Hz, 1H), 7.94 (d, J = 6.0 Hz, 1H), 7.73-7.50 (m, 3H), 5.12 (br, 2H), 3.40 (s, 2H). |
| 67 | 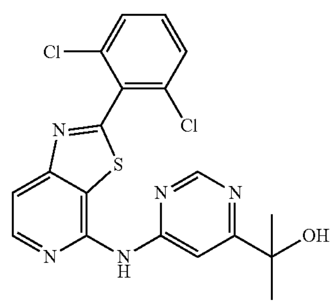 [SMILES: CC(C)(O)c1cc(Nc2nccc3nc(-c4c(Cl)cccc4Cl)sc23)ncn1] | 2-(6-(2-(2,6-dichlorophenyl)thiazolo[5,4-c]pyridin-4-ylamino)pyrimidin-4-yl)propan-2-ol | 1 | 432.0 | A | 5.53 | ¹H NMR (500 MHz, DMSO-d$_6$): δ 8.66 (s, 1H), 8.46 (d, J = 5.5 Hz, 1H), 7.87-7.67 (m, 5H), 5.33 (s, 1H), 1.42 (s, 6H). |
| 68 | 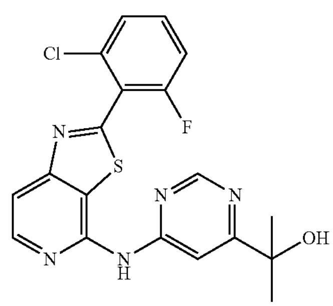 [SMILES: CC(C)(O)c1cc(Nc2nccc3nc(-c4c(F)cccc4Cl)sc23)ncn1] | 2-(6-(2-(2-chloro-6-fluorophenyl)thiazolo[5,4-c]pyridin-4-ylamino)pyrimidin-4-yl)propan-2-ol | 1 | 416.1 | A | 5.29 | ¹H NMR (500 MHz, DMSO-d$_6$): δ 8.66 (s, 1H), 8.46 (d, J = 6.0 Hz, 1H), 7.86-7.53 (m, 5H), 5.33 (s, 1H), 1.42 (s, 6H). |
| 69 | 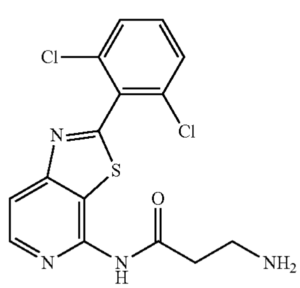 [SMILES: NCCC(=O)Nc1nccc2nc(-c3c(Cl)cccc3Cl)sc12] | 3-amino-N-(2-(2,6-dichlorophenyl)thiazolo[5,4-c]pyridin-4-yl)propanamide | 1 | 367.1 | A | 4.26 | ¹H NMR (500 MHz, DMSO-d$_6$): δ 8.44 (d, J = 5.5 Hz, 1H), 7.92 (d, J = 5.5 Hz, 1H), 7.74-7.66 (m, 3H), 2.89 (m, 2H), 2.51 (m, 2H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 70 | 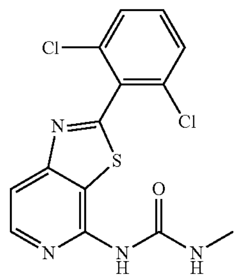 [SMILES: CNC(=O)Nc1nccc2nc(-c3c(Cl)cccc3Cl)sc12] | 1-(2-(2,6-dichlorophenyl)thiazolo[5,4-c]pyridin-4-yl)-3-methylurea | 1 | 353.1 | B | 5.41 | ¹H NMR (500 MHz, DMSO-d$_6$): δ 8.31 (d, J = 6.0 Hz, 1H), 7.95 (m, 1H), 7.74-7.72 (m, 3H), 7.68-7.66 (m, 1H), 2.76 (d, J = 5.0 Hz, 3H). |
| 71 | 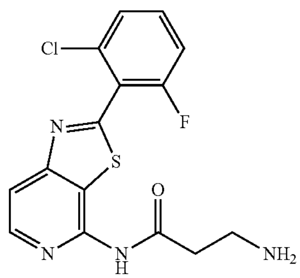 [SMILES: NCCC(=O)Nc1nccc2nc(-c3c(F)cccc3Cl)sc12] | 3-amino-N-(2-(2-chloro-6-fluorophenyl)thiazolo[5,4-c]pyridin-4-yl)propanamide | 1 | 351.0 | A | 4.45 | ¹H NMR (500 MHz, DMSO-d$_6$): δ 8.44 (d, J = 5.5 Hz, 1H), 7.92 (d, J = 5.5 Hz, 1H), 7.73-7.68 (m, 1H), 7.60 (d, J = 8.5 Hz, 1H), 7.53-7.49 (m, 1H), 5.00 (br, 2H), 2.88 (t, J = 6.0 Hz, 2H), 2.54-2.52 (m, 2H). |
| 72 | 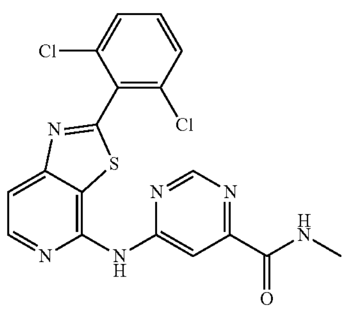 [SMILES: CNC(=O)c1cc(Nc2nccc3nc(-c4c(Cl)cccc4Cl)sc23)ncn1] | 6-(2-(2,6-dichlorophenyl)thiazolo[5,4-c]pyridin-4-ylamino)-N-methylpyrimidine-4-carboxamide | 1 | 431.1 | B | 5.51 | ¹H NMR (500 MHz, DMSO-d$_6$): δ 11.13 (br, 1H), 8.89 (d, J = 5.5 Hz, 1H), 8.84 (d, J = 1.0 Hz, 1H), 8.51 (d, J = 5.5 Hz, 1H), 8.23 (s, 1H), 7.90 (d, J = 5.5 Hz, 1H), 7.75-7.66 (m, 3H), 2.83 (d, J = 5.0 Hz, 3H). |
| 73 | 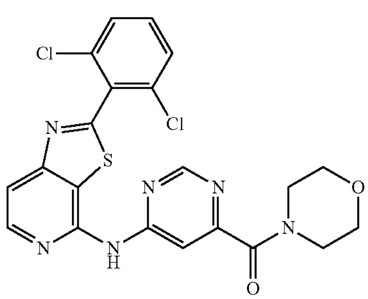 [SMILES: O=C(c1cc(Nc2nccc3nc(-c4c(Cl)cccc4Cl)sc23)ncn1)N1CCOCC1] | (6-(2-(2,6-dichlorophenyl)thiazolo[5,4-c]pyridin-4-ylamino)pyrimidin-4-yl)(morpholino)methanone | 1 | 487.0 | A | 5.16 | ¹H NMR (500 MHz, DMSO-d$_6$): δ 10.97 (s, 1H), 8.80 (s, 1H), 8.49 (d, J = 5.5 Hz, 1H), 7.76-7.74 (m, 2H), 7.70-7.68 (m, 1H), 3.68-3.64 (m, 4H), 3.58-3.60 (m, 2H), 3.45-3.44 (m, 2H). |
| 74 | 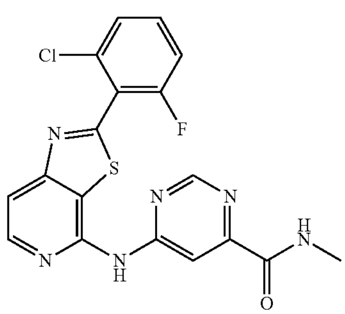 [SMILES: CNC(=O)c1cc(Nc2nccc3nc(-c4c(F)cccc4Cl)sc23)ncn1] | 6-(2-(2-chloro-6-fluorophenyl)thiazolo[5,4-c]pyridin-4-ylamino)-N-methylpyrimidine-4-carboxamide | 1 | 415.1 | B | 5.28 | ¹H NMR (500 MHz, DMSO-d$_6$): δ 10.93 (s, 1H), 8.89-8.84 (m, 2H), 8.52 (m, 1H), 8.21 (s, 1H), 7.93 (m, 1H), 7.74-7.51 (m, 3H), 2.82 (d, J = 5.0 Hz, 3H). |

TABLE 1-continued

| Example | Structure | Name | Synth. Method | LCMS (ESI) m/z [M + H+] | LCMS Method | R_T (min) | NMR |
|---|---|---|---|---|---|---|---|
| 75 | 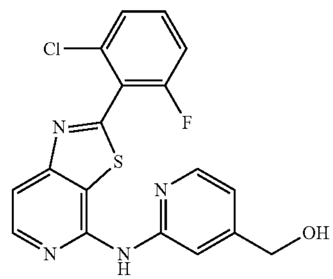 [SMILES: OCc1ccnc(Nc2nccc3nc(-c4c(F)cccc4Cl)sc23)c1] | (2-(2-(2-chloro-6-fluorophenyl)thiazolo[5,4-c]pyridin-4-ylamino)pyridin-4-yl)methanol | 1 | 387.0 | A | 5.16 | $^1$H NMR (500 MHz, DMSO-d$_6$): δ 10.18 (s, 1H), 8.34 (d, J = 5.0 Hz, 1H), 8.16 (d, J = 5.0 Hz), 7.71-7.49 (m, 5H), 6.90 (d, J = 5.0 Hz), 5.43 (t, J = 5.0 Hz, 1H), 4.53 (d, J = 5.5 Hz, 2H). |
| 76 | 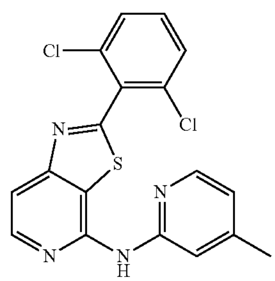 [SMILES: Cc1ccnc(Nc2nccc3nc(-c4c(Cl)cccc4Cl)sc23)c1] | 2-(2,6-dichlorophenyl)-N-(4-methylpyridin-2-yl)thiazolo[5,4-c]pyridin-4-amine | 1 | 387.1 | B | 6.89 | $^1$H NMR (500 MHz, DMSO-d$_6$): δ 10.12 (s, 1H), 8.35 (d, J = 5.0 Hz, 1H), 8.11 (d, J = 5.0 Hz), 7.73-7.66 (m, 4H), 7.47 (s, 1H), 6.82 (d, J = 5.0 Hz, 1H), 2.31 (s, 3H). |
| 77 | 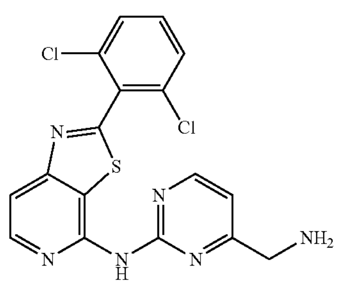 [SMILES: NCc1ccnc(Nc2nccc3nc(-c4c(Cl)cccc4Cl)sc23)n1] | N-(4-(aminomethyl)pyrimidin-2-yl)-2-(2,6-dichlorophenyl)thiazolo[5,4-c]pyridin-4-amine | 1 | 403.1 | B | 4.58 | $^1$H NMR (500 MHz, DMSO-d$_6$): δ 8.60 (br, 1H), 8.45 (d, J = 5.5 Hz, 1H), 7.85 (d, J = 5.0 Hz), 7.75-7.69 (m, 4H), 3.73 (br, 2H). |
| 78 | 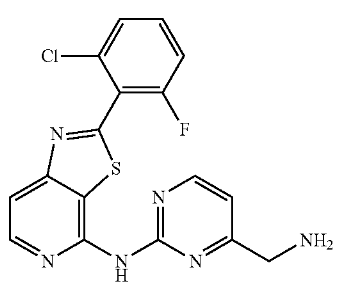 [SMILES: NCc1ccnc(Nc2nccc3nc(-c4c(F)cccc4Cl)sc23)n1] | N-(4-(aminomethyl)pyrimidin-2-yl)-2-(2-chloro-6-fluorophenyl)thiazolo[5,4-c]pyridin-4-amine | 1 | 387.1 | B | 4.39 | $^1$H NMR (500 MHz, DMSO-d$_6$): δ 8.64 (s, 1H), 8.46 (d, J = 5.5 Hz, 1H), 7.85 (d, J = 5.0 Hz), 7.72-7.51 (m, 4H), 3.72 (br, 2H). |
| 79 | 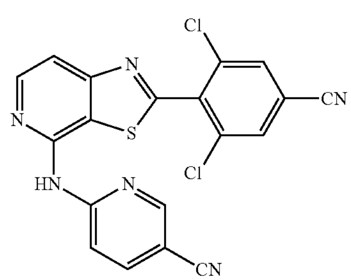 [SMILES: N#Cc1ccc(Nc2nccc3nc(-c4c(Cl)cc(C#N)cc4Cl)sc23)nc1] | 6-[2-(2,6-Dichloro-4-cyano-phenyl)-thiazolo[5,4-c]pyridine-4-ylamino]-nicotinonitrile | 2 | 423 | C | 4.70 | $^1$H NMR (400 MHz, DMSO-d$_6$): δ 10.94 (br s, 1H), 8.70 (dd, J = 2.3, 0.8 Hz, 1H), 8.45 (d, J = 5.6 Hz, 1H), 8.39 (s, 2H), 8.13 (dd, J = 8.8, 2.3 Hz, 1H), 7.85 (d, J = 5.6 Hz, 1H), 7.82 (d, J = 8.9 Hz, 1H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 80 | 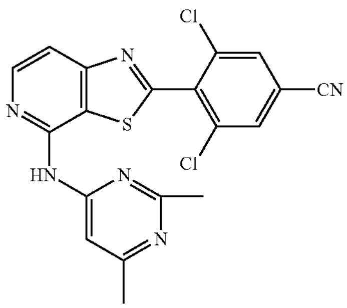 [SMILES: Cc1cc(Nc2nccc3nc(-c4c(Cl)cc(C#N)cc4Cl)sc23)nc(C)n1] | 3,5-Dichloro-4-[4-(2,6-dimethyl-pyrimidin-4-ylamino)-thiazolo[5,4-c]pyridine-2-yl]-benzonitrile | 2 | 427 | C | 3.25 | $^1$H NMR (400 MHz, DMSO-d$_6$): δ 10.63 (br s, 1H), 8.44 (d, J = 5.6 Hz, 1H), 8.38 (s, 2H), 7.83 (d, J = 5.6 Hz, 1H), 7.24 (s, 1H), 2.43 (s, 3H), 2.34 (s, 3H). |
| 81 | 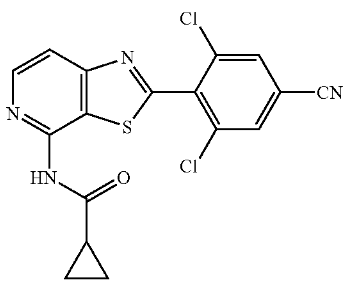 [SMILES: N#Cc1cc(Cl)c(-c2nc3ccnc(NC(=O)C4CC4)c3s2)c(Cl)c1] | Cyclopropane-carboxylic acid [2-(2,6-dichloro-4-cyano-phenyl)-thiazolo[5,4-c]pyridin-4-yl]-amide | 2 | 389 | C | 4.58 | $^1$H NMR (400 MHz, DMSO-d$_6$): δ 11.44 (br s, 1H), 8.46 (d, J = 5.5 Hz, 1H), 8.36 (s, 2H), 7.92 (d, J = 5.5 Hz, 1H), 2.07-1.99 (m, 1H), 0.89-0.79 (m, 4H). |
| 82 | 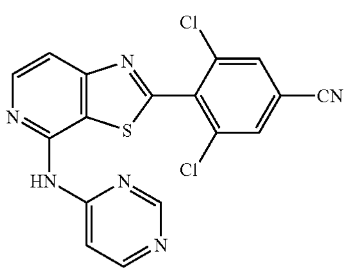 [SMILES: N#Cc1cc(Cl)c(-c2nc3ccnc(Nc4ccncn4)c3s2)c(Cl)c1] | 3,5-Dichloro-4-[4-(pyrimidin-4-ylamino)-thiazolo[5,4-c]pyridin-2-yl]-benzonitrile | 2 | 399 | C | 3.55 | $^1$H NMR (400 MHz, DMSO-d$_6$): δ 10.82 (br s, 1H), 8.76 (d, J = 1.2 Hz, 1H), 8.52 (d, J = 5.9 Hz, 1H), 8.47 (d, J = 5.6 Hz, 1H), 8.39 (s, 2H), 7.87 (d, J = 5.6 Hz, 1H), 7.76 (dd, J = 5.9, 1.3 Hz, 1H). |
| 83 | 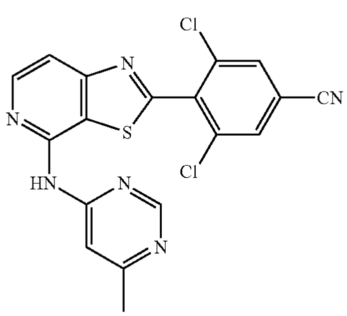 [SMILES: Cc1cc(Nc2nccc3nc(-c4c(Cl)cc(C#N)cc4Cl)sc23)ncn1] | 3,5-Dichloro-4-[4-(6-methyl-pyrimidin-4-ylamino)-thiazolo[5,4-c]pyridin-2-yl]-benzonitrile | 2 | 413 | C | 3.47 | $^1$H NMR (400 MHz, DMSO-d$_6$): δ 10.69 (br s, 1H), 8.62 (d, J = 1.2 Hz, 1H), 8.46 (d, J = 5.6 Hz, 1H), 8.38 (s, 2H), 7.84 (d, J = 5.6 Hz, 1H), 7.57 (s, 1H), 2.39 (s, 3H). |
| 84 | 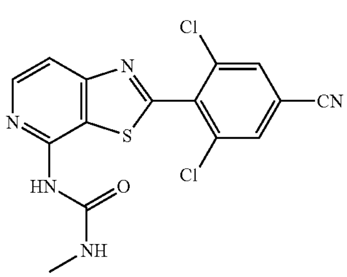 [SMILES: CNC(=O)Nc1nccc2nc(-c3c(Cl)cc(C#N)cc3Cl)sc12] | 1-[2-(2,6-Dichloro-4-cyano-phenyl)-thiazolo[5,4-c]pyridine-4-yl]-3-methyl-urea | 2 | 378 | C | 4.12 | $^1$H NMR (400 MHz, CDCl$_3$): δ 8.27 (s, 1H), 7.78 (s, 2H), 7.70 (d, J = 5.8 Hz, 1H), 3.02 (d, J = 4.6 Hz, 3H). |

TABLE 1-continued

| Example | Structure | Name | Synth. Method | LCMS (ESI) m/z [M + H+] | LCMS Method | R$_T$ (min) | NMR |
|---|---|---|---|---|---|---|---|
| 85 | 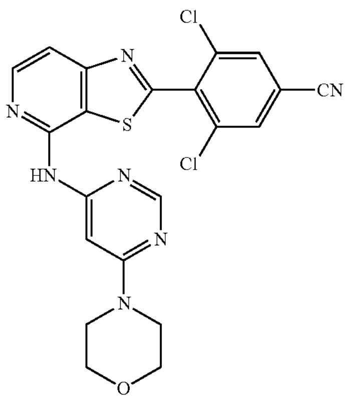 [SMILES: N#Cc1cc(Cl)c(-c2nc3ccnc(Nc4cc(N5CCOCC5)ncn4)c3s2)c(Cl)c1] | 3,5-Dichloro-4-[4-(6-morpholin-4-yl-pyrimidin-4-ylamino)-thiazolo[5,4-c]pyridine-2-yl]-benzonitrile | 2 | 484 | C | 3.52 | $^1$H NMR (400 MHz, DMSO-d$_6$): δ 10.30 (s, 1H), 8.41 (d, J = 5.6 Hz, 1H), 8.38 (s, 2H), 8.28 (d, J = 0.9 Hz, 1H), 7.77 (d, J = 5.6 Hz, 1H), 7.01 (br s, 1H), 3.69 (t, J = 4.8 Hz, 4H), 3.53 (t, J = 4.7 Hz, 4H). |
| 86 | 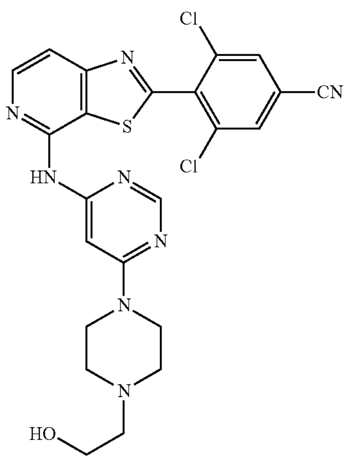 [SMILES: N#Cc1cc(Cl)c(-c2nc3ccnc(Nc4cc(N5CCN(CCO)CC5)ncn4)c3s2)c(Cl)c1] | 3,5-Dichloro-4-(4-{6-(2-hydroxy-ethyl)-piperazin-1-yl]-pyrimidin-4-ylamino}-thiazolo[5,4-c]pyridine-2-yl)-benzonitrile | 2 | 527 | C | 2.70 | $^1$H NMR (400 MHz, DMSO-d$_6$): δ 10.23 (br s, 1H), 8.40 (d, J = 5.6 Hz, 1H), 8.37 (s, 2H), 8.25 (s, 1H), 7.75 (d, J = 5.6 Hz, 1H), 6.97 (s, 1H), 4.44 (br s, 1H), 3.53-3.52 (m, 8H), 2.43-2.40 (m, 4H). |
| 87 | 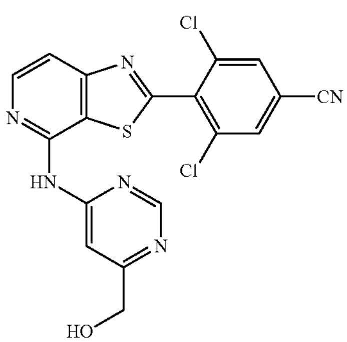 [SMILES: N#Cc1cc(Cl)c(-c2nc3ccnc(Nc4cc(CO)ncn4)c3s2)c(Cl)c1] | 3,5-Dichloro-4-[4-(5-hydroxymethyl-pyrimidin-4-ylamino)-thiazolo[5,4-c]pyridine-2-yl}-benzonitrile | 2 | 429 | C | 3.35 | $^1$H NMR (400 MHz, DMSO-d$_6$): δ 10.76 (s, 1H), 8.62 (s, 1H), 8.46 (d, J = 5.6 Hz, 1H), 8.38 (s, 2H), 7.85 (d, J = 5.6 Hz, 1H), 7.74 (s, 1H), 5.56 (t, J = 5.8 Hz, 1H), 4.48 (d, J = 5.7 Hz, 2H) |
| 88 | 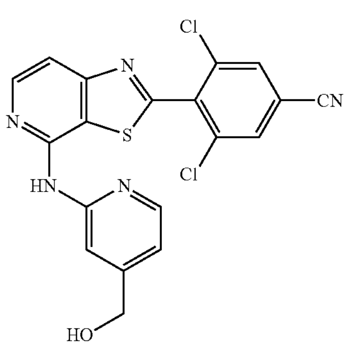 [SMILES: N#Cc1cc(Cl)c(-c2nc3ccnc(Nc4cc(CO)ccn4)c3s2)c(Cl)c1] | 3,5-Dichloro-4-[4-(4-hydroxymethyl-pyridin-2-ylamino)-thiazolo[5,4-c]pyridin-2-yl]-benzonitrile | 2 | 462 | C | 3.13 | $^1$H NMR (400 MHz, DMSO-d$_6$): δ 8.52 (d, J = 5.9 Hz, 1H), 8.43 (s, 2H), 8.38 (d, J = 6.2 Hz, 1H), 7.99 (d, J = 5.9 Hz, 1H), 7.86 (s, 1H), 7.28 (d, J = 6.2 Hz 1H), 4.70 (s, 2H). |

TABLE 1-continued

| Example | Structure | Name | Synth. Method | LCMS (ESI) m/z [M + H+] | LCMS Method | R_T (min) | NMR |
|---|---|---|---|---|---|---|---|
| 89 | 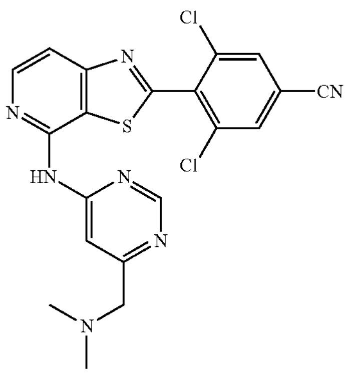 [SMILES: CN(C)Cc1cc(Nc2nccc3nc(-c4c(Cl)cc(C#N)cc4Cl)sc23)ncn1] | 3,5-Dichloro-4-[4-(6-dimethylamino-methyl-pyrimidin-4-ylamino)-thiazolo[5,4-c]pyridin-2-yl]-benzonitrile | 2 | 456 | C | 3.01 | $^1$H NMR (400 MHz, DMSO-$d_6$): δ 10.73 (s, 1H), 8.65 (d, J = 1.2 Hz, 1H), 8.46 (d, J = 5.6 Hz, 1H), 8.38 (s, 2H), 7.85 (d, J = 5.6 Hz, 1H), 7.69 (br s, 1H), 3.45 (s, 2H), 2.24 (s, 6H). |
| 90 | 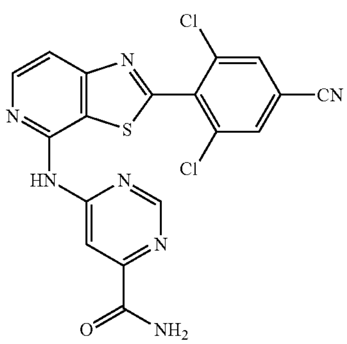 [SMILES: N#Cc1cc(Cl)c(-c2nc3ccnc(Nc4cc(C(N)=O)ncn4)c3s2)c(Cl)c1] | 6-[2-(2,6-Dichloro-4-cyano-phenyl)-thiazolo[5,4-c]pyridin-4-ylamino]-pyrimidine-4-carboxylic acid amide | 2 | 442 | C | 3.88 | $^1$H NMR (400 MHz, DMSO-$d_6$): δ 11.10 (s, 1H), 8.83 (d, J = 1.2 Hz, 1H), 8.51 (d, J = 5.6 Hz, 1H), 8.39 (s, 2H), 8.24 (d, J = 1.2 Hz, 1H), 8.18 (s, 1H), 7.91 (d, J = 5.6 Hz, 1H), 7.87 (s, 1H). |
| 91 | 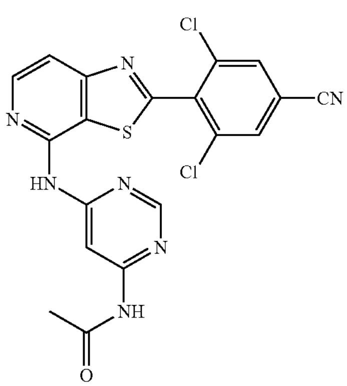 [SMILES: CC(=O)Nc1cc(Nc2nccc3nc(-c4c(Cl)cc(C#N)cc4Cl)sc23)ncn1] | N-{6-[2-(2,6-Dichloro-4-cyano-phenyl)-thiazolo[5,4-c]pyridin-4-ylamino]-pyrimidin-4-yl}-acetamide | 2 | 456 | C | 3.75 | $^1$H NMR (400 MHz, DMSO-$d_6$): δ 10.68 (s, 1H), 10.64 (s, 1H), 8.47 (d, J = 1.1 Hz, 1H), 8.43 (d, J = 5.6 Hz, 1H), 8.38 (s, 2H), 8.25-8.23 (m, 1H), 7.84 (d, J = 5.6 Hz, 1H), 2.11 (s, 3H). |
| 92 | 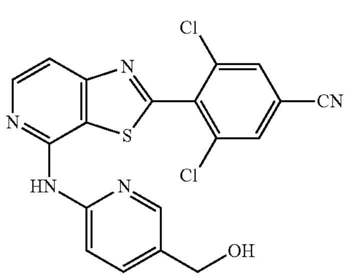 [SMILES: N#Cc1cc(Cl)c(-c2nc3ccnc(Nc4ccc(CO)cn4)c3s2)c(Cl)c1] | 3,5-Dichloro-4-[4-(5-hydoxymethyl-pyridin-2-ylamino)-thiazolo[5,4-c]pyridin-2-yl]-benzonitrile | 2 | 428 | C | 3.06 | $^1$H NMR (400 MHz, DMSO-$d_6$): δ 10.23 (s, 1H), 8.37 (s, 2H), 8.33 (d, J = 5.6 Hz, 1H), 8.18 (d, J = 2.2 Hz, 1H), 7.65-7.64 (m, 3H), 5.16 (t, J = 5.5 Hz, 1H), 4.45 (d, J = 5.2 Hz, 2H). |

TABLE 1-continued

| Example | Structure | Name | Synth. Method | LCMS (ESI) m/z [M + H+] | LCMS Method | R$_T$ (min) | NMR |
|---|---|---|---|---|---|---|---|
| 93 | 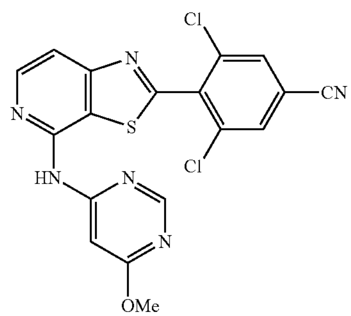 [SMILES: COc1cc(Nc2nccc3nc(-c4c(Cl)cc(C#N)cc4Cl)sc23)ncn1] | 3,5-Dichloro-4-[4-(6-methoxy-pyrimidin-4-ylamino)-thiazolo[5,4-c]pyridin-2-yl]-benzonitrile | 2 | 429 | C | 4.69 | $^1$H NMR (400 MHz, DMSO-d$_6$): δ 10.67 (s, 1H), 8.49 (d, J = 0.9 Hz, 1H), 8.45 (d, J = 5.6 Hz, 1H), 8.39 (s, 2H), 7.81 (d, J = 5.6 Hz, 1H), 7.33-7.30 (s, 1H), 3.91 (s, 3H). |
| 94 | 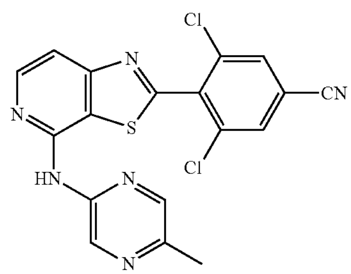 [SMILES: Cc1cnc(Nc2nccc3nc(-c4c(Cl)cc(C#N)cc4Cl)sc23)cn1] | 3,5-Dichloro-4-[4-(5-methyl-pyrazin-2-ylamino)-thiazolo[5,4-c]pyridin-2-yl]-benzonitrile | 2 | 413 | C | 4.09 | $^1$H NMR (400 MHz, DMSO-d$_6$): δ 10.42 (s, 1H), 9.07 (s, 1H), 8.38 (s, 2H), 8.36 (d, J = 5.7 Hz, 1H), 8.22-8.20 (m, 1H), 7.72 (d, J = 5.6 Hz, 1H), 2.44 (s, 3H). |
| 95 | 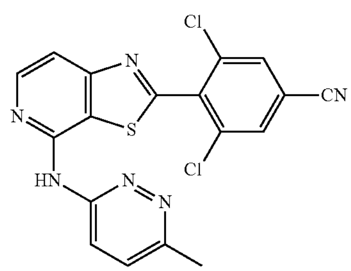 [SMILES: Cc1ccc(Nc2nccc3nc(-c4c(Cl)cc(C#N)cc4Cl)sc23)nn1] | 3,5-Dichloro-4-[4-(6-methyl-pyridazin-3-ylamino)-thiazolo[5,4-c]pyridin-2-yl]-benzonitrile | 2 | 413 | C | 3.57 | $^1$H NMR (400 MHz, DMSO-d$_6$): δ 10.60 (s, 1H), 8.38 (s, 2H), 8.34 (d, J = 5.6 Hz, 1H), 7.98-7.90 (m, 1H), 7.72 (d, J = 5.6 Hz, 1H), 7.51 (d, J = 9.1 Hz, 1H), 2.53 (s, 3H). |
| 96 | 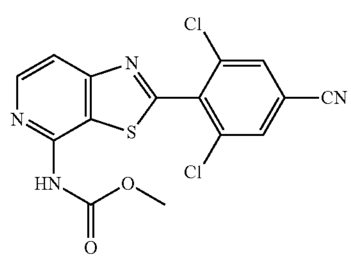 [SMILES: COC(=O)Nc1nccc2nc(-c3c(Cl)cc(C#N)cc3Cl)sc12] | [2-(2,6-Dichloro-4-cyano-phenyl)-thiazolo[5,4-c]pyridin-4-yl]-carbamic acid methyl ester | 2 | 379 | C | 4.37 | $^1$H NMR (400 MHz, CDCl$_3$): δ 8.45 (s, 1H), 8.39 (d, J = 5.6 Hz, 1H), 7.84 (d, J = 5.6 Hz, 1H), 7.76 (s, 2H), 3.87 (s, 3H). |
| 97 | 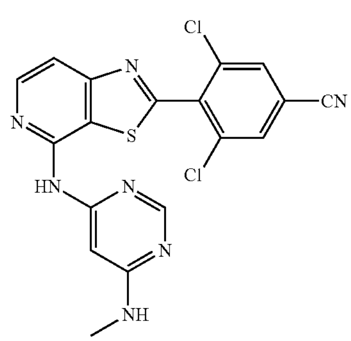 [SMILES: CNc1cc(Nc2nccc3nc(-c4c(Cl)cc(C#N)cc4Cl)sc23)ncn1] | 3,5-Dichloro-4-[4-(6-methylamino-pyrimidin-4-ylamino)-thiazolo[5,4-c]pyridin-2-yl]-benzonitrile | 3 | 428 | C | 3.32 | $^1$H NMR (400 MHz, DMSO-d$_6$): δ 10.13 (s, 1H), 8.39-8.35 (m, 3H), 8.17 (s, 1H), 7.73 (d, J = 5.6 Hz, 1H), 7.16 (s, 1H), 6.79 (s, 1H), 2.78 (d, J = 4.7 Hz, 3H). |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 98 | 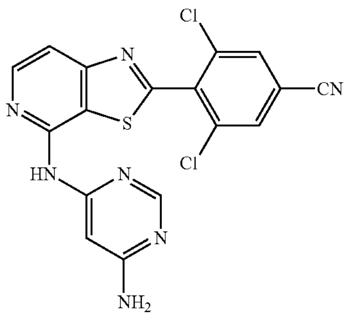 [SMILES: N#Cc1cc(Cl)c(-c2nc3ccnc(Nc4cc(N)ncn4)c3s2)c(Cl)c1] | 4-[4-(6-Amino-pyrimidin-4-ylamino)-thiazolo[5,4-c]pyridin-2-yl]-3,5-dichloro-benzonitrile | 3 | 414 | C | 3.18 | ¹H NMR (400 MHz, DMSO-d$_6$): δ 8.52 (s, 1H), 8.49 (d, J = 5.7 Hz, 1H), 8.41 (s, 2H), 7.95 (d, J = 5.7 Hz, 1H). |
| 99 | 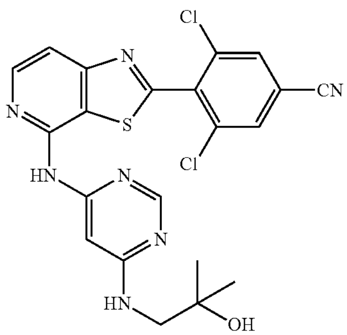 [SMILES: CC(C)(O)CNc1cc(Nc2nccc3nc(-c4c(Cl)cc(C#N)cc4Cl)sc23)ncn1] | 3,5-Dichloro-4-{4-[6-(2-hydroxy-2-methyl-propylamino)-pyrimidin-4-ylamino]-thiazolo[5,4-c]pyridin-2-yl}-benzonitrile | 3 | 486 | C | 3.33 | ¹H NMR (400 MHz, DMSO-d$_6$): δ 10.12 (s, 1H), 8.40-8.36 (m, 3H), 8.15 (s, 1H), 7.73 (d, J = 5.6 Hz, 1H), 7.12 (br s, 1H), 6.94 (br s, 1H), 4.57 (s, 1H), 3.31-3.24 (m, 2H), 1.11 (s, 6H). |
| 100 | 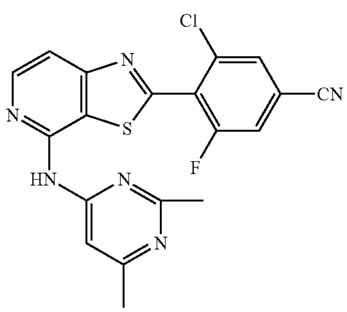 [SMILES: Cc1cc(Nc2nccc3nc(-c4c(F)cc(C#N)cc4Cl)sc23)nc(C)n1] | 3-Chloro-4-[4-(2,6-dimethyl-pyrimidin-4-ylamino)-thiazolo[5,4-c]pyridin-2-yl]-5-fluoro-benzonitrile | 4 | 411 | C | 3.11 | ¹H NMR (400 MHz, DMSO-d$_6$): δ 8.61 (d, J = 5.6 Hz, 1H), 8.30 (t, J = 1.2 Hz, 1H), 8.24 (dd, J = 9.1, 1.4 Hz, 1H), 8.09 (d, J = 5.6 Hz, 1H), 7.59 (br s, 1H), 2.65 (s, 3H), 2.56 (s, 3H). |
| 101 | 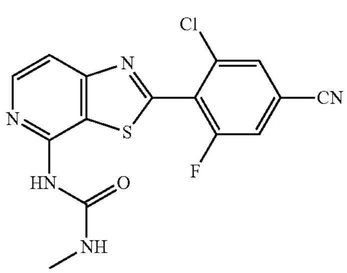 [SMILES: CNC(=O)Nc1nccc2nc(-c3c(F)cc(C#N)cc3Cl)sc12] | 1-[2-(2-Chloro-4-cyano-6-fluoro-phenyl)-thiazolo[5,4-c]pyridin-4-yl]-3-methyl-urea | 4 | 362 | C | 3.94 | ¹H NMR (400 MHz, DMSO-d$_6$): δ 9.82 (s, 1H), 8.31 (d, J = 5.7 Hz, 1H), 8.26 (t, J = 1.3 Hz, 1H), 8.20 (dd, J = 9.0, 1.5 Hz, 1H), 7.75-7.70 (m, 2H), 2.75 (d, J = 4.6 Hz, 3H). |
| 102 | 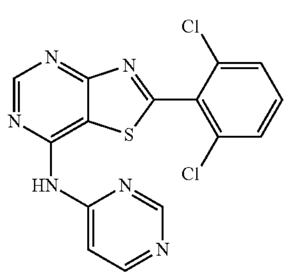 [SMILES: Clc1cccc(Cl)c1-c1nc2ncnc(Nc3ccncn3)c2s1] | 2-(2,6-dichlorophenyl)-N-(pyrimidin-4-yl)thiazolo[4,5-d]pyrimidin-7-amine | 5 | 374.9 | B | 3.84 | ¹H NMR (400 MHz, DMSO-d$_6$): δ 11.45 (s, 1H), 8.91 (d, J = 14.7 Hz, 2H), 8.63 (d, J = 5.8 Hz, 1H), 7.84 (d, J = 5.8 Hz, 1H), 7.79-7.72 (m, 2H), 7.68 (dd, J = 9.3, 6.7 Hz, 1H). |

TABLE 1-continued

| Example | Structure | Name | Synth. Method | LCMS (ESI) m/z [M + H+] | LCMS Method | R_T (min) | NMR |
|---|---|---|---|---|---|---|---|
| 103 | 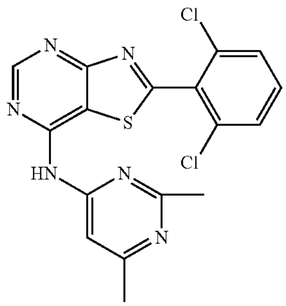 [SMILES: Cc1cc(Nc2ncnc3nc(-c4c(Cl)cccc4Cl)sc23)nc(C)n1] | 2-(2,6-dichlorophenyl)-N-(2,6-dimethylpyrimidin-4-yl)thiazolo[4,5-d]pyrimidin-7-amine | 5 | 403.0 | B | 3.55 | $^1$H NMR (400 MHz, DMSO-d$_6$): δ 11.26 (s, 1H), 8.92 (s, 1H), 7.78-7.71 (m, 2H), 7.68 (dd, J = 9.3, 6.7 Hz, 1H), 7.41 (s, 1H), 2.35 (s, 3H), 2.39 (s, 3H). |
| 104 | 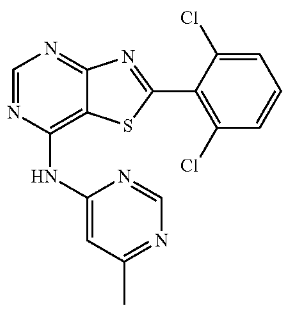 [SMILES: Cc1cc(Nc2ncnc3nc(-c4c(Cl)cccc4Cl)sc23)ncn1] | [2-(2,6-dichlorophenyl)-N-(6-methylpyrimidin-4-yl)thiazolo[4,5-d]pyrimidin-7-amine | 5 | 389.0 | B | 3.79 | $^1$H NMR (400 MHz, DMSO-d$_6$): δ 11.35 (s, 1H), 8.92 (s, 1H), 8.77 (d, J = 0.8 Hz, 1H), 7.78 (7.72 (m, 2H), 7.71 (7.61 (m, 2H), 2.44 (s, 3H). |
| 105 | 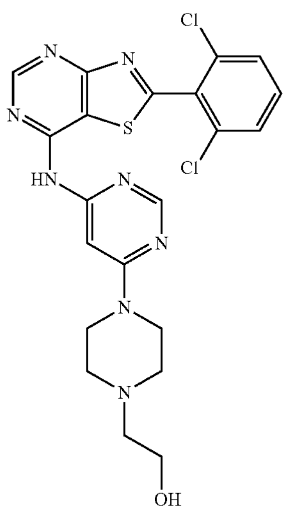 [SMILES: OCCN1CCN(c2cc(Nc3ncnc4nc(-c5c(Cl)cccc5Cl)sc34)ncn2)CC1] | 2-(4-(6-(2-(2,6-dichlorophenyl)thiazolo[4,5-d]pyrimidin-7-ylamino)pyrimidin-4-yl)piperazin-1-yl)ethanol | 5 | 503.1 | B | 3.35 | $^1$H NMR (400 MHz, DMSO-d$_6$): δ 10.90 (s, 1H), 8.86 (s, 1H), 8.35 (s, 1H), 7.78-7.71 (m, 2H), 7.67 (dd, J = 9.3, 6.7 Hz, 1H), 6.94 (s, 1H), 4.45 (t, J = 5.4 Hz, 1H), 3.65-3.47 (m, 6H), 3.33 (m, 4H), 2.43 (t, J = 6.2 Hz, 2H). |
| 106 | 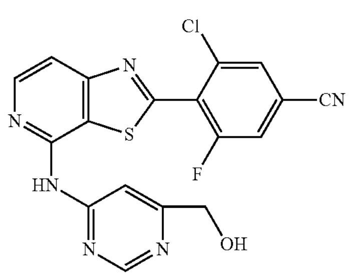 [SMILES: N#Cc1cc(F)c(-c2nc3ccnc(Nc4cc(CO)ncn4)c3s2)c(Cl)c1] | 3-Chloro-5-fluoro-4-[4-(6-hydroxymethyl-pyrimidin-4-ylamino)-thiazolo[5,4-c]pyridin-2-yl]-benzonitrile | 4 | 413 | C | 3.17 | $^1$H NMR (400 MHz, DMSO-d$_6$): δ 10.78 (s, 1H), 8.62 (s, 1H), 8.47 (d, J = 5.6 Hz, 1H), 8.28 (s, 1H), 8.22 (d, J = 9.1 Hz, 1H), 7.87 (d, J = 5.6 Hz, 1H), 7.74 (s, 1H), 5.56 (t, J = 5.8 Hz, 1H), 4.48 (d, J = 5.8 Hz, 2H). |

TABLE 1-continued

| Example | Structure | Name | Synth. Method | LCMS (ESI) m/z [M + H⁺] | LCMS Method | R_T (min) | NMR |
|---|---|---|---|---|---|---|---|
| 107 | 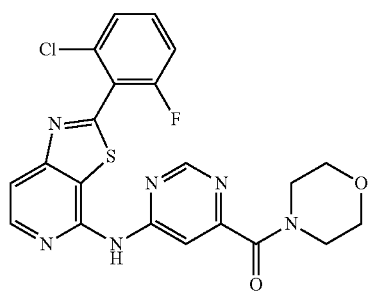 [SMILES: O=C(c1cc(Nc2nccc3nc(-c4c(F)cccc4Cl)sc23)ncn1)N1CCOCC1] | (6-(2-(2-chloro-6-fluorophenyl)thiazolo[5,4-c]pyridin-4-ylamino)pyrimidin-4-yl)(morpholino)methanone | 1 | 471.0 | A | 4.99 | ¹H-NMR (500 MHz, DMSO-d₆): δ 11.03 (br, 1H), 8.80 (s, 1H), 8.50 (d, J = 6.0 Hz, 1H), 7.89 (s, 2H), 7.74-7.52 (m, 3H), 3.68-3.65 (m, 4H), 3.58-3.32 (m, 4H) |
| 108 | 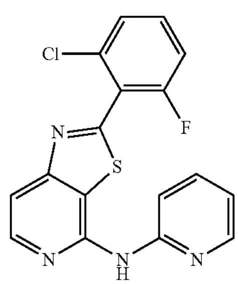 [SMILES: Fc1cccc(Cl)c1-c1nc2ccnc(Nc3ccccn3)c2s1] | 2-(2-chloro-6-fluorophenyl)-N-(pyridin-2-yl)thiazolo[5,4-c]pyridin-4-amine | 1 | 357.1 | B | 6.29 | ¹H-NMR (500 MHz, DMSO-d₆): δ 10.19 (s, 1H), 8.35 (d, J = 5.5 Hz, 1H), 8.26 (d, J = 4.5 Hz, 1H), 7.74-7.67 (m, 4H), 7.53-7.50 (m, 2H), 6.98 (m, 1H) |
| 109 | 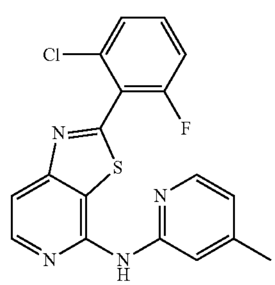 [SMILES: Cc1ccnc(Nc2nccc3nc(-c4c(F)cccc4Cl)sc23)c1] | 2-(2-chloro-6-fluorophenyl)-N-(4-methylpyridin-2-yl)thiazolo[5,4-c]pyridin-4-amine | 1 | 371.1 | B | 6.62 | ¹H-NMR (500 MHz, DMSO-d₆): δ 10.12 (s, 1H), 8.35 (d, J = 5.5 Hz, 1H), 8.11 (d, J = 5.0 Hz, 1H), 7.71-7.45 (m, 5H), 6.82 (d, J = 5.0 Hz, 1H), 2.31 (s, 3H) |
| 110 | 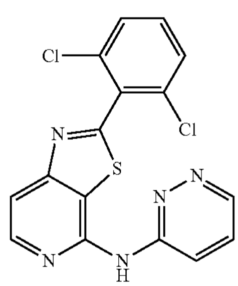 [SMILES: Clc1cccc(Cl)c1-c1nc2ccnc(Nc3cccnn3)c2s1] | 2-(2,6-dichlorophenyl)-N-(pyridazin-3-yl)thiazolo[5,4-c]pyridin-4-amine | 1 | 374.0 | A | 5.62 | ¹H- NMR (500 MHz, DMSO-d₆): δ 10.69 (s, 1H), 8.80 (s, 1H), 8.37 (d, J = 6.0 Hz, 1H), 8.12 (d, J = 9.0 Hz, 1H), 7.75-7.61 (m, 5H) |
| 111 | 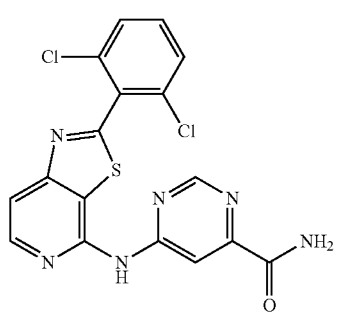 [SMILES: NC(=O)c1cc(Nc2nccc3nc(-c4c(Cl)cccc4Cl)sc23)ncn1] | 6-(2-(2,6-dichlorophenyl)thiazolo[5,4-c]pyridin-4-ylamino)pyrimidine-4-carboxamide | 1 | 417.0 | A | 5.09 | ¹H-NMR (500 MHz, DMSO-d₆): δ 11.02 (br, 1H), 8.83 (s, 1H), 8.51 (d, J = 5.5 Hz, 1H), 8.26 (s, 1H), 8.19 (s, 1H), 7.88 (m, 2H), 7.74-7.66 (m, 3H) |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 112 | 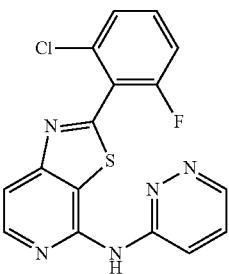 [SMILES: Fc1cccc(Cl)c1-c1nc2ccnc(Nc3cccnn3)c2s1] | 2-(2-chloro-6-fluorophenyl)-N-(pyridazin-3-yl)thiazolo[5,4-c]pyridin-4-amine | 1 | 358.0 | A | 5.38 | ¹H-NMR (500 MHz, DMSO-d₆): δ 10.70 (br, 1H), 8.85 (s, 1H), 8.38 (d, J = 5.5 Hz, 1H), 8.10 (d, J = 8.0 Hz, 1H), 7.78-7.51 (m, 5H) |
| 113 | 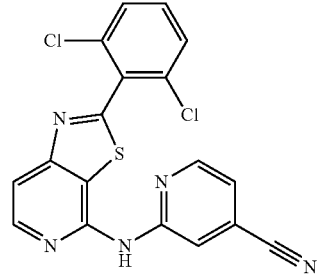 [SMILES: N#Cc1ccnc(Nc2nccc3nc(-c4c(Cl)cccc4Cl)sc23)c1] | 2-(2-(2,6-dichlorophenyl)thiazolo[5,4-c]pyridin-4-ylamino)isonicotinonitrile | 1 | 398.1 | B | 6.72 | ¹H-NMR (500 MHz, DMSO-d₆): δ 10.70 (s, 1H), 8.51 (d, J = 5.5 Hz, 1H), 8.44 (d, J = 6.0 Hz, 1H), 8.27 (s, 1H), 7.79-7.66 (m, 4H), 7.38 (m, 1H) |
| 114 | 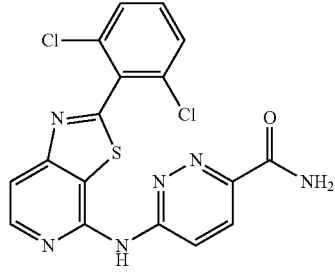 [SMILES: NC(=O)c1ccc(Nc2nccc3nc(-c4c(Cl)cccc4Cl)sc23)nn1] | 6-(2-(2,6-dichlorophenyl)thiazolo[5,4-c]pyridin-4-ylamino)pyridazine-3-carboxamide | 1 | 417.0 | A | 5.18 | ¹H-NMR (500 MHz, DMSO-d₆): δ 11.06 (br, 1H), 8.43 (d, J = 5.5 Hz, 1H), 8.30 (m, 1H), 8.21 (d, J = 9.0 Hz, 1H), 8.13 (d, J = 4.5 Hz, 1H), 7.84 (d, J = 5.5 Hz, 1H), 7.76-7.66 (m, 4H) |
| 115 | 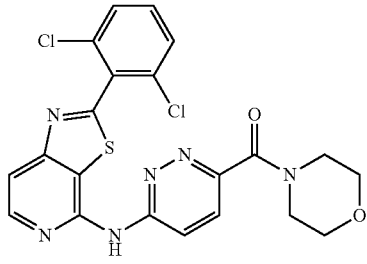 [SMILES: O=C(c1ccc(Nc2nccc3nc(-c4c(Cl)cccc4Cl)sc23)nn1)N1CCOCC1] | (6-(2-(2,6-dichlorophenyl)thiazolo[5,4-c]pyridin-4-ylamino)pyridazin-3-yl)(morpholino)methanone | 1 | 487.1 | B | 5.35 | ¹H-NMR (500 MHz, DMSO-d₆): δ 8.28 (d, J = 5.5 Hz, 1H), 8.11 (m, 1H), 7.72-7.54 (m, 5H), 3.57 (s, 4H), 3.47 (s, 4H) |
| 116 | 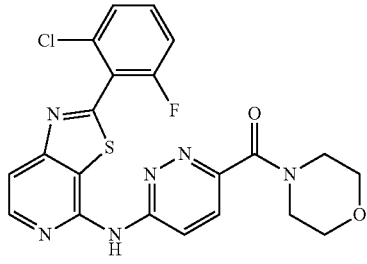 [SMILES: O=C(c1ccc(Nc2nccc3nc(-c4c(F)cccc4Cl)sc23)nn1)N1CCOCC1] | (6-(2-(2-chloro-6-fluorophenyl)thiazolo[5,4-c]pyridin-4-ylamino)pyridazin-3-yl)(morpholino)methanone | 1 | 471.2 | B | 5.14 | ¹H-NMR (500 MHz, DMSO-d₆): δ 10.95 (br, 1H), 8.40 (d, J = 5.5 Hz, 1H), 8.22 (d, J = 8.0 Hz, 1H), 7.74-7.51 (m, 5H), 3.69 (s, 4H), 3.59 (s, 4H) |

TABLE 1-continued

| Example | Structure | Name | Synth. Method | LCMS (ESI) m/z [M + H⁺] | LCMS Method | R$_T$ (min) | NMR |
|---|---|---|---|---|---|---|---|
| 117 | 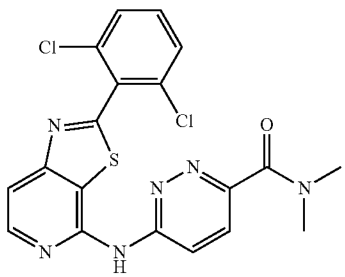 [SMILES: CN(C)C(=O)c1ccc(Nc2nccc3nc(-c4c(Cl)cccc4Cl)sc23)nn1] | 6-(2-(2,6-dichlorophenyl)thiazolo[5,4-c]pyridin-4-ylamino)-N,N-dimethylpyridazine-3-carboxamide | 1 | 445.1 | A | 5.42 | ¹H-NMR (500 MHz, DMSO-d$_6$): δ 10.95 (br, 1H), 8.41 (d, J = 5.5 Hz, 1H), 8.22 (d, J = 6.0 Hz, 1H), 7.80-7.66 (m, 5H), 3.07 (s, 3H), 3.06 (s, 3H) |
| 118 | 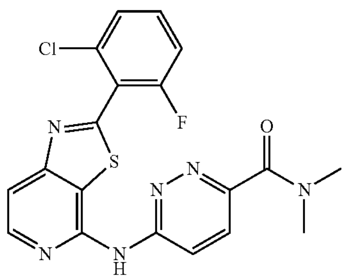 [SMILES: CN(C)C(=O)c1ccc(Nc2nccc3nc(-c4c(F)cccc4Cl)sc23)nn1] | 6-(2-(2-chloro-6-fluorophenyl)thiazolo[5,4-c]pyridin-4-ylamino)-N,N-dimethylpyridazine-3-carboxamide | 1 | 429.0 | A | 5.42 | ¹H-NMR (500 MHz, DMSO-d$_6$): δ 10.95 (br, 1H), 8.41 (d, J = 6.0 Hz, 1H) 8.19 (s, 1H), 7.80-7.51 (m, 5H), 3.07 (s, 3H), 3.06 (s, 3H) |
| 119 | 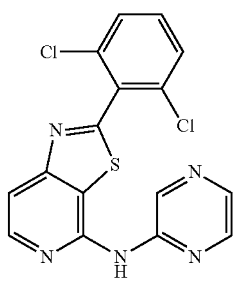 [SMILES: Clc1cccc(Cl)c1-c1nc2ccnc(Nc3cnccn3)c2s1] | 2-(2,6-dichlorophenyl)-N-(pyrazin-2-yl)thiazolo[5,4-c]pyridin-4-amine | 1 | 374.0 | A | 5.72 | ¹H-NMR (500 MHz, DMSO-d$_6$): δ 10.55 (s, 1H), 9.18 (s, 1H), 8.41 (d, J = 6.0 Hz, 1H), 8.32 (s, 1H), 8.21 (d, J = 2.5 Hz, 1H), 7.78-7.66 (m, 4H) |
| 120 | 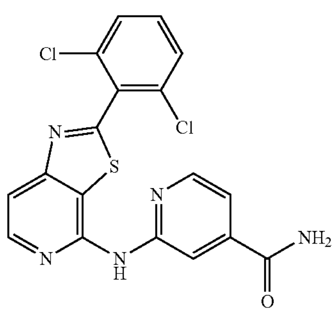 [SMILES: NC(=O)c1ccnc(Nc2nccc3nc(-c4c(Cl)cccc4Cl)sc23)c1] | 2-(2-(2,6-dichlorophenyl)thiazolo[5,4-c]pyridin-4-ylamino)isnicotinamide | 1 | 416.1 | B | 5.04 | ¹H-NMR (500 MHz, DMSO-d$_6$): δ 10.37 (s, 1H), 8.39 (m, 2H), 8.15 (s, 1H), 8.06 (s, 1H), 7.75-7.67 (m, 5H), 7.34 (m, 1H) |
| 121 | 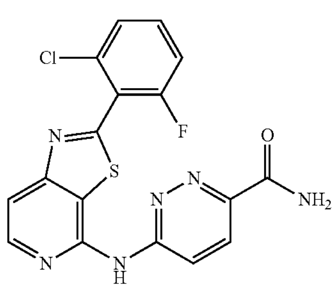 [SMILES: NC(=O)c1ccc(Nc2nccc3nc(-c4c(F)cccc4Cl)sc23)nn1] | 6-(2-(2-chloro-6-fluorophenyl)thiazolo[5,4-c]pyridin-4-ylamino)pyridazine-3-carboxamide | 1 | 401.0 | A | 4.90 | ¹H-NMR (500 MHz, DMSO-d$_6$): δ 11.05 (br, 1H), 8.42-8.13 (m, 4H), 7.84-7.53 (m, 5H) |

TABLE 1-continued

| Example | Structure | Name | Synth. Method | LCMS (ESI) m/z [M + H+] | LCMS Method | R_T (min) | NMR |
|---|---|---|---|---|---|---|---|
| 122 | 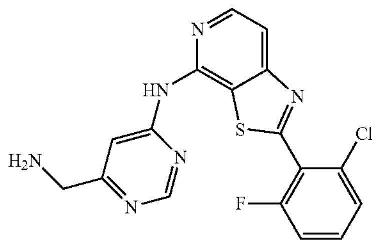 [SMILES: NCc1cc(Nc2nccc3nc(-c4c(F)cccc4Cl)sc23)ncn1] | N-(6-(aminomethyl)pyrimidin-4-yl)-2-(2-chloro-6-fluorophenyl)thiazolo[5,4-c]pyridin-4-amine | 1 | 387.1 | B | 4.42 | $^1$H-NMR (500 MHz, DMSO-d$_6$): δ 8.64 (s, 1H), 8.6 (d, J = 5.0 Hz, 1H), 7.85 (d, J = 5.0 Hz, 1H), 7.73-7.70 (m, 2H), 7.62-7.51 (m, 2H), 3.73 (s, 2H) |
| 123 | 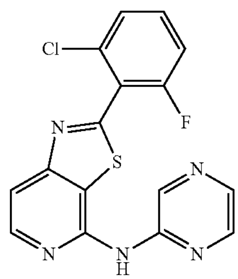 [SMILES: Fc1cccc(Cl)c1-c1nc2ccnc(Nc3cnccn3)c2s1] | 2-(2-chloro-6-fluorophenyl)-N-(pyrazin-2-yl)thiazolo[5,4-c]pyridin-4-amine | 1 | 358.0 | A | 5.46 | $^1$H-NMR (500 MHz, DMSO-d$_6$): δ 10.56 (s, 1H), 9.16 (s, 1H), 8.41 (d, J = 5.5 Hz, 1H), 8.32 (s, 1H), 8.21 (s, 1H), 7.78-7.53 (m, 4H) |
| 124 | 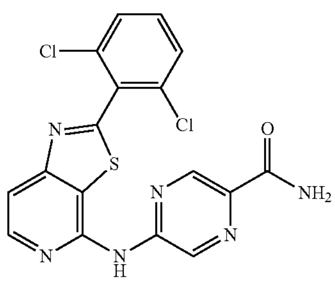 [SMILES: NC(=O)c1cnc(Nc2nccc3nc(-c4c(Cl)cccc4Cl)sc23)cn1] | 5-(2-(2,6-dichlorophenyl)thiazolo[5,4-c]pyridin-4-ylamino)pyrazine-2-carboxamide | 1 | 417.1 | B | 5.32 | $^1$H-NMR (500 MHz, DMSO-d$_6$): δ 11.06 (br, 1H), 9.11 (s, 1H), 8.81 (s, 1H), 8.43 (d, J = 5.0 Hz, 1H), 7.98 (s, 1H), 7.81-7.58 (m, 5H) |
| 125 | 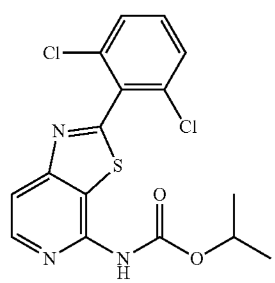 [SMILES: CC(C)OC(=O)Nc1nccc2nc(-c3c(Cl)cccc3Cl)sc12] | isopropyl 2-(2,6-dichlorophenyl)thiazolo[5,4-c]pyridin-4-ylcarbamate | 1 | 382.1 | B | 6.62 | $^1$H-NMR (500 MHz, DMSO-d$_6$): δ 10.67 (br, 1H), 8.43 (d, J = 5.5 Hz, 1H), 7.91 (d, J = 5.5 Hz, 1H), 7.74-7.61 (m, 3H), 4.93 (m, 1H), 1.29 (d, J = 6.5 Hz, 6H) |
| 126 | 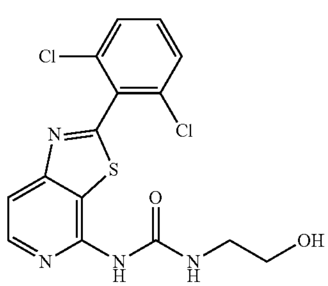 [SMILES: O=C(NCCO)Nc1nccc2nc(-c3c(Cl)cccc3Cl)sc12] | 1-(2-(2,6-dichlorophenyl)thiazolo[5,4-c]pyridin-4-yl)-3-(2-hydroxyethyl)urea | 1 | 383.1 | B | 4.74 | $^1$H-NMR (500 MHz, DMSO-d$_6$): δ 9.78 (br, 1H), 8.32 (d, J = 5.5 Hz, 1H), 8.03 (s, 1H), 7.74-7.65 (m, 4H), 4.82 (s, 1H), 3.52 (m, 2H), 3.28 (m, 2H) |

Method F: Experiments performed on a VG Platform II quadrupole mass spectrometer linked to a Hewlett Packard HP1050 LC system with diode array detector and 100 position autosampler., using a Phenomenex Luna 3 μm $C_{18}$(2) 30×4.6 mm and a 2 mL/minute flow rate. The mobile phase consisted of formic acid 0.1% in water (solvent A) and formic acid 0.1% in acetonitrile (solvent B). The initial solvent system was 95% solvent A and 5% solvent B for the first 0.3 minute followed by a gradient up to 5% solvent A and 95% solvent B over the next 4 minutes. The final solvent system was held constant for a further 1 minute.

Example 127

4-[4-(6-Amino-2-methylpyrimidin-4-ylamino)thiazolo[5,4-c]pyridin-2-yl]-3,5-dichloro-benzonitrile hydrochloride salt

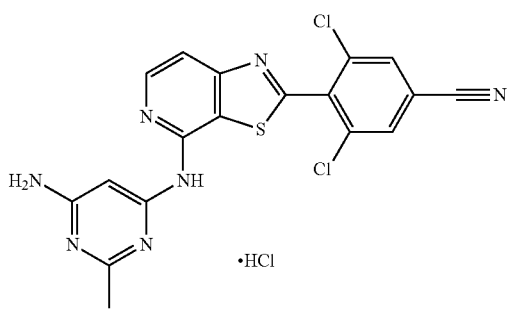 [SMILES: Cc1nc(N)cc(Nc2nccc3nc(-c4c(Cl)cc(C#N)cc4Cl)sc23)n1 ; Cl]

Step 1.
(6-Chloro-2-methylpyrimidin-4-yl)-bis-carbamic acid tert-butyl ester

To a solution of 6-chloro-2-methylpyrimidin-4-ylamine (1.36 g, 9.48 mmol) in THF (40 mL) under a nitrogen atmosphere was added di-tert-butyl dicarbonate (4.15 g, 18.95 mmol) followed by DMAP (166 mg, 0.95 mmol). The reaction mixture was stirred at room temperature for 3 hours and was then partitioned between water and EtOAc. The aqueous layer was extracted with EtOAc (×2) and the combined organic phases were washed with brine, dried ($MgSO_4$) and concentrated under reduced pressure. The resultant residue was purified by column chromatography on silica gel eluting with 0-10% EtOAc in cyclohexane to afford the title compound as a white solid (2.4 g, 73% yield). LCMS (Method D): RT=4.43 min, m/z: 344 [M+H$^+$].

Step 2. {6-[2-(2,6-Dichloro-4-cyanophenyl)thiazolo[5,4-c]pyridin-4-ylamino]-2-methylpyrimidin-4-yl}-bis-carbamic acid tert-butyl ester A mixture of 4-(4-aminothiazolo[5,4-c]pyridin-2-yl)-3,5-dichlorobenzonitrile (0.102 g, 0.318 mmol), (6-chloro-2-methylpyrimidin-4-yl)-bis-carbamic acid tert-butyl ester (0.126 g, 0.365 mmol), $Pd_2(dba)_3$ (0.015 g, 0.016 mmol), XantPhos (0.018 g, 0.032 mmol) and $Cs_2CO_3$ (0.259 g, 0.795 mmol) in dioxane (3 mL) was degassed with a stream of argon. The reaction mixture was heated at 80° C. for 1 hour in a sealed vial. After cooling to room temperature, the crude mixture was filtered through Celite® washing with EtOAc and the filtrate concentrated under reduced pressure. The resultant residue was purified by column chromatography on silica gel eluting with 0-30% EtOAc in cyclohexane to afford the title compound as a yellow glass (58 mg, 29% yield). $^1$H NMR (400 MHz, $CDCl_3$): δ 8.44 (d, J=5.6 Hz, 1H), 7.97 (s, 1H), 7.80-7.73 (m, 3H), 7.70 (s, 1H), 2.52 (s, 3H), 1.53 (s, 18H).

Step 3. 4-[4-(6-Amino-2-methylpyrimidin-4-ylamino)thiazolo[5,4-c]pyridin-2-yl]-3,5-dichlorobenzonitrile hydrochloride salt A mixture of {6-[2-(2,6-dichloro-4-cyanophenyl)thiazolo[5,4-c]pyridin-4-ylamino]-2-methylpyrimidin-4-yl}-bis-carbamic acid tert-butyl ester (0.058 g, 0.092 mmol) in HCl (4N in dioxane, 1 mL) was heated at 50° C. for 2 hours in a sealed vial. After cooling to room temperature, the crude reaction mixture was filtered through a PTFE filter. The resultant solid was washed with EtOAc and dried under reduced pressure to afford the title compound as a pink solid (38 mg, 89% yield). $^1$H NMR (400 MHz, DMSO-$d_6$): δ 11.40 (s, 1H), 8.51 (d, J=5.7 Hz, 1H), 8.41 (s, 2H), 7.95 (d, J=5.7 Hz, 1H), 7.14 (s, 1H), 2.49 (s, 3H). LCMS (Method C): RT=3.23 min, m/z: 428 [M+H$^+$].

Example 128

3,5-Dichloro-4-[4-(6-ethylpyrimidin-4-ylamino)thiazolo[5,4-c]pyridin-2-yl]-benzonitrile

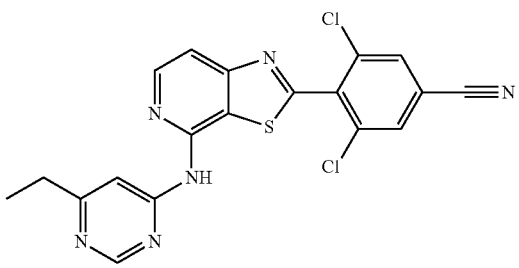 [SMILES: CCc1cc(Nc2nccc3nc(-c4c(Cl)cc(C#N)cc4Cl)sc23)ncn1]

A mixture of 4-(4-bromothiazolo[5,4-c]pyridin-2-yl)-3,5-dichlorobenzonitrile (0.095 g, 0.25 mmol), 6-ethylpyrimidin-4-ylamine (29 mg, 0.23 mmol), $Pd_2(dba)_3$ (11 mg, 0.012 mmol), XantPhos (14 mg, 0.025 mmol) and cesium carbonate (0.201 g, 0.62 mmol) in dioxane (2.5 mL) was degassed with a stream of nitrogen. The reaction mixture was heated at 70° C. for 16 hours. After cooling to room temperature, the resultant mixture was diluted with water and filtered through Celite® washing with DCM. The aqueous phase was further extracted with DCM and the combined organic layers were dried ($MgSO_4$) and concentrated under reduced pressure. The resultant residue was purified by silica gel flash $C_{18}$ column chromatography eluting with 0-100% EtOAc in pentane followed by a 20-60% gradient MeOH in $H_2O$+1M HCl (1.25 mL in each 25 mL of eluent). The product containing fractions were combined and concentrated under reduced pressure. The resultant solid was suspended in a mixture DCM/EtOAc/MeOH and washed with a saturated solution of $NaHCO_3$, then dried and concentrated under reduced pressure. Further column chromatography purification on silica gel, eluting with 0-50% EtOAc in DCM, afforded the title compound as a pale yellow solid (30 mg, 28% yield). $^1$H NMR (400 MHz, DMSO-$d_6$): δ 10.70 (br s, 1H), 8.66 (d, J=1.2 Hz, 1H), 8.46 (d, J=5.6 Hz, 1H), 8.39 (s, 2H); 7.84 (d, J=5.6 Hz, 1H), 7.56 (s, 1H), 2.67 (q, J=7.6 Hz, 2H), 1.23 (t, J=7.6 Hz, 3H). LCMS (Method C): RT=3.81 min, m/z: 427 [M+H⁺].

Example 129

3,5-Dichloro-4-[4-(6-ethylpyrimidin-4-ylamino)thiazolo[5,4-c]pyridin-2-yl]-benzamide

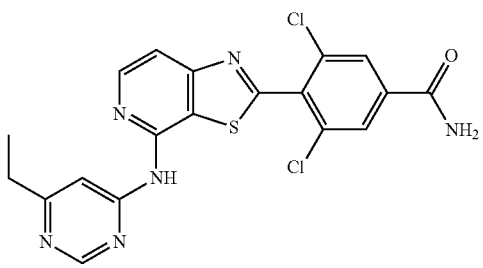 [SMILES: CCc1cc(Nc2nccc3nc(-c4c(Cl)cc(C(N)=O)cc4Cl)sc23)ncn1]

The column from which 3,5-dichloro-4-[4-(6-ethylpyrimidin-4-ylamino)thiazolo[5,4-c]pyridin-2-yl]-benzonitrile was isolated was then further eluted with 0-10% MeOH in DCM to afford the title compound as a yellow solid (8 mg, 7% yield). ¹H NMR (300 MHz, DMSO-d₆): δ 10.65 (s, 1H), 8.65 (d, J=1.2 Hz, 1H), 8.45 (d, J=5.6 Hz, 1H), 8.32 (br s, 1H), 8.13 (s, 2H), 7.86-7.80 (m, 2H), 7.56 (s, 1H), 2.66 (q, J=7.6 Hz, 2H), 1.22 (t, J=7.6 Hz, 3H). LCMS (Method C): RT=2.95 min, m/z: 445 [M+H⁺].

Example 130

4-[4-(6-Aminopyrimidin-4-ylamino)thiazolo[5,4-c]pyridin-2-yl]-3-chloro-5-fluorobenzonitrile hydrochloride salt

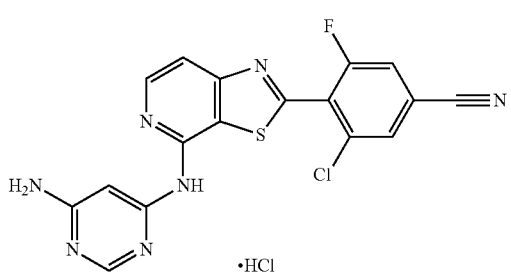 [SMILES: N#Cc1cc(F)c(-c2nc3ccnc(Nc4cc(N)ncn4)c3s2)c(Cl)c1 ; Cl]

Step 1. [2-(2-Chloro-4-cyano-6-fluorophenyl)thiazolo[5,4-c]pyridin-4-yl]-carbamic acid tert-butyl ester A mixture of 4-(4-bromothiazolo[5,4-c]pyridin-2-yl)-3-chloro-5-fluorobenzonitrile (0.118 g, 0.320 mmol) carbamic acid tert-butyl ester (0.187 g, 1.60 mmol), Pd₂(dba)₃ (0.015 g, 0.016 mmol), XantPhos (0.019 g, 0.032 mmol) and potassium phosphate tribasic (0.136 g, 0.64 mmol) in toluene (2.0 mL) and water (0.3 mL) was degassed with a stream of argon. The reaction mixture was heated at 60° C. for 4 hours. After cooling to room temperature, the crude mixture was filtered through Celite® washing with EtOAc and the filtrate was concentrated under reduced pressure. The resultant residue was purified by column chromatography on silica gel eluting with 0-20% EtOAc in cyclohexane to afford the title compound as a yellow solid (173 mg, quantitative). ¹H NMR (400 MHz, CDCl₃): δ 8.35 (d, J=5.6 Hz, 1H), 7.86 (s, 1H), 7.80 (d, J=5.6 Hz, 1H), 7.68 (t, J=1.4 Hz, 1H), 7.47 (dd, J=8.1, 1.5 Hz, 1H), 1.56 (s, 9H).

Step 2. 4-(4-Aminothiazolo[5,4-c]pyridin-2-yl)-3-chloro-5-fluorobenzonitrile

A mixture of [2-(2-chloro-4-cyano-6-fluorophenyl)thiazolo[5,4-c]pyridin-4-yl]-carbamic acid tert-butyl ester (0.320 mmol) in HCl (4N in dioxane, 2.5 mL) was heated at 50° C. for 3 hours in a sealed vial. After cooling to room temperature, the volatiles were removed under reduced pressure and the resultant residue was partitioned between EtOAc and a saturated solution of NaHCO₃. The aqueous phase was extracted with EtOAc, and the combined organic layers were washed with brine, dried (Na₂SO₄) and concentrated to dryness under reduced pressure to afford the title compound as a yellow solid (76 mg, 78% yield over two steps). ¹H NMR (400 MHz, CDCl₃): δ 8.21 (d, J=5.8 Hz, 1H), 7.69 (t, J=1.4 Hz, 1H), 7.53-7.46 (m, 2H), 4.84 (s, 2H).

Step 3. {6-[2-(2-Chloro-4-cyano-6-fluorophenyl)thiazolo[5,4-c]pyridin-4-ylamino]-pyrimidin-4-yl}-bis-carbamic acid tert-butyl ester A mixture of 4-(4-aminothiazolo[5,4-c]pyridin-2-yl)-3-chloro-5-fluorobenzonitrile (0.068 g, 0.224 mmol), (6-chloropyrimidin-4-yl)-bis-carbamic acid tert-butyl ester (0.085 g, 0.257 mmol), XantPhos (0.013 g, 0.022 mmol) and Cs₂CO₃ (0.182 g, 0.56 mmol) in dioxane (2.5 mL) was degassed with a stream of argon. Pd₂(dba)₃ (0.010 g, 0.011 mmol) was added and the reaction mixture was heated at 80° C. for 1 hour. After cooling to room temperature, the crude reaction mixture was filtered through Celite®, washing with EtOAc, and the filtrate was concentrated under reduced pressure. The resultant residue was purified by column chromatography on silica gel eluting with 0-30% EtOAc in cyclohexane to afford the title compound as a yellow oil (58 mg, 43% yield). ¹H NMR (400 MHz, CDCl₃): δ 8.60 (s, 1H), 8.45 (d, J=5.7 Hz, 1H), 8.29 (s, 1H), 7.87 (s, 1H), 7.78 (d, J=5.6 Hz, 1H), 7.70 (t, J=1.4 Hz, 1H), 7.50 (dd, J=8.2, 1.5 Hz, 1H), 1.54 (s, 18H).

Step 4. 4-[4-(6-Aminopyrimidin-4-ylamino)thiazolo[5,4-c]pyridin-2-yl]-3-chloro-5-fluorobenzonitrile hydrochloride salt A mixture of {6-[2-(2-chloro-4-cyano-6-fluorophenyl)thiazolo[5,4-c]pyridin-4-ylamino]-pyrimidin-4-yl}-bis-carbamic acid tert-butyl ester (0.058 g, 0.097 mmol) in HCl (1.25N in isopropanol, 2 mL) was heated at 45° C. for 24 hours. After cooling to room temperature, the crude mixture was filtered and the resultant solid was washed with isopropanol and then dried under reduced pressure. The solid thus obtained was sonicated in isopropanol for 1 hour, then filtered and dried under reduced pressure to afford the title compound as a yellow solid (35 mg, 91% yield). ¹H NMR (400 MHz, DMSO-d₆): δ 11.48 (s, 1H), 8.52-8.46 (m, 2H), 8.32-8.6 (m, 3H), 7.94 (d, J=5.7 Hz, 1H), 6.97 (s, 2H). LCMS (Method C): RT=3.04 min, m/z: 398 [M+H⁺].

Example 131

N-[2-(4-Amino-2,6-dichlorophenyl)thiazolo[5,4-c]pyridin-4-yl]-pyrimidine-4,6-diamine hydrochloride salt

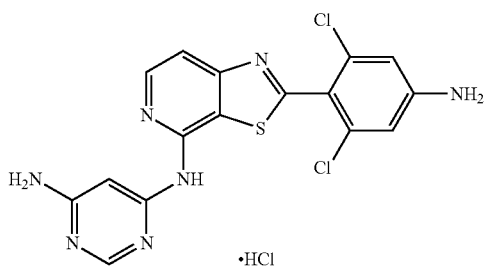 [SMILES: Nc1cc(Cl)c(-c2nc3ccnc(Nc4cc(N)ncn4)c3s2)c(Cl)c1 ; Cl]

Step 1. [3,5-Dichloro-4-(4-chlorothiazolo[5,4-c]pyridin-2-yl)-phenyl]-carbamic acid tert-butyl ester A mixture of 4-chloro-2-(2,6-dichloro-4-iodophenyl)thiazolo[5,4-c]pyridine (0.40 g, 0.905 mmol), carbamic acid tert-butyl ester (0.159 g, 1.36 mmol), XantPhos (0.053 g, 0.091 mmol) and $K_3PO_4$ (0.384 g, 1.81 mmol) in toluene (9 mL) and water (1.5 mL), was degassed with a stream of argon. $Pd_2(dba)_3$ (0.041 g, 0.045 mmol) was then added and the reaction mixture was heated at 85° C. for 2 hours using microwave irradiation and then thermally at 100° C. for 18 hours. After cooling to room temperature, the crude residue was partitioned between water and EtOAc. The aqueous phase was further extracted with EtOAc (×2) and the combined organic layers were washed with brine, dried ($MgSO_4$) and concentrated under reduced pressure. The resultant residue was purified by column chromatography on silica gel eluting with 0-10% EtOAc in cyclohexane to afford the title compound as an off-white solid (0.352 g, 90% yield). LCMS (Method D): RT=4.68 min, m/z: 430 [M+H$^+$].

Step 2. {6-[2-(4-tert-Butoxycarbonylamino-2,6-dichlorophenyl)thiazolo[5,4-c]pyridin-4-ylamino]-pyrimidin-4-yl}-bis-carbamic acid tert-butyl ester A mixture of [3,5-dichloro-4-(4-chlorothiazolo[5,4-c]pyridin-2-yl)-phenyl]-carbamic acid tert-butyl ester (0.150 g, 0.35 mmol), (6-aminopyrimidin-4-yl)-bis-carbamic acid tert-butyl ester (0.118 g, 0.38 mmol), XantPhos (0.020 g, 0.035 mmol) and $Cs_2CO_3$ (0.285 g, 0.875 mmol) in dioxane (4 mL) was degassed with a stream of argon. $Pd_2(dba)_3$ (0.016 g, 0.017 mmol) was then added and the reaction mixture was heated at 80° C. for 2 hours in a sealed vial. After standing at room temperature for 18 hours, the resultant mixture was heated at 80° C. for 5 hours. After cooling to room temperature, the crude reaction mixture was partitioned between water and EtOAc. The aqueous phase was further extracted with EtOAc (×2) and the combined organic layers were washed with brine, then dried ($MgSO_4$) and concentrated under reduced pressure. The resultant residue was purified by column chromatography on silica gel eluting with 0-20% EtOAc in cyclohexane to afford the title compound as a yellow solid (86 mg, 35% yield). LCMS (Method D): RT=4.80 min, m/z: 704 [M+H$^+$].

Step 3. N-[2-(4-Amino-2,6-dichlorophenyl)thiazolo[5,4-c]pyridin-4-yl]-pyrimidine-4,6-diamine hydrochloride salt A solution of {6-[2-(4-tert-butoxycarbonylamino-2,6-dichloro-phenyl)thiazolo[5,4-c]pyridin-4-ylamino]-pyrimidin-4-yl}-bis-carbamic acid tert-butyl ester (86 mg, 0.122 mmol) in HCl (4N in dioxane, 3 mL) was heated at 50° C. for 3 hours, under a nitrogen atmosphere. After cooling to room temperature, the reaction mixture was filtered and the solid collected and washed with dioxane followed by 1% MeOH/DCM to afford the title compound as an off-white solid (55 mg, 100% yield). $^1$H NMR (400 MHz, DMSO-d$_6$): δ 11.40 (br s, 1H), 8.21 (br s, 1H), 8.50 (s, 1H), 8.44 (d, J=5.7 Hz, 1H), 7.88 (d, J=5.7 Hz, 1H), 6.78 (s, 2H), 6.28 (br s, 2H). LCMS (Method C): RT=2.81 min, m/z: 404 [M+H$^+$].

Example 132

[2-(4-Amino-2,6-dichlorophenyl)thiazolo[5,4-c]pyridin-4-yl]-(6-methylpyrimidin-4-yl)-amine

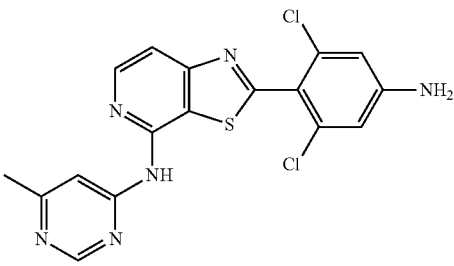 [SMILES: Cc1cc(Nc2nccc3nc(-c4c(Cl)cc(N)cc4Cl)sc23)ncn1]

Step 1. {3,5-Dichloro-4-[4-(6-methylpyrimidin-4-ylamino)thiazolo[5,4-c]pyridin-2-yl]-phenyl}-carbamic acid tert-butyl ester A mixture of [3,5-dichloro-4-(4-chlorothiazolo[5,4-c]pyridin-2-yl)-phenyl]-carbamic acid tert-butyl ester (0.30 g, 0.697 mmol), 6-methylpyrimidin-4-ylamine (0.073 g, 0.77 mmol), XantPhos (0.040 g, 0.0696 mmol) and $Cs_2CO_3$ (0.454 g, 1.39 mmol) in dioxane (10 mL) was degassed with a stream of argon. $Pd_2(dba)_3$ (0.032 g, 0.035 mmol) was added and the reaction mixture was heated at 85° C. for 18 hours. After cooling to room temperature, the crude reaction mixture was filtered through Celite® washing with EtOAc and the filtrate was concentrated under reduced pressure. The resultant residue was purified by column chromatography on silica gel eluting with 0-30% EtOAc in petroleum ether to afford the title compound as a yellow solid (0.238 g, 68% yield). LCMS (Method D): RT=3.14 min, m/z: 503 [M+H$^+$].

Step 2. [2-(4-Amino-2,6-dichlorophenyl)thiazolo[5,4-c]pyridin-4-yl]-(6-methylpyrimidin-4-yl)-amine A solution of {3,5-dichloro-4-[4-(6-methylpyrimidin-4-ylamino)thiazolo[5,4-c]pyridin-2-yl]-phenyl}-carbamic acid tert-butyl ester (235 mg, 0.467 mmol) in 4N HCl in dioxane (10 mL) was heated at 50° C. for 3 hours under a nitrogen atmosphere. After cooling to room temperature, the reaction mixture was filtered and the precipitate collected.

The solid thus obtained was purified by column chromatography on silica gel eluting with 0-5% 2N NH₃/MeOH in EtOAc to afford the title compound as a pale yellow solid (142 mg, 75% yield). ¹H NMR (400 MHz, DMSO-d₆): δ 10.54 (s, 1H), 8.62 (d, J=1.2 Hz, 1H), 8.41 (d, J=5.6 Hz, 1H), 7.77 (d, J=5.6 Hz, 1H), 7.63 (s, 1H), 6.77 (s, 2H), 6.22 (s, 2H), 2.39 (s, 3H). LCMS (Method C): RT=2.97 min, m/z: 403 [M+H⁺].

Example 133

{4-[4-(6-Aminopyrimidin-4-ylamino)thiazolo[5,4-c]pyridin-2-yl]-3,5-dichlorophenyl}-methanol formate salt

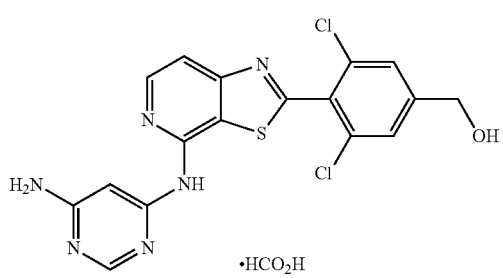 [SMILES: Nc1cc(Nc2nccc3nc(-c4c(Cl)cc(CO)cc4Cl)sc23)ncn1 ; "·HCO2H"]

Step 1. {6-[2-(2,6-Dichloro-4-hydroxymethylphenyl)thiazolo[5,4-c]pyridine-4-ylamino]-pyrimidin-4-yl}-bis-carbamic acid tert-butyl ester A mixture of [3,5-dichloro-4-(4-chlorothiazolo[5,4-c]pyridine-2-yl)phenyl]-methanol (0.270 g, 0.78 mmol), (6-aminopyrimidin-4-yl)-bis-carbamic acid tert-butyl ester (0.267 g, 0.86 mmol), XantPhos (0.045 g, 0.078 mmol) and Cs₂CO₃ (0.635 g, 1.954 mmol) in dioxane (6 mL) was degassed with a stream of argon. Pd₂(dba)₃ (0.036 g, 0.039 mmol) was added and the reaction mixture was heated at 80° C. for 5 hours. After cooling to room temperature, the crude residue was left standing at room temperature for 18 hours and then was filtered through Celite® washing with EtOAc. The organic layer was washed with water and the aqueous phase was further extracted with EtOAc (×2). The combined organic layers were dried (MgSO₄) and concentrated under reduced pressure. The resultant residue was purified by column chromatography on silica gel eluting with 0-30% EtOAc in cyclohexane to afford the title compound as a pale yellow solid (0.150 g, 31% yield). LCMS (Method D): RT=3.99 min, m/z: 619 [M+H⁺].

Step 2. {4-[4-(6-Aminopyrimidin-4-ylamino)thiazolo[5,4-c]pyridin-2-yl]-3,5-dichlorophenyl}methanol formate salt A solution of {6-[2-(2,6-dichloro-4-hydroxymethylphenyl)thiazolo[5,4-c]pyridine-4-ylamino]-pyrimidin-4-yl}-bis-carbamic acid tert-butyl ester (147 mg, 0.24 mmol) in HCl (1.25N in isopropanol, 3 mL) was heated at 50° C. for 18 hours, under a nitrogen atmosphere. After cooling to room temperature, the reaction mixture was filtered and the solid collected and washed with isopropanol. The solid was purified by reverse phase HPLC (Phenomenex Gemini 5 μm C18 on a 25 minute gradient 20-60%, 0.1% HCO₂H in MeOH/H₂O) to afford the title compound as a yellow solid/foam (45 mg, 41% yield). ¹H NMR (400 MHz, DMSO-d₆): δ 10.08 (s, 1H), 8.38 (d, J=5.6 Hz, 1H), 8.20 (s, 1H), 8.12 (s, 1H), 7.73 (d, J=5.6 Hz, 1H), 7.64 (s, 2H), 6.86 (s, 1H), 6.65 (s, 2H), 4.63 (s, 2H). LCMS (Method C): RT=2.70 min, m/z: 419 [M+H⁺].

Example 134

N-[2-(4-Aminomethyl-2,6-dichlorophenyl)thiazolo[5,4-c]pyridin-4-yl]-pyrimidine-4,6-diamine hydrochloride salt

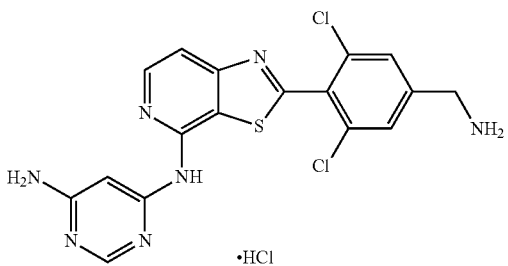 [SMILES: NCc1cc(Cl)c(-c2nc3ccnc(Nc4cc(N)ncn4)c3s2)c(Cl)c1 ; Cl]

Step 1. {6-[2-(2,6-Dichloro-4-cyanophenyl)thiazolo[5,4-c]pyridin-4-ylamino]-pyrimidin-4-yl}-bis-carbamic acid tert-butyl ester A mixture of 4-(4-aminothiazolo[5,4-c]pyridin-2-yl)-3,5-dichlorobenzonitrile (0.370 g, 1.15 mmol), (6-chloropyrimidin-4-yl)-bis-carbamic acid tert-butyl ester (0.437 g, 1.32 mmol), XantPhos (0.067 g, 0.115 mmol) and Cs₂CO₃ (0.938 g, 2.88 mmol) in dioxane (6 mL) was degassed with a stream of argon. Pd₂(dba)₃ (0.053 g, 0.058 mmol) was added and the reaction mixture was heated at 80° C. for 1 hour. After cooling to room temperature, the crude residue was filtered through Celite® washing with diethyl ether. A precipitate formed in the filtrate and was collected by filtration (42 mg). The organic layer was washed with water and the aqueous phase was further extracted with diethyl ether (×3). The combined organic layers were dried (MgSO₄) and concentrated under reduced pressure. The resultant residue was combined with the solid obtained by filtration (42 mg) and purified by column chromatography on silica gel eluting with 0-40% diethyl ether in petroleum ether to afford the title compound as a yellow solid/foam (0.293 g, 42% yield). LCMS (Method D): RT=4.46 min, m/z: 614 [M+H⁺].

Step 2. {6-[2-(4-Aminomethyl-2,6-dichlorophenyl)thiazolo[5,4-c]pyridin-4-ylamino]-pyrimidin-4-yl}-bis-carbamic acid tert-butyl ester To a solution of {6-[2-(2,6-dichloro-4-cyanophenyl)thiazolo[5,4-c]pyridin-4-ylamino]-pyrimidin-4-yl}-bis-carbamic acid tert-butyl ester (0.10 g, 0.163 mmol) in MeOH (1 mL) at 0° C., and under a nitrogen atmosphere, were added 2N NH₃ in MeOH (0.407 mL, 0.815 mmol) and CoCl₂.6H₂O (39 mg, 0.163 mmol) followed by sodium borohydride (31 mg, 0.815 mmol). The reaction mixture was stirred at 0° C. for 15 minutes and then was quenched by addition of HCl (1N, 2 mL). The volatiles were removed under reduced pressure and the resultant residue was loaded onto an Isolute® SCX-2 cartridge. The cartridge was washed with MeOH and the product eluted with 0.2N NH₃ in MeOH. The basic fractions were combined and concentrated under reduced pressure to afford the title compound (60 mg) which was combined with the crude material obtained following the same method using {6-[2-(2,6-dichloro-4-cyanophenyl)thiazolo[5,4-c]pyridin-4-ylamino]-pyrimidin-4-yl}-bis-carbamic acid tert-butyl ester (0.164 g, 0.270 mmol). The resultant residue was purified by column chromatography on silica gel eluting with 2% NH₃/MeOH in EtOAc to afford the title compound (48 mg, 18% yield). LCMS (Method D): RT=2.71 min, m/z: 618 [M+H⁺].

Step 3. N-[2-(4-Aminomethyl-2,6-dichlorophenyl)thiazolo[5,4-c]pyridin-4-yl]-pyrimidine-4,6-diamine hydrochloride salt A suspension of {6-[2-(4-aminomethyl-2,6-dichlorophenyl)thiazolo[5,4-c]pyridin-4-ylamino]-pyrimidin-4-yl}-bis-carbamic acid tert-butyl ester (47 mg, 0.076 mmol) in HCl (4N in dioxane, 3 mL) was heated at 45° C. for 3 hours, under a nitrogen atmosphere. After cooling to room temperature, the reaction mixture was filtered and the solid was collected and then washed with dioxane, then diethyl ether, DCM, EtOAc and finally with CH₃CN to afford the title compound as a pale yellow solid (31 mg, 90% yield). ¹H NMR (400 MHz, DMSO-d₆): δ 8.63-8.40 (m, 5H), 7.93-7.87 (m, 3H), 4.19 (q, J=5.4 Hz, 2H). LCMS (Method C): RT=1.93 min, m/z: 418 [M+H⁺].

Example 135

[2-(4-Aminomethyl-2,6-dichlorophenyl)thiazolo[5,4-c]pyridin-4-yl]-(6-methylpyrimidin-4-yl)-amine bis formate salt

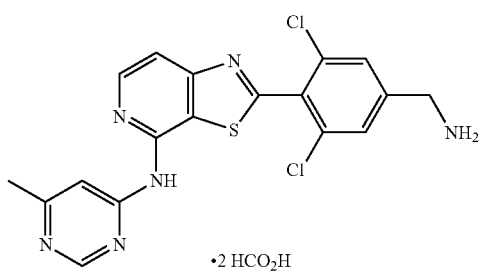 [SMILES: Cc1cc(Nc2nccc3nc(-c4c(Cl)cc(CN)cc4Cl)sc23)ncn1 ; "·2 HCO2H"]

NaBH₄ (0.137 g, 3.63 mmol) was added in one portion to a solution of 3,5-dichloro-4-[4-(6-methylpyrimidin-4-ylamino)thiazolo[5,4-c]pyridin-2-yl]benzonitrile, 0.50 g, 1.21 mmol), 2N NH₃ in MeOH (3.03 mL, 6.05 mmol) and CoCl₂.6H₂O (0.288 g, 1.21 mmol) in a mixture of MeOH (10 mL) and THF (15 mL) at 0° C. under a nitrogen atmosphere. After stirring at 0° C. for 0.5 hour, the reaction mixture was quenched by addition of 1N HCl (15 mL) and then concentrated under reduced pressure. The resultant residue was loaded onto an Isolute® SCX-2 cartridge that was washed with MeOH and the product eluted with 0.2M NH₃ in MeOH. The relevant fractions were combined and concentrated under reduced pressure. This crude product was combined with the further product obtained by reacting 3,5-dichloro-4-[4-(6-methylpyrimidin-4-ylamino)thiazolo[5,4-c]pyridin-2-yl]-benzonitrile, 0.050 g, 0.121 mmol) under the same reaction conditions. The resultant combined crude residues were purified by silica gel flash chromatography eluting with 0-2% 2M NH₃/MeOH in EtOAc, followed by reverse phase HPLC (Phenomenex Gemini 5 μm C18 on a gradient 10-40%, 0.1% HCO₂H in MeOH/H₂O) to give the title compound as a pale yellow solid (0.072 g, 13% yield). ¹H NMR (400 MHz, DMSO-d₆): δ 8.63 (d, J=1.2 Hz, 1H), 8.45 (d, J=5.6 Hz, 1H), 8.24 (s, 2H), 7.83 (d, J=5.6 Hz, 1H), 7.74 (s, 2H), 7.60 (s, 1H), 3.93 (s, 2H), 2.40 (s, 3H). LCMS (Method C): RT=2.10 min, m/z: 417 [M+H⁺].

Example 136

[2-(2,6-Dichloro-4-methoxyphenyl)thiazolo[5,4-c]pyridin-4-yl]-(6-methylpyrimidin-4-yl)-amine

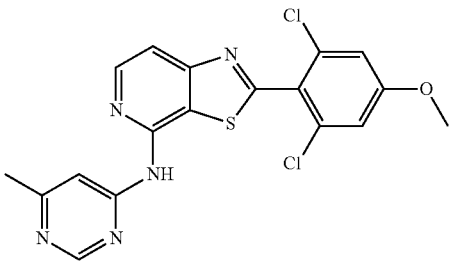

Step 1. 4-Chloro-2-(2,6-dichloro-4-methoxyphenyl)thiazolo[5,4-c]pyridine

A mixture of 4-chloro-2-(2,6-dichloro-4-iodophenyl)thiazolo[5,4-c]pyridine (0.300 g, 0.68 mmol), racemic-2-di-t-butylphosphino-1,1'-binaphthyl (0.035 g, 0.0884 mmol), Pd(OAc)₂ (0.015 g, 0.068 mmol), Cs₂CO₃ (0.332 g, 1.02 mmol) and MeOH (0.275 mL, 6.8 mmol) in toluene (3 mL) was degassed with a stream of argon and the reaction mixture was heated at 70° C. for 18 hours. After cooling to room temperature, additional racemic-2-di-t-butylphosphino-1,1'-binaphthyl (0.035 g) and Pd(OAc)₂ (0.015 g) were added. The resulting mixture was then degassed with a stream of argon and heated at 70° C. for 18 hours. The crude reaction mixture was filtered through Celite® and the filtrate was combined with two crude reaction mixtures obtained following the same method using 4-chloro-2-(2,6-dichloro-4-iodophenyl)thiazolo[5,4-c]pyridine (0.46 mmol). The volatiles were removed under reduced pressure and the resultant residue was purified by column chromatography on silica gel eluting with 0-10% diethyl ether in petroleum ether to afford the title compound as an off-white solid (116 mg, 30% yield). LCMS (Method D): RT=4.34 min, m/z: 345 [M+H⁺].

Step 2. [2-(2,6-Dichloro-4-methoxyphenyl)thiazolo[5,4-c]pyridin-4-yl]-(6-methylpyrimidin-4-yl)-amine A mixture of 4-chloro-2-(2,6-dichloro-4-methoxyphenyl)thiazolo[5,4-c]pyridine (0.113 g, 0.328 mmol), 6-methylpyrimidin-4-ylamine (0.031 g, 0.328 mmol), XantPhos (0.019 g, 0.033 mmol), Pd₂(dba)₃ (0.015 g, 0.0164 mmol) and Cs₂CO₃ (0.213 g, 0.655 mmol) in dioxane (3 mL) was degassed with a stream of argon and the reaction mixture was heated at 85° C. for 18 hours. After cooling to room temperature and standing at room temperature for 56 hours, additional XantPhos (0.019 g) and Pd₂(dba)₃ (0.015 g) were added. The resultant mixture was then degassed with a stream of argon and heated at 110° C. for 1 hour using microwave irradiation. Additional XantPhos (0.010 g), Pd₂(dba)₃ (0.008 g) and 6-methylpyrimidin-4-ylamine (0.006 g) were added and the resulting suspension was then degassed with a stream of argon and heated at 110° C. for 1 hour using microwave irradiation. The crude reaction mixture was filtered through Celite® and the filtrate was concentrated under reduced pressure. The resultant residue was purified by column chromatography on silica gel eluting with 0-2% MeOH in DCM followed by reverse phase HPLC (Phenomenex Gemini 5 μm C18 on a 30 minute gradient 10-80%, 0.1% HCO₂H in CH₃CN/H₂O) to afford the title compound as an off-white solid (36 mg, 26% yield). $^1$H NMR (400 MHz, DMSO-d$_6$): δ 8.91 (s, 1H), 8.54 (d, J=5.6 Hz, 1H), 7.98 (d, J=5.6 Hz, 1H), 7.73 (s, 1H), 7.36 (s, 2H), 3.92 (s, 3H), 2.49 (s, 3H). LCMS (Method D): RT=3.65 min, m/z: 418 [M+H⁺].

Example 137

[2-(4-Azetidin-3-yl-2,6-dichlorophenyl)thiazolo[5,4-c]pyridin-4-yl]-(6-methylpyrimidin-4-yl)-amine

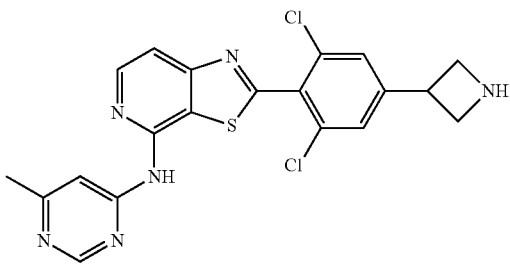 [SMILES: Cc1cc(Nc2nccc3nc(-c4c(Cl)cc(C5CNC5)cc4Cl)sc23)ncn1]

Step 1. 3-[3,5-Dichloro-4-(4-chlorothiazolo[5,4-c]pyridin-2-yl)-phenyl]-azetidine-1-carboxylic acid tert-butyl ester Zinc dust (0.116 g, 1.77 mmol) and celpure P65 (0.025 g) were stirred under an argon atmosphere for 30 minutes. N,N-dimethylacetamide (0.5 mL) was added followed by 1,2-dibromoethane (0.014 mL, 0.163 mmol) and trimethylsilyl chloride (0.021 mL, 0.163 mmol). The reaction mixture was stirred at room temperature for 15 minutes, then a solution of 3-iodoazetidine-1-carboxylic acid tert-butyl ester (0.385 g, 1.36 mmol) in N,N-dimethylacetamide (1 mL) was added and stirring at room temperature was continued for 1.5 hours. The resultant mixture was filtered and the filtrate was added to a suspension of 4-chloro-2-(2,6-dichloro-4-iodophenyl)-thiazolo[5,4-c]pyridine (0.30 g, 0.68 mmol), PdCl₂(dppf)•DCM (0.052 g, 0.068 mmol) and CuI (0.016 g, 0.088 mmol) in N,N-dimethylacetamide (4 mL) previously degassed with a stream of argon. The reaction mixture was heated at 80° C. for 2 hours and then allowed to cool to room temperature. The crude mixture was partitioned between diethyl ether and water and the aqueous phase was extracted with diethyl ether (×2). The combined organic layers were washed with brine, dried (MgSO₄) and concentrated under reduced pressure. The resultant residue was purified by column chromatography on silica gel eluting with 0-70% Et₂O in petroleum ether to afford the title compound as an off-white solid (108 mg, 34%). LCMS (Method D): RT=4.66 min, m/z: 470 [M+H⁺].

Step 2. 3-{3,5-Dichloro-4-[4-(6-methylpyrimidin-4-ylamino)thiazolo[5,4-c]pyridin-2-yl]-phenyl}-azetidine-1-carboxylic acid tert-butyl ester A mixture of 3-[3,5-dichloro-4-(4-chlorothiazolo[5,4-c]pyridin-2-yl)-phenyl]-azetidine-1-carboxylic acid tert-butyl ester (0.106 g, 0.225 mmol), 6-methylpyrimidin-4-ylamine (0.024 g, 0.248 mmol), XantPhos (0.013 g, 0.023 mmol), Pd₂(dba)₃ (0.010 g, 0.0113 mmol) and Cs₂CO₃ (0.147 g, 0.45 mmol) in dioxane (2 mL) was degassed with a stream of argon. The reaction mixture was heated at 85° C. for 18 hours. Additional Pd₂(dba)₃ (0.005 g), XantPhos (0.007 g) and 6-methylpyrimidin-4-ylamine (0.006 g) were added and the mixture was heated at 85° C. for 18 hours. After cooling to room temperature, the crude reaction mixture was filtered through Celite® and the filtrate was concentrated under reduced pressure. The resultant residue was purified by column chromatography on silica gel eluting with 0-90% EtOAc in petroleum ether to afford the title compound as a pale yellow glass (64 mg, 52% yield). $^1$H NMR (400 MHz, CDCl₃): δ 8.71 (s, 1H), 8.45 (d, J=5.7 Hz, 1H), 8.15 (s, 1H), 7.76 (d, J=5.6 Hz, 1H), 7.51-7.41 (m, 3H), 4.39 (t, J=8.7 Hz, 2H), 4.02-3.92 (m, 2H), 3.80-3.70 (m, 1H), 2.56 (s, 3H), 1.48 (s, 9H).

Step 3. [2-(4-Azetidin-3-yl-2,6-dichlorophenyl)thiazolo[5,4-c]pyridin-4-yl]-(6-methylpyrimidin-4-yl)-amine HCl (4N in dioxane, 5 mL) was added to 3-{3,5-dichloro-4-[4-(6-methylpyrimidin-4-ylamino)thiazolo[5,4-c]pyridin-2-yl]-phenyl}-azetidine-1-carboxylic acid tert-butyl ester (0.062 g, 0.114 mmol). The suspension was heated at 40° C. for 1 hour and then cooled to room temperature. The volatiles were removed under reduced pressure and the resultant residue was triturated with a mixture of EtOAc/DCM and then purified by column chromatography on silica gel eluting with 0-5% 2N NH₃/MeOH in DCM to afford the title compound as an off-white solid (20 mg, 40% yield). $^1$H NMR (400 MHz, CDCl₃): δ 8.65 (d, J=1.2 Hz, 1H), 8.46 (d, J=5.6 Hz, 1H), 7.84 (d, J=5.6 Hz, 1H), 7.75 (s, 2H), 7.63 (s, 1H), 3.99-3.90 (m, 1H), 3.85 (t, J=7.6 Hz, 2H), 3.61 (t, J=6.9 Hz, 2H), 2.41 (s, 3H). LCMS (Method C): RT=2.21 min, m/z: 443 [M+H⁺].

Example 138

[2-(2,6-Dichloro-4-cyclopropylphenyl)thiazolo[5,4-c]pyridin-4-yl]-(6-methylpyrimidin-4-yl)-amine

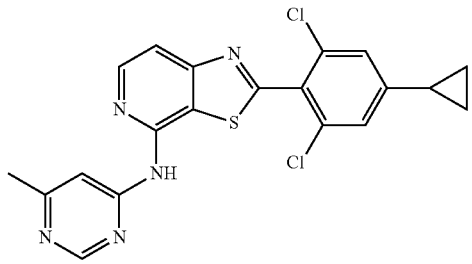 [SMILES: Cc1cc(Nc2nccc3nc(-c4c(Cl)cc(C5CC5)cc4Cl)sc23)ncn1]

Step 1. 4-Chloro-2-(2,6-dichloro-4-cyclopropylphenyl)thiazolo[5,4-c]pyridine

A mixture of 4-chloro-2-(2,6-dichloro-4-iodophenyl)thiazolo[5,4-c]pyridine (0.20 g, 0.45 mmol), cyclopropyl boronic acid (0.051 g, 0.59 mmol), Pd(OAc)₂ (0.005 g, 0.023 mmol), P(Cy)₃ (tricyclohexylphosphine) (0.013 g, 0.045 mmol) and potassium phosphate tribasic (0.336 g, 1.58 mmol) in toluene (4 mL) and water (0.2 mL) was degassed with a stream of argon and then heated at 100° C. for 18 hours. After cooling to room temperature, the crude reaction mixture was filtered through Celite® washing with EtOAc. The aqueous layer was extracted with EtOAc and the combined organic layers were washed with brine, then dried (MgSO$_4$) and concentrated under reduced pressure. The resultant residue was combined with the crude reaction mixture (79 mg) obtained by reacting 4-chloro-2-(2,6-dichloro-4-iodophenyl)-thiazolo[5,4-c]pyridine (0.10 g, 0.23 mmol) under the same reaction conditions and purified by column chromatography on silica gel eluting with 0-30% Et$_2$O in petroleum ether (40-60° C.) to afford the title compound as a yellow/orange solid (148 mg, 61%). LCMS (Method D): RT=4.69 min, m/z: 355 [M+H$^+$].

Step 2. [2-(2,6-Dichloro-4-cyclopropylphenyl)thiazolo[5,4-c]pyridin-4-yl]-(6-methylpyrimidin-4-yl)-amine A mixture of 4-chloro-2-(2,6-dichloro-4-cyclopropylphenyl)thiazolo[5,4-c]pyridine (0.148 g, 0.416 mmol), 6-methylpyrimidin-4-ylamine (0.044 g, 0.458 mmol), XantPhos (0.024 g, 0.0416 mmol), Cs$_2$CO$_3$ (0.271 g, 0.832 mmol) and Pd$_2$(dba)$_3$ (0.019 g, 0.021 mmol) in dioxane (1 mL) was degassed with a stream of argon and was then irradiated at 150° C. for 0.5 hour in a microwave reactor. After cooling to room temperature, the crude reaction mixture was filtered through Celite® washing with DCM and the filtrate was concentrated under reduced pressure. The resultant residue was purified by column chromatography on silica gel eluting with 0-2% MeOH in DCM followed by reverse phase HPLC (Phenomenex Gemini 5 μm C18 on a 30 minute gradient 50-90%, 0.1% HCO$_2$H in MeOH/H$_2$O) to afford the title compound (7 mg, 4% yield). $^1$H NMR (400 MHz, DMSO-d$_6$): δ 10.63 (s, 1H), 8.63 (d, J=1.2 Hz, 1H), 8.45 (d, J=5.6 Hz, 1H), 7.82 (d, J=5.6 Hz, 1H), 7.62 (s, 1H), 7.45 (s, 2H), 2.40 (s, 3H), 2.14-2.05 (m, 1H), 1.13-1.07 (m, 2H), 0.94-0.89 (m, 2H). LCMS (Method C): RT=4.17 min, m/z: 428 [M+H$^+$].

Example 139

N-(3,5-dichloro-4-(4-(6-methylpyrimidin-4-ylamino)thiazolo[5,4-c]pyridin-2-yl)phenyl)acetamide

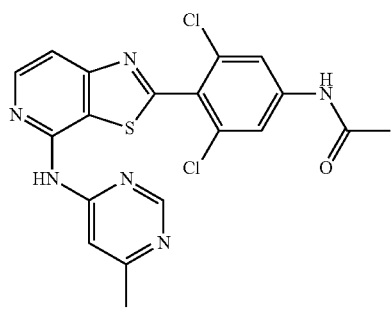 [SMILES: CC(=O)Nc1cc(Cl)c(-c2nc3ccnc(Nc4cc(C)ncn4)c3s2)c(Cl)c1]

Step 1. I-[3,5-Dichloro-4-(4-chlorothiazolo[5,4-c]pyridin-2-yl)phenyl]-acetamide A mixture of 4-chloro-2-(2,6-dichloro-4-iodophenyl)thiazolo[5,4-c]pyridine (0.150 g, 0.34 mmol), acetamide (0.024 g, 0.41 mmol), copper(I) iodide (0.010 g, 0.05 mmol), dimethylamino-acetic acid (0.007 g, 0.068 mmol) and potassium phosphate (0.360 g, 1.70 mmol) in DMSO (1 mL) was degassed with a stream of nitrogen and then heated at 80° C. for 16 hours. After cooling to room temperature, the crude reaction mixture was partitioned between EtOAc and water.

The organic layer was washed with brine, then dried (Na$_2$SO$_4$) and concentrated under reduced pressure. The resultant residue was purified by column chromatography on silica gel eluting with 50% EtOAc in cyclohexane to afford the title compound as a pale yellow solid (52 mg, 45% yield). $^1$H NMR (400 MHz, CDCl$_3$): δ 8.52 (d, J=5.6 Hz, 1H), 8.06 (s, 1H), 7.98 (d, J=5.6 Hz, 1H), 7.72 (s, 2H), 2.23 (s, 3H).

Step 2. N-{3,5-Dichloro-4-[4-(6-methylpyrimidin-4-ylamino)thiazolo[5,4-c]pyridin-2-yl]-phenyl}-acetamide A mixture of N-[3,5-dichloro-4-(4-chlorothiazolo[5,4-c]pyridin-2-yl)-phenyl]-acetamide (0.057 g, 0.15 mmol), 6-methylpyrimidin-4-ylamine (0.020 g, 0.18 mmol), Pd$_2$(dba)$_3$ (0.007 g, 0.0075 mmol), XantPhos (0.017 g, 0.03 mmol) and Cs$_2$CO$_3$ (0.098 g, 0.30 mmol) in dioxane (2 mL) was degassed with a stream of N$_2$ and then subjected to microwave irradiation at 150° C. for 30 minutes. After cooling to room temperature, the crude reaction mixture was partitioned between EtOAc and water. The organic layer was washed with brine, then dried (Na$_2$SO$_4$) and concentrated under reduced pressure. The resultant residue was purified by column chromatography on silica gel eluting with 50-100% EtOAc in cyclohexane followed by 1% MeOH in EtOAc to afford the title compound as a pale yellow solid (21 mg, 31% yield). $^1$H NMR (400 MHz, DMSO-d$_6$): δ 10.62 (s, 1H), 10.53 (s, 1H), 8.63 (d, J=1.2 Hz, 1H), 8.44 (d, J=5.6 Hz, 1H), 7.89 (s, 2H), 7.82 (d, J=5.6 Hz, 1H), 7.61 (s, 1H), 2.39 (s, 3H), 2.13 (s, 3H). LCMS (Method C): RT=3.02 min, m/z: 445 [M+H$^+$].

Example 140

[2-(2-Chloro-6-fluorophenyl)-7-fluorothiazolo[5,4-c]pyridin-4-yl]-(6-methylpyrimidin-4-yl)-amine

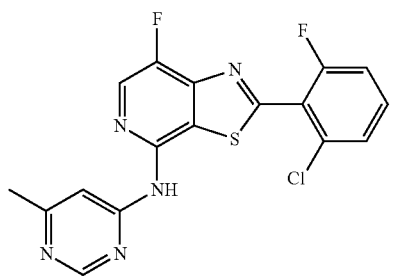 [SMILES: Cc1cc(Nc2ncc(F)c3nc(-c4c(F)cccc4Cl)sc23)ncn1]

Step 1. 2-Chloro-N-(3,5-difluoropyridin-4-yl)-6-fluorobenzamide

2-Chloro-6-fluorobenzoyl chloride (13.6 g, 71.6 mmol) was added dropwise, over 10 minutes, to a solution of 3,5-difluoro-pyridin-4-ylamine (7.7 g, 59.3 mmol) in pyridine (100 mL) at 0° C. under argon and the reaction mixture was stirred at 0° C. for 3 hours. The volatiles were removed under reduced pressure and the resultant residue was treated with 1N HCl (100 mL). The resultant suspension was stirred at room temperature for 2 hours and then the solid was collected by filtration, washing with water. A mixture of 2-chloro-N-(3,5-difluoropyridin-4-yl)-6-fluorobenzamide, LCMS (Method E): RT=2.83 min, m/z: 287 [M+H$^+$], and of 2-chloro-N-(2-chloro-6-fluorobenzoyl)-N-(3,5-difluoropyridin-4-yl)-6-fluorobenzamide LCMS (Method E): RT=3.96 min, m/z: 443 [M+H$^+$], (23 g) was obtained which was used in the following step without further purification.

A suspension of the crude mixture (23 g) and 1M NaOH (200 mL) in MeOH (200 mL) was stirred at room temperature for 2 hours. Additional amounts of 1M NaOH (200 mL) and of MeOH (200 mL) were added and stirring at room temperature was continued for 2 hours and then at 80° C. for 1 hour. After cooling to room temperature, the mixture was made acidic by addition of conc HCl (33 mL). The suspension was evaporated in vacuo to half of the original volume and the residue was collected by filtration, washed with water and dried to afford the title compound as a cream solid (11.6 g, 68%). LCMS (Method E): RT=2.76 min, m/z: 287 [M+H$^+$].

Step 2. 2-Chloro-N-(3,5-difluoropyridin-4-yl)-6-fluorobenzimidoyl chloride

A stirred suspension of 2-chloro-N-(3,5-difluoropyridin-4-yl)-6-fluorobenzamide (11.4 g, 0.04 mol) in thionyl chloride (100 mL) was heated at 100° C. for 18 hours. After cooling to room temperature, the volatiles were removed under reduced pressure. The resulting residue was azeotroped with toluene (100 mL). The crude residue was triturated with diethyl ether to afford the title compound as an off-white solid (12.1 g, quantitative). LCMS (Method E): RT=3.88 min, m/z: 305 [M+H$^+$].

Step 3. 2-(2-Chloro-6-fluorophenyl)-7-fluorothiazolo[5,4-c]pyridine

A stirred suspension of 2-chloro-N-(3,5-difluoropyridin-4-yl)-6-fluorobenzimidoyl chloride (12.0 g, 39.4 mmol), thiourea (9.0 g, 118 mmol) and pyridine (12.7 mL, 198 mmol) in isopropanol (200 mL) was heated at 150° C. for 3.5 hours. After stirring for one additional hour, the resulting precipitate was collected by filtration. The filtrate was treated with Et$_3$N (27 mL, 0.197 mol) and heating was continued at 150° C. for 18 hours. After cooling to room temperature, the volatiles were removed under reduced pressure and the resultant residue was partitioned between EtOAc (300 mL) and water (500 mL). The aqueous phase was extracted with EtOAc (2×300 mL) and the combined organic layers were dried and concentrated under reduced pressure. The resultant residue was purified by column chromatography on silica gel eluting with 0-100% Et$_2$O in petroleum ether and then triturated with a mixture 3:1 diethyl ether:pentane (25 mL) to afford the title compound as a cream coloured solid (4.6 g, 41%). LCMS (Method F): RT=3.39 min, m/z: 283 [M+H$^+$].

Step 4. 2-(2-Chloro-6-fluorophenyl)-7-fluorothiazolo[5,4-c]pyridine 5-oxide

To an ice-cooled solution of 2-(2-chloro-6-fluorophenyl)-7-fluorothiazolo[5,4-c]pyridine (4.0 g, 14.16 mmol) in DCM (50 mL) was added m-CPBA (4.82 g, 0.028 mol) and the mixture was stirred at 5° C. for 1 hour. Additional m-CPBA (4.82 g, 28.0 mmol) was added and stirring at room temperature was continued for 18 hours. The suspension was diluted with DCM (50 mL) and washed with a potassium carbonate solution (100 mL). The aqueous phase was extracted with DCM (2×50 mL) and the combined organic layers were washed with water (100 mL), then dried (Na$_2$SO$_4$) and concentrated under reduced pressure. The resultant residue was triturated with diethyl ether (25 mL) to afford the title compound as a white solid (3.1 g, 73%). LCMS (Method E): RT=2.70 min, m/z: 299 [M+H$^+$].

Step 5. 4-Chloro-2-(2-chloro-6-fluorophenyl)-7-fluoro thiazolo[5,4-c]pyridine A stirred solution of 2-(2-chloro-6-fluorophenyl)-7-fluorothiazolo[5,4-c]pyridine 5-oxide (3.0 g, 10.5 mmol) in phosphoryl chloride (50 mL) was heated at 110° C. for 45 minutes. After cooling to room temperature, the volatiles were removed under reduced pressure and the resultant residue was partitioned between a potassium carbonate saturated solution (100 mL) and EtOAc (50 mL). The aqueous phase was extracted with EtOAc (2×50 mL) and the combined organic layers were washed with water (100 mL), dried and concentrated under reduced pressure. The resultant residue was purified by column chromatography on silica gel eluting with 10% diethyl ether in pentane to afford the title compound as a colourless solid (0.71 g, 22% yield). $^1$H NMR (400 MHz, CDCl$_3$): δ 8.38 (s, 1H), 7.56-7.46 (m, 1H), 7.41 (d, J=8.2 Hz, 1H), 7.21 (t, J=8.6 Hz, 1H).

Step 6. 4-Bromo-2-(2-chloro-6-fluorophenyl)-7-fluorothiazolo[5,4-c]pyridine

Trimethylsilyl bromide (0.4 mL, 3 mmol) was added to a solution of 4-chloro-2-(2-chloro-6-fluorophenyl)-7-fluorothiazolo[5,4-c]pyridine (0.317 g, 10 mmol) in propionitrile (10 mL) at room temperature under an argon atmosphere. The reaction mixture was heated at 85° C. in a sealed vial for three days then it was poured in an ice-cooled saturated solution of potassium carbonate. The resultant mixture was extracted with DCM (×2). The combined organic washings were dried (Na$_2$SO$_4$) and concentrated under reduced pressure to afford the title compound as an off-white solid (0.365 g, quantitative). $^1$H NMR (400 MHz, CDCl$_3$): δ 8.39 (d, J=1.9 Hz, 1H), 7.51 (td, J=8.3, 5.8 Hz, 1H), 7.41 (dt, J=8.2, 1.1 Hz, 1H), 7.25-7.16 (m, 1H).

Step 7. [2-(2-Chloro-6-fluorophenyl)-7-fluorothiazolo[5,4-c]pyridin-4-yl]-(6-methylpyrimidin-4-yl)-amine A mixture of 4-bromo-2-(2-chloro-6-fluorophenyl)-7-fluorothiazolo[5,4-c]pyridine (0.09 g, 0.25 mmol), 6-methylpyrimidin-4-ylamine (0.027 g, 0.25 mmol), XantPhos (0.015 g, 0.025 mmol) and Cs$_2$CO$_3$ (0.206 g, 0.625 mmol) in dioxane (2 mL) was degassed with a stream of argon. Pd$_2$(dba)$_3$ (0.012 g, 0.0125 mmol) was added and the reaction mixture was heated in a sealed vial at 70° C. for 5 hours. After allowing to cool to room temperature, a stream of argon was bubbled through the suspension and additional amounts of Pd$_2$(dba)$_3$ (0.010 g) and XantPhos (0.010 g) were added. The reaction mixture was heated at 80° C. for 18 hours. After cooling to room temperature, the crude mixture was filtered through Celite® washing with EtOAc and the filtrate was concentrated under reduced pressure. The resultant residue was purified by column chromatography on silica gel eluting with 0-100% EtOAc in pentane and then triturated with diethyl ether to afford the title compound as an off-white solid (41 mg, 42% yield). $^1$H NMR (400 MHz, CDCl$_3$): δ 8.71 (s, 1H), 8.30 (d, J=1.9 Hz, 1H), 7.87 (s, 1H), 7.57-7.45 (m, 2H), 7.40 (d, J=8.2 Hz, 1H), 7.21 (t, J=8.7 Hz, 1H), 2.55 (s, 3H). LCMS (Method C): RT=3.54 min, m/z: 390 [M+H$^+$].

Example 141

N-[2-(2-Chloro-6-fluorophenyl)-7-fluorothiazolo[5,4-c]pyridin-4-yl]-pyrimidine-4,6-diamine hydrochloride salt

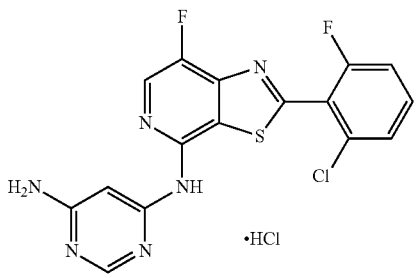 [SMILES: Nc1cc(Nc2ncc(F)c3nc(-c4c(F)cccc4Cl)sc23)ncn1 ; Cl]

Step 1. [2-(2-Chloro-6-fluorophenyl)-7-fluorothiazolo[5,4-c]pyridin-4-yl]-carbamic acid tert-butyl ester A mixture of 4-bromo-2-(2-chloro-6-fluorophenyl)-7-fluorothiazolo[5,4-c]pyridine (0.440 g, 1.22 mmol), carbamic acid tert-butyl ester (0.714 g, 6.1 mmol), XantPhos (0.071 g, 0.122 mmol) and K$_3$PO$_4$ (0.530 g, 2.5 mmol) in toluene (8 mL) and water (1.2 mL) was degassed with a stream of argon. Pd$_2$(dba)$_3$ (0.056 g, 0.061 mmol) was added and the reaction mixture was heated in a sealed vial at 70° C. for 3 hours. After cooling to room temperature, the crude mixture was filtered through Celite® washing with EtOAc. The organic layer was washed with brine, then dried (Na$_2$SO$_4$) and concentrated under reduced pressure. The resultant residue was purified by column chromatography on silica gel eluting with 0-50% EtOAc in pentane to afford the title compound as a white solid (350 mg, 72% yield). LCMS (Method D): RT=4.08 min, m/z: 398 [M+H$^+$].

Step 2. 2-(2-Chloro-6-fluorophenyl)-7-fluorothiazolo[5,4-c]pyridin-4-ylamine

HCl (4N in dioxane, 10 mL) was added to [2-(2-chloro-6-fluorophenyl)-7-fluorothiazolo[5,4-c]pyridin-4-yl]-carbamic acid tert-butyl ester (0.350 g, 0.88 mmol) and the reaction mixture was heated at 50° C. for 3 hours. After cooling to room temperature, the volatiles were removed under reduced pressure to afford the title compound as an off-white solid (270 mg, quantitative). $^1$H NMR (400 MHz, CDCl$_3$): δ 7.84 (s, 1H), 7.61-7.49 (m, 1H), 7.44 (d, J=8.1 Hz, 1H), 7.25 (t, J=8.7 Hz, 1H), 2.90 (br s, 2H).

Step 3. {6-[2-(2-Chloro-6-fluorophenyl)-7-fluorothiazolo[5,4-c]pyridin-4-ylamino]-pyrimidin-4-yl}-bis-carbamic acid tert-butyl ester A mixture of 2-(2-chloro-6-fluorophenyl)-7-fluorothiazolo[5,4-c]pyridin-4-ylamine (0.130 g, 0.440 mmol), (6-chloropyrimidin-4-yl)-bis-carbamic acid tert-butyl ester (0.189 g, 0.57 mmol), XantPhos (0.025 g, 0.049 mmol) and Cs$_2$CO$_3$ (0.360 g, 1.10 mmol) in dioxane (4.5 mL) was degassed with a stream of argon. Pd$_2$(dba)$_3$ (0.070 g, 0.022 mmol) was added and the reaction mixture was heated at 70° C. for 7 hours. The resultant mixture was diluted with DMF (1.5 mL) and degassed with a stream of argon prior to addition of Pd$_2$(dba)$_3$ (0.020 g) and XantPhos (0.025 g). The suspension was heated at 80° C. for 18 hours and then cooled to room temperature. The crude reaction mixture was filtered through Celite® washing with EtOAc (50 mL) and the filtrate was washed with brine, then dried (Na$_2$SO$_4$) and concentrated under reduced pressure. The resultant residue was purified by column chromatography on silica gel eluting with 0-50% EtOAc in pentane followed by 0-20% EtOAc in DCM to afford the title compound as a yellow glass (186 mg). LCMS (Method D): RT=4.60 min, m/z: 591 [M+H$^+$].

Step 4. N-[2-(2-Chloro-6-fluorophenyl)-7-fluorothiazolo[5,4-c]pyridin-4-yl]-pyrimidine-4,6-diamine hydrochloride salt To a mixture of {6-[2-(2-chloro-6-fluorophenyl)-7-fluorothiazolo[5,4-c]pyridin-4-ylamino]-pyrimidin-4-yl}-bis-carbamic acid tert-butyl ester (0.186 g) in DCM (5 mL) was added TFA (0.5 mL) at room temperature under argon. The reaction mixture was stirred at room temperature for 18 hours. The volatiles were removed under reduced pressure and the resultant residue was dissolved in DCM and washed with a saturated solution of NaHCO$_3$, by brine and then dried (Na$_2$SO$_4$) and concentrated under reduced pressure. The resultant residue was purified by reverse phase HPLC (Phenomenex Gemini 5 μm C18 on a 35 minute gradient 20-80%, 0.1% NH$_4$OH in CH$_3$CN/H$_2$O) to afford N-[2-(2-chloro-6-fluorophenyl)-7-fluorothiazolo[5,4-c]pyridin-4-yl]-pyrimidine-4,6-diamine as an off-white solid (58 mg). The product thus obtained was stirred in HCl (1.25N in isopropanol) at room temperature for 18 hours. The volatiles were removed under reduced pressure to afford the title compound as a white solid (64 mg, 34% over three steps). $^1$H NMR (400 MHz, DMSO-d$_6$): δ 11.69 (br s, 1H), 8.51 (d, J=11.5 Hz, 1H), 8.32 (br s, 1H), 7.80-7.71 (m, 1H), 7.64 (d, J=8.1 Hz, 1H), 7.55 (t, J=8.9 Hz, 1H), 7.05 (br s, 1H). LCMS (Method C): RT=3.18 min, m/z: 391 [M+H$^+$].

Example 142

[2-(2,6-Dichlorophenyl)-7-fluorothiazolo[5,4-c]pyridin-4-yl]-(6-methylpyrimidin-4-yl)-amine

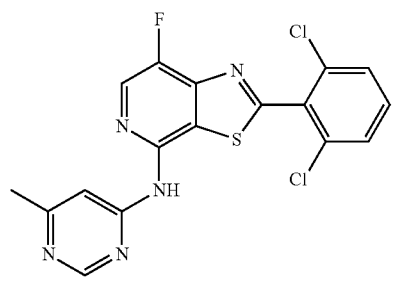 [SMILES: Cc1cc(Nc2ncc(F)c3nc(-c4c(Cl)cccc4Cl)sc23)ncn1]

Step 1. 2,6-Dichloro-N-(3,5-difluoropyridin-4-yl)-benzamide 2,6-Dichlorobenzoyl chloride (13.7 mL, 95.6 mmol) was added dropwise, over 10 minutes, to a solution of 3,5-difluoropyridin-4-ylamine (10.37 g, 79.7 mmol) in pyridine (160 mL) at a temperature of between 3 and 5° C., under argon. The reaction mixture was allowed to warm to room temperature over 1 hour and then stirred at room temperature for 2 hours. The volatiles were removed under reduced pressure and the resultant residue was treated with HCl (1N, 120 mL). The resultant suspension was stirred at room temperature for 45 minutes and the precipitate was collected by filtration, washing with water. A mixture of 2,6-dichloro-N-(3,5-difluoropyridin-4-yl)-benzamide and of 2,6-dichloro-N-(2,6-dichlorobenzoyl)-N-(3,5-difluoropyridin-4-yl)-benzamide (22.0 g) was obtained. A suspension of this mixture (22.0 g) in 1N NaOH (200 mL) and MeOH (200 mL) was heated at 65° C. for 7 hours then slowly cooled to room temperature. The pH of the mixture was adjusted to 4-5 by dropwise addition of 12N HCl, controlling the exotherm by the use of an ice-bath. The residue was left standing at room temperature for 18 hours and then the resultant solid was collected by filtration, washing with water, to afford the title compound as an off-white solid (14.65 g, 61% yield over two steps). LCMS (Method D): RT=2.93 min, m/z: 303 [M+H$^+$].

Step 2. 2,6-Dichloro-N-(3,5-difluoropyridin-4-yl)-benzimidoyl chloride

A stirred suspension of 2,6-dichloro-N-(3,5-difluoropyridin-4-yl)-benzamide (14.5 g, 47.8 mmol) in thionyl chloride (130 mL) was heated at 85° C. for 20 hours and then at 90° C. for 26 hours under argon. After cooling to room temperature, the volatiles were removed under reduced pressure, azeotroped with toluene (×3) to afford the title compound as a yellow solid (15.7 g, quantitative). LCMS (Method D): RT=4.16 min, m/z: 321 [M+H$^+$].

Step 3. 2-(2,6-Dichlorophenyl)-7-fluorothiazolo[5,4-c]pyridine

A stirred suspension of 2,6-dichloro-N-(3,5-difluoropyridin-4-yl)-benzimidoyl chloride (15.4 g, 47.8 mmol), thiourea (14.5 g, 0.191 mol) and pyridine (19.3 mL, 0.239 mol) in isopropanol (250 mL) was heated at 85° C. for 4 hours under argon. To the mixture was added Et$_3$N (40 mL, 0.287 mol) and heating at 85° C. was continued for 18 hours. After cooling to room temperature, the volatiles were removed under reduced pressure and the resultant residue was partitioned between EtOAc (500 mL) and water (500 mL). The aqueous phase was extracted with EtOAc (300 mL) and the combined organic layers were washed with water, then dried (Na$_2$SO$_4$) and concentrated under reduced pressure. The resultant residue was purified by column chromatography on silica gel eluting with 0-50% EtOAc in pentane to afford the title compound as a pale yellow solid (8.5 g, 59%). LCMS (Method D): RT=3.56 min, m/z: 299 [M+H$^+$].

Step 4. 2-(2,6-Dichlorophenyl)-7-fluorothiazolo[5,4-c]pyridine 5-oxide

To an ice-cooled solution of 2-(2,6-dichlorophenyl)-7-fluorothiazolo[5,4-c]pyridine (5.1 g, 17.1 mmol) in DCM (70 mL), was added m-CPBA (11.77 g, 68.2 mmol) over 3 minutes, at 0° C. under argon. The reaction mixture was slowly warmed to room temperature over 1 hour and then stirred at room temperature for 4 hours. The resultant mixture was diluted with DCM (150 mL) and washed with a saturated solution of potassium carbonate (100 mL). Additional amounts of DCM and water were added, followed by MeOH (50 mL). The organic layer was separated, washed with water (300 mL), dried (Na$_2$SO$_4$) and concentrated under reduced pressure. The resultant residue was triturated with water, dried under reduced pressure to afford the title compound as a white solid (6.50 g, quantitative). LCMS (Method F): RT=2.76 min, m/z: 315 [M+H$^+$].

Step 5. 4-Chloro-2-(2,6-dichlorophenyl)-7-fluorothiazolo[5,4-c]pyridine

A stirred solution of 2-(2,6-dichlorophenyl)-7-fluorothiazolo[5,4-c]pyridine 5-oxide (0.095 g, 0.30 mmol) in phosphoryl chloride (3 mL) was heated under reflux for 0.5 hour and then at 110° C. for 15 minutes. The reaction was repeated on a larger scale by reacting 2-(2,6-dichlorophenyl)-7-fluorothiazolo[5,4-c]pyridine 5-oxide (6.4 g, 17.0 mmol) with phosphoryl chloride (100 mL) and by heating the mixture under reflux for 30 minutes. After cooling to room temperature, the mixture was left standing at room temperature for 18 hours and then heated at reflux temperature for 15 minutes. The two crude reaction mixtures were combined and the volatiles were removed under reduced pressure. The crude residue was dissolved in EtOAc (200 mL) and washed with a saturated solution of potassium carbonate, followed by water, then dried (Na$_2$SO$_4$) and concentrated under reduced pressure. The resultant residue was purified by column chromatography on silica gel eluting with 0-20% EtOAc in pentane to afford the title compound as a white solid (3.42 g, 49% yield). $^1$H NMR (400 MHz, CDCl$_3$): δ 8.39 (d, J=1.9 Hz, 1H), 7.53-7.41 (m, 3H).

Step 6. 4-Bromo-2-(2,6-dichlorophenyl)-7-fluorothiazolo[5,4-c]pyridine

Trimethylsilyl bromide (1.2 mL, 9.0 mmol) was added to a solution of 4-chloro-2-(2,6-dichlorophenyl)-7-fluorothiazolo[5,4-c]pyridine (1.0 g, 3.0 mmol) in propionitrile (30 mL) at room temperature under argon. The reaction mixture was heated at 85° C. in a sealed vial for 16 hours. The resultant mixture was poured in an ice-cooled saturated solution of potassium carbonate. The product was extracted with DCM (×2) and the combined organic layers were dried (Na$_2$SO$_4$) and concentrated under reduced pressure to afford the title compound as an off-white solid (1.17 g, quantitative). LCMS (Method E): RT=4.32 min, m/z: 379 [M+H$^+$].

Step 7. [2-(2,6-Dichlorophenyl)-7-fluorothiazolo[5,4-c]pyridin-4-yl]-(6-methylpyrimidin-4-yl)-amine A mixture of 4-bromo-2-(2,6-dichlorophenyl)-7-fluorothiazolo[5,4-c]pyridine (0.113 g, 0.30 mmol), 6-methylpyrimidin-4-ylamine (0.036 g, 0.33 mmol), XantPhos (0.018 g, 0.030 mmol) and Cs$_2$CO$_3$ (0.247 g, 0.75 mmol) in dioxane (2.5 mL) was degassed with a stream of argon. Pd$_2$(dba)$_3$ (0.014 g, 0.015 mmol) was added and the reaction mixture was heated in a sealed vial at 80° C. for 3 hours. After cooling to room temperature, the crude reaction mixture was filtered through Celite® washing with EtOAc and the filtrate was concentrated under reduced pressure. The resultant residue was purified by column chromatography on silica gel eluting with 0-100% EtOAc in pentane and then triturated with diethyl ether to afford the title compound as an off-white solid (71 mg, 58% yield). $^1$H NMR (400 MHz, DMSO-d$_6$): δ 10.68 (s, 1H), 8.61 (d, J=1.1 Hz, 1H), 8.49 (d, J=1.9 Hz, 1H), 7.77-7.72 (m, 2H), 7.71-7.66 (m, 1H), 7.42 (s, 1H), 2.38 (s, 3H). LCMS (Method C): RT=3.73 min, m/z: 406 [M+H⁺].

Example 143

[2-(2,6-Dichlorophenyl)-7-fluorothiazolo[5,4-c]pyridin-4-yl]-carbamic acid methyl ester

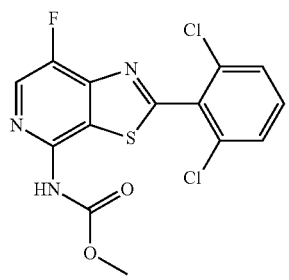

Step 1. 2-(2,6-Dichlorophenyl)-7-fluorothiazolo[5,4-c]pyridin-4-yl]-carbamic acid tert-butyl ester A mixture of 4-bromo-2-(2,6-dichlorophenyl)-7-fluorothiazolo[5,4-c]pyridine (0.60 g, 1.6 mmol), carbamic acid tert-butyl ester (0.936 g, 8.0 mmol), XantPhos (0.093 g, 0.16 mmol) and $K_3PO_4$ (0.678 g, 3.2 mmol), in toluene (10 mL) and water (2 mL), was degassed with a stream of argon. $Pd_2(dba)_3$ (0.073 g, 0.08 mmol) was added and the reaction mixture was heated at 70° C. for 3 hours in a sealed vial. After cooling to room temperature, the crude reaction mixture was filtered through Celite® washing with EtOAc. The aqueous phase was further extracted with EtOAc and the combined organic layers were washed with brine, then dried ($Na_2SO_4$) and concentrated under reduced pressure. The resultant residue was purified by column chromatography on silica gel eluting with 0-40% EtOAc in pentane to afford the title compound as an off-white/yellow solid (0.74 g). LCMS (Method D): RT=4.26 min, m/z: 414 [M+H⁺].

Step 2. 2-(2,6-Dichlorophenyl)-7-fluorothiazolo[5,4-c]pyridin-4-ylamine

To a solution of 2-(2,6-dichlorophenyl)-7-fluorothiazolo[5,4-c]pyridin-4-yl]-carbamic acid tert-butyl ester (0.70 g) in DCM (12 mL) under an argon atmosphere at room temperature was added TFA (3.0 mL). The reaction mixture was stirred for 1 hour and 15 minutes. The volatiles were removed under reduced pressure and the resultant residue was loaded onto an Isolute® SCX-2 cartridge. The cartridge was washed with DCM:MeOH (1:1) and then with MeOH and the product eluted with 2N $NH_3$ in MeOH. The basic fractions were combined and concentrated under reduced pressure to afford the title compound as a white solid (305 mg, 60% over two steps). LCMS (Method F): RT=2.87 min, m/z: 314 [M+H⁺].

Step 3. [2-(2,6-Dichlorophenyl)-7-fluorothiazolo[5,4-c]pyridin-4-yl]-carbamic acid methyl ester To a solution of methyl chloroformate (18 mg, 0.191 mmol) and DIPEA (42 µL, 0.24 mmol) in THF (1.0 mL) was added 2-(2,6-dichlorophenyl)-7-fluorothiazolo[5,4-c]pyridin-4-ylamine (50 mg, 0.159 mmol). The reaction mixture was stirred at room temperature for 2.5 hours, then heated at 50° C. for 2 hours and left standing at room temperature for 18 hours. The crude reaction mixture was partitioned between EtOAc and brine. The aqueous phase was extracted with EtOAc and the combined organic layers were dried ($Na_2SO_4$) and concentrated under reduced pressure. The resultant residue was purified by column chromatography on silica gel eluting with 0-50% EtOAc in pentane to afford the title compound as a white solid (12 mg, 20%). ¹H NMR (400 MHz, DMSO-d₆): δ 10.87 (s, 1H), 8.48 (d, J=1.8 Hz, 1H), 7.77-7.65 (m, 3H), 3.73 (s, 3H). LCMS (Method C): RT=4.74 min, m/z: 372 [M+H⁺].

Example 144

3,5-Dichloro-4-[7-fluoro-4-(6-methylpyrimidin-4-ylamino)thiazolo[5,4-c]pyridin-2-yl]-benzonitrile formate salt

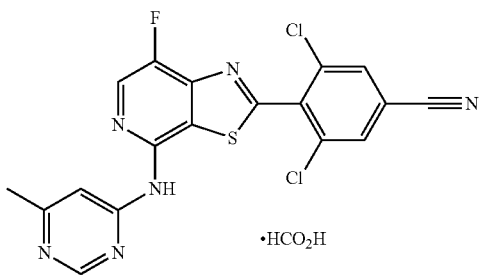 [SMILES: Cc1cc(Nc2ncc(F)c3nc(-c4c(Cl)cc(C#N)cc4Cl)sc23)ncn1 ; "·HCO2H"]

Step 1. 2,6-Dichloro-4-cyano-N-(3,5-difluoropyridin-4-yl)-benzamide

NaH (461 mg, 11.54 mmol) was added portionwise to a solution of 3,5-difluoropyridin-4-ylamine (1.0 g, 7.69 mmol) in DMF (20 mL) at 0° C. under a nitrogen atmosphere. A solution of 2,6-dichloro-4-cyano-benzoyl chloride (1.98 g, 8.46 mmol) in DMF (15 mL) was then added whilst maintaining the internal temperature below 10° C. Stirring was continued for 1.5 hours. The reaction mixture was quenched by addition of a saturated solution of $NH_4Cl$ and partitioned between water and EtOAc. The aqueous phase was further extracted with EtOAc (×2) and the combined organic layers were washed with water, then with brine, dried ($MgSO_4$) and concentrated under reduced pressure. The resultant residue was combined with the crude reaction mixture obtained following the same method starting from 3,5-difluoro-pyridin-4-ylamine (100 mg, 0.77 mmol) and purified by column chromatography on silica gel eluting with 0-50% EtOAc in cyclohexane to afford the title compound as an off-white solid (1.35 g, 49% yield). LCMS (Method D): RT=3.02 min, m/z: 328 [M+H⁺].

Step 2. 2,6-Dichloro-4-cyano-N-(3,5-difluoropyridin-4-yl)-benzimidoyl chloride

A stirred suspension of 2,6-dichloro-4-cyano-N-(3,5-difluoropyridin-4-yl)-benzamide (1.35 g, 4.12 mmol) in thionyl chloride (14 mL) was heated at 85° C. for 5 hours and then at 80° C. for 56 hours under a nitrogen atmosphere. After cooling to room temperature, the volatiles were removed under reduced pressure to afford the title compound as an orange solid (1.5 g, quantitative). LCMS (Method D): RT=4.01 min, m/z: 346 [M+H⁺].

Step 3. 3,5-Dichloro-4-(7-fluorothiazolo[5,4-c]pyridin-2-yl)-benzonitrile

A stirred suspension of 2,6-dichloro-4-cyano-N-(3,5-difluoropyridin-4-yl)-benzimidoyl chloride (1.5 g, 4.33 mmol), thiourea (1.32 g, 17.34 mmol) and pyridine (1.19 mL, 14.72 mmol) in isopropanol (13 mL) under a nitrogen atmosphere was heated at 90° C. for 4 hours. After cooling to 60° C., Et$_3$N (3.62 mL, 25.98 mmol) was added and heating at 85° C. was continued for 18 hours, then at 90° C. for a further 18 hours. After cooling to room temperature, the volatiles were removed under reduced pressure and the resultant residue was partitioned between EtOAc and water. The aqueous phase was extracted with EtOAc (×2) and the combined organic layers were dried (MgSO$_4$) and concentrated under reduced pressure. The resultant residue was purified by column chromatography on silica gel eluting with 0-90% EtOAc in cyclohexane to afford the title compound as a yellow solid (417 mg, 30%). LCMS (Method D): RT=3.53 min, m/z: 324 [M+H$^+$].

Step 4. 3,5-Dichloro-4-(7-fluoro-5-oxythiazolo[5,4-c]pyridin-2-yl)-benzonitrile To a solution of 3,5-dichloro-4-(7-fluorothiazolo[5,4-c]pyridin-2-yl)-benzonitrile (413 mg, 1.27 mmol) in DCM (5 mL) under a nitrogen atmosphere was added methyltrioxorhenium(VII) (32 mg, 0.127 mmol) followed by 30% aq. hydrogen peroxide (0.26 mL, 2.54 mmol). The reaction mixture was stirred at room temperature for 18 hours and then was quenched by addition of a saturated solution of NaHCO$_3$. The aqueous layer was extracted with DCM (×2). The combined organic phases were washed with brine, dried (MgSO$_4$) and concentrated under reduced pressure to afford the title compound as a yellow solid (259 mg, 60% yield). LCMS (Method D): RT=2.78 min, m/z: 340 [M+H$^+$].

Step 5. 3,5-Dichloro-4-(4-chloro-7-fluorothiazolo[5,4-c]pyridin-2-yl)-benzonitrile A stirred solution of 3,5-dichloro-4-(7-fluoro-5-oxythiazolo[5,4-c]pyridin-2-yl)-benzonitrile (0.259 g, 0.76 mmol) in phosphoryl chloride (2.6 mL) was heated at 110° C. for 1 hour under a nitrogen atmosphere. After cooling to room temperature, the volatiles were removed under reduced pressure and the resultant residue was partitioned between EtOAc and a saturated solution of NaHCO$_3$. The aqueous phase was extracted with EtOAc (×2) and the combined organic layers were dried (MgSO$_4$) and concentrated under reduced pressure. The resultant residue was combined with the crude mixture obtained following the same method and using 3,5-dichloro-4-(7-fluoro-5-oxythiazolo[5,4-c]pyridin-2-yl)-benzonitrile (0.154 g, 0.453 mmol). The crude material (215 mg) was purified by column chromatography on silica gel eluting with 0-10% EtOAc in petroleum ether to afford the title compound as a yellow solid (132 mg, 30% yield). $^1$H NMR (400 MHz, CDCl$_3$): δ 8.42 (d, J=1.8 Hz, 1H), 7.79 (s, 2H).

Step 6. 4-(4-Bromo-7-fluorothiazolo[5,4-c]pyridin-2-yl)-3,5-dichlorobenzonitrile Trimethylsilyl bromide (0.14 mL, 1.08 mmol) was added to a solution of 3,5-dichloro-4-(4-chloro-7-fluorothiazolo[5,4-c]pyridin-2-yl)-benzonitrile (0.130 g, 0.36 mmol) in propionitrile (3 mL) at room temperature under a nitrogen atmosphere. The reaction mixture was heated at 85° C. for 18 hours then allowed to stand at room temperature for 48 hours. The resultant mixture was poured into an ice-cooled saturated solution of NaHCO$_3$ and extracted with EtOAc (×2). The combined organic layers were dried (MgSO$_4$) and concentrated under reduced pressure to afford the title compound as an off-white solid (131 mg, 90% yield). $^1$H NMR (400 MHz, CDCl$_3$): δ 8.42 (d, J=1.8 Hz, 1H), 7.78 (s, 2H).

Step 7. 3,5-Dichloro-4-[7-fluoro-4-(6-methylpyrimidin-4-ylamino)-thiazolo[5,4-c]pyridin-2-yl]-benzonitrile formate salt A mixture of 4-(4-bromo-7-fluorothiazolo[5,4-c]pyridin-2-yl)-3,5-dichlorobenzonitrile (0.128 g, 0.318 mmol), 6-methylpyrimidin-4-ylamine (0.033 g, 0.35 mmol), XantPhos (0.019 g, 0.032 mmol) and Cs$_2$CO$_3$ (0.207 g, 0.635 mmol) in dioxane (4 mL) was degassed with a stream of argon. Pd$_2$(dba)$_3$ (0.015 g, 0.016 mmol) was added and the reaction mixture was heated at 80° C. for 18 hours. After cooling to room temperature, the crude reaction mixture was partitioned between EtOAc and water. The aqueous phase was extracted with EtOAc (×2) and the combined organic layers were washed with brine, dried (MgSO$_4$) and concentrated under reduced pressure. The resultant residue was purified by column chromatography on silica gel eluting with 0-5% MeOH in DCM and then by reverse phase HPLC (Phenomenex Gemini 5 μm C18 on a 30 minute gradient 40-90%, 0.1% HCO$_2$H in MeOH/H$_2$O) to afford the title compound as an off-white solid (44 mg, 30% yield). $^1$H NMR (400 MHz, DMSO-d$_6$): δ 10.72 (s, 1H), 8.61 (d, J=1.1 Hz, 1H), 8.50 (d, J=1.8 Hz, 1H), 8.40 (s, 2H), 8.31 (s, 1H), 7.39 (s, 1H), 2.38 (s, 3H). LCMS (Method C): RT=3.71 min, m/z: 431 [M+H$^+$].

Example 145

2-[4-(6-Aminopyrimidin-4-ylamino)thiazolo[5,4-c]pyridin-2-yl]-3-chlorobenzonitrile

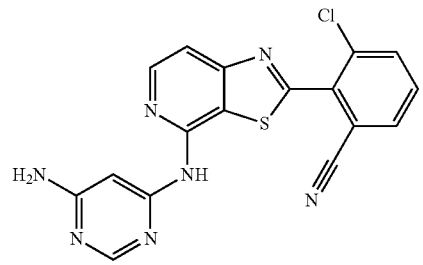 [SMILES: N#Cc1cccc(Cl)c1-c1nc2ccnc(Nc3cc(N)ncn3)c2s1]

Step 1. 2-Bromo-6-chloro-N-(2-chloro-3-fluoropyridin-4-yl)-benzamide

A mixture of 2-chloro-3-fluoro-4-iodopyridine (9.0 g, 35 mmol), 2-bromo-6-chlorobenzamide (9.0 g, 38.3 mmol), XantPhos (0.81 g, 1.40 mmol), Cs$_2$CO$_3$ (19.8 g, 60.7 mmol) and Pd$_2$(dba)$_3$ (0.90 g, 1.0 mmol) in dioxane (200 mL) was degassed with a stream of argon and then was heated under reflux for 1.5 hours. After cooling to room temperature, the crude reaction mixture was poured into a rapidly stirred mixture of water (1200 mL) and EtOAc (300 mL) and filtered through Celite® washing with EtOAc. The filtrate was partitioned between water (1.2 L) and EtOAc (300 mL) and the organic layer was washed with additional water (300 mL), then dried and concentrated to dryness under reduced pressure. The resultant residue was heated in isopropanol (100 mL) under reflux for 30 minutes and the suspension was allowed to cool and then filtered to yield a pale brown solid (3.1 g). The filtrate was concentrated to dryness and then triturated with diethyl ether (40 mL) to afford an off-white solid (4.80 g). The two batches of solid were combined and triturated with methanol (30 mL) to afford the title compound as a pale brown solid (4.8 g, 38% yield). LCMS (Method E): RT=3.48 min, m/z: 365 [M+H$^+$].

Step 2. 2-Bromo-6-chloro-N-(2-chloro-3-fluoropyridin-4-yl)-benzimidoyl chloride A stirred solution of 2-bromo-6-chloro-N-(2-chloro-3-fluoropyridin-4-yl)-benzamide (4.8 g, 13.2 mmol) in thionyl chloride (100 mL) was heated at 100° C. for 18 hours under a nitrogen atmosphere. After cooling to room temperature, the volatiles were removed under reduced pressure and the resultant residue was purified by column chromatography on silica gel eluting with 30% diethyl ether in pentane to afford the title compound as a pale yellow solid (4.2 g, 83% yield). LCMS (Method D): RT=4.47 min, m/z: 383 [M+H$^+$].

Step 3. 2-(2-Bromo-6-chlorophenyl)-4-chlorothiazolo[5,4-c]pyridine

A stirred solution of 2-bromo-6-chloro-N-(2-chloro-3-fluoropyridin-4-yl)-benzimidoyl chloride (4.2 g, 11.0 mmol), thiourea (2.5 g, 33.0 mmol) and pyridine (3.1 mL, 38.4 mmol) in isopropanol (50 mL) under a nitrogen atmosphere was heated under reflux for 3 hours. Et$_3$N (7.6 mL, 54.6 mmol) was added and the reaction mixture was heated under reflux for 1.5 hours. After cooling to room temperature, the volatiles were removed under reduced pressure. The resultant residue was triturated with water (100 mL) and then boiled in isopropanol (15 mL) for 10 minutes. After cooling to room temperature, the resultant solid was collected by filtration and then purified by column chromatography on silica gel eluting with 25% diethyl ether in pentane to afford the title compound as a colourless solid (2.1 g, 53%). LCMS (Method E): RT=4.16 min, m/z: 361 [M+H$^+$].

Step 4. 3-Chloro-2-(4-chlorothiazolo[5,4-c]pyridine-2-yl)-benzonitrile

A stirred mixture of 2-(2-bromo-6-chlorophenyl)-4-chlorothiazolo[5,4-c]pyridine (1.48 g, 4.11 mmol) and copper(I) cyanide (0.45 g, 5.0 mmol) in NMP (20 mL) was heated at 150° C. for 20 minutes. After cooling to room temperature, the mixture was poured into water (250 mL) and the insoluble material was collected by filtration. The solid was then suspended in EtOAc (300 mL) and, after vigorous stirring, was collected by filtration. The filtrate was concentrated under reduced pressure and the resultant residue was purified by column chromatography on silica gel eluting with 25-33% diethyl ether in pentane followed by 0-10% MeOH in DCM to afford the title compound as a pale yellow solid (0.364 g, 29% yield). LCMS (Method E): RT=3.59 min, m/z: 306 [M+H$^+$].

Step 5. 2-(4-Bromothiazolo[5,4-c]pyridin-2-yl)-3-chlorobenzonitrile

Trimethylsilyl bromide (1 mL) was added to a solution of 3-chloro-2-(4-chlorothiazolo[5,4-c]pyridine-2-yl)-benzonitrile (0.364 g, 1.18 mmol) in propionitrile (15 mL) at room temperature under a nitrogen atmosphere. The reaction mixture was heated at 85° C. for 2 hours and then the volatiles were removed under reduced pressure. The resultant residue was purified by column chromatography on silica gel eluting with 0-100% methanol in DCM to afford the title compound as a pale brown solid (230 mg, 56% yield). LCMS (Method D): RT=3.70 min, m/z: 337 [M+H$^+$].

Step 6. (6-Azidopyrimidin-4-yl)-bis-carbamic acid tert-butyl ester

To a mixture of (6-chloropyrimidin-4-yl)-bis-carbamic acid tert-butyl ester (2.0 g, 6.0 mmol) in DMF (10 mL) was added sodium azide (780 mg, 12.0 mmol). The resultant mixture was heated at 70° C. for 4 hours. After allowing to cool to room temperature, the crude mixture was partitioned between water and EtOAc. The organic layer was washed with brine (×2), dried (Na$_2$SO$_4$) and concentrated to dryness. The resultant residue was purified by column chromatography on silica gel eluting with 20% EtOAc in cyclohexane to afford the title compound as a pale yellow solid (1.33 g, 66% yield). $^1$H NMR (400 MHz, DMSO-d$_6$): δ 8.63 (s, 1H), 7.18 (s, 1H), 1.53 (s, 18H).

Step 7. (6-Aminopyrimidin-4-yl)-bis-carbamic acid tert-butyl ester

A suspension of (6-azidopyrimidin-4-yl)-bis-carbamic acid tert-butyl ester (1.33 g, 4.0 mmol) and 5% Pd/C (1.0 g) in IMS (10 mL) and EtOAc (3 mL) was stirred under a hydrogen atmosphere for 18 hours at room temperature. The reaction mixture was then filtered through Celite® washing with EtOAc. The filtrate was concentrated to dryness under reduced pressure and the resultant residue was titurated with diethyl ether to afford the title compound as a white solid (1.21 g, 95%). $^1$H NMR (400 MHz, DMSO-d$_6$): δ 8.17 (s, 1H), 6.96 (br s, 2H), 6.49 (s, 1H), 1.45 (s, 18H).

Step 8. {6-[2-(2-Chloro-6-cyanophenyl)-thiazolo[5,4-c]pyridin-4-ylamino]-pyrimidin-4-yl}-bis-carbamic acid tert-butyl ester A mixture of 2-(4-bromothiazolo[5,4-c]pyridin-2-yl)-3-chlorobenzonitrile (0.105 g, 0.30 mmol), (6-aminopyrimidin-4-yl)-bis-carbamic acid tert-butyl ester (77 mg, 0.36 mmol), XantPhos (0.018 g, 0.03 mmol) and Cs$_2$CO$_3$ (247 mg, 0.75 mmol) in dioxane (2.5 mL) was degassed with a stream of argon. Pd$_2$(dba)$_3$ (0.014 g, 0.015 mmol) was added and the reaction mixture was heated at 80° C. for 3 hours in a sealed vial. Additional amounts of XantPhos (0.018 g), Pd$_2$(dba)$_3$ (0.015 g), (6-aminopyrimidin-4-yl)-bis-carbamic acid tert-butyl ester (100 mg) and dioxane (1 mL) were added and the mixture was degassed with a stream of argon. Heating at 80° C. was continued for 18 hours. After cooling to room temperature, the crude reaction mixture was filtered through Celite® washing with DCM (100 mL). The filtrate was concentrated to dryness under reduced pressure and the resultant residue was purified by column chromatography on silica gel eluting with 0-80% EtOAc in pentane followed by 0-30% EtOAc in DCM to afford the title compound as a yellow oil (56 mg, 32% yield). LCMS (Method F): RT=4.20 min, m/z: 580 [M+H$^+$].

Step 9. 2-[4-(6-Aminopyrimidin-4-ylamino)thiazolo[5,4-c]pyridin-2-yl]-3-chlorobenzonitrile A mixture of {6-[2-(2-chloro-6-cyanophenyl)thiazolo[5,4-c]pyridin-4-ylamino]-pyrimidin-4-yl}-bis-carbamic acid tert-butyl ester (53 mg, 0.09 mmol) in HCl (4N in dioxane, 5 mL) was heated at 50° C. under a nitrogen atmosphere for 1 hour and then was stirred at room temperature for 18 hours.

The volatiles were removed under reduced pressure and the resultant residue was triturated with isopropanol to afford the title compound as a white solid (33 mg, 88% yield). $^1$H NMR (400 MHz, DMSO-$d_6$): δ 11.75 (s, 1H), 8.57-8.47 (m, 2H), 8.18-8.08 (m, 2H), 7.98 (d, J=5.7 Hz, 1H), 7.88 (t, J=8.1 Hz, 1H), 7.06 (br s, 1H). LCMS (Method C): RT=2.86 min, m/z: 380 [M+H$^+$].

Example 146

3-Chloro-2-[4-(6-hydroxymethylpyrimidin-4-ylamino)thiazolo[5,4-c]pyridin-2-yl]-benzonitrile

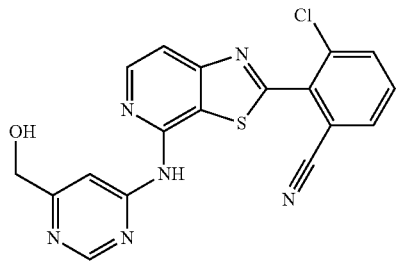 [SMILES: N#Cc1cccc(Cl)c1-c1nc2ccnc(Nc3cc(CO)ncn3)c2s1]

Step 1. 2-Chloro-3-fluoro-4-iodopyridine

A solution of lithium di-isopropylamide (2N in tetrahydrofuran/ethylbenzene/heptane, 155 mL, 310 mmol) was added dropwise over 40 minutes to solution of 2-chloro-3-fluoropyridine (31.0 g, 235 mmol) in tetrahydrofuran (200 mL) at −70° C. and the resulting mixture stirred for 4 hours. A solution of iodine (69.0 g, 200 mmol) in tetrahydrofuran (100 mL) was added dropwise over 30 minutes and the resultant mixture was stirred for 30 minutes at −70° C. then allowed to warm to room temperature over 1 hour. The reaction mixture was poured onto aqueous sodium metabisulphite solution (20% w/v, 2 L) and extracted with diethyl ether (3×300 mL). The combined organic extracts were washed with aqueous sodium metabisulphite solution (20% w/v, 2 L) and water (200 mL), dried over $Na_2SO_4$ and evaporated under reduced pressure to yield an oil. The resultant oil was triturated with diethyl ether to yield the title compound as a red/brown solid (28 g, 46% yield). $^1$H NMR (400 MHz, CDCl$_3$): δ 7.87 (d, J=5.0 Hz, 1H), 7.66 (ddd, J=5.0, 4.0, 0.4 Hz, 1H).

Step 2. 2-Chloro-N-(2-chloro-3-fluoropyridin-4-yl)-6-nitrobenzamide

A mixture of 2-chloro-3-fluoro-4-iodopyridine (4.78 g, 18.6 mmol), 2-chloro-6-nitrobenzamide (3.91 g, 19.5 mmol), ethane-1,2-diamine (0.2 mL, 2.97 mmol), copper(I) iodide (0.57 g, 2.97 mmol) and K$_3$PO$_4$ (7.90 g, 37.2 mmol) in dioxane (80 mL), was degassed with a stream of argon and the reaction mixture was then heated under reflux for 4 hours. After cooling to room temperature, the crude reaction mixture was filtered through Celite® washing with dioxane. The filtrate was concentrated to dryness under reduced pressure and the resultant residue was purified by column chromatography on silica gel eluting with 0-100% ethyl acetate in petroleum ether (40-60° C.), to afford the title compound as a pale yellow solid (1.87 g, 31% yield). $^1$H NMR (400 MHz, DMSO-$d_6$): δ 11.42-11.37 (br s, 1H), 8.35-8.24 (m, 3H), 8.08 (dd, J=1.1, 8.1 Hz, 1H), 7.81 (t, J=8.2 Hz, 1H).

Step 3. 2-Chloro-N-(2-chloro-3-fluoropyridin-4-yl)-6-nitrobenzimidoyl chloride

A stirred solution of 2-chloro-N-(2-chloro-3-fluoropyridin-4-yl)-6-nitrobenzamide (4.27 g, 12.9 mmol) in thionyl chloride (60 mL) was heated at 85° C. for 2 days under a nitrogen atmosphere. After cooling to room temperature, the volatiles were removed under reduced pressure and the resultant residue was purified by column chromatography on silica gel eluting with 0-30% ethyl acetate in petroleum ether (40-60° C.), to afford the title compound as a cream solid (3.90 g, 87% yield). $^1$H NMR (400 MHz, CDCl$_3$): δ 8.27-8.20 (m, 2H), 7.88 (dd, J=1.1, 8.1 Hz, 1H), 7.66 (t, J=8.2 Hz, 1H), 6.95 (t, J=5.2 Hz, 1H).

Step 4. 4-Chloro-2-(2-chloro-6-nitrophenyl)thiazolo[5,4-c]pyridine

A stirred suspension of 2-chloro-N-(2-chloro-3-fluoropyridin-4-yl)-6-nitrobenzamide (3.90 g, 11.2 mmol), thiourea (3.40 g, 44.8 mmol) and pyridine (3.1 mL, 38.1 mmol) in isopropanol (35 mL) under a nitrogen atmosphere, was heated under reflux for 4 hours. After this time, Et$_3$N (9.4 mL, 67.2 mmol) was added and the reaction mixture was heated under reflux for 16 hours. After cooling to room temperature, the volatiles were removed under reduced pressure. The crude residue was triturated with ethyl acetate and the solid was removed by filtration. The resultant filtrate was washed with 10% citric acid, brine, dried over MgSO$_4$ and evaporated under reduced pressure to afford the title compound as a pale orange solid (3.55 g, 97%). $^1$H NMR (400 MHz, CDCl$_3$): δ 8.51 (d, J=5.5 Hz, 1H), 8.13 (dd, J=1.2, 8.4 Hz, 1H), 7.91 (d, J=5.7 Hz, 1H), 7.87 (dd, J=1.2, 8.3 Hz, 1H), 7.72 (t, J=8.1 Hz, 1H).

Step 5. 3-Chloro-2-(4-chlorothiazolo[5,4-c]pyridin-2-yl)-phenylamine

Iron powder (6.08 g, 109 mmol) was added to a solution of 4-chloro-2-(2-chloro-6-nitrophenyl)thiazolo[5,4-c]pyridine (3.55 g, 10.9 mmol) in AcOH (100 mL). The reaction mixture was heated at 100° C. for 30 minutes and then allowed to cool to room temperature. The volatiles were removed under reduced pressure and the resultant residue was dissolved in DCM/MeOH and filtered through Celite® washing further with MeOH. The combined washings were concentrated under reduced pressure and the resultant residue was triturated with 10% MeOH in DCM to afford the title compound as an orange/red solid (2.55 g, 79% yield). $^1$H NMR (400 MHz, CDCl$_3$): δ 8.44 (d, J=5.6 Hz, 1H), 7.83 (d, J=5.7 Hz, 1H), 7.16 (t, J=7.9 Hz, 1H), 6.89 (dd, J=1.2, 7.8 Hz, 1H), 6.73 (dd, J=1.2, 8.3 Hz, 1H), 6.14 (br s, 2H).

Step 6. 3-Chloro-2-(4-chlorothiazolo[5,4-c]pyridine-2-yl)-benzonitrile

A solution of sodium nitrite (334 mg, 4.85 mmol) in water (4.8 mL) was added dropwise to a suspension of 3-chloro-2-(7-fluorothiazolo[5,4-c]pyridin-2-yl)-phenylamine (1.42 g, 4.8 mmol) in CH$_3$CN (23.6 mL), conc. HCl (12N, 4.8 mL) and water (21.3 mL) at 0° C. The resultant mixture was stirred between 0 and 5° C. for 1 hour.

Simultaneously, in a separate flask, CuSO$_4$.5H$_2$O (1.44 g, 5.76 mmol) in water (5.76 mL) was added dropwise to a solution of KCN (1.44 g, 22.1 mmol) in water (7.8 mL) at 0° C., followed by toluene (15.8 mL) and the reaction mixture was heated at 60° C. for 1 hour.

The pH of the diazonium suspension was adjusted to 6-7 by careful addition of a saturated solution of NaHCO$_3$ (~40 mL) at 0° C. The resultant mixture was then added dropwise over 20 minutes to the copper cyanide mixture at 60° C. The resultant suspension was heated at 70° C. for 50 minutes and then allowed to cool to room temperature. The reaction mixture was filtered through Celite® washing with EtOAc (200 mL). The combined organic extracts were washed with brine, dried (MgSO$_4$), filtered and concentrated under reduced pressure. The crude residue was firstly purified by column chromatography on silica gel eluting with 0-20% EtOAc in petroleum ether (40-60° C.), then by a second column eluting with 0-1% MeOH in DCM to afford the title compound as a yellow solid (574 mg, 39% yield). $^1$H NMR (400 MHz, CDCl$_3$): δ 8.54 (d, J=5.6 Hz, 1H), 8.02 (d, J=5.6 Hz, 1H), 7.85-7.80 (m, 2H), 7.63 (t, J=8.1 Hz, 1H).

Step 7. 3-Chloro-2-(4-chlorothiazolo[5,4-c]pyridine-2-yl)-benzonitrile

A mixture of 3-chloro-2-(4-chlorothiazolo[5,4-c]pyridin-2-yl)benzonitrile (100 mg, 0.33 mmol), (6-aminopyrimidin-4-yl)methanol (45 mg, 0.36 mmol), XantPhos (0.019 g, 0.033 mmol) and Cs$_2$CO$_3$ (215 mg, 0.66 mmol) in dioxane (4 mL) was degassed with a stream of argon. Pd$_2$(dba)$_3$ (0.015 g, 0.0163 mmol) was added and the reaction mixture was heated at 85° C. for 18 hours. After cooling to room temperature, the crude mixture was filtered through Celite®, washing with DCM/MeOH and the filtrate was concentrated to dryness under reduced pressure. The resultant residue was purified by column chromatography on silica gel, eluting with 0-3% MeOH in EtOAc, and then by reverse phase HPLC (Phenomenex Gemini 5 µm C18 on a 30 minute gradient 20-80%, 0.1% HCO$_2$H in MeOH/H$_2$O) to afford the title compound as an off-white solid (30 mg, 23% yield). $^1$H NMR (400 MHz, DMSO-d$_6$): δ 10.80 (br s, 1H), 8.64 (d, J=1.2 Hz, 1H), 8.49 (d, J=5.6 Hz, 1H), 8.15-8.07 (m, 2H), 7.90-7.82 (m, 2H), 7.76 (br s, 1H), 5.58 (t, J=5.7 Hz, 1H), 4.49 (d, J=4.8 Hz, 2H). LCMS (Method C): RT=2.97 min, m/z: 395 [M+H$^+$].

Example 147

2-[4-(6-Amino-2-methylpyrimidin-4-ylamino)-thiazolo[5,4-c]pyridin-2-yl]-3-chlorobenzonitrile hydrochloride salt

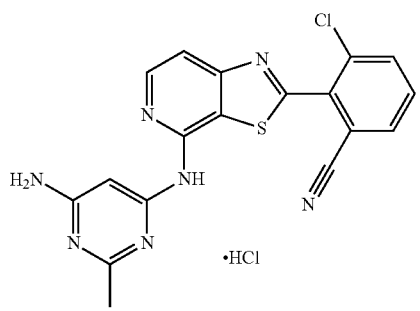 [SMILES: Cc1nc(N)cc(Nc2nccc3nc(-c4c(Cl)cccc4C#N)sc23)n1 ; Cl]

Step 1.
(6-Azido-2-methylpyrimidin-4-yl)-bis-carbamic acid tert-butyl ester

To a mixture of (6-chloro-2-methylpyrimidin-4-yl)-bis-carbamic acid tert-butyl ester (2.0 g, 5.8 mmol) in DMSO (10 mL) was added sodium azide (757 mg, 11.6 mmol). The resultant mixture was heated at 50° C. for 16 hours. After cooling to room temperature, the crude mixture was partitioned between water and EtOAc. The aqueous layer was washed with EtOAc (×2). The combined organic extracts were washed with brine (×2), dried (Na$_2$SO$_4$) and concentrated to dryness to afford the title compound as an oil (1.64 g, 80% yield). LCMS (Method D): RT=3.76 min, m/z: 351 [M+H$^+$].

Step 2.
(6-Amino-2-methylpyrimidin-4-yl)-bis-carbamic acid tert-butyl ester

A suspension of (6-azido-2-methylpyrimidin-4-yl)-bis-carbamic acid tert-butyl ester (1.64 g, 4.7 mmol) and 5% Pd/C (0.5 g) in IMS (36 mL) and EtOAc (12 mL) was stirred under a hydrogen atmosphere for 18 hours at room temperature. The reaction mixture was then filtered through Celite® washing with EtOAc. The filtrate was concentrated to dryness under reduced pressure and the resultant residue was purified by column chromatography on silica gel eluting with 0-60% EtOAc in petroleum ether (40-60° C.) to afford the title compound as a white solid (0.74 g, 49%). LCMS (Method D): RT=2.72 min, m/z: 325 [M+H$^+$].

Step 3. {6-[2-(2-Chloro-6-cyanophenyl)-thiazolo[5,4-c]pyridin-4-ylamino]-2-methylpyrimidin-4-yl}-bis-carbamic acid tert-butyl ester A mixture of 2-(4-chlorothiazolo[5,4-c]pyridin-2-yl)-3-chlorobenzonitrile (0.27 g, 0.88 mmol), (6-amino-2-methylpyrimidin-4-yl)-bis-carbamic acid tert-butyl ester (314 mg, 0.97 mmol), XantPhos (0.051 g, 0.09 mmol) and Cs$_2$CO$_3$ (722 mg, 2.20 mmol) in dioxane (10 mL) was degassed with a stream of argon. Pd$_2$(dba)$_3$ (0.040 g, 0.044 mmol) was added and the reaction mixture was heated at 80° C. for 16 hours in a sealed vial. After cooling to room temperature, the crude reaction mixture was filtered through Celite® washing with DCM (100 mL). The filtrate was concentrated to dryness under reduced pressure and the resultant residue was purified by column chromatography on silica gel eluting with 0-60% EtOAc in pentane followed by 0-25% EtOAc in DCM to afford the title compound as a yellow oil (305 mg, 59% yield). LCMS (Method D): RT=4.38 min, m/z: 594 [M+H$^+$].

Step 4. 2-[4-(6-Amino-2-methylpyrimidin-4-ylamino)-thiazolo[5,4-c]pyridin-2-yl]-3-chlorobenzonitrile hydrochloride salt A mixture of {6-[2-(2-chloro-6-cyanophenyl)-thiazolo[5,4-c]pyridin-4-ylamino]-2-methylpyrimidin-4-yl}-bis-carbamic acid tert-butyl ester (305 mg, 0.51 mmol) in HCl (4N in dioxane, 10 mL) was heated at 50° C. under a nitrogen atmosphere for 5 hours. After cooling to room temperature, the volatiles were removed under reduced pressure and the resultant residue was triturated with isopropanol to afford the title compound as an off-white solid (236 mg, quantitative yield). $^1$H NMR (400 MHz, DMSO-d$_6$): δ 11.44 (br s, 1H), 8.53 (d, J=5.5 Hz, 1H), 8.16-8.10 (m, 2H), 7.97 (d, J=5.5 Hz, 1H), 7.87 (t, J=8.1 Hz, 1H), 7.15 (br s, 1H), 4.05 (br s, 3H), 3.57 (s, 3H). LCMS (Method C): RT=2.92 min, m/z: 394 [M+H$^+$].

Example 148

3-Chloro-2-[7-fluoro-4-(6-methylpyrimidin-4-ylamino)thiazolo[5,4-c]pyridin-2-yl]-benzonitrile

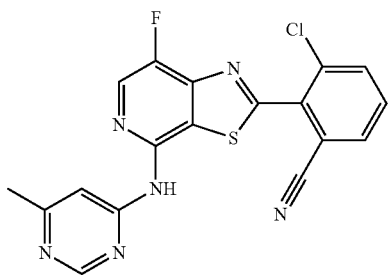 [SMILES: Cc1cc(Nc2ncc(F)c3nc(-c4c(Cl)cccc4C#N)sc23)ncn1]

Step 1. 2-Chloro-N-(3,5-difluoropyridin-4-yl)-6-nitrobenzamide

A solution of 2-chloro-6-nitrobenzoyl chloride (7.63 g, 34.7 mmol) in dioxane (12 mL) was added dropwise over 5 minutes to a solution of 3,5-difluoropyridin-4-ylamine (3.77 g, 29.0 mmol) in pyridine (40 mL) at room temperature under argon. The reaction mixture was stirred at room temperature for 19 hours then the volatiles were removed under reduced pressure. To the resultant residue, HCl (1N, 60 mL) was added and the suspension was sonicated and then stirred at room temperature for 30 minutes. The resultant solid was filtered to afford a mixture of 2-chloro-N-(3,5-difluoropyridin-4-yl)-6-nitrobenzamide {LCMS (Method D): RT=2.76 min, m/z: 314 [M+H$^+$]} and 2-chloro-N-(2-chloro-6-nitrobenzoyl)-N-(3,5-difluoropyridin-4-yl)-6-nitrobenzamide {LCMS (Method D): RT=3.77 min, m/z: 498 [M+H$^+$]}. NaOH (1N, 60 mL) was added to a suspension of this solid in MeOH (60 mL) at room temperature under argon. The reaction mixture was heated at 50° C. for 1.5 hours, allowed to cool to room temperature, and then the organic solvent was removed in vacuo. The resultant mixture was made acidic (pH 2-3) by addition of 12N HCl and was then cooled to 0° C. The resultant solid was filtered and dried to afford the title compound as a pale yellow solid (5.25 g, 58% yield) which was used in the following step without further purification. LCMS (Method D): RT=2.76 min, m/z: 314 [M+H$^+$].

Step 2. 2-Chloro-N-(3,5-difluoropyridin-4-yl)-6-nitrobenzimidoyl chloride

A mixture of 2-chloro-N-(3,5-difluoropyridin-4-yl)-6-nitrobenzamide (5.25 g, 16.7 mmol) in thionyl chloride (40 mL) was heated under reflux for 18 hours under a nitrogen atmosphere. After cooling to room temperature, the volatiles were removed under reduced pressure and the resultant residue was azeotroped with toluene (×3) to afford the title compound as a yellow/brown solid (5.5 g, quantitative). LCMS (Method D): RT=3.77 min, m/z: 332 [M+H$^+$].

Step 3. 2-(2-Chloro-6-nitrophenyl)-7-fluorothiazolo[5,4-c]pyridine

A suspension of 2-chloro-N-(3,5-difluoropyridin-4-yl)-6-nitrobenzimidoyl chloride (5.53 g, 16.6 mmol), thiourea (5.05 g, 0.066 mol) and pyridine (6.7 mL, 83 mmol) in isopropanol (90 mL), under nitrogen, was heated under reflux for 6 hours. After this time, Et$_3$N (14 mL, 100 mmol) was added over 5 minutes and the reaction mixture was heated under reflux for 18 hours. Upon cooling to room temperature, the volatiles were removed under reduced pressure and the resultant residue was partitioned between water and EtOAc. The aqueous phase was further extracted with EtOAc (×2) and the combined organic layers were dried (Na$_2$SO$_4$) and concentrated to dryness. The resultant residue was purified by column chromatography on silica gel eluting with 0-80% EtOAc in pentane followed by 0-50% EtOAc in DCM to afford the title compound as a yellow solid (2.55 g, 50% yield). LCMS (Method D): RT=3.29 min, m/z: 310 [M+H$^+$].

Step 4. 3-Chloro-2-(7-fluorothiazolo[5,4-c]pyridin-2-yl)-phenylamine

Iron powder (7.95 g, 141 mmol) was added to a solution of 2-(2-chloro-6-nitrophenyl)-7-fluorothiazolo[5,4-c]pyridine (4.35 g, 14.1 mmol) in AcOH (130 mL). The reaction mixture was heated at 100° C. for 30 minutes and then allowed to cool to room temperature. The volatiles were removed under reduced pressure and the resultant residue was dissolved in DCM/MeOH and filtered through Celite® washing the filter pad thoroughly with further DCM/MeOH. The filtrate was concentrated under reduced pressure and the resultant residue was purified by column chromatography on silica gel eluting with 0-5% MeOH in DCM to afford the title compound as a yellow solid (3.63 g, 92% yield). $^1$H NMR (300 MHz, CDCl$_3$): δ 9.03 (s, 1H), 8.52 (d, J=2.4 Hz, 1H), 7.16 (t, J=8.2 Hz, 1H), 6.89 (d, J=7.8 Hz, 1H), 6.75 (d, J=8.3 Hz, 1H), 6.28 (br s, 2H). LCMS (Method D): RT=3.51 min, m/z: 280 [M+H$^+$].

Step 5. 3-Chloro-2-(7-fluorothiazolo[5,4-c]pyridin-2-yl)-benzonitrile

Sodium nitrite (0.89 g, 12.9 mmol) in water (17 mL) was added dropwise to a suspension of 3-chloro-2-(7-fluorothiazolo[5,4-c]pyridin-2-yl)-phenylamine (3.43 g, 12.3 mmol) and 37% hydrochloric acid (16.1 mL) in water (34 mL) and acetonitrile (62 mL) at 0° C. The resultant mixture was stirred at 0° C. for 1.5 hours until all of the solid had dissolved.

Simultaneously, in a separate flask, a solution of CuSO$_4$.5H$_2$O (3.77 g, 15.1 mmol) in water (17 mL) was added dropwise to a solution of KCN (3.77 g, 58.3 mmol) in water (21 mL) at 0° C. Toluene (41 mL) was then added and the reaction mixture was heated at 60° C. for 1.5 hours.

The diazonium salt solution, still at 0° C., was treated cautiously with aqeuous sodium bicarbonate to achieve pH 6-7. The resultant mixture was then added, dropwise over 15 min, to the copper cyanide mixture at 60° C. The reaction mixture was heated at 70° C. for 1.5 hours, allowed to cool to room temperature and was then partitioned between ethyl acetate and water and the aqueous layer was extracted with ethyl acetate (×3). The combined organic extracts were dried (sodium sulphate) and evaporated. The crude product was triturated twice with 1:1 diethyl ether/cyclohexane (100 mL) and the solid was filtered off and dried under vacuum to give the title compound as an off-white solid (2.31 g). The trituration liquors were evaporated and the crude residue was purified by column chromatography on silica gel, eluting with 0-40% ethyl acetate in cyclohexane to give a further crop of the title compound as an off-white solid (0.49 g). Combined yield: (2.80 g, 79%). $^1$H NMR (300 MHz, DMSO-d$_6$): δ 9.44

(s, 1H), 8.80-8-77 (m, 1H), 8.13 (t, J=8.0 Hz, 2H), 7.88 (t, J=8.0 Hz, 1H). LCMS (Method F): RT=3.10 min, m/z: 290 [M+H⁺].

Step 6. 3-Chloro-2-(7-fluoro-5-oxythiazolo[5,4-c]pyridin-2-yl)-benzonitrile

To a solution of 3-chloro-2-(7-fluorothiazolo[5,4-c]pyridin-2-yl)-benzonitrile (880 mg, 3.04 mmol) in DCM (15 mL) and methyltrioxorhenium(VII) (76 mg, 0.3 mmol) under argon was added 27.5% aq. hydrogen peroxide (0.68 mL, 6.08 mmol). The reaction mixture was stirred at room temperature for 72 hours. The crude mixture was diluted with DCM (40 mL) and MeOH (10 mL) and washed with water (60 mL). The aqueous phase was extracted with EtOAc and the combined organic extracts were washed with brine, dried (Na₂SO₄) and concentrated under reduced pressure to afford the title compound as a yellow solid (930 mg, quantitative). LCMS (Method D): RT=2.51 min, m/z: 306 [M+H⁺].

Step 7. 3-Chloro-2-(4-chloro-7-fluorothiazolo[5,4-c]pyridin-2-yl)-benzonitrile

To a suspension of 3-chloro-2-(7-fluoro-5-oxy-thiazolo[5,4-c]pyridin-2-yl)-benzonitrile (2.11 g, 6.92 mmol) in 1,2-dichloroethane (34 mL) was added phosphorus oxychloride (2.0 mL, 22.2 mmol). The reaction mixture was heated at 70° C. for 16 hours. Upon cooling, the resultant mixture was treated cautiously with aqueous sodium bicarbonate to achieve pH 6-7, and then extracted with dichloromethane (×5). The combined organic extracts were dried (Na₂SO₄) and concentrated under reduced pressure. The crude product was purified by column chromatography on silica gel eluting with 0-50% ethyl acetate in cyclohexane to afford the title compound as a white solid 1.43 g (64% yield). ¹H NMR (300 MHz, CDCl₃): δ 8.42 (d, J=1.8 Hz, 1H), 7.86-7.79 (m, 2H), 7.66 (t, J=8.0 Hz, 1H).

Step 8. 2-(4-Bromo-7-fluorothiazolo[5,4-c]pyridin-2-yl)-3-chlorobenzonitrile

Trimethylsilyl bromide (1.8 mL, 13.2 mmol) was added to a suspension of 3-chloro-2-(4-chloro-7-fluorothiazolo[5,4-c]pyridin-2-yl)-benzonitrile (1.43 g, 4.40 mmol) in propionitrile (40 mL) at room temperature, under argon. The reaction mixture was heated at 50° C. for 7 hours. The reaction mixture was adjusted to pH 7 by careful addition of a saturated aqueous solution of sodium bicarbonate. The resultant mixture was extracted with DCM (×3) and the combined organic layers were dried (Na₂SO₄) and concentrated under reduced pressure to afford the title compound as an off-white solid (1.65 g, 100% yield). ¹H NMR (300 MHz, CDCl₃): δ 8.42 (d, J=1.8 Hz, 1H), 7.86-7.79 (m, 2H), 7.66 (t, J=8.0 Hz, 1H).

Step 9. 3-Chloro-2-[7-fluoro-4-(6-methylpyrimidin-4-ylamino)thiazolo[5,4-c]pyridin-2-yl]-benzonitrile A mixture of 2-(4-bromo-7-fluorothiazolo[5,4-c]pyridin-2-yl)-3-chlorobenzonitrile (0.110 g, 0.30 mmol), 6-methylpyrimidin-4-ylamine (35 mg, 0.32 mmol), XantPhos (0.018 g, 0.03 mmol) and Cs₂CO₃ (247 mg, 0.75 mmol) in dioxane (2.5 mL) was degassed with a stream of argon. Pd₂(dba)₃ (0.014 g, 0.015 mmol) was added and the reaction mixture was heated at 80° C. for 2 hours in a sealed vial. After cooling to room temperature, the crude reaction mixture was filtered through Celite® washing with EtOAc (50 mL). The filtrate was concentrated to dryness under reduced pressure. The resultant residue was purified by column chromatography on silica gel eluting with 0-100% EtOAc in DCM, then triturated with diethyl ether (×2), to afford the title compound as a pale yellow solid (43 mg, 36% yield). ¹H NMR (400 MHz, CDCl₃): δ 8.73 (d, J=1.2 Hz, 1H), 8.34 (d, J=1.8 Hz, 1H), 7.86-7.76 (m, 3H), 7.66 (t, J=8.0 Hz, 1H), 7.57 (br s, 1H), 2.56 (s, 3H). LCMS (Method C): RT=3.31 min, m/z: 397 [M+H⁺].

Example 149

3-Chloro-2-[7-fluoro-4-(6-hydroxymethyl-pyrimidin-4-ylamino)-thiazolo[5,4-c]pyridin-2-yl]-benzonitrile

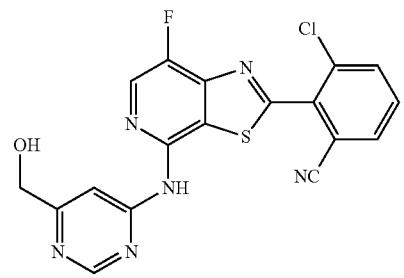 [SMILES: N#Cc1cccc(Cl)c1-c1nc2c(F)cnc(Nc3cc(CO)ncn3)c2s1]

A mixture of 2-(4-bromo-7-fluorothiazolo[5,4-c]pyridin-2-yl)-3-chlorobenzonitrile (0.35 g, 0.95 mmol), (6-aminopyrimidin-4-yl)methanol (125 mg, 1.0 mmol), XantPhos (0.055 g, 0.095 mmol) and Cs₂CO₃ (780 mg, 2.38 mmol) in dioxane (11 mL) was degassed with a stream of argon. Pd₂(dba)₃ (0.048 g, 0.047 mmol) was added and the reaction mixture was heated at 80° C. for 6 hours in a sealed vial. After cooling to room temperature, the crude reaction mixture was diluted with EtOAc (100 mL) and water (20 mL) and the resultant mixture was filtered through Celite® washing with EtOAc (50 mL). The combined organic extracts were washed with brine, dried (Na₂SO₄) and concentrated under reduced pressure The resultant residue was purified by column chromatography on silica gel eluting with 0-10% MeOH in DCM, then triturated with diethyl ether (×2), to afford the title compound as a pale yellow solid (203 mg, 52% yield). ¹H NMR (400 MHz, DMSO-d₆): δ 10.79 (br s, 1H), 8.61 (d, J=1.2 Hz, 1H), 8.52 (d, J=1.8 Hz, 1H), 8.16-8.08 (m, 2H), 7.86 (t, J=8.0 Hz, 1H), 7.58 (s, 1H), 5.57 (t, J=5.7 Hz, 1H), 4.48 (d, J=5.7 Hz, 2H). LCMS (Method C): RT=3.29 min, m/z: 413 [M+H⁺].

Example 150

3-Fluoro-2-[7-fluoro-4-(6-methylpyrimidin-4-ylamino)-thiazolo[5,4-c]pyridin-2-yl]-benzonitrile hydrochloride salt

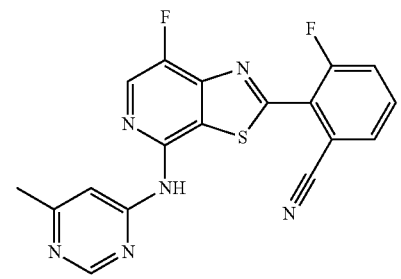 [SMILES: Cc1cc(Nc2ncc(F)c3nc(-c4c(F)cccc4C#N)sc23)ncn1]

Step 1. 2-Fluoro-N-(3,5-difluoropyridin-4-yl)-6-nitrobenzamide

A solution of 2-fluoro-6-nitrobenzoyl chloride (10.97 g, 52.4 mmol) in dioxane (20 mL) was added dropwise over 5 minutes to a solution of 3,5-difluoropyridin-4-ylamine (6.19 g, 47.6 mmol) in pyridine (80 mL) at room temperature under argon. The reaction mixture was stirred at room temperature for 18 hours then the volatiles were removed under reduced pressure. To the resultant residue, HCl (1N, 100 mL) was added and the suspension was sonicated and then stirred at room temperature for 30 minutes. The resultant solid was filtered and dried to afford a mixture of 2-fluoro-N-(3,5-difluoropyridin-4-yl)-6-nitrobenzamide {LCMS (Method D): RT=2.67 min, m/z: 298 [M+H$^+$]} and 2-chloro-N-(2-fluoro-6-nitrobenzoyl)-N-(3,5-difluoropyridin-4-yl)-6-nitrobenzamide {LCMS (Method D): RT=3.63 min, m/z: 465 [M+H$^+$]}.

NaOH (1N, 100 mL) was added to a suspension of this solid in MeOH (100 mL) at room temperature under argon. The reaction mixture was heated at 60° C. for 1.5 hours, allowed to cool to room temperature, and then the organic solvent was removed in vacuo. The resultant mixture was made acidic (pH 2-3) by addition of 12N HCl and was then cooled to 0° C. The resultant solid was filtered and dried to afford the title compound as a pale yellow solid (10.81 g, 76% yield). LCMS (Method D): RT=2.66 min, m/z: 298 [M+H$^+$].

Step 2. 2-Fluoro-N-(3,5-difluoropyridin-4-yl)-6-nitrobenzimidoyl chloride

A mixture of 2-fluoro-N-(3,5-difluoropyridin-4-yl)-6-nitrobenzamide (10.81 g, 36.4 mmol) in thionyl chloride (95 mL) was heated under reflux for 3 days under a nitrogen atmosphere. After cooling to room temperature, the volatiles were removed under reduced pressure and the resultant residue was azeotroped with toluene (×3) to afford the title compound as a yellow/pale brown solid (12.05 g, quantitative). LCMS (Method D): RT=3.64 min, m/z: 316 [M+H$^+$].

Step 3. 2-(2-Fluoro-6-nitrophenyl)-7-fluorothiazolo[5,4-c]pyridine

A suspension of 2-fluoro-N-(3,5-difluoropyridin-4-yl)-6-nitrobenzimidoyl chloride (12.05 g, 36.4 mmol), thiourea (12.05 g, 159 mmol) and pyridine (16 mL, 200 mmol) in isopropanol (200 mL) under a nitrogen atmosphere was heated under reflux for 4 hours. Et$_3$N (33.2 mL, 239 mmol) was added over 5 minutes and the reaction mixture was heated under reflux for 18 hours. After cooling to room temperature, the volatiles were removed under reduced pressure and the resultant residue was partitioned between water and EtOAc. The aqueous phase was further extracted with EtOAc (×5) and the combined organic layers were dried (Na$_2$SO$_4$) and concentrated to dryness. The resultant residue was purified by column chromatography on silica gel eluting with 0-50% EtOAc in cyclohexane to afford the title compound as a yellow solid (4.33 g, 41% yield). LCMS (Method D): RT=3.21 min, m/z: 294 [M+H$^+$].

Step 4. 3-Fluoro-2-(7-fluorothiazolo[5,4-c]pyridin-2-yl)-phenylamine

Iron powder (8.29 g, 148 mmol) was added to a solution of 2-(2-fluoro-6-nitrophenyl)-7-fluorothiazolo[5,4-c]pyridine (4.33 g, 14.8 mmol) in AcOH (144 mL). The reaction mixture was heated at 100° C. for 30 minutes and then allowed to cool to room temperature. The volatiles were removed under reduced pressure and the resultant residue was dissolved in DCM/MeOH and filtered through Celite® washing the filter pad thoroughly with further DCM/MeOH. The filtrate was concentrated under reduced pressure and the resultant residue was purified by column chromatography on silica gel eluting with 0-2% MeOH in DCM, then triturated with DCM and then dried to afford the title compound as a yellow solid (2.23 g, 57% yield). LCMS (Method D): RT=3.62 min, m/z: 264 [M+H$^+$].

Step 5. 3-Fluoro-2-(7-fluorothiazolo[5,4-c]pyridin-2-yl)-benzonitrile

Sodium nitrite (0.54 g, 7.82 mmol) in water (7.0 mL) was added dropwise to a suspension of 3-fluoro-2-(7-fluorothiazolo[5,4-c]pyridin-2-yl)-phenylamine (2.03 g, 7.72 mmol) and 37% hydrochloric acid (9.54 mL) in water (20 mL) and acetonitrile (36 mL) at 0° C. The resultant mixture was stirred at 0° C. for 1 hour until all of the solid had dissolved.

Simultaneously, in a separate flask, a solution of CuSO$_4$.5H$_2$O (2.34 g, 9.24 mmol) in water (10 mL) was added dropwise to a solution of KCN (2.23 g, 34.5 mmol) in water (12 mL) at 0° C. Toluene (24 mL) was then added and the reaction mixture was heated at 60° C. for 1 hour.

The diazonium salt solution, still at 0° C., was treated cautiously with aqeuous sodium bicarbonate to achieve pH 6-7. The resultant mixture was then added, dropwise over 15 min, to the copper cyanide mixture at 60° C. The reaction mixture was heated at 70° C. for 1.5 hours, allowed to cool to room temperature and was then partitioned between ethyl acetate and water and the aqueous layer was extracted with ethyl acetate (×3). The combined organic extracts were dried (sodium sulphate) and evaporated. The crude product was triturated twice with 1:1 diethyl ether/cyclohexane (40 mL) and the solid was filtered off and dried under vacuum to give the title compound as a yellow solid (1.09 g, 52%). LCMS (Method C): RT=3.15 min, m/z: 274 [M+H$^+$].

Step 6. 3-Fluoro-2-(7-fluoro-5-oxythiazolo[5,4-c]pyridin-2-yl)-benzonitrile

To a solution of 3-fluoro-2-(7-fluorothiazolo[5,4-c]pyridin-2-yl)-benzonitrile (1.09 g, 3.99 mmol) in DCM (14 mL) and methyltrioxorhenium(VII) (100 mg, 0.41 mmol) under argon was added 27.5% aq. hydrogen peroxide (1.18 mL, 9.47 mmol). The reaction mixture was stirred at room temperature for 72 hours adding further portions of methyltrioxorhenium(VII) (100 mg, 0.41 mmol) and 27.5% aq. hydrogen peroxide (1.18 mL, 9.47 mmol) after each 24 hour period. The crude mixture was diluted with DCM (60 mL) and MeOH (15 mL) and washed with aqeuous sodium bicarbonate (60 mL). The aqueous phase was extracted with DCM/MeOH and the combined organic extracts were dried (Na$_2$SO$_4$) and concentrated under reduced pressure to afford the title compound as a pale yellow solid (1.01 g, 88%). LCMS (Method F): RT=2.32 min, m/z: 290 [M+H$^+$].

Step 7. 3-Fluoro-2-(4-chloro-7-fluorothiazolo[5,4-c]pyridin-2-yl)-benzonitrile To a suspension of 3-fluoro-2-(7-fluoro-5-oxy-thiazolo[5,4-c]pyridin-2-yl)-benzonitrile (1.13 g, 3.90 mmol) in 1,2-dichloroethane (20 mL) was added phosphorus oxychloride (1.14 mL, 12.5 mmol). The reaction mixture was heated at 70° C. for 18 hours. Upon cooling, the resultant mixture was treated cautiously with aqueous sodium bicarbonate to achieve pH 6-7, and then extracted with 20% MeOH in dichloromethane (×5). The combined organic extracts were dried (Na$_2$SO$_4$) and concentrated under reduced pressure. The crude product was purified by column chromatography on silica gel eluting with 0-50% ethyl acetate in cyclohexane to afford the title compound as a white solid 0.70 g (61% yield). LCMS (Method D): RT=3.82 min, m/z: 308 [M+H$^+$].

Step 8. 2-(4-Bromo-7-fluorothiazolo[5,4-c]pyridin-2-yl)-3-fluorobenzonitrile

Trimethylsilyl bromide (0.92 mL, 6.85 mmol) was added to a suspension of 3-fluoro-2-(4-chloro-7-fluorothiazolo[5,4-c]pyridin-2-yl)-benzonitrile (0.70 g, 2.28 mmol) in propionitrile (20 mL) at room temperature, under argon. The reaction mixture was heated at 50° C. for 16 hours. The reaction mixture was adjusted to pH 7 by careful addition of a saturated aqueous solution of sodium bicarbonate. The resultant mixture was extracted with DCM (×3) and the combined organic layers were dried (Na$_2$SO$_4$) and concentrated under reduced pressure. The resultant solid was triturated with diethyl ether and dried under vacuum to afford the title compound as an off-white solid (0.76 g, 95% yield). LCMS (Method D): RT=3.87 min, m/z: 352 [M+H$^+$].

Step 9. 3-Fluoro-2-[7-fluoro-4-(6-methylpyrimidin-4-ylamino)thiazolo[5,4-c]pyridin-2-yl]-benzonitrile hydrochloride salt A mixture of 2-(4-bromo-7-fluorothiazolo[5,4-c]pyridin-2-yl)-3-chlorobenzonitrile (0.100 g, 0.28 mmol), 6-methylpyrimidin-4-ylamine (33 mg, 0.30 mmol), XantPhos (0.016 g, 0.028 mmol) and Cs$_2$CO$_3$ (173 mg, 0.53 mmol) in dioxane (2.0 mL) was degassed with a stream of argon. Pd$_2$(dba)$_3$ (0.013 g, 0.014 mmol) was added and the reaction mixture was heated at 80° C. for 24 hours in a sealed vial. After cooling to room temperature, the crude reaction mixture was partitioned between EtOAc and water. The aqueous layer was extracted with EtOAc (×3) and the combined organic extracts were dried (Na$_2$SO$_4$) and concentrated under reduced pressure. The resultant residue was purified by column chromatography on silica gel eluting with 50-100% EtOAc in cyclohexane. The resultant residue was dissolved in DCM (10 mL) and HCl (1.25N in propan-2-ol, 0.1 mL) was added and the mixture was concentrated to dryness. The crude solid obtained was triturated with diethyl ether (×2), acetonitrile (×3) and cyclohexane (×3), before drying to afford the title compound as an off white solid (19 mg, 16% yield). $^1$H NMR (400 MHz, DMSO-d$_6$): δ 11.82 (s, 1H), 8.93 (s, 1H), 8.62 (d, J=1.8 Hz, 1H), 8.08-8.02 (m, 1H), 7.99-7.89 (m, 2H), 7.59 (s, 1H), 2.49 (s, 3H). LCMS (Method C): RT=3.12 min, m/z: 381 [M+H$^+$].

Example 151

7-bromo-2-(2-chloro-6-fluorophenyl)-N-(6-methylpyrimidin-4-yl)thiazolo[5,4-c]pyridin-4-amine

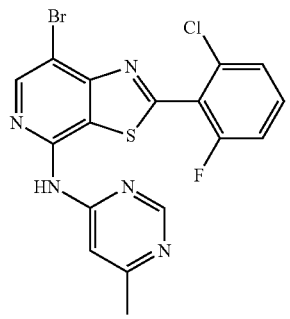 [SMILES: Cc1cc(Nc2ncc(Br)c3nc(-c4c(F)cccc4Cl)sc23)ncn1]

Step 1. N-(3-bromo-5-fluoropyridin-4-yl)-2-chloro-6-fluorobenzamide

To a solution of 3-bromo-5-fluoro-pyridin-4-amine (20.0 mmol, 3.82 g) in DMF (40 mL) was added NaH (40.0 mmol, 1.6 g). The mixture was stirred at room temperature for 30 min, then cooled to 0° C. A solution of 2-chloro-6-fluoro-benzoyl chloride (30.0 mmol, 5.79 g) in DCM (10 mL) was then added dropwise. The reaction mixture was stirred at room temperature for 16 hours. The reaction was then quenched with ice water, extracted with EtOAc. The combined organics were dried (Na$_2$SO$_4$), filtered and concentrated.

The resultant oil was dissolved in MeOH (40 mL) and THF (40 mL). 2N NaOH (30 mL) was added. The mixture was stirred at room temperature for 16 hours. The volatile solvents were then removed under reduced pressure. Water (100 mL) was added. The aqueous layer was saturated with NaCl, extracted with CHCl$_3$/iPrOH (3/1). The combined organics were dried (Na$_2$SO$_4$), filtered and concentrated. The crude product was purified by silica gel chromatography (0-8% EtOAc/DCM) to give the title compound as an off-white solid (3.4 g, 49% yield). $^1$H NMR (400 MHz, DMSO) δ 11.07 (s, 1H), 8.74 (s, 1H), 8.71 (s, 1H), 7.59 (dd, J=14.8, 7.8 Hz, 1H), 7.47 (d, J=8.1 Hz, 1H), 7.40 (t, J=8.6 Hz, 1H). LCMS (ESI) m/z 348.9 [M+H$^+$].

Step 2. 7-bromo-2-(2-chloro-6-fluorophenyl)thiazolo[5,4-c]pyridine

To a suspension of N-(3-bromo-5-fluoro-4-pyridyl)-2-chloro-6-fluoro-benzamide (6.891 mmol, 2.395 g) in 1,2-dichloroethane (100 mL) was added thionyl chloride (45 mL). The mixture was heated at reflux for 3 days under nitrogen when monitoring the reaction by LCMS showed incomplete conversion. More thionyl chloride (21 mL) was added. The reaction mixture was heated at reflux for additional 44 hours. The reaction mixture was then concentrate, azeotroped with toluene twice to give a light yellow solid which was used in the next step directly.

A mixture of (1Z)—N-(3-bromo-5-fluoro-4-pyridyl)-2-chloro-6-fluoro-benzimidoyl chloride, thiourea (103.4 mmol, 7.869 g) and pyridine (137.8 mmol, 10.9 g, 2.3 mL) in anhydrous isopropanol (50 mL) was heated at reflux for 17 hours. Triethylamine (13.78 mmol, 1.395 g) was then added. The mixture was heated at reflux for another 1 hour, cooled to room temperature. A solid precipitated and was filtered off. The filtrate was concentrated to give a solid residue which was partitioned between EtOAc (150 mL) and water (100 mL). The aqueous layer was extracted with EtOAc (100 mL). Combined organics were dried (Na$_2$SO$_4$), filtered and concentrated. The crude product was purified by silica gel chromatography (0-20% EtOAc/hexane) to give the title compound as an off-white solid (1.88 g, 79% yield). LCMS (ESI) m/z 344.0 [M+H$^+$].

Step 3: 7-bromo-2-(2-chloro-6-fluorophenyl)thiazolo[5,4-c]pyridine 5-oxide

To a solution of 7-bromo-2-(2-chloro-6-fluoro-phenyl)thiazolo[5,4-c]pyridine (2.0 mmol, 690 mg) in DCM (20 mL) was added mCPBA (5. 2 mmol, 890 mg). The mixture was stirred at room temperature for 5 hours. A solution of 1 M Na$_2$SO$_3$ (10 mL) was then added. The mixture was then stirred at room temperature for 1 hour. A solution of sat. NaHCO$_3$ was added. The layers were separated. The aqueous layer was extracted with DCM. Then the combined organics were dried (Na$_2$SO$_4$), filtered and concentrated to give the title compound as an off-white solid which was used in the next step without purification. LCMS (ESI) m/z 360.9 [M+H$^+$].

Step 4. 4,7-dibromo-2-(2-chloro-6-fluorophenyl)thiazolo[5,4-c]pyridine

To a suspension of 7-bromo-2-(2-chloro-6-fluoro-phenyl)-5-oxido-thiazolo[5,4-c]pyridin-5-ium (2.0 mmol, 720 mg) in 1,2-dichloroethane (30 mL) was added POBr$_3$ (8.0 mmol, 2.3 g). The mixture was heated at 70° C. for 3 hours. The mixture was cooled to room temperature, and sat. NaHCO$_3$ solution was added. The aqueous layer was extracted with DCM. The combined organics were dried (Na$_2$SO$_4$), filtered and concentrated. The crude product was purified by silica gel chromatography (0-15% EtOAc/hexane) to give the title compound as a white solid (600 mg, 71% yield). $^1$H NMR (400 MHz, CDCl$_3$) δ 8.60 (s, 1H), 7.49 (dd, J=14.2, 8.0 Hz, 1H), 7.39 (d, J=8.2 Hz, 1H), 7.19 (t, J=8.7 Hz, 1H). LCMS (ESI) m/z 422.9 [M+H$^+$].

Step 5: 7-bromo-2-(2-chloro-6-fluorophenyl)-N-(6-methylpyrimidin-4-yl)thiazolo[5,4-c]pyridin-4-amine The mixture of 4,7-dibromo-2-(2-chloro-6-fluoro-phenyl)thiazolo[5,4-c]pyridine (0.227 mmol; 96 mg), 6-methylpyrimidin-4-amine (0.34 mmol, 37 mg), Pd$_2$(dba)$_3$ (0.011 mmol, 10 mg), XantPhos (0.0227 mmol; 14 mg) and Cs$_2$CO$_3$ (0.4544 mmol, 148 mg) in 1,4-dioxane (3 mL) was heated at 75° C. under nitrogen in an oil bath for 4.5 hours. The reaction mixture was then cooled to room temperature, filtered through celite, washed with EtOAc. The filtrate was concentrated and the resulting crude product was purified by silica gel chromatography (30-100% EtOAc/hexane) to give the title compound as an off-white solid (80 mg, 78% yield). $^1$H NMR (400 MHz, DMSO-d$_6$) δ 10.76 (s, 1H), 8.64 (s, 1H), 8.59 (s, 1H), 7.77-7.68 (m, 1H), 7.62 (d, J=8.1 Hz, 1H), 7.56-7.48 (m, 2H), 2.39 (s, 3H). LCMS (Method B): RT=4.39 min, m/z 450.0 [M+H$^+$].

Example 152

2-(2-chloro-6-fluorophenyl)-4-(6-methylpyrimidin-4-ylamino)thiazolo[5,4-c]pyridine-7-carbonitrile

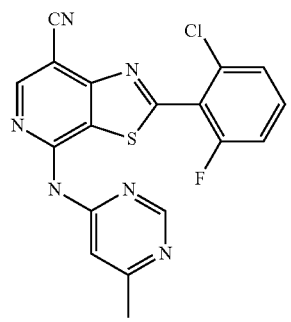

A mixture of 7-bromo-2-(2-chloro-6-fluoro-phenyl)-N-(6-methylpyrimidin-4-yl)thiazolo[5,4-c]pyridin-4-amine (0.15 mmol, 69 mg), Zn(CN)$_2$ (0.30 mmol, 36 mg), Pd$_2$(dba)$_3$ (0.015 mmol, 13.8 mg), and dppf (0.030 mmol, 16.5 mg) in a 10 mL microwave vial was purged with nitrogen for 5 min.

DMF (3 mL) and TMEDA (0.03 mmol; 3.6 mg) were added. The vial was sealed and heated at 140° C. in a microwave reactor for 20 min. The reaction mixture was filtered through celite, washed with EtOAc. Filtrate was concentrated to give a crude product which was purified by reverse phase HPLC to give the title compound as an off-white solid (5.7 mg, 9.6% yield). $^1$H NMR (400 MHz, DMSO-d$_6$) δ 11.33 (s, 1H), 8.89 (s, 1H), 8.74 (s, 1H), 7.75 (td, J=8.3, 6.2 Hz, 1H), 7.68 (s, 1H), 7.63 (d, J=8.2 Hz, 1H), 7.54 (t, J=8.9 Hz, 1H), 2.43 (s, 3H). LCMS (Method B): RT=4.33 min, m/z 397.1 [M+H$^+$].

Example 153

2-(2-cyano-6-fluorophenyl)-4-(6-methylpyrimidin-4-ylamino)thiazolo[5,4-c]pyridine-7-carbonitrile

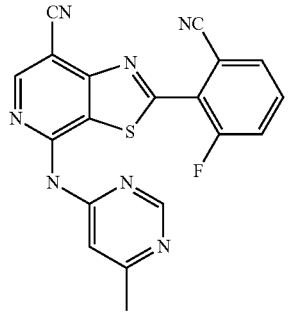 [SMILES: Cc1cc(Nc2ncc(C#N)c3nc(-c4c(F)cccc4C#N)sc23)ncn1]

The title compound was obtained from the purification of Example 151 as an off-white solid (9.9 mg, 17% yield). $^1$H NMR (400 MHz, DMSO-d$_6$) δ 8.83 (s, 1H), 8.71 (s, 1H), 8.05-8.00 (m, 1H), 7.92 (dt, J=13.0, 6.5 Hz, 2H), 7.70 (s, 1H), 6.54 (s, 1H), 2.42 (s, 3H). LCMS (Method B): RT=3.98 min, m/z 388.1 [M+H$^+$].

Example 154

(2-(2-chloro-6-fluorophenyl)-4-(6-methylpyrimidin-4-ylamino)thiazolo[5,4-c]pyridin-7-yl)methanol

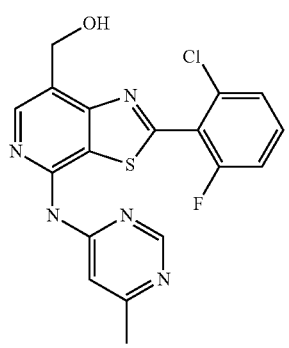 [SMILES: Cc1cc(Nc2ncc(CO)c3nc(-c4c(F)cccc4Cl)sc23)ncn1]

Step 1: 2-(2-chloro-6-fluorophenyl)-4-(6-methylpyrimidin-4-ylamino)thiazolo[5,4-c]pyridine-7-carbaldehyde To a solution of 2-(2-chloro-6-fluoro-phenyl)-4-[(6-methylpyrimidin-4-yl)amino]thiazolo[5,4-c]pyridine-7-carbonitrile (0.0500 mmol, 61.8 mg) in formic acid (2.25 mL) and water (0.75 mL) was added Al—Ni Alloy (130 mg). The mixture was heated at 100° C. for 4 hours. The mixture was then cooled to room temperature and filtered through celite, washed with 95% EtOH, concentrated via rotavap to give a yellow solid which was used in the next step without purification. LCMS (ESI) m/z 400.1 [M+H$^+$].

Step 2: (2-(2-chloro-6-fluorophenyl)-4-(6-methylpyrimidin-4-ylamino)thiazolo[5,4-c]pyridin-7-yl)methanol To a solution of 2-(2-chloro-6-fluoro-phenyl)-4-[(6-methylpyrimidin-4-yl)amino]thiazolo[5,4-c]pyridine-7-carbaldehyde (0.0500 mmol, 20.0 mg) in MeOH (2 mL) at 0° C. was added NaBH$_4$ (0.15 mmol, 6 mg). The mixture was stirred at room temperature for 2 hours. The reaction was then quenched with water, extracted with EtOAc and then DCM. The combined organics were dried (Na$_2$SO$_4$), filtered and concentrated to a yellow oil.

The resultant oil was dissolved in THF (2 mL) and MeOH (0.1 mL). A solution of 1 N NaOH (0.2 mL) was added. The mixture was stirred at room temperature for 1 hour. The mixture was then diluted with water, extracted with EtOAc. The combined organics were dried (Na$_2$SO$_4$), filtered and concentrated. The crude product was purified by reverse phase HPLC to give the title compound as a yellow solid (3.6 mg, 18% yield). $^1$H NMR (300 MHz, DMSO-d$_6$) δ 8.60 (s, 1H), 8.44 (s, 1H), 8.27 (s, 1H), 7.72 (dd, J=14.5, 8.1 Hz, 1H), 7.60 (d, J=8.1 Hz, 1H), 7.55-7.45 (m, 3H), 5.48 (t, J=5.3 Hz, 1H), 4.98 (d, J=4.8 Hz, 2H), 2.39 (s, 3H). LCMS (Method B): RT=3.78 min, m/z 402.1 [M+H$^+$].

Example 155 and 156

(1S,2S)—N-(2-(2,6-dichlorophenyl)thiazolo[5,4-c]pyridin-4-yl)-2-fluorocyclopropanecarboxamide and (1R,2R)—N-(2-(2,6-dichlorophenyl)thiazolo[5,4-c]pyridin-4-yl)-2-fluorocyclopropanecarboxamide

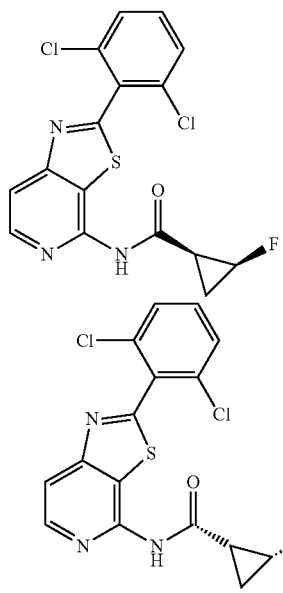

and

Step 1. 2-(2,6-Dichlorophenyl)thiazolo[5,4-c]pyridin-4-amine

To a microwave tube was added 4-bromo-2-(2,6-dichlorophenyl)thiazolo[5,4-c]pyridine (1.00 g, 2.80 mmol), diphenylmethanimine (607 mg., 3.40 mmol), Pd$_2$(dba)$_3$ (128 mg, 0.140 mmol), BINAP (174 mg, 0.280 mmol), sodium tert-butoxide (403 mg, 4.20 mmol), and toluene (15.0 mL). The mixture was degassed with nitrogen for 10 min. The resulting mixture was irradiated in a microwave reactor at 130° C. for 1 hour and then cooled to room temperature. The mixture was filtered through Celite and the filtrate was concentrated. The residue was purified by column chromatography eluting with ethyl acetate/petroleum ether (1:10 to 1:2) to give the desired product as a solid (320 mg, 38.7% yield). LCMS (ESI) m/z: 296 [M+H$^+$].

Step 2. (1S,2S)—N-(2-(2,6-dichlorophenyl)thiazolo[5,4-c]pyridin-4-yl)-2-fluorocyclopropanecarboxamide and (1R,2R)—N-(2-(2,6-dichlorophenyl)thiazolo[5,4-c]pyridin-4-yl)-2-fluorocyclopropanecarboxamide To a microwave tube was added 2-(2,6-dichlorophenyl)thiazolo[5,4-c]pyridin-4-amine (200 mg, 0.680 mmol), cis-2-fluorocyclopropanecarboxylic acid (106 mg., 1.02 mmol), HATU (517 mg, 1.36 mmol), DIPEA (263 mg, 1.36 mmol), and DMF (3 mL). The resulting mixture was irradiated in a microwave reactor at 120° C. for 4 hours and then cooled to room temperature. Water (10 mL) was added and the aqueous layer was extracted with ethyl acetate (3×10 mL). The combined organic layers were washed with brine (10 mL) and dried over anhydrous sodium sulfate. After concentration by rotavap, the residue was purified by silica gel column chromatography eluting with ethyl acetate/petroleum ether (1:10 to 1:2) to give a racemic mixture, which was purified by chiral HPLC (AD-H, SFC with MeOH as co-solvent) to give two desired products as following:

First eluting peak: 23.5 mg, 9.1% yield. >98% ee (3.66 min, AD-H, SFC with MeOH as co-solvent, 8 min) $^1$H NMR (500 MHz, MeOH-d$_4$): δ 8.44 (d, J=5.5 Hz, 1H), 7.86 (d, J=5 Hz, 1H), 7.62-7.55 (m, 3H), 4.99-4.83 (m, 1H), 2.21-2.17 (m, 1H), 1.86-1.78 (m, 1H), 1.28-1.23 (m, 1H). LCMS (Method A): RT=5.58 min, m/z: 382.0 [M+H$^+$].

Second eluting peak: 35 mg, 14% yield. >98% ee (5.04 min, AD-H, SFC with MeOH as co-solvent, 8 min). $^1$H NMR (500 MHz, MeOH-d$_4$): δ 8.45 (d, J=5.5 Hz, 1H), 7.87 (d, J=5.5 Hz, 1H), 7.63-7.56 (m, 3H), 5.00-4.84 (m, 1H), 2.22-2.16 (m, 1H), 1.87-1.79 (m, 1H), 1.28-1.22 (m, 1H). LCMS (Method B): RT=5.64 min, m/z: 382.1 [M+H$^+$].

Example 157 and 158

(1R,2S)—N-(2-(2,6-dichlorophenyl)thiazolo[5,4-c]pyridin-4-yl)-2-(hydroxymethyl)cyclopropanecarboxamide and (1S,2R)—N-(2-(2,6-dichlorophenyl)thiazolo[5,4-c]pyridin-4-yl)-2-(hydroxymethyl)cyclopropanecarboxamide

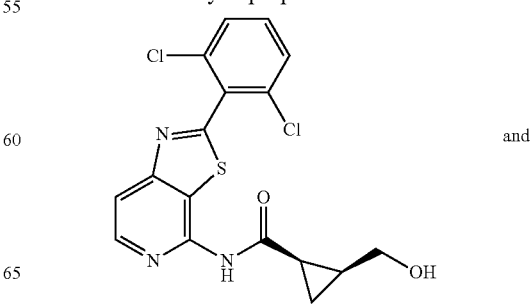

and

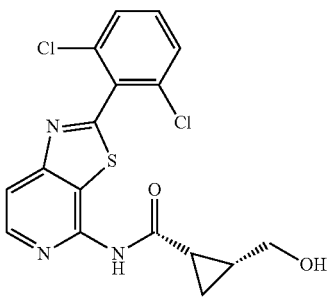

Step 1. 3-(2-(2,6-dichlorophenyl)thiazolo[5,4-c]pyridin-4-yl)-3-aza-bicyclo[3.1.0]hexane-2,4-dione A solution of 2-(2,6-dichlorophenyl)thiazolo[5,4-c]pyridin-4-amine (550 mg, 1.86 mmol) and 3-oxabicyclo[3.1.0]hexane-2,4-dione (835 mg, 7.46 mmol) in 1,4-dioxane (10 mL) was heated at 90° C. for 2 hours. The reaction mixture was then cooled to room temperature and concentrated. The residue was purified by column chromatography eluting with ethyl acetate/petroleum ether (1:10 to 1:2) to give the desired product as a solid. (570 mg, 78.8% yield). LCMS (ESI) m/z: 390.0 [M+H$^+$].

Step 2. (1R,2S)—N-(2-(2,6-dichlorophenyl)thiazolo[5,4-c]pyridin-4-yl)-2-(hydroxymethyl)cyclopropanecarboxamide and (1S,2R)—N-(2-(2,6-dichlorophenyl)thiazolo[5,4-c]pyridin-4-yl)-2-(hydroxymethyl)cyclopropanecarboxamide To a suspension of 3-(2-(2,6-dichlorophenyl)thiazolo[5,4-c]pyridin-4-yl)-3-aza-bicyclo[3.1.0]hexane-2,4-dione (570 mg, 1.46 mmol) in isopropanol (15 mL) and water (3.0 mL) was added NaBH$_4$ (278 mg, 7.32 mmol). The reaction mixture was stirred at room temperature for 1 hour. The volatile solvent was removed under reduced pressure. The residue was diluted with water, extracted with EtOAc (3×10 mL). The combined organics were dried (Na$_2$SO$_4$), filtered, and concentrated. The crude product was purified by column chromatography eluting with ethyl acetate/petroleum ether (1:5 to 1:2) to give a racemic mixture, which was purified by chiral HPLC (AD-H, SFC with MeOH as co-solvent) to give two desired products as following:

First eluting peak: 27.5 mg, 4.8% yield. >98% ee (3.46 min, AD-H, SFC with MeOH as co-solvent, 8 min) $^1$H NMR (500 MHz, DMSO-d$_6$): δ 8.42 (d, J=6.0 Hz, 1H), 7.83 (d, J=6.0 Hz, 1H), 7.62-7.56 (m, 3H), 3.86-3.83 (m, 1H), 3.74-3.69 (m, 1H), 2.15-2.10 (m, 1H), 1.69-1.66 (m, 1H), 1.18-1.15 (m, 2H). LCMS (Method A): RT=4.90 min, m/z: 394.0 [M+H$^+$].

Second eluting peak: 23.5 mg, 3.3% yield. >98% ee (5.06 min, AD-H, SFC with MeOH as co-solvent, 8 min) $^1$H NMR (500 MHz, DMSO-d$_6$): δ 8.42 (d, J=5.5 Hz, 1H), 7.83 (d, J=5 Hz, 1H), 7.62-7.56 (m, 3H), 3.86-3.83 (m, 1H), 3.74-3.69 (m, 1H), 2.15-2.10 (m, 1H), 1.69-1.66 (m, 1H), 1.18-1.15 (m, 2H). LCMS (Method A): RT=4.90 min, m/z: 394.0 [M+H$^+$].

Example 159

2-(4-amino-2-chloro-6-fluorophenyl)-N-(6-methylpyrimidin-4-yl)thiazolo[5,4-c]pyridin-4-amine

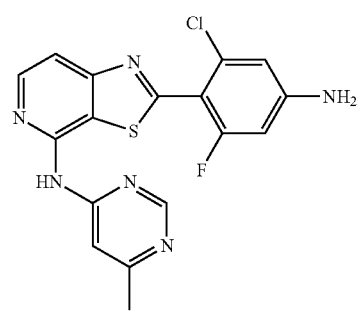 [SMILES: Cc1cc(Nc2nccc3nc(-c4c(F)cc(N)cc4Cl)sc23)ncn1]

Step 1: Dimethyl 2-chloro-6-fluoroterephthalate

An autoclave equipped with a stir bar was charged with 2,5-dibromo-1-chloro-3-fluorobenzene (5.0 g, 17.3 mmol), triethylamine (12.1 mL, 86.7 mmol), bis(diphenylphosphino)ferrocene)palladium(II) Chloride (0.86 mmol, 708 mg) and methanol (100 mL) was degassed with nitrogen for 10 min. Then the container was sealed and filled with CO to 400 psi. The reaction mixture was heated at 100° C. with stirring for 12 hours. The reaction mixture was filtered through Celite, washed with MeOH, and the filtrate was concentrated. The crude product was purified by silica gel chromatography (0-10% EtOAc/hexane) to afford the title compound as a colorless oil which solidified in high vacuum (3.06 g, 71% yield). $^1$H NMR (400 MHz, CDCl$_3$) δ 7.90 (s, 1H), 7.69 (dd, J=9.0, 1.2 Hz, 1H), 3.99 (s, 3H), 3.95 (s, 3H). LCMS (APCI+) 247.0 [M+H]$^+$.

Step 2: 3-Chloro-5-fluoro-4-(methoxycarbonyl)benzoic acid

To a solution of dimethyl 2-chloro-6-fluoroterephthalate (6.19 g, 25.1 mmol) in tetrahydrofuran (75 mL) was added a solution of 1 N NaOH (27.6 mmol, 27.6 mL). The reaction mixture was stirred at room temperature for 30 min. After the volatiles were removed under reduced pressure, water (30 mL) was added. The aqueous solution was acidified with 1 N HCl to pH 3.0. A white solid precipitated and was collected by filtration, washed with water and diethyl ether, dried in high vacuum to afford the title compound as a white solid (5.54 g, 95% yield). $^1$H NMR (400 MHz, CDCl$_3$) δ 7.96 (s, 1H), 7.76 (dd, J=8.8, 1.3 Hz, 1H), 4.01 (s, 3H). LCMS (APCI+) 233.0 [M+H]$^+$.

Step 3: Methyl 4-(tert-butoxycarbonylamino)-2-chloro-6-fluorobenzoate

To a solution of 3-chloro-5-fluoro-4-methoxycarbonylbenzoic acid (5.55 g, 23.84 mmol) in tert-butanol (48 mL) was added diphenyl phosphorylazide (7.22 g, 26.2 mmol) and triethylamine (2.65 g, 26.2 mmol). The mixture was heated at 85° C. for 20 hours, then concentrated via rotavap. The crude product was purified by silica gel chromatography (0-20%

EtOAc/hexane) to give the title compound. (6.53 g, 90.2% yield) as a colorless oil. $^1$H NMR (400 MHz, CD$_2$Cl$_2$) δ 7.32 (dd, J=11.7, 1.7 Hz, 1H), 7.28 (s, 1H), 7.05 (s, 1H), 3.95 (s, 3H), 1.54 (s, 9H). LCMS (ESI) m/z 304.0 [M+H$^+$].

Step 4: Methyl 4-amino-2-chloro-6-fluorobenzoate

To a solution of methyl 4-(tert-butoxycarbonylamino)-2-chloro-6-fluoro-benzoate (6.53 g, 21.5 mmol) in dichloromethane (40 mL) was added TFA (9.94 mL). The mixture was stirred at room temperature for 4 hours. The mixture was then concentrated. Water (30 mL) was added to the residue, and pH was adjusted 10 with 25% NaOH. The resulting suspension was extracted with EtOAc (3×). The combined organics were dried (Na$_2$SO$_4$), filtered and concentrated to give the title compound (4.41 g, quantitative yield) as an off-white solid. $^1$H NMR (400 MHz, CD$_2$Cl$_2$) δ 6.54 (s, 1H), 6.34 (dd, J=11.6, 2.1 Hz, 1H), 4.19 (s, 2H), 3.90 (s, 3H). LCMS (ESI) m/z 204.0 [M+H$^+$].

Step 5: Methyl 2-chloro-6-fluoro-4-iodobenzoate

Methyl 4-amino-2-chloro-6-fluoro-benzoate (3.74 g, 18.4 mmol) was added to conc. HCl (110 mL). The mixture was cooled to 0° C. A solution of NaNO$_2$ (2.53 g, 36.7 mmol) in water (7 mL) was added dropwise with vigorous stirring. After stirring at 0° C. for 1.5 hours, a solution of KI (15.2 g, 91.8 mmol) in water (18 mL)) was added dropwise. The mixture was warmed up to room temperature and stirred overnight. The mixture was then extracted with DCM (3×). The combined organics were washed with 10% Na$_2$S$_2$O$_3$ (50 mL), brine, dried (Na$_2$SO$_4$), filtered and concentrated. The crude product was purified by silica gel chromatography (0-10% EtOAc/hexane) to give the title compound (4.48 g, 77.6% yield) as a light yellow oil. $^1$H NMR (400 MHz, CD$_2$Cl$_2$) δ 7.69 (s, 1H), 7.52 (dd, J=8.3, 1.2 Hz, 1H), 3.97 (s, 3H). LCMS (ESI) m/z 314.8 [M+H$^+$].

Step 6: 2-Chloro-6-fluoro-4-iodobenzoic acid

To a solution of methyl 2-chloro-6-fluoro-4-iodo-benzoate (4.48 g, 14.2 mmol) in pyridine (28 mL) was added LiI (4.0 g, 29.9 mmol). The reaction mixture was heated at 115° C. for 4 hours. The solvent was removed under vacuum. The resultant solid was dissolved in water, and extracted with EtOAc. The aqueous layer was acidified with 1 N HCl to pH=4, extracted with EtOAc (3×30 mL). The combined organic phases were washed with 10% citric acid (2×30 mL), brine, dried (Na$_2$SO$_4$), filtered and concentrated to give the title compound (4.77 g, quantitative yield) as a yellow solid. $^1$H NMR (400 MHz, methanol-d$_4$) δ 7.73 (s, 1H), 7.62 (dd, J=8.4, 1.1 Hz, 1H). LCMS (ESI) m/z 300.8 [M+H$^+$].

Step 7: 2-Chloro-N-(2-chloro-3-fluoropyridin-4-yl)-6-fluoro-4-iodobenzamide

To a 250 ml RB flask was added 2-chloro-6-fluoro-4-iodo-benzoic acid (4.53 g, 15.1 mmol), followed by toluene (30 mL) and thionyl chloride (11 mL). The mixture was heated at 80° C. for 2 hours before being cooled to room temperature and concentrated to dryness. The crude product was azeotroped from anhydrous toluene twice (10 ml) and directly carried to the next step.
To a solution of 2-chloro-3-fluoro-pyridin-4-amine (3.31 g, 22.6 mmol) in THF (50 mL) at 0° C. was slowly added LiHMDS in THF (1.0 M, 45 mL). The mixture was warmed to room temperature and allowed to stir for 1 hour. It was then cooled to −78° C. A THF solution of 2-chloro-6-fluoro-4-iodo-benzoyl chloride (15.1 mmol, 15 mL) was added dropwise. The mixture was stirred at −78° C. for 1 hour. The reaction was then quenched with sat. NH$_4$Cl, extracted with EtOAc (3×). The combined organics were dried over Na$_2$SO$_4$, concentrated. The crude product was purified by silica gel column chromatography (0-25% EtOAc/hexane) to give the title compound (4.97 g, 76.8% yield) as an off-white solid. $^1$H NMR (400 MHz, methanol-d$_4$) δ 8.37 (t, J=5.4 Hz, 1H), 8.18 (d, J=5.5 Hz, 1H), 7.80 (s, 1H), 7.69 (dd, J=8.2, 1.2 Hz, 1H). LCMS (ESI) m/z 429.0 [M+H$^+$].

Step 8: 4-Chloro-2-(2-chloro-6-fluoro-4-iodophenyl)thiazolo[5,4-c]pyridine

The solution of 2-chloro-N-(2-chloro-3-fluoro-4-pyridyl)-6-fluoro-4-iodo-benzamide (2.4 g, 5.59 mmol) in thionyl chloride (40.6 mL) was heated at 90° C. for 5 days. The solvent was removed under reduced pressure, azeotroped with toluene twice to give an off-white solid which was directly used in the next step.
To the solid from last step was added isopropanol (20 mL), thiourea (1.72 g, 22.4 mmol) and pyridine (1.77 g, 22.4 mmol). The mixture was heated at 85° C. for 4 hours. Triethylamine (2.83 g, 28.0 mmol) was then added, and the mixture was heated at 85° C. for additional 4 hours. The mixture was concentrated. The residue was partitioned between DCM and water. The layers were separated and the aqueous layer was extracted with DCM two more times. The combined organics were dried (Na$_2$SO$_4$), filtered and concentrated. The crude product was purified by silica gel chromatography (0-15% EtOAc/hexane) to give the title compound (1.515 g, 63.7% yield) as a white solid. $^1$H NMR (400 MHz, CDCl$_3$) δ 8.51 (d, J=5.6 Hz, 1H), 7.98 (d, J=5.6 Hz, 1H), 7.79 (s, 1H), 7.59 (dd, J=8.3, 1.1 Hz, 1H). LCMS (ESI) m/z 425.0 [M+H$^+$].

Step 9: tert-Butyl 3-chloro-4-(4-chlorothiazolo[5,4-c]pyridin-2-yl)-5-fluorophenylcarbamate A mixture of 4-chloro-2-(2-chloro-6-fluoro-4-iodo-phenyl)thiazolo[5,4-c]pyridine (715 mg, 1.682 mmol), tert-butyl carbamate (394 mg, 3.365 mmol), Pd$_2$(dba)$_3$ (77 mg, 0.084 mmol), and XantPhos (97 mg, 0.168 mmol) in toluene (17 mL) and K$_3$PO$_4$ (2.65 mL, 1.27 M) was heated at 90° C. under nitrogen for 20 hours. The reaction mixture was diluted with water, extracted with EtOAc (2×). The combined organics were dried (Na$_2$SO$_4$), filtered and concentrated. The crude product was purified by silica gel flash chromatography (0-25% EtOAc/hexane) to give the title compound (550 mg, 78.9% yield) as an off-white solid. $^1$H NMR (400 MHz, CDCl$_3$) δ 8.48 (d, J=5.6 Hz, 1H), 7.95 (d, J=5.6 Hz, 1H), 7.46-7.33 (m, 2H), 6.70 (s, 1H), 1.55 (s, 9H). LCMS (ESI) m/z 414.1 [M+H$^+$].

Step 10: 2-(4-Amino-2-chloro-6-fluoro-phenyl)-N-(6-methylpyrimidin-4-yl)thiazolo[5,4-c]pyridin-4-amine A mixture of tert-butyl N-[3-chloro-4-(4-chlorothiazolo[5,4-c]pyridin-2-yl)-5-fluoro-phenyl]carbamate (56 mg, 0.135 mmol), 6-methylpyrimidin-4-amine (44 mg, 0.40 mmol), Pd$_2$(dba)$_3$ (6.2 mg, 0.00676 mmol), XantPhos (7.8 mg, 0.0135 mmol) and Cs$_2$CO$_3$ (88 mg, 0.27 mmol) in 1,4-Dioxane (2 mL) was heated at 150° C. in a microwave reactor for 20 min, The mixture was filtered through Celite, washed with EtOAc, concentrated. The crude product was purified by reverse phase HPLC to give the title compound (5.4 mg, 10% yield) as a yellow solid. $^1$H NMR (400 MHz, DMSO-$d_6$) δ 10.48 (s, 1H), 8.61 (s, 1H), 8.39 (d, J=5.6 Hz, 1H), 7.75 (d, J=5.6 Hz, 1H), 7.58 (s, 1H), 6.66 (s, 1H), 6.49 (dd, J=12.7, 2.0 Hz, 1H), 6.34 (s, 2H), 2.38 (s, 3H). LCMS (Method B): RT=3.43 min, m/z 387.0 [M+H$^+$].

Additional compounds shown in Table 2 were also made according to the above procedures.

TABLE 2

| Example | Structure | Name | Synth. Method | LCMS (ESI) m/z [M + H$^+$] | LCMS Method | R$_T$ (min) | NMR |
|---|---|---|---|---|---|---|---|
| 160 | 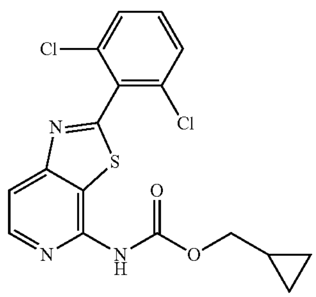 [SMILES: O=C(Nc1nccc2nc(-c3c(Cl)cccc3Cl)sc12)OCC1CC1] | Cyclopropylmethyl 2-(2,6-dichlorophenyl)thiazolo[5,4-c]pyridin-4-ylcarbamate | 2 | 394.1 | B | 6.67 | $^1$H-NMR (500 MHz, DMSO-$d_6$): δ 10.78 (br s, 1H), 8.43 (d, J = 5.5 Hz, 1H), 7.91 (d, J = 5.5 Hz, 1H), 7.74-7.65 (m, 3H), 4.00 (d, J = 7.5 Hz 2H), 1.23-1.17 (m, 1H), 0.56-0.54 (m, 2H), 0.34-0.33 (m, 2H). |
| 161 | 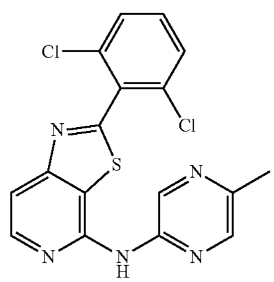 [SMILES: Cc1cnc(Nc2nccc3nc(-c4c(Cl)cccc4Cl)sc23)cn1] | 2-(2,6-Dichlorophenyl)-N-(5-methylpyrazin-2-yl)thiazolo[5,4-c]pyridin-4-amine | 2 | 388.1 | B | 6.11 | $^1$H-NMR (500 MHz, DMSO-$d_6$): δ 10.37 (br s, 1H), 9.10 (s, 1H), 8.36 (d, J = 6.0 Hz, 1H), 8.22 (s, 1H), 7.74-7.65 (m, 4H), 2.43 (s, 3H). |
| 162 | 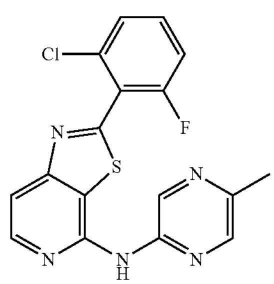 [SMILES: Cc1cnc(Nc2nccc3nc(-c4c(F)cccc4Cl)sc23)cn1] | 2-(2-Chloro-6-fluorophenyl)-N-(5-methylpyrazin-2-yl)thiazolo[5,4-c]pyridin-4-amine | 2 | 372.0 | A | 5.74 | $^1$H-NMR (500 MHz, DMSO-$d_6$): δ 10.38 (br s, 1H), 9.08 (d, J = 0.5 Hz, 1H), 8.36 (d, J = 5.5 Hz, 1H), 8.21 (s, 1H), 7.74-7.50 (m, 4H), 2.43 (s, 3H). |
| 163 | 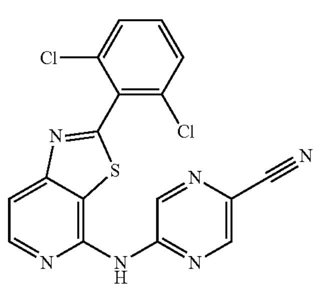 [SMILES: N#Cc1cnc(Nc2nccc3nc(-c4c(Cl)cccc4Cl)sc23)cn1] | 5-(2-(2,6-Dichlorophenyl)thiazolo[5,4-c]pyridin-4-ylamino)pyrazine-2-carbonitrile | 2 | 399.1 | B | 6.49 | $^1$H-NMR (500 MHz, DMSO-$d_6$): δ 11.35 (br s, 1H), 9.16 (s, 1H), 8.84 (s, 1H), 8.50 (d, J = 3.5 Hz, 1H), 7.92 (s, 1H), 7.75-7.67 (m, 3H). |

TABLE 2-continued

| Example | Structure | Name | Synth. Method | LCMS (ESI) m/z [M + H⁺] | LCMS Method | R$_T$ (min) | NMR |
|---|---|---|---|---|---|---|---|
| 164 | 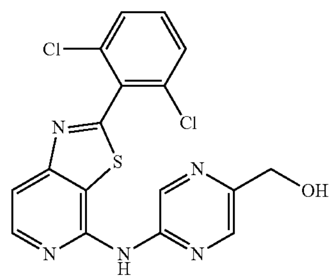 [SMILES: OCc1cnc(Nc2nccc3nc(-c4c(Cl)cccc4Cl)sc23)cn1] | (5-(2-(2,6-Dichlorophenyl)thiazolo[5,4-c]pyridin-4-ylamino)pyrazin-2-yl)methanol | 2 | 404.0 | B | 5.06 | ¹H-NMR (500 MHz, DMSO-d$_6$): δ 9.10 (s, 1H), 8.37 (d, J = 3.5 Hz, 1H), 8.34 (s, 1H), 7.74-7.67 (m, 4H), 4.57 (s, 2H). |
| 165 | 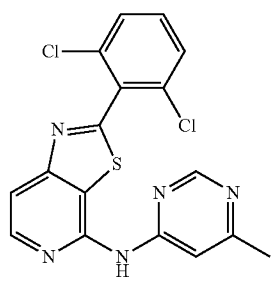 [SMILES: Cc1cc(Nc2nccc3nc(-c4c(Cl)cccc4Cl)sc23)ncn1] | 2-(2,6-Dichlorophenyl)-N-(6-methylpyrimidin-4-yl)thiazolo[5,4-c]pyridin-4-amine | 2 | 388.0 | B | 5.71 | ¹H-NMR (500 MHz, DMSO-d$_6$): δ 8.64 (s, 1H), 8.46 (d, J = 5.5 Hz, 1H), 7.84 (d, J = 5.5 Hz, 1H), 7.75-7.61 (m, 4H), 2.40 (s, 3H). |
| 166 | 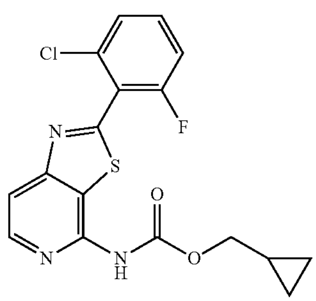 [SMILES: O=C(Nc1nccc2nc(-c3c(F)cccc3Cl)sc12)OCC1CC1] | Cyclopropylmethyl 2-(2-chloro-6-fluorophenyl)thiazolo[5,4-c]pyridin-4-ylcarbamate | 2 | 378.0 | B | 6.42 | ¹H-NMR (500 MHz, DMSO-d$_6$): δ 10.80 (br s, 1H), 8.44 (d, J = 5.5 Hz, 1H), 7.91 (d, J = 5.5 Hz, 1H), 7.72-7.50 (m, 3H), 4.00 (d, J = 7.5 Hz 2H), 1.23-1.16 (m, 1H), 0.56-0.53 (m, 2H), 0.34-0.33 (m, 2H). |
| 167 | 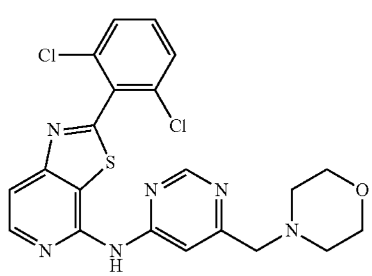 [SMILES: Clc1cccc(Cl)c1-c1nc2ccnc(Nc3cc(CN4CCOCC4)ncn3)c2s1] | 2-(2,6-Dichlorophenyl)-N-(6-(morpholinomethyl)pyrimidin-4-yl)thiazolo[5,4-c]pyridin-4-amine | 2 | 473.1 | B | 5.46 | ¹H-NMR (500 MHz, DMSO-d$_6$): δ 10.71 (br s, 1H), 8.66 (s, 1H), 8.45 (d, J = 5.0 Hz, 1H), 7.84-7.65 (m, 5H), 3.64-3.62 (m, 4H), 3.53 (s, 2H), 2.50-2.47 (m, 4H). |
| 168 | 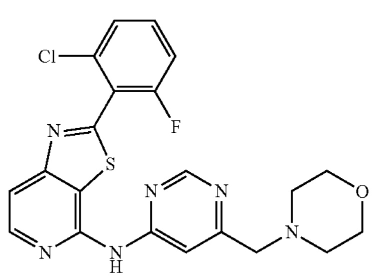 [SMILES: Fc1cccc(Cl)c1-c1nc2ccnc(Nc3cc(CN4CCOCC4)ncn3)c2s1] | 2-(2-Chloro-6-fluorophenyl)-N-(6-(morpholinomethyl)pyrimidin-4-yl)thiazolo[5,4-c]pyridin-4-amine | 2 | 457.1 | B | 5.22 | ¹H-NMR (500 MHz, DMSO-d$_6$): δ 10.72 (br s, 1H), 8.66 (s, 1H), 8.45 (d, J = 6.0 Hz, 1H), 7.85-7.51 (m, 5H), 3.64-3.62 (m, 4H), 3.53 (s, 2H), 2.50-2.47 (m, 4H). |

TABLE 2-continued

| Example | Structure | Name | Synth. Method | LCMS (ESI) m/z [M + H⁺] | LCMS Method | R_T (min) | NMR |
|---|---|---|---|---|---|---|---|
| 169 | 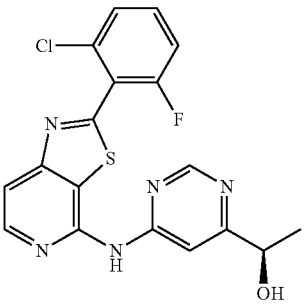 [SMILES: C[C@@H](O)c1cc(Nc2nccc3nc(-c4c(F)cccc4Cl)sc23)ncn1] | (R)-1-(6-(2-(2-Chloro-6-fluorophenyl)thiazolo[5,4-c]pyridin-4-ylamino)pyrimidin-4-yl)ethanol | 2 | 402.0 | A | 4.89 | ¹H-NMR (500 MHz, DMSO-d₆): δ 10.73 (br s, 1H), 8.65 (s, 1H), 8.47 (d, J = 5.5 Hz, 1H), 7.86-7.51 (m, 5H), 5.53 (d, J = 5.0 Hz, 1H), 4.60 (t, J = 5.5 Hz, 1H), 1.38 (t, J = 6.0 Hz, 3H). |
| 170 | 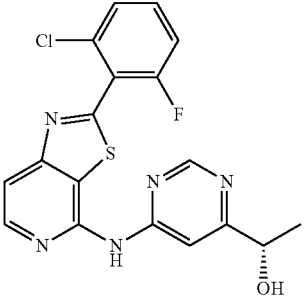 [SMILES: C[C@H](O)c1cc(Nc2nccc3nc(-c4c(F)cccc4Cl)sc23)ncn1] | (S)-1-(6-(2-(2-Chloro-6-fluorophenyl)thiazolo[5,4-c]pyridin-4-ylamino)pyrimidin-4-yl)ethanol | 2 | 402.0 | A | 4.89 | ¹H-NMR (500 MHz, DMSO-d₆): δ 10.73 (br s, 1H), 8.65 (s, 1H), 8.47 (d, J = 5.5 Hz, 1H), 7.86-7.51 (m, 5H), 5.53 (d, J = 5.0 Hz, 1H), 4.60 (t, J = 5.5 Hz, 1H), 1.37 (t, J = 6.0 Hz, 3H). |
| 171 | 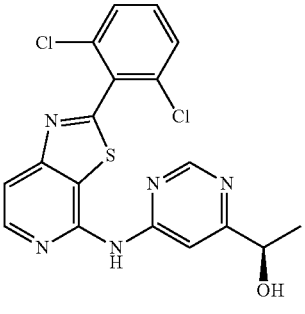 [SMILES: C[C@@H](O)c1cc(Nc2nccc3nc(-c4c(Cl)cccc4Cl)sc23)ncn1] | (R)-1-(6-(2-(2,6-Dichlorophenyl)thiazolo[5,4-c]pyridin-4-ylamino)pyrimidin-4-yl)ethanol | 2 | 418.0 | A | 5.11 | ¹H-NMR (500 MHz, DMSO-d₆): δ 10.73 (br s, 1H), 8.65 (s, 1H), 8.46 (d, J = 6.0 Hz, 1H), 7.86-7.66 (m, 5H), 5.53 (d, J = 4.5 Hz, 1H), 4.60 (t, J = 5.5 Hz, 1H), 1.37 (d, J = 6.5 Hz, 3H). |
| 172 | 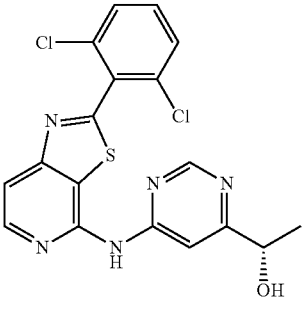 [SMILES: C[C@H](O)c1cc(Nc2nccc3nc(-c4c(Cl)cccc4Cl)sc23)ncn1] | (S)-1-(6-(2-(2,6-Dichlorophenyl)thiazolo[5,4-c]pyridin-4-ylamino)pyrimidin-4-yl)ethanol | 2 | 418.0 | A | 5.11 | ¹H-NMR (500 MHz, DMSO-d₆): δ 10.73 (br s, 1H), 8.65 (s, 1H), 8.46 (d, J = 6.0 Hz, 1H), 7.86-7.66 (m, 5H), 5.53 (d, J = 4.5 Hz, 1H), 4.60 (t, J = 5.5 Hz, 1H), 1.37 (d, J = 6.5 Hz, 3H). |
| 173 | 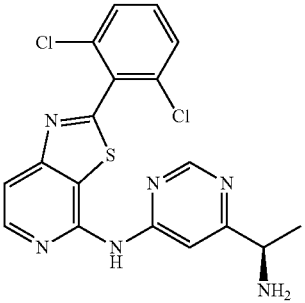 [SMILES: C[C@@H](N)c1cc(Nc2nccc3nc(-c4c(Cl)cccc4Cl)sc23)ncn1] | (R)-N-(6-(1-Aminoethyl)pyrimidin-4-yl)-2-(2,6-dichlorophenyl)thiazolo[5,4-c]pyridin-4-amine | 2 | 417.0 | A | 4.95 | ¹H-NMR (500 MHz, DMSO-d₆): δ 10.69 (br s, 1H), 8.66 (d, J = 1 Hz, 1H), 8.45 (d, J = 5.0 Hz, 1H), 7.84-7.65 (m, 4H), 3.90-3.87 (m, 1H), 1.29 (d, J = 6.5 Hz, 3H). |

TABLE 2-continued

| Example | Structure | Name | Synth. Method | LCMS (ESI) m/z [M + H⁺] | LCMS Method | R$_T$ (min) | NMR |
|---|---|---|---|---|---|---|---|
| 174 | 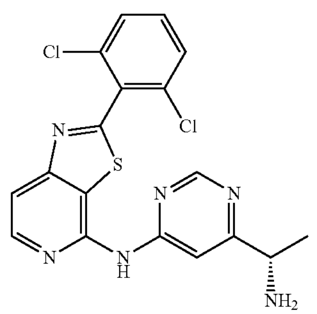 [SMILES: C[C@H](N)c1cc(Nc2nccc3nc(-c4c(Cl)cccc4Cl)sc23)ncn1] | (S)-N-(6-(1-Aminoethyl)pyrimidin-4-yl)-2-(2,6-dichlorophenyl)thiazolo[5,4-c]pyridin-4-amine | 2 | 417.0 | A | 4.95 | $^1$H-NMR (500 MHz, DMSO-d$_6$): δ 10.76 (br s, 1H), 8.66 (d, J = 1 Hz, 1H), 8.45 (d, J = 5.0 Hz, 1H), 7.84-7.65 (m, 4H), 3.90-3.86 (m, 1H), 1.28 (d, J = 6.5 Hz, 3H). |
| 175 | 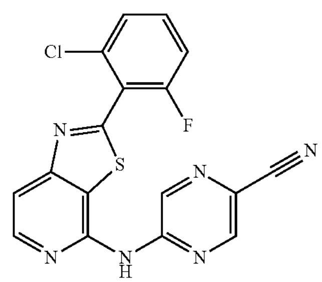 [SMILES: N#Cc1cnc(Nc2nccc3nc(-c4c(F)cccc4Cl)sc23)cn1] | 5-(2-(2-Chloro-6-fluorophenyl)thiazolo[5,4-c]pyridin-4-ylamino)pyrazine-2-carbonitrile | 2 | 383.0 | A | 5.98 | $^1$H NMR (500 MHz, DMSO-d$_6$): δ 9.10 (s, 1H), 8.83 (s, 1H), 8.47 (d, J = 5.5 Hz, 1H), 7.90 (d, J = 5.5 Hz, 1H), 7.75-7.70 (m, 3H). |
| 176 | 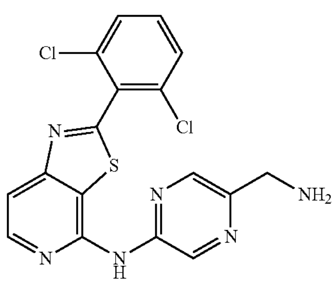 [SMILES: NCc1cnc(Nc2nccc3nc(-c4c(Cl)cccc4Cl)sc23)cn1] | N-(5-(Aminomethyl)pyrazin-2-yl)-2-(2,6-dichlorophenyl)thiazolo[5,4-c]pyridin-4-amine | 2 | 403.0 | A | 4.96 | $^1$H NMR (500 MHz, DMSO-d$_6$): δ 9.13 (br s, 1H), 8.39-8.37 (m, 2H), 7.75-7.66 (m, 5H), 3.94 (s, 2H), 3.50 (br s, 2H). |
| 177 | 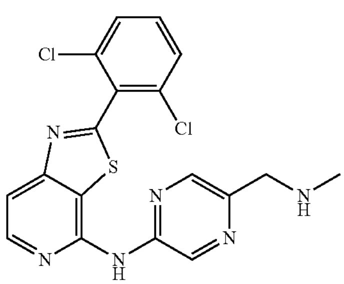 [SMILES: CNCc1cnc(Nc2nccc3nc(-c4c(Cl)cccc4Cl)sc23)cn1] | 2-(2,6-Dichlorophenyl)-N-(5-((methylamino)methyl)pyrazin-2-yl)thiazolo[5,4-c]pyridin-4-amine | 2 | 417.1 | B | 4.79 | $^1$H NMR (500 MHz, DMSO-d$_6$): δ 10.47 (br s, 1H), 9.12 (s, 1H), 8.36 (d, J = 5.5 Hz, 1H), 8.31 (s, 1H), 7.75-7.73 (m, 3H), 7.69-7.66 (m, 1H), 3.73 (s, 2H), 2.31 (s, 3H). |
| 178 | 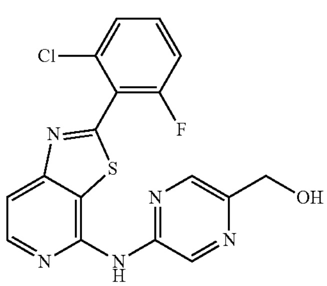 [SMILES: OCc1cnc(Nc2nccc3nc(-c4c(F)cccc4Cl)sc23)cn1] | (5-(2-(2-Chloro-6-fluorophenyl)thiazolo[5,4-c]pyridin-4-ylamino)pyrazin-2-yl)methanol | 2 | 388.0 | B | 4.84 | $^1$H NMR (500 MHz, DMSO-d$_6$): δ 10.48 (br s, 1H), 9.10 (s, 1H), 8.37 (d, J = 5.5 Hz, 1H), 8.34 (s, 1H), 7.75-7.69 (m, 2H), 7.62-7.50 (m, 2H), 5.43 (t, J = 6.0 Hz, 1H), 4.57 (d, J = 6.0 Hz, 2H). |

TABLE 2-continued

| Example | Structure | Name | Synth. Method | LCMS (ESI) m/z [M + H⁺] | LCMS Method | R_T (min) | NMR |
|---|---|---|---|---|---|---|---|
| 179 | 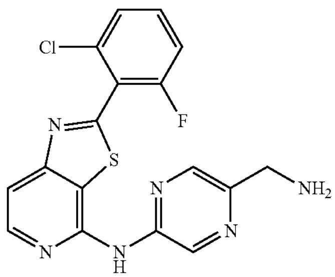 [SMILES: NCc1cnc(Nc2nccc3nc(-c4c(F)cccc4Cl)sc23)cn1] | N-(5-(Aminomethyl)pyrazin-2-yl)-2-(2-chloro-6-fluorophenyl)thiazolo[5,4-c]pyridin-4-amine | 2 | 386.9 | B | 4.51 | $^1$H NMR (500 MHz, DMSO-d$_6$): δ 9.10 (m, 1H), 8.36-8.23 (m, 2H), 7.74-7.51 (m, 4H), 4.23 (d, J = 5.5 Hz, 1H), 3.82 (s, 2H). |
| 180 | 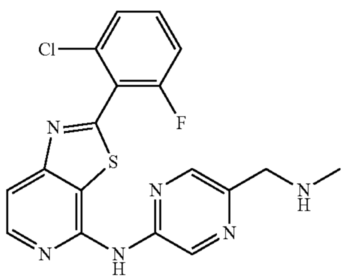 [SMILES: CNCc1cnc(Nc2nccc3nc(-c4c(F)cccc4Cl)sc23)cn1] | 2-(2-Chloro-6-fluorophenyl)-N-(5-((methylamino)methyl)pyrazin-2-yl)thiazolo[5,4-c]pyridin-4-amine | 2 | 401.1 | A | 5.13 | $^1$H NMR (500 MHz, DMSO-d$_6$): δ 10.48 (br s, 1H), 9.11 (s, 1H), 8.37 (d, J = 5.0 Hz, 1H), 8.32 (s, 1H), 7.74-7.69 (m, 2H), 7.61 (d, J = 8.0 Hz, 1H), 7.53 (t, J = 8.5 Hz, 1H), 3.75 (s, 2H), 2.32 (s, 3H). |
| 181 | 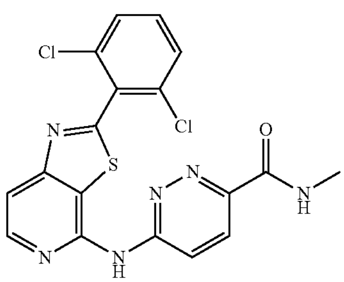 [SMILES: CNC(=O)c1ccc(Nc2nccc3nc(-c4c(Cl)cccc4Cl)sc23)nn1] | 6-(2-(2,6-Dichlorophenyl)thiazolo[5,4-c]pyridin-4-ylamino)-N-methylpyridazine-3-carboxamide | 2 | 431.0 | A | 5.40 | $^1$H NMR (500 MHz, DMSO-d$_6$): δ 11.06 (s, 1H), 8.92 (d, J = 5.5 Hz, 1H), 8.41 (d, J = 7.0 Hz, 1H), 8.18 (d, J = 11.5 Hz, 1H), 8.10 (d, J = 11.5 Hz, 1H), 7.83-7.45 (m, 4H), 2.83 (d, J = 6.0 Hz, 3H). |
| 182 | 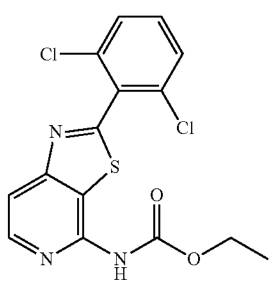 [SMILES: CCOC(=O)Nc1nccc2nc(-c3c(Cl)cccc3Cl)sc12] | Ethyl 2-(2,6-dichlorophenyl)thiazolo[5,4-c]pyridin-4-ylcarbamate | 2 | 368.0 | B | 6.16 | $^1$H NMR (500 MHz, DMSO-d$_6$): δ 10.74 (br s, 1H), 8.43 (d, J = 5.5 Hz, 1H), 7.91 (d, J = 6.0 Hz, 1H), 7.74-7.72 (m, 2H), 7.68-7.64 (m, 1H), 4.21-4.16 (m, 2H), 1.27 (t, J = 7.0 Hz, 3H). |
| 183 | 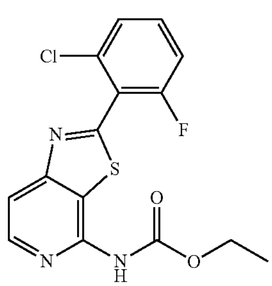 [SMILES: CCOC(=O)Nc1nccc2nc(-c3c(F)cccc3Cl)sc12] | Ethyl 2-(2-chloro-6-fluorophenyl)thiazolo[5,4-c]pyridin-4-ylcarbamate | 2 | 352.0 | B | 5.89 | $^1$H NMR (500 MHz, DMSO-d$_6$): δ 10.75 (br s, 1H), 8.44 (d, J = 5.5 Hz, 1H), 7.92 (d, J = 5.5 Hz, 1H), 7.74-7.69 (m, 1H), 7.61 (d, J = 8.5 Hz, 1H), 7.54-7.50 (m, 1H), 4.22-4.18 (m, 2H), 1.27 (t, J = 7.5 Hz, 3H). |

TABLE 2-continued

| Example | Structure | Name | Synth. Method | LCMS (ESI) m/z [M + H+] | LCMS Method | R$_T$ (min) | NMR |
|---|---|---|---|---|---|---|---|
| 184 | 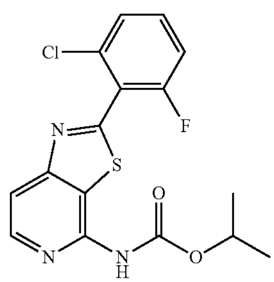 [SMILES: CC(C)OC(=O)Nc1nccc2nc(-c3c(F)cccc3Cl)sc12] | Isopropyl 2-(2-chloro-6-fluorophenyl)thiazolo[5,4-c]pyridin-4-ylcarbamate | 2 | 366.0 | B | 6.34 | $^1$H NMR (500 MHz, DMSO-d$_6$): δ 10.67 (s, 1H), 8.43 (d, J = 5.5 Hz, 1H), 7.91 (d, J = 6.0 Hz, 1H), 7.74-7.69 (m, 1H), 7.61 (d, J = 8.5 Hz, 1H), 7.54-7.50 (m, 1H), 4.97-4.91 (m, 1H), 1.29 (d, J = 6.0 Hz, 6H). |
| 185 | 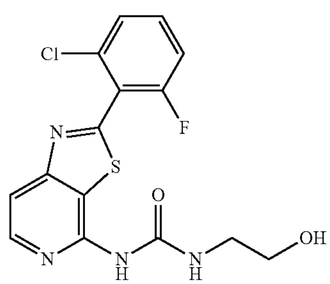 [SMILES: O=C(NCCO)Nc1nccc2nc(-c3c(F)cccc3Cl)sc12] | 1-(2-(2-Chloro-6-fluorophenyl)thiazolo[5,4-c]pyridin-4-yl)-3-(2-hydroxyethyl)urea | 2 | 367.1 | B | 4.54 | $^1$H NMR (500 MHz, DMSO-d$_6$): δ 9.76 (br s, 1H), 8.31 (d, J = 5.5 Hz, 1H), 8.01 (br s, 1H), 7.74-7.68 (m, 2H), 7.60 (d, J = 8.0 Hz, 1H), 7.51 (t, J = 9.0 Hz, 1H), 4.81 (br s, 1H), 3.52-3.48 (m, 2H), 3.28-3.24 (m, 2H). |
| 186 | 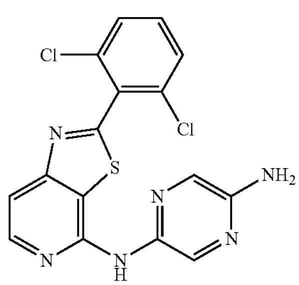 [SMILES: Nc1cnc(Nc2nccc3nc(-c4c(Cl)cccc4Cl)sc23)cn1] | N$^2$-(2-(2,6-Dichlorophenyl)thiazolo[5,4-c]pyridin-4-yl)pyrazine-2,5-diamine | 2 | 389.0 | B | 1.90 | $^1$H NMR (500 MHz, DMSO-d$_6$): δ 9.62 (s, 1H), 8.48 (d, J = 1.5 Hz, 1H), 8.21 (d, J = 6.0 Hz, 1H), 7.73-7.65 (m, 4H), 7.52 (d, J = 5.0 Hz, 1H), 6.14 (s, 2H). |
| 187 | 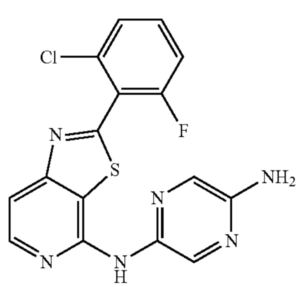 [SMILES: Nc1cnc(Nc2nccc3nc(-c4c(F)cccc4Cl)sc23)cn1] | N$^2$-(2-(2-Chloro-6-fluorophenyl)thiazolo[5,4-c]pyridin-4-yl)pyrazine-2,5-diamine | 2 | 373.1 | B | 4.78 | $^1$H NMR (500 MHz, DMSO-d$_6$): δ 9.63 (br s, 1H), 8.47 (d, J = 1.0 Hz, 1H), 8.21 (d, J = 5.5 Hz, 1H), 7.71-7.70 (m, 2H), 7.59 (d, J = 8.0 Hz, 1H), 7.53-7.50 (m, 2H), 6.14 (s, 2H). |
| 188 | 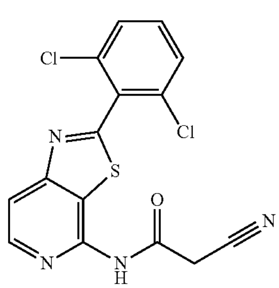 [SMILES: N#CCC(=O)Nc1nccc2nc(-c3c(Cl)cccc3Cl)sc12] | 2-Cyano-N-(2-(2,6-dichlorophenyl)thiazolo[5,4-c]pyridin-4-yl)acetamide | 2 | 363.0 | B | 5.19 | $^1$H NMR (500 MHz, DMSO-d$_6$): δ 9.63 (br s, 1H), 8.49 (d, J = 6.0 Hz, 1H), 7.99 (d, J = 5.5 Hz, 1H), 7.75-7.66 (m, 3H), 4.12 (s, 2H). |

TABLE 2-continued

| Example | Structure | Name | Synth. Method | LCMS (ESI) m/z [M + H⁺] | LCMS Method | R$_T$ (min) | NMR |
|---|---|---|---|---|---|---|---|
| 189 | 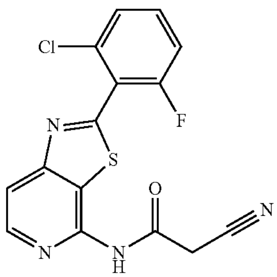 [SMILES: N#CCC(=O)Nc1nccc2nc(-c3c(F)cccc3Cl)sc12] | N-(2-(2-Chloro-6-fluorophenyl)thiazolo[5,4-c]pyridin-4-yl)-2-cyanoacetamide | 2 | 347.1 | B | 4.94 | $^1$H NMR (500 MHz, DMSO-d$_6$): δ 11.48 (br s, 1H), 8.49 (d, J = 5.5 Hz, 1H), 8.00 (d, J = 6.0 Hz, 1H), 7.73-7.50 (m, 3H), 4.12 (s, 2H). |
| 190 | 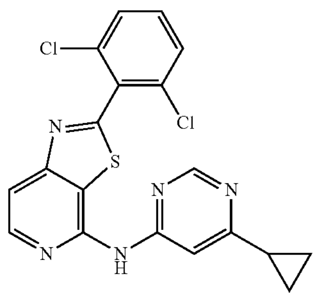 [SMILES: Clc1cccc(Cl)c1-c1nc2ccnc(Nc3cc(C4CC4)ncn3)c2s1] | N-(6-Cyclopropylpyrimidin-4-yl)-2-(2,6-dichlorophenyl)thiazolo[5,4-c]pyridin-4-amine | 2 | 414.1 | B | 6.64 | $^1$H NMR (500 MHz, DMSO-d$_6$): δ 8.56 (s, 1H), 8.45 (d, J = 5.5 Hz, 1H), 7.83-7.65 (m, 5H), 2.03 (t, J = 6.5 Hz, 1H), 1.00 (d, J = 6.5 Hz, 4H). |
| 191 | 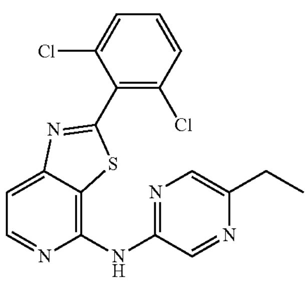 [SMILES: CCc1cnc(Nc2nccc3nc(-c4c(Cl)cccc4Cl)sc23)cn1] | 2-(2,6-Dichlorophenyl)-N-(5-ethylpyrazin-2-yl)thiazolo[5,4-c]pyridin-4-amine | 2 | 402.1 | B | 6.64 | $^1$H NMR (500 MHz, DMSO-d$_6$): δ 10.40 (s, 1H), 9.10 (s, 1H), 8.35 (d, J = 6.0 Hz, 1H), 8.23 (s, 1H), 7.74-7.66 (m, 4H), 2.76-2.71 (m, 2H), 1.24 (t, J = 8.0 Hz, 3H). |
| 192 | 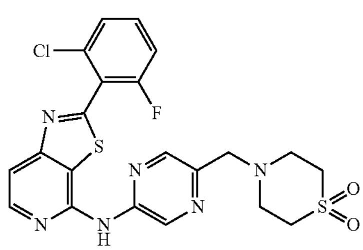 [SMILES: O=S1(=O)CCN(Cc2cnc(Nc3nccc4nc(-c5c(F)cccc5Cl)sc34)cn2)CC1] | 4-[(5-{[2-(2-Chloro-6-fluorophenyl)-[1,3]thiazolo[5,4-c]pyridin-4-yl]amino}pyrazin-2-yl)methyl]-1λ$^6$,4-thiomorpholine-1,1-dione | 2 | 504.9 | B | 5.20 | 1H-NMR (500 MHz, DMSO-d$_6$): δ 9.12 (s, 1H), 8.38-8.36 (m, 2H), 7.76-7.53 (m, 4H), 6.31 (s, 1H), 3.79 (s, 2H), 3.13-3.12 (m, 4H), 2.97-2.95 (m, 4H). |
| 193 | 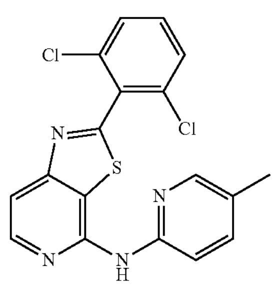 [SMILES: Cc1ccc(Nc2nccc3nc(-c4c(Cl)cccc4Cl)sc23)nc1] | 2-(2,6-Dichlorophenyl)-N-(5-methylpyridin-2-yl)thiazolo[5,4-c]pyridin-4-amine | 2 | 388.7 | B | 6.96 | $^1$H-NMR (500 MHz, DMSO-d$_6$): δ 10.08 (br s, 1H), 8.31 (d, J = 5.0 Hz, 1H), 8.10 (s, 1H), 7.74-7.59 (m, 6H), 2.24 (s, 3H). |

TABLE 2-continued

| Example | Structure | Name | Synth. Method | LCMS (ESI) m/z [M + H+] | LCMS Method | R$_T$ (min) | NMR |
|---|---|---|---|---|---|---|---|
| 194 | 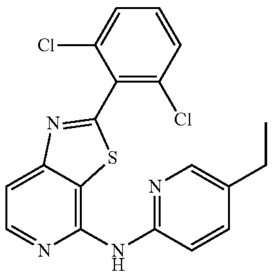 [SMILES: CCc1ccc(Nc2nccc3nc(-c4c(Cl)cccc4Cl)sc23)nc1] | 2-(2,6-Dichlorophenyl)-N-(5-ethylpyridin-2-yl)thiazolo[5,4-c]pyridin-4-amine | 2 | 401.7 | B | 7.40 | $^1$H-NMR (500 MHz, DMSO-d$_6$): δ 10.10 (br s, 1H), 8.31 (d, J = 5.5 Hz, 1H), 8.11 (s, 1H), 7.73-7.60 (m, 6H), 2.58-2.54 (m, 2H), 1.18 (t, J = 7.5 Hz, 3H). |
| 195 | 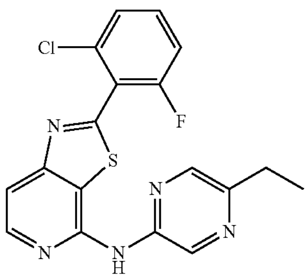 [SMILES: CCc1cnc(Nc2nccc3nc(-c4c(F)cccc4Cl)sc23)cn1] | 2-(2-Chloro-6-fluorophenyl)-N-(5-ethylpyrazin-2-yl)thiazolo[5,4-c]pyridin-4-amine | 2 | 386.1 | B | 6.42 | $^1$H-NMR (500 MHz, DMSO-d$_6$): δ 10.40 (br s, 1H), 9.09 (s, 1H), 8.45-8.35 (m, 1H), 8.22 (s, 1H), 7.74-7.50 (m, 4H), 2.76-2.63 (m, 2H), 1.24 (t, J = 7.5 Hz, 3H). |
| 196 | 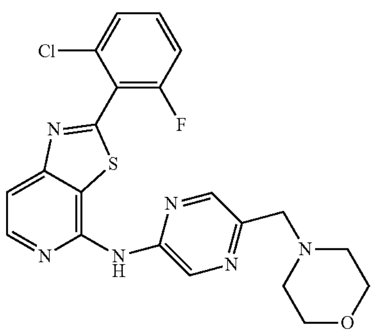 [SMILES: Fc1cccc(Cl)c1-c1nc2ccnc(Nc3cnc(CN4CCOCC4)cn3)c2s1] | 2-(2-Chloro-6-fluorophenyl)-N-(5-(morpholinomethyl)pyrazin-2-yl)thiazolo[5,4-c]pyridin-4-amine | 2 | 457.1 | A | 5.43 | $^1$H-NMR (500 MHz, DMSO-d$_6$): δ 9.09 (s, 1H), 8.25 (br, 2H), 7.71-7.50 (m, 4H), 3.60-3.53 (m, 6H), 2.45-2.36 (m, 4H). |
| 197 | 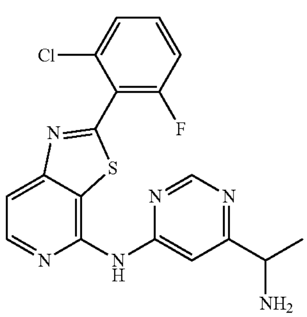 [SMILES: CC(N)c1cc(Nc2nccc3nc(-c4c(F)cccc4Cl)sc23)ncn1] | N-(6-(1-Aminoethyl)pyrimidin-4-yl)-2-(2-chloro-6-fluorophenyl)thiazolo[5,4-c]pyridin-4-amine | 2 | 401.1 | B | 4.63 | $^1$H-NMR (500 MHz, MeOD-d$_4$): δ 8.70 (s, 1H), 8.48 (d, J = 5.5 Hz, 1H), 7.87 (s, 1H), 7.81 (d, J = 5.5 Hz, 1H), 7.68-7.63 (m, 1H), 7.53 (d, J = 8 Hz, 1H), 7.39-7.36 (m, 1H), 4.08-4.03 (m, 1H), 1.47 (d, J = 6.5 Hz, 3H). |
| 198 | 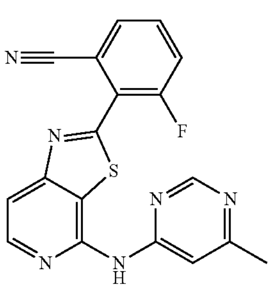 [SMILES: Cc1cc(Nc2nccc3nc(-c4c(F)cccc4C#N)sc23)ncn1] | 3-Fluoro-2-(4-(6-methylpyrimidin-4-ylamino)thiazolo[5,4-c]pyridin-2-yl)benzonitrile | 2 | 363.2 | B | 4.88 | $^1$H-NMR (500 MHz, DMSO-d$_6$): δ 10.70 (br s, 1H), 8.63 (s, 1H), 8.46 (d, J = 5.5 Hz, 1H), 8.02 (d, J = 7.0 Hz, 1H) 7.94-7.83 (m, 3H), 7.60 (s, 1H), 2.40 (s, 3H). |

TABLE 2-continued

| Example | Structure | Name | Synth. Method | LCMS (ESI) m/z [M + H+] | LCMS Method | R$_T$ (min) | NMR |
|---|---|---|---|---|---|---|---|
| 199 | 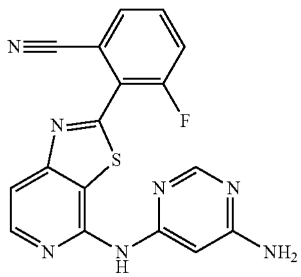 [SMILES: N#Cc1cccc(F)c1-c1nc2ccnc(Nc3cc(N)ncn3)c2s1] | 2-(4-(6-Aminopyrimidin-4-ylamino)thiazolo[5,4-c]pyridin-2-yl)-3-fluorobenzonitrile | 2 | 364.1 | B | 4.24 | $^1$H-NMR (500 MHz, DMSO-d$_6$): δ 10.15 (br s, 1H), 8.39 (d, J = 5.5 Hz, 1H), 8.12 (s, 1H), 8.02-7.87 (m, 3H), 7.75 (d, J = 5.5 Hz 1H), 6.82 (s, 1H), 6.67 (br s, 2H). |
| 200 | 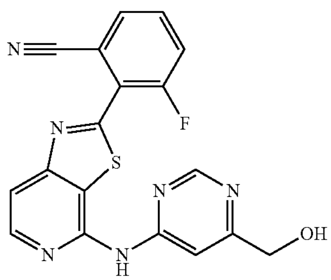 [SMILES: N#Cc1cccc(F)c1-c1nc2ccnc(Nc3cc(CO)ncn3)c2s1] | 3-Fluoro-2-(4-(6-(hydroxymethyl)pyrimidin-4-ylamino)thiazolo[5,4-c]pyridin-2-yl)benzonitrile | 2 | 379.1 | B | 4.22 | $^1$H-NMR (500 MHz, DMSO-d$_6$): δ 8.63 (s, 1H), 8.47 (d, J = 5.5 Hz, 1H), 8.02 (d, J =7.0 Hz, 1H), 7.93-7.86 (m, 3H), 7.77 (s, 1H), 5.58 (m, 1H), 4.49 (d, J = 5.5 Hz, 2H). |
| 201 | 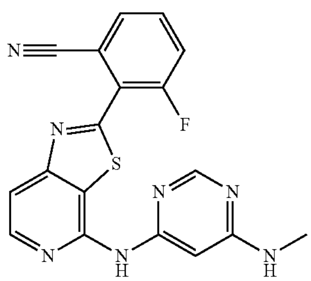 [SMILES: CNc1cc(Nc2nccc3nc(-c4c(F)cccc4C#N)sc23)ncn1] | 3-Fluoro-2-(4-(6-(methylamino)pyrimidin-4-ylamino)thiazolo[5,4-c]pyridin-2-yl)benzonitrile | 2 | 378.1 | B | 4.85 | $^1$H-NMR (500 MHz, DMSO-d$_6$): δ 10.15 (br s, 1H), 8.39 (d, J = 5.5 Hz, 1H), 8.19 (s, 1H), 8.01 (d, J = 7.5 Hz, 1H), 7.93-7.88 (m, 2H), 7.75 (d, J = 6.0 Hz 1H), 7.19 (br s, 1H), 6.84 (br s, 1H), 2.80 (d, J = 4.5 Hz, 3H) |
| 202 | 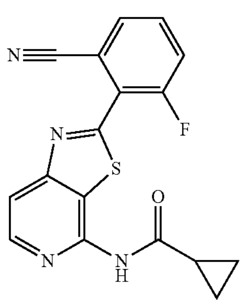 [SMILES: N#Cc1cccc(F)c1-c1nc2ccnc(NC(=O)C3CC3)c2s1] | N-(2-(2-Cyano-6-fluorophenyl)thiazolo[5,4-c]pyridin-4-yl)cyclopropanecarboxamide | 2 | 339.1 | B | 5.13 | $^1$H-NMR (500 MHz, DMSO-d$_6$): δ 11.45 (br s 1H), 8.47 (d, J = 6.0 Hz, 1H), 8.01-7.87 (m, 4H), 2.11-2.08 (m, 1H), 0.93-0.91 (m, 4H). |
| 203 | 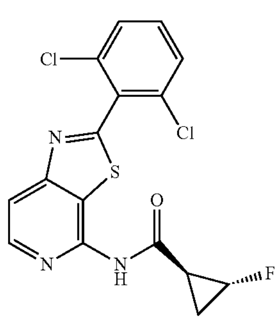 [SMILES: O=C(Nc1nccc2nc(-c3c(Cl)cccc3Cl)sc12)[C@@H]1C[C@H]1F] | (1S,2R)-N-(2-(2,6-Dichlorophenyl)thiazolo[5,4-c]pyridin-4-yl)-2-fluorocyclopropanecarboxamide | 2 | 382.0 | B | 6.08 | $^1$H-NMR (500 MHz, MeOH-d$_4$): δ 8.34 (d, J = 5.5 Hz, 1H), 7.76 (d, J = 6.0 Hz, 1H), 7.52-7.46 (m, 3H), 4.87-4.72 (m, 1H), 2.40-2.33 (m, 1H), 1.49-1.45 (m, 1H), 1.33-1.29 (m, 1H). |

TABLE 2-continued

| Example | Structure | Name | Synth. Method | LCMS (ESI) m/z [M + H⁺] | LCMS Method | R$_T$ (min) | NMR |
|---|---|---|---|---|---|---|---|
| 204 | 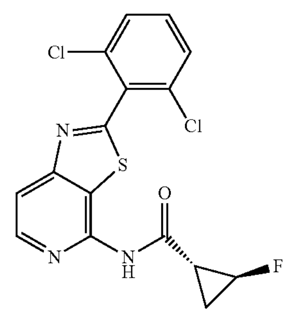 [SMILES: O=C(Nc1nccc2nc(-c3c(Cl)cccc3Cl)sc12)[C@H]1C[C@@H]1F] | (1R,2S)-N-(2-(2,6-Dichlorophenyl)thiazolo[5,4-c]pyridin-4-yl)-2-fluorocyclopropane carboxamide | 2 | 382.0 | B | 6.08 | ¹H-NMR (500 MHz, MeOH-d$_4$): δ 8.46 (d, J = 6.0 Hz, 1H), 7.87 (d, J = 5.5 Hz, 1H), 7.64-7.57 (m, 3H), 4.99-4.84 (m, 1H), 2.50-2.45 (m, 1H), 1.61-1.57 (m, 1H), 1.45-1.41 (m, 1H). |
| 205 | 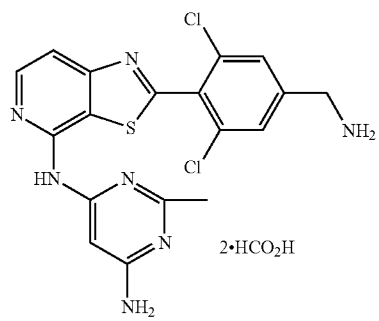 [SMILES: Cc1nc(N)cc(Nc2nccc3nc(-c4c(Cl)cc(CN)cc4Cl)sc23)n1] | N-[2-(4-Aminomethyl-2,6-dichlorophenyl)-thiazolo[5,4-c]pyridin-4-yl]-2-methylpyrimidine-4,6-diamine diformate salt | 2 | 432 | C | 2.04 | ¹H NMR (400 MHz, DMSO-d$_6$): δ 8.34 (d, J = 5.6 Hz, 1H), 8.24 (s, 2H), 7.70 (t, J = 2.8 Hz, 3H), 6.57-6.48 (m, 3H), 3.87 (br s, 2H), 2.24 (s, 3H). |
| 206 | 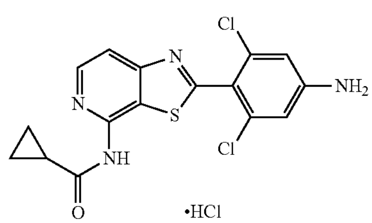 [SMILES: Nc1cc(Cl)c(-c2nc3ccnc(NC(=O)C4CC4)c3s2)c(Cl)c1 ; Cl] | Cyclopropanecarboxylic acid [2-(4-amino-2,6-dichlorophenyl)-thiazolo[5,4-c]pyridin-4-yl]-amide hydrochloride salt | 2 | 379 | C | 3.90 | ¹H NMR (400 MHz, DMSO-d$_6$): δ 11.41 (s, 1H), 8.41 (d, J = 5.6 Hz, 1H), 7.87 (d, J = 5.6 Hz, 1H), 6.76 (s, 2H), 2.12-2.02 (m, 1H), 0.95-0.84 (m, 4H). |
| 207 | 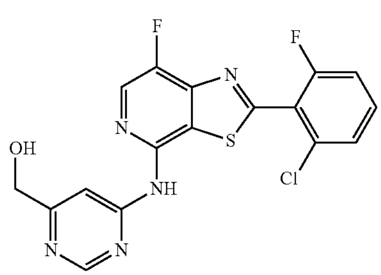 [SMILES: OCc1cc(Nc2ncc(F)c3nc(-c4c(F)cccc4Cl)sc23)ncn1] | {6-[2-(2-Chloro-6-fluorophenyl)-7-fluorothiazolo[5,4-c]pyridin-4-ylamino]-pyrimidin-4-yl}-methanol | 2 | 406 | C | 3.51 | ¹H NMR (400 MHz, DMSO-d$_6$): δ 10.75 (br s, 1H), 8.61 (d, J = 1.2 Hz, 1H), 8.49 (d, J = 1.9 Hz, 1H), 7.77-7.69 (m, 1H), 7.66-7.49 (m, 3H), 5.56 (t, J = 5.7 Hz, 1H), 4.47 (d, J = 5.7 Hz, 2H). |
| 208 | 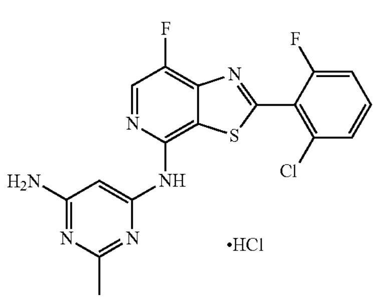 [SMILES: Cc1nc(N)cc(Nc2ncc(F)c3nc(-c4c(F)cccc4Cl)sc23)n1 ; Cl] | N-[2-(2-Chloro-6-fluorophenyl)-7-fluorothiazolo[5,4-c]pyridin-4-yl]-2-methylpyrimidine-4,6-diamine-hydrochloride salt | 2 | 405 | C | 3.26 | ¹H NMR (400 MHz, DMSO-d$_6$): δ 11.34 (s, 1H), 8.52 (d, J = 1.8 Hz, 1H), 7.79-7.70 (m, 1H), 7.64 (d, J = 8.1 Hz, 1H), 7.55 (t, J = 8.9 Hz, 1H), 7.02 (s, 1H), 2.47 (s, 3H). |

TABLE 2-continued

| Example | Structure | Name | Synth. Method | LCMS (ESI) m/z [M + H+] | LCMS Method | R_T (min) | NMR |
|---|---|---|---|---|---|---|---|
| 209 | 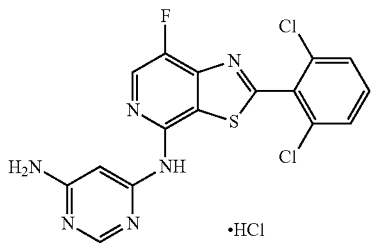 [SMILES: Nc1cc(Nc2ncc(F)c3nc(-c4c(Cl)cccc4Cl)sc23)ncn1 ; Cl] | N-[2-(2,6-Dichlorophenyl)-7-fluorothiazolo[5,4-c]pyridin-4-yl]-pyrimidine-4,6-diamine hydrochloride salt | 2 | 407 | C | 3.31 | $^1$H NMR (400 MHz, DMSO-d$_6$): δ 11.67 (br s, 1H), 8.53-7.47 (m, 2H), 7.79-7.70 (m, 3H), 7.04 (s, 1H). |
| 210 | 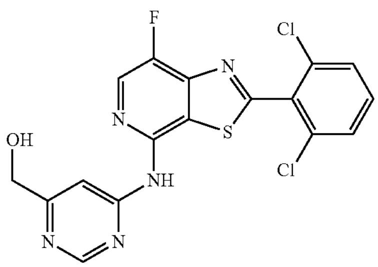 [SMILES: OCc1cc(Nc2ncc(F)c3nc(-c4c(Cl)cccc4Cl)sc23)ncn1] | {6-[2-(2,6-Dichlorophenyl)-7-fluorothiazolo[5,4-c]pyridin-4-ylamino]-pyrimidin-4-yl}-methanol | 2 | 422 | C | 3.68 | $^1$H NMR (400 MHz, DMSO-d$_6$): δ 10.76 (s, 1H), 8.61 (s, 1H), 8.50 (d, J = 1.8 Hz, 1H), 7.78-7.73 (m, 2H), 7.72-7.65 (m, 1H), 7.60 (s, 1H), 5.56 (t, J = 5.7 Hz, 1H), 4.48 (d, J = 5.7 Hz, 2H). |
| 211 | 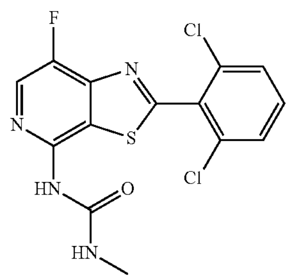 [SMILES: CNC(=O)Nc1ncc(F)c2nc(-c3c(Cl)cccc3Cl)sc12] | 1-[2-(2,6-Dichlorophenyl)-7-fluorothiazolo[5,4-c]pyridin-4-yl]-3-methyl-urea | 2 | 371 | C | 4.43 | $^1$H NMR (400 MHz, DMSO-d$_6$): δ 9.77 (s, 1H), 8.34 (d, J = 1.9 Hz, 1H), 7.76-7.72 (m, 2H), 7.70-7.65 (m, 1H), 7.31-7.24 (m, 1H), 2.73 (d, J = 4.6 Hz, 3H). |
| 212 | 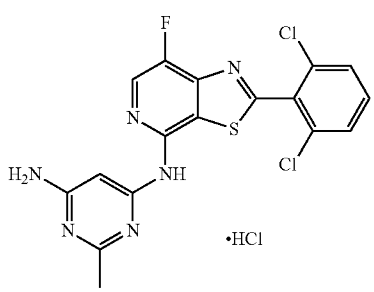 | N-[2-(2,6-Dichlorophenyl)-7-fluorothiazol[5,4-c]pyridin-4-yl]-2-methylpyrimidine-4,6-diamine-hydrochloride salt | 2 | 421 | C | 3.37 | $^1$H NMR (400 MHz, DMSO-d$_6$): δ 11.34 (s, 1H), 8.51 (d, J = 1.8 Hz, 1H), 7.77-7.65 (m, 3H), 6.99 (s, 1H), 2.44 (s, 3H). |
| 213 | 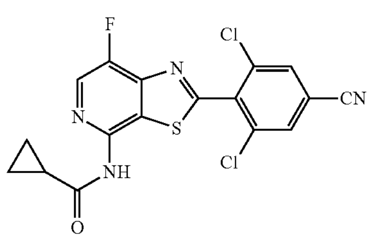 [SMILES: N#Cc1cc(Cl)c(-c2nc3c(F)cnc(NC(=O)C4CC4)c3s2)c(Cl)c1] | Cyclopropane-carboxylic acid [2-(2,6-dichloro-4-cyano-phenyl)-7-fluorothiazolo[5,4-c]pyridin-4-yl]-amide | 2 | 407 | C | 4.83 | $^1$H NMR (400 MHz, DMSO-d$_6$): δ 11.50 (s, 1H), 8.51 (d, J = 1.7 Hz, 1H), 8.38 (s, 2H), 2.10-2.02 (m, 1H), 0.95-0.83 (m, 4H). |
| 214 | 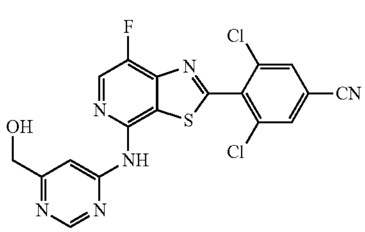 [SMILES: N#Cc1cc(Cl)c(-c2nc3c(F)cnc(Nc4cc(CO)ncn4)c3s2)c(Cl)c1] | 3,5-Dichloro-4-[7-fluoro-4-(6-hydroxymethyl-pyrimidin-4-ylamino)-thiazolo[5,4-c]pyridin-2-yl]-benzonitrile | 2 | 447 | C | 3.67 | $^1$H NMR (400 MHz, DMSO-d$_6$): δ 10.80 (s, 1H), 8.61 (d, J = 1.2 Hz, 1H), 8.51 (d, J = 1.7 Hz, 1H), 8.40 (s, 2H), 7.58 (s, 1H), 5.57 (t, J = 5.7 Hz, 1H), 4.48 (d, J = 5.7 Hz, 2H). |

TABLE 2-continued

| Example | Structure | Name | Synth. Method | LCMS (ESI) m/z [M + H+] | LCMS Method | R_T (min) | NMR |
|---|---|---|---|---|---|---|---|
| 215 | 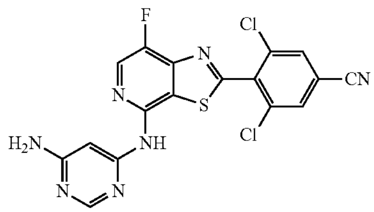 [SMILES: N#Cc1cc(Cl)c(-c2nc3c(F)cnc(Nc4cc(N)ncn4)c3s2)c(Cl)c1] | 4-[4-(6-Aminopyrimidin-4-ylamino)-7-fluorothiazolo[5,4-c]pyridin-2-yl]-3,5-dichlorobenzonitrile | 2 | 432 | C | 3.28 | $^1$H NMR (400 MHz, DMSO-d$_6$): δ 10.19 (s, 1H), 8.40-8.37 (m, 3H), 8.10 (d, J = 1.0 Hz, 1H), 6.66 (br s, 2H), 6.55 (d, J = 1.1 Hz, 1H). |
| 216 | 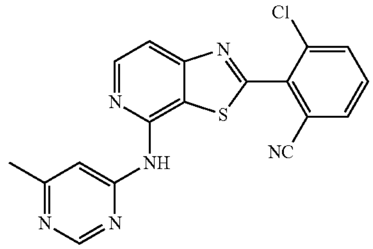 [SMILES: Cc1cc(Nc2nccc3nc(-c4c(Cl)cccc4C#N)sc23)ncn1] | 3-Chloro-2-[4-(6-methylpyrimidin-4-ylamino)-thiazolo[5,4-c]pyridin-2-yl]benzonitrile | 2 | 379 | C | 3.08 | $^1$H NMR (400 MHz, DMSO-d$_6$): δ 10.71 (br s, 1H), 8.64 (d, J = 1.2 Hz, 1H), 8.48 (d, J = 5.6 Hz, 1H), 8.16-8.05 (m, 2H), 7.89-7.81 (m, 2H), 7.58 (s, 1H), 2.40 (s, 3H). |
| 217 | 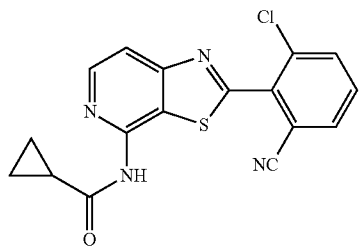 [SMILES: N#Cc1cccc(Cl)c1-c1nc2ccnc(NC(=O)C3CC3)c2s1] | Cyclopropane-carboxylic acid [2-(2-chloro-6-cyanophenyl)-thiazolo[5,4-c]pyridin-4-yl]-amide | 2 | 355 | C | 4.18 | $^1$H NMR (400 MHz, DMSO-d$_6$): δ 11.47 (s, 1H), 8.48 (d, J = 5.5 Hz, 1H), 8.13-8.05 (m, 2H), 7.96 (d, J = 5.5 Hz, 1H), 7.83 (t, J = 8.0 Hz, 1H), 2.13-2.05 (m, 1H), 0.95-0.86 (m, 4H). |
| 218 | 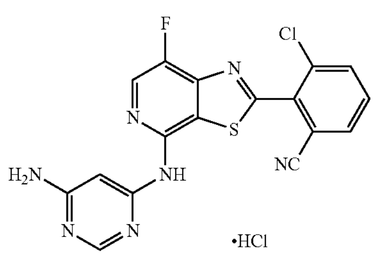 [SMILES: N#Cc1cccc(Cl)c1-c1nc2c(F)cnc(Nc3cc(N)ncn3)c2s1 ; Cl] | 2-[4-(6-Aminopyrimidin-4-ylamino)-7-fluorothiazolo[5,4-c]pyridin-2-yl]-3-chlorobenzonitrile hydrochloride salt | 2 | 398 | C | 3.01 | $^1$H NMR (400 MHz, DMSO-d$_6$): δ 11.71 (br s, 1H), 8.55-8.50 (m, 2H), 8.18-8.09 (m, 2H), 7.91-7.86 (m, 1H), 7.05 (br s, 1H). |
| 219 | 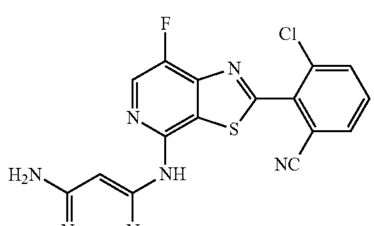 | 2-[4-(6-Amino-2-methyl-pyrimidin-4-ylamino)-7-fluorothiazol[5,4-c]pyridin-2-yl]-3-chlorobenzonitrile hydrochloride salt | 2 | 412 | C | 3.07 | $^1$H NMR (400 MHz, DMSO-d$_6$): δ 11.37 (br s, 1H), 8.56 (d, J = 2.0 Hz, 1H), 8.17-8.11 (m, 2H), 7.88 (t, J = 8.0 Hz, 1H), 6.98 (br s, 1H), 3.81 (br s, 3H), 2.47 (s, 3H). |
| 220 | 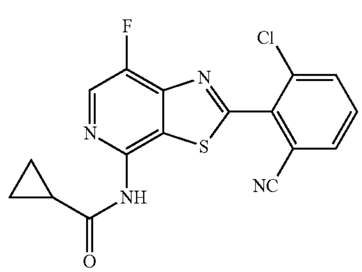 [SMILES: N#Cc1cccc(Cl)c1-c1nc2c(F)cnc(NC(=O)C3CC3)c2s1] | Cyclopropane-carboxylic acid [2-(2-chloro-6-cyanophenyl)-7-fluorothiazol0[5,4-c]pyridin-4-yl]-amide | 2 | 373 | C | 4.43 | $^1$H NMR (400 MHz, CDCl$_3$): δ 8.45 (br s, 1H), 8.22 (d, J = 1.8 Hz, 1H), 7.79-7.74 (m, 2H), 7.58 (t, J = 8.0 Hz, 1H), 1.70-1.61 (m, 1H), 1.19-1.14 (m, 2H), 1.02-0.96 (m, 2H). |

TABLE 2-continued

| Example | Structure | Name | Synth. Method | LCMS (ESI) m/z [M + H+] | LCMS Method | R_T (min) | NMR |
|---|---|---|---|---|---|---|---|
| 221 | 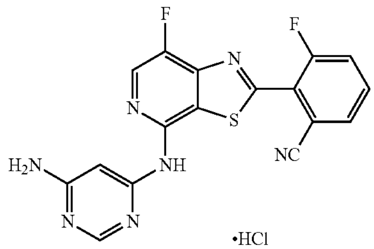 [SMILES: N#Cc1cccc(F)c1-c1nc2c(F)cnc(Nc3cc(N)ncn3)c2s1 ; Cl] | 2-[4-(6-Aminopyrimidin-4-ylamino)-7-fluorothiazolo[5,4-c]pyridin-2-yl]-3-fluorobenzonitrile hydrochloride salt | 2 | 382 | C | 2.91 | $^1$H NMR (400 MHz, DMSO-$d_6$): δ 11.55 (br s, 1H), 8.55-8.48 (m, 2H), 8.08-8.03 (m, 1H), 8.01-7.89 (m, 2H), 7.01 (br s, 1H). |
| 222 | 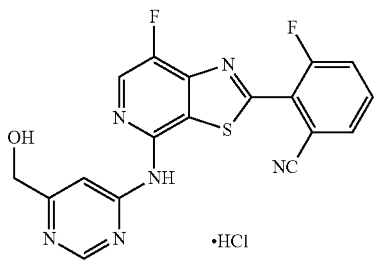 [SMILES: N#Cc1cccc(F)c1-c1nc2c(F)cnc(Nc3cc(CO)ncn3)c2s1 ; Cl] | 3-Fluoro-2-[7-fluoro-4-(6-hydroxymethyl-pyrimidin-4-ylamino)thiazolo[5,4-c]pyridin-2-yl]-benzonitrile hydrochloride salt | 2 | 397 | C | 3.10 | $^1$H NMR (400 MHz, DMSO-$d_6$): δ 11.72 (br s, 1H), 8.87 (s, 1H), 8.61 (d, J = 2.0 Hz, 1H), 8.07-8.03 (m, 1H), 7.98-7.88 (m, 2H), 7.71 (s, 1H), 4.61 (s, 2H). |
| 223 | 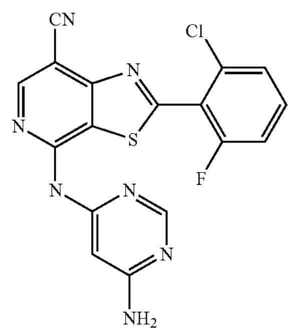 [SMILES: N#Cc1cnc(Nc2cc(N)ncn2)c2sc(-c3c(F)cccc3Cl)nc12] | 4-(6-aminopyrimidin-4-ylamino)-2-(2-chloro-6-fluorophenyl)thiazolo[5,4-c]pyridine-7-carbonitrile | 2 | 398.1 | B | 4.17 | $^1$H NMR (400 MHz, DMSO-$d_6$): δ 8.78 (s, 1H), 8.19 (s, 1H), 7.78-7.68 (m, 1H), 7.62 (d, J = 8.1 Hz, 1H), 7.53 (t, J = 8.9 Hz, 1H), 6.82 (s, 2H), 6.75 (s, 1H), 6.54 (s, 1H). |
| 224 | 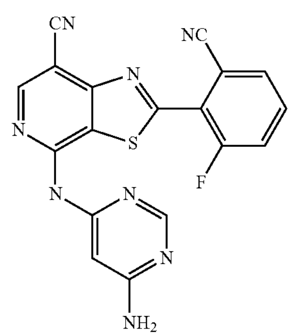 [SMILES: N#Cc1cccc(F)c1-c1nc2c(C#N)cnc(Nc3cc(N)ncn3)c2s1] | 4-(6-aminopyrimidin-4-ylamino)-2-(2-cyano-6-fluorophenyl)thiazolo[5,4-c]pyridine-7-carbonitrile | 2 | 398.1 | B | 3.93 | $^1$H NMR (400 MHz, DMSO-$d_6$): δ 10.85 (s, 1H), 8.81 (s, 1H), 8.20 (s, 1H), 8.02 (d, J = 6.5 Hz, 1H), 7.91 (t, J = 6.5 Hz, 2H), 6.87 (s, 2H), 6.80 (s, 1H). |
| 225 | 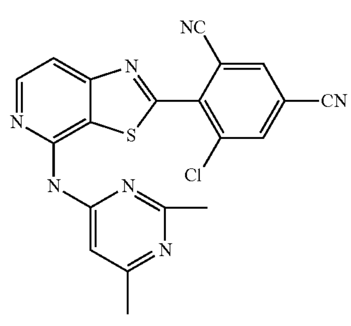 [SMILES: Cc1cc(Nc2nccc3nc(-c4c(Cl)cc(C#N)cc4C#N)sc23)nc(C)n1] | 5-chloro-4-(4-(2,6-dimethylpyrimidin-4-ylamino)thiazolo[5,4-c]pyridine-2-yl)isophthalonitrile | 2 | 418.1 | B | 3.72 | $^1$H NMR (400 MHz, DMSO-$d_6$): δ 10.65 (s, 1H), 8.73 (d, J = 7.8 Hz, 2H), 8.47 (d, J = 5.6 Hz, 1H), 7.86 (d, J = 5.6 Hz, 1H), 7.21 (s, 1H), 2.45 (s, 3H), 2.34 (s, 3H). |

TABLE 2-continued

| Example | Structure | Name | Synth. Method | LCMS (ESI) m/z [M + H⁺] | LCMS Method | R$_T$ (min) | NMR |
|---|---|---|---|---|---|---|---|
| 226 | 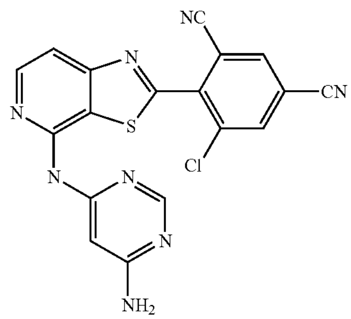 [SMILES: N#Cc1cc(Cl)c(-c2nc3ccnc(Nc4cc(N)ncn4)c3s2)c(C#N)c1] | 4-(4-(6-aminopyrimidin-4-ylamino)thiazolo[5,4-c]pyridin-2-yl)-5-chloro-isophthalonitrile | 2 | 405.1 | B | 3.69 | ¹H NMR (500 MHz, DMSO-d$_6$): δ 10.23 (s, 1H), 8.75 (d, J = 1.4 Hz, 1H), 8.73 (d, J = 1.4 Hz, 1H), 8.40 (d, J = 5.6 Hz, 1H), 8.12 (s, 1H), 7.77 (d, J = 5.6 Hz, 1H) 6.75 (s, 1H), 6.68 (s, 2H). |
| 227 | 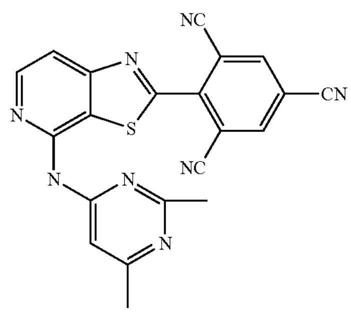 [SMILES: Cc1cc(Nc2nccc3nc(-c4c(C#N)cc(C#N)cc4C#N)sc23)nc(C)n1] | 2-(4-(2,6-dimethylpyrimidin-4-ylamino)thiazolo[5,4-c]pyridin-2-yl)benzene-1,3,5-tricarbonitrile | 2 | 409.1 | B | 3.51 | ¹H NMR (400 MHz, DMSO-d$_6$): δ 10.74 (s, 1H), 9.06 (s, 2H), 8.49 (d, J = 5.6 Hz, 1H), 7.90 (d, J = 5.6 Hz, 1H), 7.20 (s, 1H), 2.49 (s, 3H), 2.35 (s, 3H). |
| 228 | 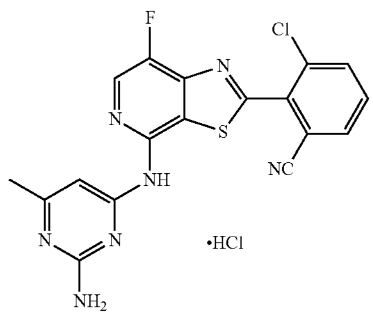 [SMILES: Cc1cc(Nc2ncc(F)c3nc(-c4c(Cl)cccc4C#N)sc23)nc(N)n1 ; Cl] | 2-[4-(2-Amino-6-methylpyrimidin-4-ylamino)-7-fluoro-thiazolo[5,4-c]pyridin-2-yl]-3-chlorobenzonitrile hydrochloride salt | 2 | 412 | C | 2.99 | ¹H NMR (400 MHz, DMSO-d$_6$): δ 11.59 (br s, 1H), 8.64 (d, J = 1.7 Hz, 1H), 8.17-8.15 (m, 1H), 8.13-8.10 (m, 1H), 7.87 (t, J = 7.9 Hz, 1H), 7.81 (br s, 3H), 6.53 (br s, 1H), 2.35 (s, 3H). |
| 229 | 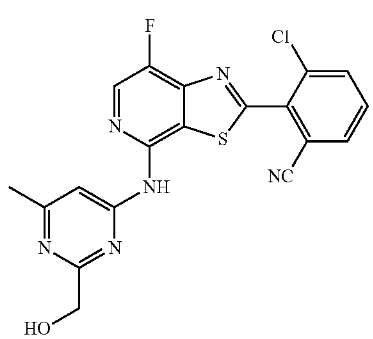 [SMILES: Cc1cc(Nc2ncc(F)c3nc(-c4c(Cl)cccc4C#N)sc23)nc(CO)n1] | 3-Chloro-2-[7-fluoro-4-(2-hydroxymethyl-6-methylpyrimidin-4-ylamino)-thiazolo[5,4-c]pyridin-2-yl]-benzonitrile | 2 | 427 | C | 3.07 | ¹H NMR (400 MHz, DMSO-d$_6$): δ 10.75 (br s, 1H), 8.51 (d, J = 1.8 Hz, 1H), 8.16-8.08 (m, 2H), 7.87 (t, J = 8.0 Hz, 1H), 7.22 (s, 1H), 4.96 (t, J = 6.1 Hz, 1H), 4.48 (d, J = 6.1 Hz, 2H), 2.28 (s, 3H). |

TABLE 2-continued

| Example | Structure | Name | Synth. Method | LCMS (ESI) m/z [M + H⁺] | LCMS Method | R_T (min) | NMR |
|---|---|---|---|---|---|---|---|
| 230 | 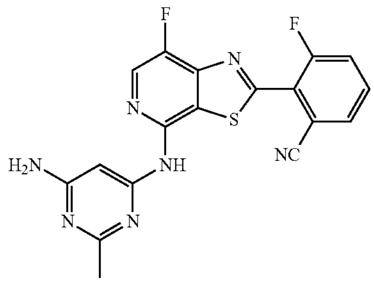 [SMILES: Cc1nc(N)cc(Nc2ncc(F)c3nc(-c4c(F)cccc4C#N)sc23)n1] | 2-[4-(6-Amino-2-methylpyrimidin-4-ylamino)-7-fluorothiazolo[5,4-c]pyridin-2-yl]-3-fluorobenzonitrile | 2 | 396 | C | 2.97 | $^1$H NMR (400 MHz, DMSO-d$_6$): δ 10.12 (br s, 1H), 8.37 (d, J = 1.8 Hz, 1H), 8.03-8.00 (m, 1H), 7.96-7.85 (m, 2H), 6.56 (br s, 1H), 6.29 (s, 1H), 2.39 (s, 3H). |

Example 231

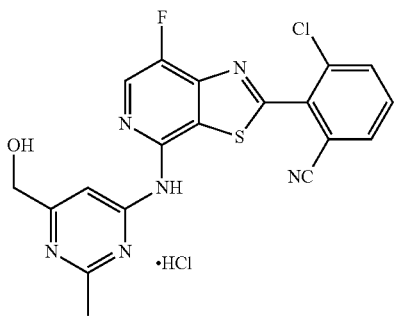 [SMILES: Cc1nc(CO)cc(Nc2ncc(F)c3nc(-c4c(Cl)cccc4C#N)sc23)n1 ; Cl]

3-Chloro-2-[7-fluoro-4-(6-hydroxymethyl-2-methylpyrimidin-4-ylamino)-thiazolo[5,4-c]pyridin-2-yl]benzonitrile hydrochloride

Step 1. (2-Methyl-6-vinyl-aminopyrimidin-4-yl)-bis-carbamic acid tert-butyl ester To a solution of (2-methyl-6-chloro-aminopyrimidin-4-yl)-bis-carbamic acid tert-butyl ester (1.50 g, 4.4 mmol), potassium vinyltrifluoroborate (884 mg, 6.6 mmol) and triethylamine (3.3 mL, 22 mmol) in nPrOH (40 mL) was added Pd(dppf)Cl$_2$ (180 mg, 0.22 mmol). The reaction mixture was degassed with nitrogen and then heated at 100° C. for 30 minutes in a sealed vial. The resulting mixture was allowed to cool and was then partitioned between EtOAc and saturated sodium bicarbonate. The organic layer was washed with brine, dried (Na$_2$SO$_4$), filtered and concentrated in vacuo. The resultant residue was purified by column chromatography on silica gel eluting with 10% EtOAc in cyclohexane to afford the title compound as an oil (1.99 g, 93%). $^1$H NMR (400 MHz, CDCl$_3$): δ 7.45 (s, 1H), 6.70 (dd, J=17.3, 1.3 Hz, 1H), 6.42 (dd, J=17.3, 10.7 Hz, 1H), 5.64 (dd, J=10.7, 1.3 Hz, 1H), 2.61 (s, 3H), 1.54 (s, 9H).

Step 2. (6-Hydroxymethyl-2-methyl-aminopyrimidin-4-yl)-bis-carbamic acid tert-butyl ester Ozone was bubbled through a solution of (2-methyl-6-vinyl-aminopyrimidin-4-yl)-bis-carbamic acid tert-butyl ester (1.98 g, 5.9 mmol), in DCM (50 mL) and MeOH (12 mL), at −78° C. for 60 minutes (until a permanent blue colour resulted). The flow of Ozone was stopped and then sodium borohydride (448 mg, 11.8 mmol) was added at −78° C. The reaction mixture was allowed to stir at −78° C. for 10 minutes and was then allowed to warm to room temperature and further stirred for 60 minutes. The resulting mixture was then partitioned between DCM and water. The organic layer was washed with brine, dried (Na$_2$SO$_4$), filtered and concentrated in vacuo. The resultant residue was purified by column chromatography on silica gel eluting with 40-60% EtOAc in cyclohexane to afford the title compound as an oil (1.69 g, 84%). LCMS (Method E): RT=3.19 min, m/z: 340 [M+H⁺].

Step 3. (6-Amino-2-methylpyrimidin-4-yl)-methanol

TFA (5 mL) was added to a solution of (6-hydroxymethyl-2-methyl-aminopyrimidin-4-yl)-bis-carbamic acid tert-butyl ester (1.68 g, 5.0 mmol), in DCM (20 mL) and the reaction mixture was stirred at room temperature for 16 hours. The resulting mixture was concentrated in vacuo. The crude residue was dissolved in methanol and loaded onto an Isolute® SCX-2 cartridge which was washed with MeOH and the product was then eluted with 2M ammonia in MeOH. The combined elution fractions were concentrated in vacuo and the resultant residue was triturated with diethylether to afford the title compound as a pale pink solid (540 mg, 78%). $^1$H NMR (400 MHz, DMSO-d$_6$): δ 6.64 (br s, 2H), 6.34 (s, 1H), 5.26 (t, J=5.9 Hz, 1H), 4.25 (d, J=5.9 Hz, 2H), 2.25 (s, 3H).

Step 4. 3-Chloro-2-[7-fluoro-4-(6-hydroxymethyl-2-methylpyrimidin-4-ylamino)-thiazolo[5,4-c]pyridin-2-yl]benzonitrile hydrochloride To a mixture of 2-(4-bromo-7-fluorothiazolo[5,4-c]pyridin-2-yl)-3-chlorobenzonitrile (150 mg, 0.41 mmol), (6-amino-2-methylpyrimidin-4-yl)-methanol (56 mg, 0.41 mmol), XantPhos (24 mg, 0.042 mmol) and Cs$_2$CO$_3$ (345 mg, 1.05 mmol) in 1,4-dioxane (2.5 mL) was added Pd$_2$(dba)$_3$ (20 mg, 0.022 mmol), and the reaction mixture was heated under argon at 80° C. for 24 hours. The resultant mixture was allowed to cool, diluted with water and extracted with ethyl acetate, then further extracted with 10% methanol in DCM (×5). The resultant insoluble material was filtered off, triturated twice with methanol and dried (50° C. under vacuum) to give the free base of the title compound as a solid (77 mg). The previously combined organic extracts were dried (Na$_2$SO$_4$), filtered and concentrated in vacuo. The resulting residue was purified by chromatography on silica (0-100% ethyl acetate in cyclohexane) to give a further crop of the free base of the title compound [(30 mg), total yield 107 mg, 61%]. The combined batches of free base were suspended in 2-propanol (2 mL), and a solution of hydrogen chloride in 1,4-dioxane (4 N, 2 mL) was added. The mixture was stirred for 1 hour, then the solvent was removed under reduced pressure, and the resultant residue was triturated with diethylether and dried (50° C. under vacuum) to give the title compound as an off-white solid (104 mg, 55%). $^1$H NMR (400 MHz, DMSO-$d_6$): δ 11.76 (br s, 1H), 8.63 (s, 1H), 8.17-8.09 (m, 2H), 7.88 (t, J=8.1 Hz, 1H), 7.44 (br s, 1H), 4.58 (s, 2H), 2.57 (s, 3H). LCMS (Method C): RT=3.07, m/z: 427 [M+H$^+$].

Example 232

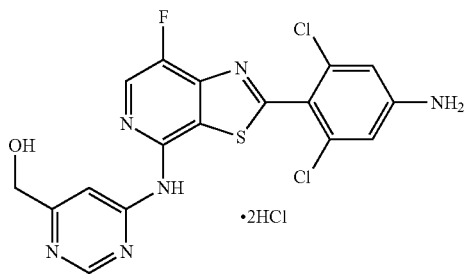 [SMILES: Nc1cc(Cl)c(-c2nc3c(F)cnc(Nc4cc(CO)ncn4)c3s2)c(Cl)c1 ; "·2HCl"]

{6-[2-(4-Amino-2,6-dichlorophenyl)-7-fluorothia-zolo[5,4-c]pyridin-4-ylamino]-pyrimidin-4-yl}-methanol dihydrochloride salt Step 1. 2,6-Dichloro-N-(3,5-difluoropyridin-4-yl)-4-iodobenzamide A suspension of 2,6-dichloro-4-iodobenzoyl chloride (24.2 g, 72.1 mmol) in THF (25 mL), was added drop-wise over 10 minutes, to a solution of 3,5-difluoropyridin-4-ylamine (10.37 g, 79.7 mmol) in pyridine (100 mL) at a temperature of between 3 and 5° C., under nitrogen. The reaction mixture was allowed to warm to room temperature over 1 hour and then stirred overnight. The volatiles were removed under reduced pressure and the resultant residue was treated with HCl (1 N, 90 mL). The resultant suspension was stirred at room temperature for 45 minutes and the precipitate obtained was collected by filtration, washing with water before drying. The resultant solid obtained was suspended in 1N NaOH (124 mL) and MeOH (124 mL), and heated at 65° C. for 5 hours then slowly cooled to room temperature. Further MeOH (50 mL) and dioxane (100 mL) were added and the reaction mixture was heated at 75° C. overnight. The resultant mixture was cooled to room temperature and the organic solvents removed under reduced pressure. The pH of the aqueous mixture was adjusted to 4-5 by drop-wise addition of 12 N HCl, controlling the exotherm by the use of an ice-bath. The residue was left standing at room temperature for 18 hours and then the resultant solid was collected by filtration, washing with water and dried under vacuum to afford the title compound as an off-white solid (21.3 g, 83% yield). LCMS (Method D): RT=3.46 min, m/z: 429 [M+H$^+$].

Step 2. 2,6-Dichloro-N-(3,5-difluoropyridin-4-yl)-4-iodobenzimidoyl chloride

A mixture of 2,6-dichloro-N-(3,5-difluoropyridin-4-yl)-4-iodobenzamide (21.3 g, 49.7 mmol) in thionyl chloride (118 mL) was heated under reflux for 20 hours under a nitrogen atmosphere. After cooling to room temperature, the volatiles were removed under reduced pressure and the resultant residue was azeotroped with toluene (×3) and dried under vacuum to afford the title compound as a brown solid (22.4 g, quantitative). LCMS (Method E): RT=4.69 min, m/z: 448 [M+H$^+$].

Step 3. 2-(2,6-Dichloro-4-iodophenyl)-7-fluorothia-zolo[5,4-c]pyridine

A suspension of 2,6-dichloro-N-(3,5-difluoropyridin-4-yl)-4-iodobenzimidoyl chloride (8.8 g, 19.7 mmol), thiourea (6.0 g, 78.8 mol) and pyridine (5.4 mL, 66.9 mmol) in iso-propanol (80 mL), under a nitrogen atmosphere, was heated under reflux for 6 hours. After this time, the reaction mixture was cooled to 70° C. and Et$_3$N (16.4 mL, 118.1 mmol) was added over 5 minutes and then the resultant mixture was heated under reflux for a further 18 hours. Upon cooling to room temperature, the precipitate obtained was collected by filtration and the filtrate was then partitioned between water and EtOAc. The aqueous phase was further extracted with EtOAc (×2) and the combined organic layers were dried (MgSO$_4$), filtered and concentrated to dryness to afford the title compound as an off-white solid (5.5 g, 66% yield). LCMS (Method D): RT=4.22 min, m/z: 426 [M+H$^+$].

Step 4. 2-(2,6-Dichloro-4-iodophenyl)-7-fluorothia-zolo[5,4-c]pyridine-5-oxide

To a solution of 2-(2,6-dichloro-4-iodophenyl)-7-fluo-rothiazolo[5,4-c]pyridine (5.3 g, 12.6 mmol) in DCM (100 mL) under a nitrogen atmosphere was added methyltrioxorhenium(VII) (313 mg, 1.3 mmol) followed by 30% aqueous hydrogen peroxide (2.6 mL, 25.1 mmol). The reaction mixture was stirred at room temperature for 48 hours with a further two additions of methyltrioxorhenium(VII) (313 mg, 1.3 mmol) and 30% aqueous hydrogen peroxide (2.6 mL, 25.1 mmol) added over this period. The precipitate obtained was collected by filtration and the filtrate was partitioned between water. The aqueous layer was extracted with DCM (×2). The combined organic phases were washed with a saturated solution of NaHCO$_3$, dried (MgSO$_4$) and concentrated under reduced pressure. The resultant residue was combined with the previously filtered solid and was purified by column chromatography on silica gel eluting with 0-90% EtOAc in petroleum ether (40-60° C.), followed by 0-10% MeOH in DCM to afford the title compound as a white solid (2.5 g, 45% yield). LCMS (Method D): RT=3.36 min, m/z: 441 [M+H$^+$].

Step 5. 4-Chloro-2-(2,6-dichloro-4-iodophenyl)-7-fluorothiazolo[5,4-c]pyridine

To a suspension of 2-(2,6-dichloro-4-iodophenyl)-7-fluo-rothiazolo[5,4-c]pyridine-5-oxide (2.8 g, 6.4 mmol) in 1,2-dichloroethane (80 mL) was added phosphorus oxychloride (1.8 mL, 19.1 mmol). The reaction mixture was heated under reflux for 16 hours. Upon cooling, the resultant mixture was treated cautiously with aqueous sodium bicarbonate to achieve pH 6-7, and then extracted with dichloromethane (×2). The combined organic extracts were dried (MgSO$_4$), filtered and concentrated under reduced pressure. The crude product was purified by column chromatography on silica gel eluting with 0-50% diethyl ether in petroleum ether to afford the title compound as a white solid (1.0 g, 34% yield). $^1$H NMR (400 MHz, CDCl$_3$): δ 8.35 (d, J=1.5 Hz, 1H), 7.82 (s, 2H).

Step 6. [3,5-Dichloro-4-(4-chloro-7-fluorothiazolo[5,4-c]pyridin-2-yl)phenyl]-carbamic acid tert-butyl ester To 4-chloro-2-(2,6-dichloro-4-iodophenyl)-7-fluorothiazolo[5,4-c]pyridine (579 mg, 1.3 mmol), in toluene (12 mL) and water (2 mL), was added tert-butyl carbamate (221 mg, 1.9 mmol), XantPhos (72.9 g, 0.13 mmol) and K₃PO₄ (534 mg, 0.34 mmol). The resulting mixture was degassed with argon for 10 minutes, Pd₂(dba)₃ (57.7 mg, 0.063 mmol) was added and the reaction mixture was heated at 100° C. for 18 hours in a sealed vial. After cooling to room temperature, the reaction mixture was filtered through Celite® washing with EtOAc (5 mL). The filtrate was partitioned between water and the organic layer separated. The aqueous phase was further extracted with EtOAc (×2). The combined organic layers were dried (MgSO₄), filtered concentrated under reduced pressure. The resultant residue was purified by column chromatography on silica gel eluting with 0-100% DCM in cyclohexane to afford the title compound as a white solid (303 mg, 54% yield). LCMS (Method D): RT=4.86 min, m/z: 448.0 [M+H⁺].

Step 7. {3,5-Dichloro-4-[7-fluoro-4-(6-hydroxymethylpyrimidin-4-ylamino)-thiazolo[5,4-c]pyridin-2-yl]phenyl}-carbamic acid tert-butyl ester To a solution of [3,5-dichloro-4-(4-chloro-7-fluorothiazolo[5,4-c]pyridin-2-yl)phenyl]-carbamic acid tert-butyl ester (150 mg, 0.33 mmol) in dioxane (5 mL), was added (6-aminopyrimidin-4-yl)methanol (45 mg, 0.36 mmol), XantPhos (19.4 mg, 0.033 mmol) and Cs₂CO₃ (218.3 mg, 0.67 mmol). The resultant mixture was degassed with argon for 10 minutes before Pd₂(dba)₃ (57.7 mg, 0.063 mmol) was added and the reaction mixture was heated at 100° C. for 18 hours in a sealed vial. After cooling to room temperature, the reaction mixture was filtered through Celite® washing with EtOAc (5 mL). The resultant residue was purified by column chromatography on silica gel eluting with 0-80% EtOAc in cyclohexane to afford the title compound as a white foam (102 mg, 58%). LCMS (Method D): RT=3.35 min, m/z: 538 [M+H⁺].

Step 8. {6-[2-(4-Amino-2,6-dichlorophenyl)-7-fluorothiazolo[5,4-c]pyridin-4-ylamino]-pyrimidin-4-yl}-methanol dihydrochloride salt A mixture of {3,5-dichloro-4-[7-fluoro-4-(6-hydroxymethylpyrimidin-4-ylamino)-thiazolo[5,4-c]pyridin-2-yl]phenyl}-carbamic acid tert-butyl ester (102 mg, 0.19 mmol) in HCl (4 N in dioxane, 3 mL) under a nitrogen atmosphere was heated at 50° C. for 5 hours. After cooling to room temperature, the precipitate was collected by filtration and then purified by column chromatography on silica gel eluting with 0-5% MeOH in EtOAc. To the resultant solid obtained was added DCM (1 mL) followed by HCl (4 N in dioxane, 1 mL) and the resulting mixture was stirred at room temperature for 1 hour and then concentrated under reduced pressure to afford the title compound as an off white solid (50 mg, 91% yield). ¹H NMR (300 MHz, DMSO-d₆): δ 11.75 (br s, 1H), 8.89 (s, 1H), 8.57 (d, J=2.1 Hz, 1H), 7.70 (s, 1H), 6.78 (s, 2H), 4.61 (s, 2H). LCMS (Method C): RT=3.11 min, m/z: 437 [M+H⁺].

Example 233

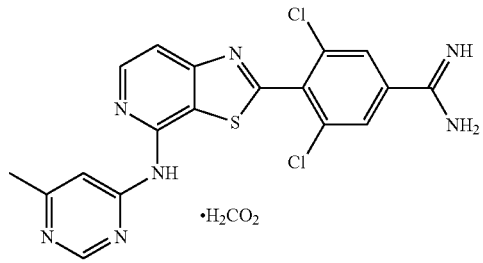

4-[4-(6-Methylpyrimidin-4-ylamino)-thiazolo[5,4-c]pyridin-2-yl]-3,5-dichlorobenzamidine bis formate salt To a solution of 3,5-dichloro-4-[4-(6-methylpyrimidin-4-ylamino)-thiazolo[5,4-c]pyridin-2-yl]benzonitrile (54 mg, 0.12 mmol) in MeOH (3 mL) was added a solution of sodium methoxide in methanol (0.054 mL, 0.24 mmol) and the reaction mixture was stirred at room temperature for 48 hours. After this time, an additional portion of sodium methoxide in methanol (0.0082 mL, 0.14 mmol) was added, stirred for 1 hour and then ammonium chloride (7.0 mg, 7.1 mmol) was added and the resultant mixture was heated at reflux overnight. After cooling to room temperature, additional ammonium chloride (11.4 mg, 0.21 mmol) was added and heated at reflux for a further 5 hours. The reaction mixture was cooled to room temperature and concentrated under reduced pressure. The resultant residue was purified by reverse phase HPLC (Phenomenex Gemini 5 μm C18 on a 25 minute gradient 5-50%, 0.1% HCO₂H in CH₃CN/H₂O) to afford the title compound (5.6 mg, 10% yield) as yellow solid. ¹H NMR (400 MHz, DMSO-d₆): δ 10.75 (br s, 1H), 9.60 (s, 2H), 9.34 (s, 2H), 8.61 (s, 1H), 8.42 (d, J=5.5 Hz, 1H), 8.14 (s, 2H), 7.82 (d, J=5.3 Hz, 1H), 7.54 (s, 1H), 2.41 (s, 3H). LCMS (Method C): RT=2.06 min, m/z: 412 [M+H⁺].

Example 234

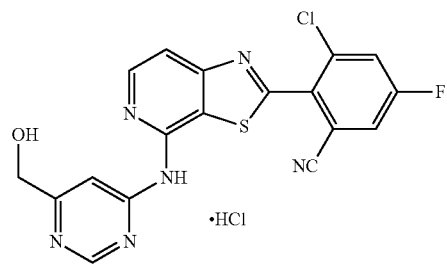 [SMILES: N#Cc1cc(F)cc(Cl)c1-c1nc2ccnc(Nc3cc(CO)ncn3)c2s1 ; Cl]

3-Chloro-5-fluoro-2-[4-(6-hydroxymethylpyrimidin-4-ylamino)-thiazolo[5,4-c]pyridin-2-yl]benzonitrile hydrochloride

Step 1. 2-Amino-3-chloro-5-fluorobenzonitrile

To a solution of 2-amino-5-fluorobenzonitrile (9.90 g, 72.8 mmol) in acetonitrile (200 mL) was added N-chlorosuccinimide (10.7 g, 80.1 mmol) in several portions. The reaction mixture was heated at 80° C. for 16 hours, then cooled and concentrated to approximately 100 mL under reduced pressure. The residue was poured into water (1 L), and the resultant precipitate was filtered, washed with water and dried (50° C. under vacuum) to give the title compound as a light brown solid (12.37 g, 100%). $^1$H NMR (300 MHz, CDCl$_3$): δ 7.27 (dd, J=7.9, 2.9 Hz, 1H), 7.09 (dd, J=7.9, 2.9 Hz, 1H), 4.69 (br s, 2H).

Step 2. 2-Bromo-3-chloro-5-fluorobenzonitrile

To a mixture of 2-amino-3-chloro-5-fluorobenzonitrile (5.0 g, 29 mmol) and copper (II) bromide (7.8 g, 35 mmol) in acetonitrile (130 mL) was added t-butyl nitrite (4.2 mL, 35 mmol), drop-wise at 0° C. The reaction mixture was stirred for 2 hours while warming slowly to room temperature. The resultant mixture was then concentrated under reduced pressure to approx. half the original volume, and the residue was poured into water (1 L) and extracted twice with ethyl acetate. The combined organic extracts were washed with water, dried (Na$_2$SO$_4$) and evaporated. The crude product was purified by chromatography on silica (20% diethylether in pentane) to give the title compound as a cream coloured solid (5.4 g, 79%). $^1$H NMR (400 MHz, CDCl$_3$): δ 7.48 (dd, J=7.8, 2.9 Hz, 1H), 7.35 (dd, J=7.8, 2.9 Hz, 1H).

Step 3. 3-Chloro-5-fluoro-2-thiazolo[5,4-c]pyridin-2-yl-benzonitrile

A mixture of thiazolo[5,4-c]pyridine (0.5 g, 3.67 mmol), 2-bromo-3-chloro-5-fluorobenzonitrile (1.3 g, 5.5 mmol), Pd(PPh$_3$)$_4$ (0.42 g, 0.36 mmol), copper(I) iodide (70 mg, 0.37 mmol) and cesium carbonate (3.9 g, 12 mmol) in dimethylformamide (15 mL) was heated at 150° C. in a microwave reactor for 5 minutes. The cooled mixture was poured into water and extracted twice with ethyl acetate. The combined organic extracts were washed with water, dried (Na$_2$SO$_4$), filtered and concentrated in vacuo. The crude product was purified by chromatography on silica (10% diethylether in DCM) to yield a pale solid (0.22 g). The reaction was repeated on the same scale, and the combined product from both reactions was purified by chromatography on silica (5% diethylether in DCM) to give the title compound as an off-white solid (0.30 g, 14%). $^1$H NMR (300 MHz, CDCl$_3$): δ 9.35 (s, 1H), 8.78 (d, J=6.2 Hz, 1H), 8.10 (d, J=6.2 Hz, 1H), 7.58 (dd, J=7.8, 2.5 Hz, 1H), 7.53 (dd, J=7.4, 2.5 Hz, 1H). LCMS (Method E): RT=2.78, m/z: 290 [M+H$^+$].

Step 4. 3-Chloro-5-fluoro-2-(5-oxythiazolo[5,4-c]pyridin-2-yl)-benzonitrile

To a solution of 3-chloro-5-fluoro-2-thiazolo[5,4-c]pyridin-2-yl-benzonitrile (163 mg, 0.56 mmol) in DCM (4 mL) was added methyltrioxorhenium (VII) (15 mg, 0.06 mmol) and hydrogen peroxide (27% in water, 0.08 mL, 1.11 mmol). The reaction mixture was stirred vigorously for 16 hours. Further portions of methyltrioxorhenium (VII) (5 mg) and hydrogen peroxide (0.04 mL) were added and stirring was continued for 5 hours. The resultant mixture was then treated with aqueous sodium bicarbonate, the phases were separated and the aqueous phase was extracted three times with DCM. The combined organic washings were dried (Na$_2$SO$_4$), filtered and concentrated in vacuo. The resultant residue was triturated twice with diethylether and dried (50° C. under vacuum) to yield the title compound as a white solid (154 mg, 90%). $^1$H NMR (300 MHz, CDCl$_3$): δ 8.85 (d, J=1.3 Hz, 1H), 8.36 (dd, J=7.0, 1.7 Hz, 1H), 8.01 (d, J=7.1 Hz, 1H), 7.59 (dd, J=7.6, 2.7 Hz, 1H), 7.55 (dd, J=7.3, 2.7 Hz, 1H). LCMS (Method F): RT=2.34, m/z: 306 [M+H$^+$].

Step 5. 3-Chloro-2-(4-chlorothiazolo[5,4-c]pyridin-2-yl)-5-fluorobenzonitrile

To a suspension of 3-chloro-5-fluoro-2-(5-oxythiazolo[5,4-c]pyridin-2-yl)-benzonitrile (154 mg, 0.50 mmol) in DCE (2.5 mL) was added phosphorus oxychloride (0.15 mL, 1.62 mmol). The resultant mixture was heated at 70° C. After 6 hours, a further portion of phosphorus oxychloride (6 drops) was added and heating was continued for 16 hours. The cooled reaction mixture was treated with aqueous sodium bicarbonate, the phases were separated and the aqueous phase was extracted five times with DCM. The combined organic washings were dried (Na$_2$SO$_4$), filtered and concentrated in vacuo. The crude residue was purified by chromatography on silica (10-50% ethyl acetate in cyclohexane) to give the title compound as a yellow solid (118 mg, 73%). $^1$H NMR (300 MHz, CDCl$_3$): δ 8.55 (d, J=5.7 Hz, 1H), 8.02 (d, J=5.7 Hz, 1H), 7.59 (dd, J=7.8, 2.5 Hz, 1H), 7.55 (dd, J=7.3, 2.5 Hz, 1H). LCMS (Method D): RT=3.84, m/z: 324 [M+H$^+$].

Step 6. 2-(4-Bromothiazolo[5,4-c]pyridin-2-yl)-3-chloro-5-fluorobenzonitrile

To a suspension of 3-chloro-2-(4-chlorothiazolo[5,4-c]pyridin-2-yl)-5-fluorobenzonitrile (118 mg, 0.36 mmol) in propionitrile (3.5 mL) was added bromotrimethylsilane (0.15 mL, 1.1 mmol) and the reaction mixture was heated at 50° C. for 7 hours. The cooled mixture was treated with aqueous sodium bicarbonate and extracted three times with DCM. The combined organic washings were dried (Na$_2$SO$_4$), filtered and concentrated in vacuo to give the title compound as a yellow solid (133 mg, 100%). $^1$H NMR (300 MHz, CDCl$_3$): δ 8.53 (d, J=5.6 Hz, 1H), 8.04 (d, J=5.6 Hz, 1H), 7.59 (dd, J=7.7, 2.5 Hz, 1H), 7.55 (dd, J=7.3, 2.5 Hz, 1H). LCMS (Method D): RT=3.88, m/z: 368 [M+H$^+$].

Step 7. 3-Chloro-5-fluoro-2-[4-(6-hydroxymethylpyrimidin-4-ylamino)-thiazolo[5,4-c]pyridin-2-yl]benzonitrile hydrochloride A mixture of 2-(4-bromothiazolo[5,4-c]pyridin-2-yl)-3-chloro-5-fluorobenzonitrile (98 mg, 0.26 mmol), (6-aminopyrimidin-4-yl)-methanol (33 mg, 0.26 mmol), Pd$_2$(dba)$_3$ (12 mg, 0.013 mmol), XantPhos (15 mg, 0.026 mmol) and cesium carbonate (219 mg, 0.67 mmol) in 1,4-dioxane (2 mL) was heated under argon at 80° C. for 16 hours. The cooled reaction mixture was diluted with water and extracted five times with ethyl acetate, then three times with 10% methanol in DCM. The combined organic extracts were dried (Na$_2$SO$_4$), filtered and concentrated in vacuo. The crude product was purified by chromatography on silica (20-100% ethyl acetate in cyclohexane) to yield the free base of the title compound (41 mg, 38%). This material was suspended in DCM (2 mL) and 2-propanol (0.5 mL), and a solution of hydrogen chloride in 2-propanol (1.25 N, 1 mL) was added and the resultant mixture was stirred for 10 minutes. The solvent was removed under reduced pressure and the resultant residue was triturated three times with diethylether and dried (50° C. under vacuum) to give the title compound as an off-white solid (44 mg). $^1$H NMR (400 MHz, DMSO-d$_6$): δ 8.93 (s, 1H), 8.59 (d, J=5.6 Hz, 1H), 8.28-8.23 (m, 2H), 8.05 (d, J=5.6 Hz, 1H), 7.87 (br s, 1H), 4.64 (s, 2H). LCMS (Method C): RT=3.14, m/z: 413 [M+H$^+$].

Additional compounds shown in Table 3 were also made according to the above procedures.

TABLE 3

| Example | Structure | Name | Synth. Method | LCMS (ESI) m/z [M + H⁺] | LCMS Method | R$_T$ (min) | NMR |
|---|---|---|---|---|---|---|---|
| 235 | 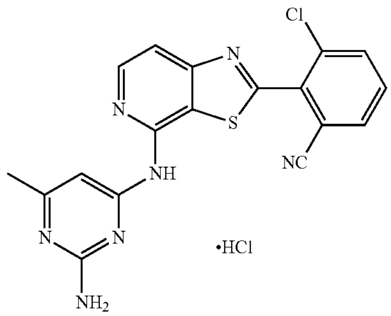 [SMILES: Cc1cc(Nc2nccc3nc(-c4c(Cl)cccc4C#N)sc23)nc(N)n1 ; Cl] | 2-[4-(2-Amino-6-methyl-pyrimidin-4-ylamino)-thiazolo[5,4-c]pyridin-2-yl]-3-chloro-benzonitrile hydrochloride salt | 2 | 394 | C | 2.88 | $^1$H NMR (400 MHz, DMSO-d$_6$): δ 13.12 (br s, 1H), 11.55 (br s, 1H), 8.52 (d, J = 5.6 Hz, 1H), 8.09 (dd, J = 0.9, 7.8 Hz, 1H), 8.04 (dd, J = 1.1, 8.3 Hz, 1H), 8.01 (d, J = 5.5 Hz, 1H), 7.08 (t, J = 8.2 Hz, 1H), 6.56 (br s, 1H), 2.27 (s, 3H). |
| 236 | 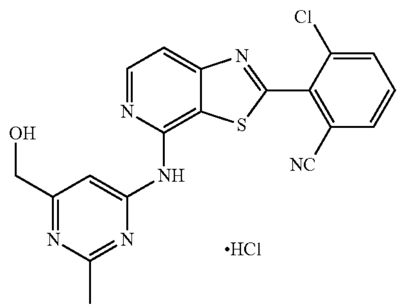 [SMILES: Cc1nc(CO)cc(Nc2nccc3nc(-c4c(Cl)cccc4C#N)sc23)n1 ; Cl] | 3-Chloro-2-[4-(6-hydroxy-methyl-2-methyl-pyrimidin-4-ylamino)-thiazolo[5,4-c]pyridin-2-yl]-benzonitrile hydrochloride salt | 2 | 409 | C | 2.85 | $^1$H NMR (400 MHz, DMSO-d$_6$): δ 11.91 (br s, 1H), 8.54 (d, J = 5.6 Hz, 1H), 8.09 (d, J = 1.0, 7.8 Hz, 1H), 8.05 (dd, J = 1.3, 8.4 Hz, 1H), 8.02 (d, J = 5.5 Hz, 1H), 7.81 (t, J = 8.3 Hz, 1H), 7.58 (br s, 1H), 4.59 (s, 2H), 2.56 (s, 3H). |
| 237 | 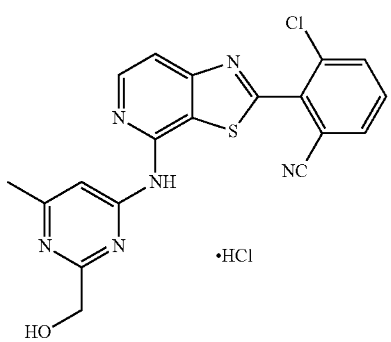 [SMILES: Cc1cc(Nc2nccc3nc(-c4c(Cl)cccc4C#N)sc23)nc(CO)n1 ; Cl] | 3-Chloro-2-[4-(2-hydroxy-methyl-6-methyl-pyrimidin-4-ylamino)-thiazolo[5,4-c]pyridin-2-yl]-benzonitrile hydrochloride salt | 2 | 409 | C | 2.91 | $^1$H NMR (400 MHz, DMSO-d$_6$): δ 11.02 (br s, 1H), 8.45 (d, J = 5.6 Hz, 1H), 8.09-8.02 (m, 2H), 7.87 (d, J = 5.6 Hz, 1H), 7.80 (t, J = 8.0 Hz, 1H), 7.39 (br s, 1H), 4.48 (s, 2H), 2.40 (s, 3H). |
| 238 | 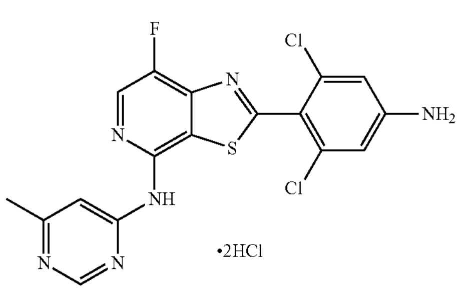 [SMILES: Cc1cc(Nc2ncc(F)c3nc(-c4c(Cl)cc(N)cc4Cl)sc23)ncn1 ; "·2HCl"] | [2-(4-Amino-2,6-dichloro-phenyl)-7-fluoro-thiazolo[5,4-c]pyridin-4-yl]-(6-methyl-pyrimidin-4-yl)-amine dihydrochloride salt | 2 | 422 | C | 3.23 | $^1$H NMR (400 MHz, DMSO-d$_6$): δ 11.75 (br s, 1H), 8.89 (s, 1H), 8.52 (d, J = 1.9 Hz, 1H), 7.53 (s, 1H), 6.74 (s, 2H), 2.50 (s, 3H). |

TABLE 3-continued

| Example | Structure | Name | Synth. Method | LCMS (ESI) m/z [M + H⁺] | LCMS Method | R_T (min) | NMR |
|---|---|---|---|---|---|---|---|
| 239 | 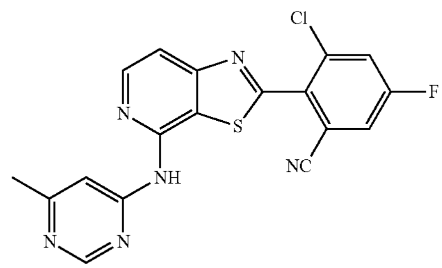 [SMILES: Cc1cc(Nc2nccc3nc(-c4c(Cl)cc(F)cc4C#N)sc23)ncn1] | 3-Chloro-5-fluoro-2-[4-(6-methyl-pyrimidin-4-ylamino)-thiazolo[5,4-c]pyridin-2-yl]benzonitrile | 2 | 397 | C | 3.26 | $^1$H NMR (400 MHz, DMSO-d$_6$): δ 10.70 (s, 1H), 8.59 (s, 1H), 8.43 (d, J = 5.6 Hz, 1H), 8.21-8.15 (m, 2H), 7.82 (d, J = 5.8 Hz, 1H), 7.52 (s, 1H), 2.35 (s, 3H). |
| 240 | 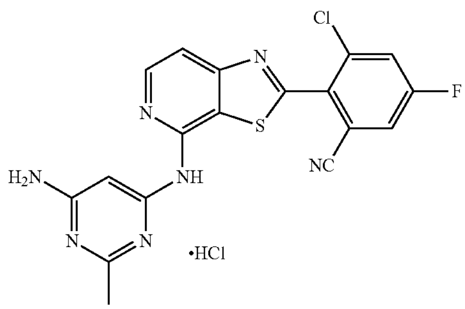 [SMILES: Cc1nc(N)cc(Nc2nccc3nc(-c4c(Cl)cc(F)cc4C#N)sc23)n1 ; Cl] | 2-[4-(6-Amino-2-methyl-pyrimidin-4-ylamino)-thiazolo[5,4-c]pyridin-2-yl]-3-chloro-5-fluoro-benzonitrile hydrochloride | 2 | 412 | C | 3.08 | $^1$H NMR (400 MHz, DMSO-d$_6$): δ 11.34 (br s, 1H), 8.49 (d, J = 5.6 Hz, 1H), 8.24-8.17 (m, 2H), 7.92 (d, J = 5.6 Hz, 1H), 7.09 (br s, 1H), 2.50 (s, 3H). |

Specific reference is made to U.S. Provisional Patent Application Ser. No. 61/383,273, filed Sep. 15, 2010, which is incorporated herein by reference in its entirety for all purposes. Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

What is claimed is:
1. A compound selected from:
2-(2,6-Dichlorophenyl)-N-(6-methyl-2-morpholinopyrimidin-4-yl)thiazolo[5,4-c]pyridin-4-amine;
2-(2,6-Dichlorophenyl)-N-(2,6-dimethylpyrimidin-4-yl)thiazolo[5,4-c]pyridin-4-amine;
N-(2-(2,6-Dichlorophenyl)thiazolo[5,4-c]pyridin-4-yl)cyclopropanecarboxamide;
N-(6-(aminomethyl)pyrimidin-4-yl)-2-(2,6-dichlorophenyl)thiazolo[5,4-c]pyridin-4-amine;
4-[4-(2-Amino-6-methyl-pyrimidin-4-ylamino)-thiazolo[5,4-c]pyridin-2-yl]-3,5-dichloro-benzonitrile;
3-(6-(2-(2,6-dichlorophenyl)thiazolo[4,5-d]pyrimidin-7-ylamino)pyrimidin-4-yl)cyclobutanol;
N-(2-(2,6-dichlorophenyl)thiazolo[4,5-d]pyrimidin-7-yl)cyclopropanecarboxamide;
3-Chloro-5-fluoro-4-[4-(6-methyl-pyrimidin-4-ylamino)-thiazolo[5,4-c]pyridin-2-yl]-benzonitrile;
{3,5-Dichloro-4-[4-(6-methyl-pyrimidin-4-ylamino)-thiazolo[5,4-c]pyridin-2-yl]-phenyl}-methanol;
3,5-Dichloro-4-{4-[6-(2-hydroxy-ethylamino)-pyrimidin-4-ylamino]-thiazolo[5,4-c]pyridin-2-yl}-benzonitrile;
3,5-Dichloro-4-{4-[5-(3-hydroxy-azetidin-1-yl)-pyrimidin-4-ylamino]-thiazolo[5,4-c]pyridine-2-yl}-benzonitrile;
2-[2-(2,6-Dichloro-4-cyano-phenyl)-thiazolo[5,4-c]pyridine-4-ylamino]-isonicotinonitrile;
(2-(2-(2,6-dichlorophenyl)thiazolo[5,4-c]pyridin-4-ylamino)pyridin-4-yl)methanol;
N-(6-(2-(2-Chloro-6-fluorophenyl)thiazolo[5,4-c]pyridin-4-ylamino)pyrimidin-4-yl)acetamide;
1-(2-(2-Chloro-6-fluorophenyl)thiazolo[5,4-c]pyridin-4-yl)-3-cyclopropylurea;
1-(6-(2-(2-Chloro-6-fluorophenyl)thiazolo[5,4-c]pyridin-4-ylamino)pyrimidin-4-yl)ethane-1,2-diol;
2-(2-Chloro-6-fluorophenyl)-N-(2-methyl-6-morpholinopyrimidin-4-yl)thiazolo[5,4-c]pyridin-4-amine;
N-(2-(2-Chloro-6-fluorophenyl)thiazolo[5,4-c]pyridin-4-yl)cyclopropanecarboxamide;
6-(2-(2,6-Dichlorophenyl)thiazolo[5,4-c]pyridin-4-ylamino)pyrimidine-4-carbonitrile;
N-(2-(2,6-Dichlorophenyl)thiazolo[5,4-c]pyridin-4-yl)-2-(dimethylamino)acetamide;
N-(2-(2,6-Dichlorophenyl)thiazolo[5,4-c]pyridin-4-yl)-2-hydroxyacetamide;
2-(2,6-Dichlorophenyl)thiazolo[5,4-c]pyridin-4-ylcarbamate;
(6-(2-(2,6-Dichlorophenyl)thiazolo[5,4-c]pyridin-4-ylamino)pyrimidin-4-yl)methanol;
2-(4-(6-(2-(2,6-Dichlorophenyl)thiazolo[5,4-c]pyridin-4-ylamino)-2-methylpyrimidin-4-yl)piperazin-1-yl)ethanol;
2-(2,6-Dichlorophenyl)-N-(1H-pyrazol-4-yl)thiazolo[5,4-c]pyridin-4-amine;
N-(2-(2,6-Dichlorophenyl)thiazolo[5,4-c]pyridin-4-yl)acetamide;
2-(2,6-dichlorophenyl)-N-(2-methyl-6-morpholinopyrimidin-4-yl)thiazolo[5,4-c]pyridin-4-amine;
2-(2,6-dichlorophenyl)-N-(6-morpholinopyrimidin-4-yl)thiazolo[5,4-c]pyridin-4-amine;
2-(4-(6-(2-(2,6-dichlorophenyl)thiazolo[5,4-c]pyridin-4-ylamino)pyrimidin-4-yl)piperazin-1-yl)ethanol;

1-(6-(2-(2,6-dichlorophenyl)thiazolo[5,4-c]pyridin-4-ylamino)pyrimidin-4-yl)azetidin-3-ol;
2-((6-(2-(2,6-dichlorophenyl)thiazolo[5,4-c]pyridin-4-ylamino)pyrimidin-4-yl)(methyl)amino)ethanol;
2,2'-(6-(2-(2,6-dichlorophenyl)thiazolo[5,4-c]pyridin-4-ylamino)pyrimidin-4-ylazanediyl)diethanol;
2-(2,6-dichlorophenyl)-N-(pyridin-2-yl)thiazolo[5,4-c]pyridin-4-amine;
2-(2,6-dichlorophenyl)-N-(pyrimidin-4-yl)thiazolo[5,4-c]pyridin-4-amine;
2-(6-(2-(2,6-dichlorophenyl)thiazolo[5,4-c]pyridin-4-ylamino)pyrimidin-4-ylamino)ethanol;
N-4-(2-(2,6-dichlorophenyl)thiazolo[5,4-c]pyridin-4-yl)pyrimidine-4,6-diamine;
2-(2-chloro-6-fluorophenyl)-N-(2,6-dimethylpyrimidin-4-yl)thiazolo[5,4-c]pyridin-4-amine;
2-(2-chloro-6-fluorophenyl)-N-(6-methyl-2-morpholinopyrimidin-4-yl)thiazolo[5,4-c]pyridin-4-amine;
2-(2-chloro-6-fluorophenyl)-N-(6-morpholinopyrimidin-4-yl)thiazolo[5,4-c]pyridin-4-amine;
2-(4-(6-(2-(2-chloro-6-fluorophenyl)thiazolo[5,4-c]pyridin-4-ylamino)-2-methylpyrimidin-4-yl)piperazin-1-yl)ethanol;
2-(4-(6-(2-(2-chloro-6-fluorophenyl)thiazolo[5,4-c]pyridin-4-ylamino)pyrimidin-4-yl)piperazin-1-yl)ethanol;
2-((6-(2-(2-chloro-6-fluorophenyl)thiazolo[5,4-c]pyridin-4-ylamino)pyrimidin-4-yl)(methyl)amino)ethanol;
2,2'-(6-(2-(2-chloro-6-fluorophenyl)thiazolo[5,4-c]pyridin-4-ylamino)pyrimidin-4-ylazanediyl)diethanol;
(6-(2-(2-chloro-6-fluorophenyl)thiazolo[5,4-c]pyridin-4-ylamino)pyrimidin-4-yl)methanol;
1-(6-(2-(2,6-dichlorophenyl)thiazolo[5,4-c]pyridin-4-ylamino)pyrimidin-4-yl)ethane-1,2-diol;
2-(6-(2-(2-chloro-6-fluorophenyl)thiazolo[5,4-c]pyridin-4-ylamino)pyrimidin-4-ylamino)ethanol;
N-(2-(2-chlorophenyl)thiazolo[5,4-c]pyridin-4-yl)cyclopropanecarboxamide;
2-(2-chloro-6-fluorophenyl)-N-(6-methylpyrimidin-4-yl)thiazolo[5,4-c]pyridin-4-amine;
methyl 2-(2,6-dichlorophenyl)thiazolo[5,4-c]pyridin-4-ylcarbamate;
methyl 2-(2-chloro-6-fluorophenyl)thiazolo[5,4-c]pyridin-4-ylcarbamate;
N-(2-(2-chloro-6-fluorophenyl)thiazolo[5,4-c]pyridin-4-yl)-2-hydroxyacetamide;
2-(2,6-dichlorophenyl)-N-(6-methylpyrimidin-4-yl)thiazolo[5,4-c]pyridin-4-amine;
N-4-(2-(2-chloro-6-fluorophenyl)thiazolo[5,4-c]pyridin-4-yl)pyrimidine-4,6-diamine;
1-cyclopropyl-3-(2-(2,6-dichlorophenyl)thiazolo[5,4-c]pyridin-4-yl)urea;
2-(2-chlorophenyl)-N-(2,6-dimethylpyrimidin-4-yl)thiazolo[5,4-c]pyridin-4-amine;
1-(2-(2-chloro-6-fluorophenyl)thiazolo[5,4-c]pyridin-4-yl)-3-methylurea;
N-4-(2-(2,6-dichlorophenyl)thiazolo[5,4-c]pyridin-4-yl)-N-6-methylpyrimidine-4,6-diamine;
N-4-(2-(2-chloro-6-fluorophenyl)thiazolo[5,4-c]pyridin-4-yl)-N-6-methylpyrimidine-4,6-diamine;
2-(2,6-dichlorophenyl)-N-(6-((dimethylamino)methyl)pyrimidin-4-yl)thiazolo[5,4-c]pyridin-4-amine;
2-(2-chloro-6-fluorophenyl)-N-(6-((dimethylamino)methyl)pyrimidin-4-yl)thiazolo[5,4-c]pyridin-4-amine;
N-(2-(2-chloro-6-fluorophenyl)thiazolo[5,4-c]pyridin-4-yl)-2-(dimethylamino)acetamide;
6-(2-(2-chloro-6-fluorophenyl)thiazolo[5,4-c]pyridin-4-ylamino)pyrimidine-4-carbonitrile;
N-(6-(2-(2,6-dichlorophenyl)thiazolo[5,4-c]pyridin-4-ylamino)pyrimidin-4-yl)acetamide;
2-amino-N-(2-(2,6-dichlorophenyl)thiazolo[5,4-c]pyridin-4-yl)acetamide;
2-amino-N-(2-(2-chloro-6-fluorophenyl)thiazolo[5,4-c]pyridin-4-yl)acetamide;
2-(6-(2-(2,6-dichlorophenyl)thiazolo[5,4-c]pyridin-4-ylamino)pyrimidin-4-yl)propan-2-ol;
2-(6-(2-(2-chloro-6-fluorophenyl)thiazolo[5,4-c]pyridin-4-ylamino)pyrimidin-4-yl)propan-2-ol;
3-amino-N-(2-(2,6-dichlorophenyl)thiazolo[5,4-c]pyridin-4-yl)propanamide;
1-(2-(2,6-dichlorophenyl)thiazolo[5,4-c]pyridin-4-yl)-3-methylurea;
3-amino-N-(2-(2-chloro-6-fluorophenyl)thiazolo[5,4-c]pyridin-4-yl)propanamide;
6-(2-(2,6-dichlorophenyl)thiazolo[5,4-c]pyridin-4-ylamino)-N-methylpyrimidine-4-carboxamide;
(6-(2-(2,6-dichlorophenyl)thiazolo[5,4-c]pyridin-4-ylamino)pyrimidin-4-yl)(morpholino)methanone;
6-(2-(2-chloro-6-fluorophenyl)thiazolo[5,4-c]pyridin-4-ylamino)-N-methylpyrimidine-4-carboxamide;
(2-(2-(2-chloro-6-fluorophenyl)thiazolo[5,4-c]pyridin-4-ylamino)pyrimidin-4-yl)methanol;
2-(2,6-dichlorophenyl)-N-(4-methylpyridin-2-yl)thiazolo[5,4-c]pyridin-4-amine;
N-(4-(aminomethyl)pyrimidin-2-yl)-2-(2,6-dichlorophenyl)thiazolo[5,4-c]pyridin-4-amine;
N-(4-(aminomethyl)pyrimidin-2-yl)-2-(2-chloro-6-fluorophenyl)thiazolo[5,4-c]pyridin-4-amine;
6-[2-(2,6-Dichloro-4-cyano-phenyl)-thiazolo[5,4-c]pyridine-4-ylamino]-nicotinonitrile;
3,5-Dichloro-4-[4-(2,6-dimethyl-pyrimidin-4-ylamino)-thiazolo[5,4-c]pyridine-2-yl]-benzonitrile;
Cyclopropanecarboxylic acid [2-(2,6-dichloro-4-cyano-phenyl)-thiazolo[5,4-c]pyridin-4-yl]-amide;
3,5-Dichloro-4-[4-(pyrimidin-4-ylamino)-thiazolo[5,4-c]pyridin-2-yl]-benzonitrile;
3,5-Dichloro-4-[4-(6-methyl-pyrimidin-4-ylamino)-thiazolo[5,4-c]pyridin-2-yl]-benzonitrile;
1-[2-(2,6,-Dichloro-4-cyano-phenyl)-thiazolo[5,4-c]pyridine-4-yl]-3-methyl-urea;
3,5-Dichloro-4-[4-(6-morpholin-4-yl-pyrimidin-4-ylamino)-thiazolo[5,4-c]pyridine-2-yl]-benzonitrile;
3,5-Dichloro-4-(4-{6-(2-hydroxy-ethyl)-piperazin-1-yl]-pyrimidin-4-ylamino}-thiazolo[5,4-c]pyridine-2-yl)-benzonitrile;
3,5-Dichloro-4-[4-(5-hydroxymethyl-pyrimidin-4-ylamino)-thiazolo[5,4-c]pyridine-2-yl}-benzonitrile;
3,5-Dichloro-4-[4-(4-hydroxymethyl-pyridin-2-ylamino)-thiazolo[5,4-c]pyridin-2-yl]-benzonitrile;
3,5-Dichloro-4-[4-(6-dimethylaminomethyl-pyrimidin-4-ylamino)-thiazolo[5,4-c]pyridin-2-yl]-benzonitrile;
6-[2-(2,6-Dichloro-4-cyano-phenyl)-thiazolo[5,4-c]pyridin-4-ylamino]-pyrimidine-4-carboxylic acid amide;
N-{6-[2-(2,6-Dichloro-4-cyano-phenyl)-thiazolo[5,4-c]pyridin-4-ylamino]-pyrimidin-4-yl}-acetamide;
3,5-Dichloro-4-[4-(5-hydroxymethyl-pyridin-2-ylamino)-thiazolo[5,4-c]pyridin-2-yl]-benzonitrile;
3,5-Dichloro-4-[4-(6-methoxy-pyrimidin-4-ylamino)-thiazolo[5,4-c]pyridin-2-yl]-benzonitrile;
3,5-Dichloro-4-[4-(5-methyl-pyrazin-2-ylamino)-thiazolo[5,4-c]pyridin-2-yl]-benzonitrile;
3,5-Dichloro-4-[4-(6-methyl-pyridazin-3-ylamino)-thiazolo[5,4-c]pyridin-2-yl]-benzonitrile;
[2-(2,6-Dichloro-4-cyano-phenyl)-thiazolo[5,4-c]pyridin-4-yl]-carbamic acid methyl ester;

3,5-Dichloro-4-[4-(6-methylamino-pyrimidin-4-ylamino)-thiazolo[5,4-c]pyridin-2-yl]-benzonitrile;
4-[4-(6-Amino-pyrimidin-4-ylamino)-thiazolo[5,4-c]pyridin-2-yl]-3,5-dichloro-benzonitrile;
3,5-Dichloro-4-{4-[6-(2-hydroxy-2-methyl-propylamino)-pyrimidin-4-ylamino]-thiazolo[5,4-c]pyridin-2-yl}-benzonitrile;
3-Chloro-4-[4-(2,6-dimethyl-pyrimidin-4-ylamino)-thiazolo[5,4-c]pyridin-2-yl]-5-fluoro-benzonitrile;
1-[2-(2-Chloro-4-cyano-6-fluoro-phenyl)-thiazolo[5,4-c]pyridin-4-yl]-3-methyl-urea;
2-(2,6-dichlorophenyl)-N-(pyrimidin-4-yl)thiazolo[4,5-d]pyrimidin-7-amine;
2-(2,6-dichlorophenyl)-N-(2,6-dimethylpyrimidin-4-yl)thiazolo[4,5-d]pyrimidin-7-amine;
[2-(2,6-dichlorophenyl)-N-(6-methylpyrimidin-4-yl)thiazolo[4,5-d]pyrimidin-7-amine;
2-(4-(6-(2-(2,6-dichlorophenyl)thiazolo[4,5-d]pyrimidin-7-ylamino)pyrimidin-4-yl)piperazin-1-yl)ethanol;
3-Chloro-5-fluoro-4-[4-(6-hydroxymethyl-pyrimidin-4-ylamino)-thiazolo[5,4-c]pyridin-2-yl]-benzonitrile;
(6-(2-(2-chloro-6-fluorophenyl)thiazolo[5,4-c]pyridin-4-ylamino)pyrimidin-4-yl)(morpholino)methanone;
2-(2-chloro-6-fluorophenyl)-N-(pyridin-2-yl)thiazolo[5,4-c]pyridin-4-amine;
2-(2-chloro-6-fluorophenyl)-N-(4-methylpyridin-2-yl)thiazolo[5,4-c]pyridin-4-amine;
2-(2,6-dichlorophenyl)-N-(pyridazin-3-yl)thiazolo[5,4-c]pyridin-4-amine;
6-(2-(2,6-dichlorophenyl)thiazolo[5,4-c]pyridin-4-ylamino)pyrimidine-4-carboxamide;
2-(2-chloro-6-fluorophenyl)-N-(pyridazin-3-yl)thiazolo[5,4-c]pyridin-4-amine;
2-(2-(2,6-dichlorophenyl)thiazolo[5,4-c]pyridin-4-ylamino)isonicotinonitrile;
6-(2-(2,6-dichlorophenyl)thiazolo[5,4-c]pyridin-4-ylamino)pyridazine-3-carboxamide;
(6-(2-(2,6-dichlorophenyl)thiazolo[5,4-c]pyridin-4-ylamino)pyridazin-3-yl)(morpholino)methanone;
(6-(2-(2-chloro-6-fluorophenyl)thiazolo[5,4-c]pyridin-4-ylamino)pyridazin-3-yl)(morpholino)methanone;
6-(2-(2,6-dichlorophenyl)thiazolo[5,4-c]pyridin-4-ylamino)-N,N-dimethylpyridazine-3-carboxamide;
6-(2-(2-chloro-6-fluorophenyl)thiazolo[5,4-c]pyridin-4-ylamino)-N,N-dimethylpyridazine-3-carboxamide;
2-(2,6-dichlorophenyl)-N-(pyrazin-2-yl)thiazolo[5,4-c]pyridin-4-amine;
2-(2-(2,6-dichlorophenyl)thiazolo[5,4-c]pyridin-4-ylamino)isonicotinamide;
6-(2-(2-chloro-6-fluorophenyl)thiazolo[5,4-c]pyridin-4-ylamino)pyridazine-3-carboxamide;
N-(6-(aminomethyl)pyrimidin-4-yl)-2-(2-chloro-6-fluorophenyl)thiazolo[5,4-c]pyridin-4-amine;
2-(2-chloro-6-fluorophenyl)-N-(pyrazin-2-yl)thiazolo[5,4-c]pyridin-4-amine;
5-(2-(2,6-dichlorophenyl)thiazolo[5,4-c]pyridin-4-ylamino)pyrazine-2-carboxamide;
isopropyl 2-(2,6-dichlorophenyl)thiazolo[5,4-c]pyridin-4-ylcarbamate;
1-(2-(2,6-dichlorophenyl)thiazolo[5,4-c]pyridin-4-yl)-3-(2-hydroxyethyl)urea;
4-[4-(6-Amino-2-methylpyrimidin-4-ylamino)thiazolo[5,4-c]pyridin-2-yl]-3,5-dichloro-benzonitrile;
3,5-Dichloro-4-[4-(6-ethylpyrimidin-4-ylamino)thiazolo[5,4-c]pyridin-2-yl]-benzonitrile;
3,5-Dichloro-4-[4-(6-ethylpyrimidin-4-ylamino)thiazolo[5,4-c]pyridin-2-yl]-benzamide;
4-[4-(6-Aminopyrimidin-4-ylamino)thiazolo[5,4-c]pyridin-2-yl]-3-chloro-5-fluorobenzonitrile;
N-[2-(4-Amino-2,6-dichlorophenyl)thiazolo[5,4-c]pyridin-4-yl]-pyrimidine-4,6-diamine;
[2-(4-Amino-2,6-dichlorophenyl)thiazolo[5,4-c]pyridin-4-yl]-(6-methylpyrimidin-4-yl)-amine;
{4-[4-(6-Aminopyrimidin-4-ylamino)thiazolo[5,4-c]pyridin-2-yl]-3,5-dichlorophenyl}-methanol;
N-[2-(4-Aminomethyl-2,6-dichlorophenyl)thiazolo[5,4-c]pyridin-4-yl]-pyrimidine-4,6-diamine;
[2-(4-Aminomethyl-2,6-dichlorophenyl)thiazolo[5,4-c]pyridin-4-yl]-(6-methylpyrimidin-4-yl)-amine;
[2-(2,6-Dichloro-4-methoxyphenyl)thiazolo[5,4-c]pyridin-4-yl]-(6-methylpyrimidin-4-yl)-amine;
[2-(4-Azetidin-3-yl-2,6-dichlorophenyl)thiazolo[5,4-c]pyridin-4-yl]-(6-methylpyrimidin-4-yl)-amine;
[2-(2,6-Dichloro-4-cyclopropylphenyl)thiazolo[5,4-c]pyridin-4-yl]-(6-methylpyrimidin-4-yl)-amine;
I-{3,5-Dichloro-4-[4-(6-methylpyrimidin-4-ylamino)thiazolo[5,4-c]pyridin-2-yl]-phenyl}-acetamide;
[2-(2-Chloro-6-fluorophenyl)-7-fluorothiazolo[5,4-c]pyridin-4-yl]-(6-methylpyrimidin-4-yl)-amine;
N-[2-(2-Chloro-6-fluorophenyl)-7-fluorothiazolo[5,4-c]pyridin-4-yl]-pyrimidine-4,6-diamine;
[2-(2,6-Dichlorophenyl)-7-fluorothiazolo[5,4-c]pyridin-4-yl]-(6-methylpyrimidin-4-yl)-amine;
[2-(2,6-Dichlorophenyl)-7-fluorothiazolo[5,4-c]pyridin-4-yl]-carbamic acid methyl ester;
3,5-Dichloro-4-[7-fluoro-4-(6-methylpyrimidin-4-ylamino)thiazolo[5,4-c]pyridin-2-yl]-benzonitrile;
2-[4-(6-Aminopyrimidin-4-ylamino)thiazolo[5,4-c]pyridin-2-yl]-3-chlorobenzonitrile;
3-Chloro-2-[4-(6-hydroxymethylpyrimidin-4-ylamino)thiazolo[5,4-c]pyridin-2-yl]-benzonitrile;
2-[4-(6-Amino-2-methylpyrimidin-4-ylamino)-thiazolo[5,4-c]pyridin-2-yl]-3-chlorobenzonitrile;
3-Chloro-2-[7-fluoro-4-(6-methylpyrimidin-4-ylamino)thiazolo[5,4-c]pyridin-2-yl]-benzonitrile;
3-Chloro-2-[7-fluoro-4-(6-hydroxymethyl-pyrimidin-4-ylamino)-thiazolo[5,4-c]pyridin-2-yl]-benzonitrile;
3-Fluoro-2-[7-fluoro-4-(6-methylpyrimidin-4-ylamino)-thiazolo[5,4-c]pyridin-2-yl]-benzonitrile;
7-bromo-2-(2-chloro-6-fluorophenyl)-N-(6-methylpyrimidin-4-yl)thiazolo[5,4-c]pyridin-4-amine;
2-(2-chloro-6-fluorophenyl)-4-(6-methylpyrimidin-4-ylamino)thiazolo[5,4-c]pyridine-7-carbonitrile;
2-(2-cyano-6-fluorophenyl)-4-(6-methylpyrimidin-4-ylamino)thiazolo[5,4-c]pyridine-7-carbonitrile;
(2-(2-chloro-6-fluorophenyl)-4-(6-methylpyrimidin-4-ylamino)thiazolo[5,4-c]pyridin-7-yl)methanol;
(1S,2S)—N-(2-(2,6-dichlorophenyl)thiazolo[5,4-c]pyridin-4-yl)-2-fluorocyclopropanecarboxamide;
(1R,2R)—N-(2-(2,6-dichlorophenyl)thiazolo[5,4-c]pyridin-4-yl)-2-fluoro-cyclopropane-carboxamide;
(1R,2S)—N-(2-(2,6-dichlorophenyl)thiazolo[5,4-c]pyridin-4-yl)-2-(hydroxymethyl)cyclopropane-carboxamide;
(1S,2R)—N-(2-(2,6-dichlorophenyl)thiazolo[5,4-c]pyridin-4-yl)-2-(hydroxymethyl)cyclopropane-carboxamide;
2-(4-amino-2-chloro-6-fluorophenyl)-N-(6-methylpyrimidin-4-yl)thiazolo[5,4-c]pyridin-4-amine;
Cyclopropylmethyl 2-(2,6-dichlorophenyl)thiazolo[5,4-c]pyridin-4-ylcarbamate;
2-(2,6-Dichlorophenyl)-N-(5-methylpyrazin-2-yl)thiazolo[5,4-c]pyridin-4-amine;

2-(2-Chloro-6-fluorophenyl)-N-(5-methylpyrazin-2-yl) thiazolo[5,4-c]pyridin-4-amine;
5-(2-(2,6-Dichlorophenyl)thiazolo[5,4-c]pyridin-4-ylamino)pyrazine-2-carbonitrile;
(5-(2-(2,6-Dichlorophenyl)thiazolo[5,4-c]pyridin-4-ylamino)pyrazin-2-yl)methanol;
2-(2,6-Dichlorophenyl)-N-(6-methylpyrimidin-4-yl)thiazolo[5,4-c]pyridin-4-amine;
Cyclopropylmethyl 2-(2-chloro-6-fluorophenyl)thiazolo[5,4-c]pyridin-4-ylcarbamate;
2-(2,6-Dichlorophenyl)-N-(6-(morpholinomethyl)pyrimidin-4-yl)thiazolo[5,4-c]pyridin-4-amine;
2-(2-Chloro-6-fluorophenyl)-N-(6-(morpholinomethyl)pyrimidin-4-yl)thiazolo[5,4-c]pyridin-4-amine;
(R)-1-(6-(2-(2-Chloro-6-fluorophenyl)thiazolo[5,4-c]pyridin-4-ylamino)pyrimidin-4-yl)ethanol;
(S)-1-(6-(2-(2-Chloro-6-fluorophenyl)thiazolo[5,4-c]pyridin-4-ylamino)pyrimidin-4-yl)ethanol;
(R)-1-(6-(2-(2,6-Dichlorophenyl)thiazolo[5,4-c]pyridin-4-ylamino)pyrimidin-4-yl)ethanol;
(S)-1-(6-(2-(2,6-Dichlorophenyl)thiazolo[5,4-c]pyridin-4-ylamino)pyrimidin-4-yl)ethanol;
(R)—N-(6-(1-Aminoethyl)pyrimidin-4-yl)-2-(2,6-dichlorophenyl)thiazolo[5,4-c]pyridin-4-amine;
(S)—N-(6-(1-Aminoethyl)pyrimidin-4-yl)-2-(2,6-dichlorophenyl)thiazolo[5,4-c]pyridin-4-amine;
5-(2-(2-Chloro-6-fluorophenyl)thiazolo[5,4-c]pyridin-4-ylamino)pyrazine-2-carbonitrile;
N-(5-(Aminomethyl)pyrazin-2-yl)-2-(2,6-dichlorophenyl)thiazolo[5,4-c]pyridin-4-amine;
2-(2,6-Dichlorophenyl)-N-(5-((methylamino)methyl) pyrazin-2-yl)thiazolo[5,4-c]pyridin-4-amine;
(5-(2-(2-Chloro-6-fluorophenyl)thiazolo[5,4-c]pyridin-4-ylamino)pyrazin-2-yl)methanol;
N-(5-(Aminomethyl)pyrazin-2-yl)-2-(2-chloro-6-fluorophenyl)thiazolo[5,4-c]pyridin-4-amine;
2-(2-Chloro-6-fluorophenyl)-N-(5-((methylamino)methyl)pyrazin-2-yl)thiazolo[5,4-c]pyridin-4-amine;
6-(2-(2,6-Dichlorophenyl)thiazolo[5,4-c]pyridin-4-ylamino)-N-methylpyridazine-3-carboxamide;
Ethyl 2-(2,6-dichlorophenyl)thiazolo[5,4-c]pyridin-4-ylcarbamate;
Ethyl 2-(2-chloro-6-fluorophenyl)thiazolo[5,4-c]pyridin-4-ylcarbamate;
Isopropyl 2-(2-chloro-6-fluorophenyl)thiazolo[5,4-c]pyridin-4-ylcarbamate;
1-(2-(2-Chloro-6-fluorophenyl)thiazolo[5,4-c]pyridin-4-yl)-3-(2-hydroxyethyl)urea;
N2-(2-(2,6-Dichlorophenyl)thiazolo[5,4-c]pyridin-4-yl)pyrazine-2,5-diamine;
N2-(2-(2-Chloro-6-fluorophenyl)thiazolo[5,4-c]pyridin-4-yl)pyrazine-2,5-diamine;
2-Cyano-N-(2-(2,6-dichlorophenyl)thiazolo[5,4-c]pyridin-4-yl)acetamide;
N-(2-(2-Chloro-6-fluorophenyl)thiazolo[5,4-c]pyridin-4-yl)-2-cyanoacetamide;
N-(6-Cyclopropylpyrimidin-4-yl)-2-(2,6-dichlorophenyl)thiazolo[5,4-c]pyridin-4-amine;
2-(2,6-Dichlorophenyl)-N-(5-ethylpyrazin-2-yl)thiazolo[5,4-c]pyridin-4-amine;
4-[(5-{[2-(2-Chloro-6-fluorophenyl)-[1,3]thiazolo[5,4-c]pyridin-4-yl]amino}pyrazin-2-yl)methyl]-1λ6,4-thiomorpholine-1,1-dione;
2-(2,6-Dichlorophenyl)-N-(5-methylpyridin-2-yl)thiazolo[5,4-c]pyridin-4-amine;
2-(2,6-Dichlorophenyl)-N-(5-ethylpyridin-2-yl)thiazolo[5,4-c]pyridin-4-amine;
2-(2-Chloro-6-fluorophenyl)-N-(5-ethylpyrazin-2-yl) thiazolo[5,4-c]pyridin-4-amine;
2-(2-Chloro-6-fluorophenyl)-N-(5-(morpholinomethyl) pyrazin-2-yl)thiazolo[5,4-c]pyridin-4-amine;
N-(6-(1-Aminoethyl)pyrimidin-4-yl)-2-(2-chloro-6-fluorophenyl)thiazolo[5,4-c]pyridin-4-amine;
3-Fluoro-2-(4-(6-methylpyrimidin-4-ylamino)thiazolo[5,4-c]pyridin-2-yl)benzonitrile;
2-(4-(6-Aminopyrimidin-4-ylamino)thiazolo[5,4-c]pyridin-2-yl)-3-fluorobenzonitrile;
3-Fluoro-2-(4-(6-(hydroxymethyl)pyrimidin-4-ylamino) thiazolo[5,4-c]pyridin-2-yl)benzonitrile;
3-Fluoro-2-(4-(6-(methylamino)pyrimidin-4-ylamino) thiazolo[5,4-c]pyridin-2-yl)benzonitrile;
N-(2-(2-Cyano-6-fluorophenyl)thiazolo[5,4-c]pyridin-4-yl)cyclopropanecarboxamide;
(1S,2R)—N-(2-(2,6-Dichlorophenyl)thiazolo[5,4-c]pyridin-4-yl)-2-fluorocyclopropanecarboxamide;
(1R,2S)—N-(2-(2,6-Dichlorophenyl)thiazolo[5,4-c]pyridin-4-yl)-2-fluorocyclopropanecarboxamide;
N-[2-(4-Aminomethyl-2,6-dichlorophenyl)-thiazolo[5,4-c]pyridin-4-yl]-2-methylpyrimidine-4,6-diamine;
Cyclopropanecarboxylic acid [2-(4-amino-2,6-dichlorophenyl)-thiazolo[5,4-c]pyridin-4-yl]-amide;
{6-[2-(2-Chloro-6-fluorophenyl)-7-fluorothiazolo[5,4-c] pyridin-4-ylamino]-pyrimidin-4-yl}-methanol;
N-[2-(2-Chloro-6-fluorophenyl)-7-fluorothiazolo[5,4-c] pyridin-4-yl]-2-methylpyrimidine-4,6-diamine;
N-[2-(2,6-Dichlorophenyl)-7-fluorothiazolo[5,4-c]pyridin-4-yl]-pyrimidine-4,6-diamine;
{6-[2-(2,6-Dichlorophenyl)-7-fluorothiazolo[5,4-c]pyridin-4-ylamino]-pyrimidin-4-yl}-methanol;
1-[2-(2,6-Dichlorophenyl)-7-fluorothiazolo[5,4-c]pyridin-4-yl]-3-methyl-urea;
N-[2-(2,6-Dichlorophenyl)-7-fluorothiazolo[5,4-c]pyridin-4-yl]-2-methylpyrimidine-4,6-diamine;
Cyclopropanecarboxylic acid [2-(2,6-dichloro-4-cyanophenyl)-7-fluorothiazolo[5,4-c]pyridin-4-yl]-amide;
3,5-Dichloro-4-[7-fluoro-4-(6-hydroxymethylpyrimidin-4-ylamino)-thiazolo[5,4-c]pyridin-2-yl]-benzonitrile;
4-[4-(6-Aminopyrimidin-4-ylamino)-7-fluorothiazolo[5,4-c]pyridin-2-yl]-3,5-dichlorobenzonitrile;
3-Chloro-2-[4-(6-methylpyrimidin-4-ylamino)-thiazolo [5,4-c]pyridin-2-yl]benzonitrile;
Cyclopropanecarboxylic acid [2-(2-chloro-6-cyanophenyl)-thiazolo[5,4-c]pyridin-4-yl]-amide;
2-[4-(6-Aminopyrimidin-4-ylamino)-7-fluorothiazolo[5,4-c]pyridin-2-yl]-3-chlorobenzonitrile;
2-[4-(6-Amino-2-methyl-pyrimidin-4-ylamino)-7-fluorothiazolo[5,4-c]pyridin-2-yl]-3-chlorobenzonitrile;
Cyclopropanecarboxylic acid [2-(2-chloro-6-cyanophenyl)-7-fluorothiazolo[5,4-c]pyridin-4-yl]-amide;
2-[4-(6-Aminopyrimidin-4-ylamino)-7-fluorothiazolo[5,4-c]pyridin-2-yl]-3-fluorobenzonitrile;
3-Fluoro-2-[7-fluoro-4-(6-hydroxymethylpyrimidin-4-ylamino)thiazolo[5,4-c]pyridin-2-yl]-benzonitrile;
4-(6-aminopyrimidin-4-ylamino)-2-(2-chloro-6-fluorophenyl)thiazolo[5,4-c]pyridine-7-carbonitrile;
4-(6-aminopyrimidin-4-ylamino)-2-(2-cyano-6-fluorophenyl)thiazolo[5,4-c]pyridine-7-carbonitrile;
5-chloro-4-(4-(2,6-dimethylpyrimidin-4-ylamino)thiazolo[5,4-c]pyridin-2-yl)isophthalonitrile;
4-(4-(6-aminopyrimidin-4-ylamino)thiazolo[5,4-c]pyridin-2-yl)-5-chloroisophthalonitrile;
2-(4-(2,6-dimethylpyrimidin-4-ylamino)thiazolo[5,4-c] pyridin-2-yl)benzene-1,3,5-tricarbonitrile;

2-[4-(2-Amino-6-methylpyrimidin-4-ylamino)-7-fluoro-thiazolo[5,4-c]pyridin-2-yl]-3-chlorobenzonitrile;

3-Chloro-2-[7-fluoro-4-(2-hydroxymethyl-6-methylpyrimidin-4-ylamino)-thiazolo[5,4-c]pyridin-2-yl]-benzonitrile;

2-[4-(6-Amino-2-methylpyrimidin-4-ylamino)-7-fluorothiazolo[5,4-c]pyridin-2-yl]-3-fluorobenzonitrile;

3-Chloro-2-[7-fluoro-4-(6-hydroxymethyl-2-methylpyrimidin-4-ylamino)-thiazolo[5,4-c]pyridin-2-yl]benzonitrile;

{6-[2-(4-Amino-2,6-dichlorophenyl)-7-fluorothiazolo[5,4-c]pyridin-4-ylamino]-pyrimidin-4-yl}-methanol;

4-[4-(6-Methylpyrimidin-4-ylamino)-thiazolo[5,4-c]pyridin-2-yl]-3,5-dichlorobenzamidine;

3-Chloro-5-fluoro-2-[4-(6-hydroxymethylpyrimidin-4-ylamino)-thiazolo[5,4-c]pyridin-2-yl]benzonitrile;

2-[4-(2-Amino-6-methylpyrimidin-4-ylamino)-thiazolo[5,4-c]pyridin-2-yl]-3-chlorobenzonitrile;

3-Chloro-2-[4-(6-hydroxymethyl-2-methylpyrimidin-4-ylamino)-thiazolo[5,4-c]pyridin-2-yl]-benzonitrile;

3-Chloro-2-[4-(2-hydroxymethyl-6-methylpyrimidin-4-ylamino)-thiazolo[5,4-c]pyridin-2-yl]-benzonitrile;

[2-(4-Amino-2,6-dichlorophenyl)-7-fluorothiazolo[5,4-c]pyridin-4-yl]-(6-methylpyrimidin-4-yl)-amine;

3-Chloro-5-fluoro-2-[4-(6-methylpyrimidin-4-ylamino)-thiazolo[5,4-c]pyridin-2-yl]benzonitrile; and 2-[4-(6-Amino-2-methylpyrimidin-4-ylamino)-thiazolo[5,4-c]pyridin-2-yl]-3-chloro-5-fluorobenzonitrile.

\* \* \* \* \*